United States Patent
Heiland

(10) Patent No.: US 11,826,423 B2
(45) Date of Patent: Nov. 28, 2023

(54) NUCLEIC ACIDS FOR TREATMENT OF ALLERGIES

(71) Applicant: Immunomic Therapeutics, Inc, Rockville, MD (US)

(72) Inventor: Teri Heiland, New Market, MD (US)

(73) Assignee: Immunomic Therapeutics, Inc., Rockville, MD (US)

( * ) Notice: Subject to any disclaimer, the term of this patent is extended or adjusted under 35 U.S.C. 154(b) by 1156 days.

(21) Appl. No.: 16/461,185

(22) PCT Filed: Nov. 15, 2017

(86) PCT No.: PCT/US2017/061847
§ 371 (c)(1),
(2) Date: May 15, 2019

(87) PCT Pub. No.: WO2018/093932
PCT Pub. Date: May 24, 2018

(65) Prior Publication Data
US 2019/0351050 A1   Nov. 21, 2019

Related U.S. Application Data

(60) Provisional application No. 62/536,088, filed on Jul. 24, 2017, provisional application No. 62/423,111, filed on Nov. 16, 2016.

(51) Int. Cl.
| | | |
|---|---|---|
| *A61K 39/35* | (2006.01) | |
| *A61P 37/08* | (2006.01) | |
| *C07K 14/415* | (2006.01) | |
| *A61K 39/00* | (2006.01) | |

(52) U.S. Cl.
CPC .............. *A61K 39/35* (2013.01); *A61P 37/08* (2018.01); *C07K 14/415* (2013.01); *A61K 2039/6031* (2013.01); *C07K 2319/06* (2013.01)

(58) Field of Classification Search
None
See application file for complete search history.

(56) References Cited

U.S. PATENT DOCUMENTS 9,040,054 B2   5/2015   Wallner et al.

FOREIGN PATENT DOCUMENTS

| CN | 1705492 A | 12/2005 | |
|---|---|---|---|
| CN | 104080481 A | 10/2014 | |
| WO | WO-9308279 A1 * | 4/1993 | ........... C07K 14/415 |
| WO | 2004019978 A1 | 3/2004 | |
| WO | 2004109291 A2 | 12/2004 | |
| WO | 2013113501 A1 | 8/2013 | |
| WO | 2013187906 A1 | 12/2013 | |
| WO | 2015200357 A2 | 12/2015 | |

OTHER PUBLICATIONS

Tan et al (Vaccine, 24:5762-5771, 2006).*
Hofmann et al., "Cor a 1-reactive T cells and IgE are predominantly cross-reactive to Bet v 1 in patients with birch pollen-associated food allergy to hazelnut," J Allergy Clin Immunol, 2013, 131(5): 1384-1392.
Su et al., "CryJ-LAMP DNA Vaccines for Japanese Red Cedar Allergy Induce Robust Th1-Type Immune Responses in Murine Model," J Immunol Res, 2016, pp. 1-15.
EPO Office Action dated Nov. 18, 2020 received in corresponding EP Application 17809419.9.
Chua et al., "DNA Vaccines for the Prevention and Treatment of Allergy", Current Opinion in Allergy and Clinical Immunology, pp. 50-54, (2009).
International Preliminary Report of Patentability dated May 31, 2019 and received in PCT/US2017/061847.
Invitation to pay additional fees discussing why the invention isn't novel dated Mar. 26, 2018.
Written Opinion and International Search Report dated May 30, 2018 in PCT/US2017/061847.

* cited by examiner

*Primary Examiner* — Brian Gangle
(74) *Attorney, Agent, or Firm* — McNeill Baur PLLC

(57) ABSTRACT

The present invention provides DNA vaccines for the treatment or prevention of an allergic response. The vaccines comprise the coding sequence for Allergen X or fragments thereof fused in-frame with the lumenal domain of the lysosomal associated membrane protein (LAMP) and the targeting sequence of LAMP. The vaccines allow for presentation of properly configured three dimensional epitopes for production of an immune response when administered to a subject. The vaccines can be multivalent molecules, and/or can be provided as part of a multivalent vaccine containing two or more DNA constructs.

21 Claims, 28 Drawing Sheets

Specification includes a Sequence Listing.

Portion of Human LAMP-1 Transmembrane/Cytoplasmic Tail Used in Constructs (amino acids 383-417 of Human Full Length Lamp-1 Sequence) (SEQ ID NO:1)

```
LIPIAVGGALAGLVLIVLIAYLVGRKRSHAGYQTI
```

Portion of Human LAMP-1 Lumenal Domain Used in Constructs (amino acids 3-381 of Full Length Lamp-1 Sequence) (SEQ ID NO:2)

```
APRSARRPLLLLLLLLLLGLMHCASAAMFMVKNGNGTACIMANFSAAFSVNYDTKSGPK
NMTLDLPSDATVVLNRSSCGKENTSDPSLVIAFGRGHTLTLNFTRNATRYSVQLMSFVY
NLSDTHLFPNASSKEIKTVESITDIRADIDKKYRCVSGTQVHMNNVTVTLHDATIQAYL
SNSSFSRGETRCEQDRPSPTTAPPAPPSPSPSPVPKSPSVDKYNVSGTNGTCLLASMGL
QLNLTYERKDNTTVTRLLNINPNKTSASGSCGAHLVTLELHSEGTTVLLFQFGMNASSS
RFFLQGIQLNTILPDARDPAFKAANGSLRALQATVGNSYKCNAEEHVRVTKAFSVNIFK
VWVQAFKVEGGQFGSVEECLLDENS
```

5' Sequence Included in Constructs (SEQ ID NO:3)

```
MAPRSARRPLLLLLLLLLLGLMHCASAAMFMVKNGNGTACIMANFSAAFSVNYDTKSGP
KNMTLDLPSDATVVLNRSSCGKENTSDPSLVIAFGRGHTLTLNFTRNATRYSVQLMSFV
YNLSDTHLFPNASSKEIKTVESITDIRADIDKKYRCVSGTQVHMNNVTVTLHDATIQAY
LSNSSFSRGETRCEQDRPSPTTAPPAPPSPSPSPVPKSPSVDKYNVSGTNGTCLLASMG
LQLNLTYERKDNTTVTRLLNINPNKTSASGSCGAHLVTLELHSEGTTVLLFQFGMNASS
SRFFLQGIQLNTILPDARDPAFKAANGSLRALQATVGNSYKCNAEEHVRVTKAFSVNIF
KVWVQAFKVEGGQFGSVEECLLDENSLE
```

Figure 1

Human LAMP-1 Protein Sequence (SEQ ID NO:4)

```
  1  maapgsarrp lllllllll glmhcasaam fmvkngNgta Cimanfsaaf svNydtksgp
 61  kNmtfdlpsd atvvlNrssC gkeNtsdpsl viafgrghtl tlNftrNatr ysvqlmsfvy
121  Nlsdthlfpn asskeiktve sitdiradid kkyrCvsgtq vhmnNvtvtl hdatiqayls
181  NssfsrgetrCeqdrpsptt appappspsp spvpkspsvd kyNvsgtNgt Clliasmglql
241  NltyerkdNt tvtrlininp NktsasgsCg ahlvtlelhs egttvllfqf gmNasssrff
301  lggiqlNtil pdardpafka aNgslralga tvgnsykCna eehvrvtkaf svnifkvwvq
361  afkveggqfg sveeCllden sMLIPIAVGG ALAGLVLIVL IAYLVgrkrs haGYQTI
```

Signal sequence (1-28aa)

First Lumenal Domain (29-194 aa)

Hinge Region (195-227 aa)

Second Lumenal Domain (228-381 aa)

Transmembrane Domain (382-405 aa)

Cytoplasmic Tail (406-417aa)

Figure 2

Mouse LAMP-1 Protein Sequence (SEQ ID NO:5)

```
  1 MAAPGARRPL LILILAGLAH GASAlfevkn NgttCimasf sasflttyet aNgsqivNis
 61 lpasaevlkN gssCgkeNvs dpsltitfgr gylltlNftk Nttrysvqhm yftyNlsdte
121 hfpnaiskei ytmdsttdik adinkayrCv sdirvymkNv tvvlrdatiq aylssgNfsk
181 eethCtqdgp spttgppsps pplvptnptv skyNvtgnNg tCllasmalq lNitylkkdN
241 ktvtrafnis pNdtssgsCg inlvtlkven knralelqfg mNasslffl qgvrlNmtlp
301 dalvptfsis Nhslkalqat vgnsykCnte ehifvskmls lnvfsvqvqa fkvdsdrfgs
361 veeCvqdgnn MLIPIAVGGA LAGLVLIVLI AYLlgrkrsh aGYQTI
```

Signal sequence (1-24aa)

First Lumenal Domain (25-188 aa)

Hinge Region (189-218 aa)

Second Lumenal Domain (219-370 aa)

Transmembrane Domain (371-394 aa)

Cytoplasmic Tail (395-406aa)

Figure 3

For the constructs, the sequences are highlighted as follows: *hLAMP Signal peptide*-hLAMP Luminal domain -CTCGAG-Antigen-GAATTC-hLAMP TM and Cyto domain

SEQ ID NO:7 Cor a 1 amino acids (1-159)

MGVFCYEDEATSVIPPARLFKSFVLDADNLIPKVAPQHFTSAENLEGNGGPGTIKKITFAEGNEFKYMKH
KVEEIDHANFKYCYSIIEGGPLGHTLEKISYEIKMAAAPHGGGSILKITSKYHTKGNASINEEEIKAGKE
KAAGLFKAVEAYLLAHPDAY

Polynucleotide sequence encoding Cor a 1(flanking XhoI-EcoRI uppercase)(SEQ ID NO:6)

CTCGAGatgggcgtgttctgctacgaggacgaggccacaagcgtgatccctcccgccagactgttcaaga
gcttcgtgctggacgccgacaatctgatccccaaagtggccccccagcacttcaccagcgccgagaatct
ggaaggcaatggcggacccggcaccatcaagaagatcacattcgccgagggcaacgagttcaagtacatg
aagcacaaagtggaagagatcgaccacgccaacttcaagtactgctacagcatcatcgaaggcggccctc
tgggccacacactggaaaagatcagctacgagatcaagatggccgctgcccctcacggcggaggcagcat
tctgaagatcaccagcaagtaccacaccaagggcaacgccagcatcaacgaggaagaaatcaaggccggc
aaagagaaagccgccggactgtttaaggccgtggaagcctatctgctggcccaccccgatgcctacGAAT
TC

SEQ ID NO:9 Cor a 9 amino acids (24-320)

INVGLRRQQQRYFGECNLDRLNALEPTNRIEAEACQIESWDHNDQQFQCAGVAVIRRTIEPNGLLLPQYS
NAPELIYIERGRGITGVLFPGCPETFEDPQQQSQQGQRQGQGQSQRSEQDRHQKIRHFREGDIIALPAGV
AHWCYNDGDSPVVTVSLLHTNNYANQLDENPRHFYLAGNPDDEHQRQGQQQFGQRRRQQQHSHGEQGEQE
QQGEGNNVFSGFDAEFLADAFNVDVDTARRLQSNQDKRRNIVKVEGRLQVVRPERSRQEWERQERQERES
EQERERQRRQGGRGRDVN

Polynucleotide encoding Cor a 9 (revised)(flanking XhoI-EcoRI uppercase) (SEQ ID NO:8)

CTCGAGatcaacgtgggactgcggagacagcagcagcggtacttcggcgagtgcaatctggaccggctga
acgctctggaacccaccaacagaatcgaggccgaggcttgccagatcgagagctgggaccacaacgacca
gcagttccagtgtgctggcgtggccgtgatcagacggaccatcgagcccaacggactgctgctgccccag
tacagcaatgccccgagctgatctacatcgagcggggcagaggaatcaccggcgtgctgtttcccggct
gccccgagacattcgaggaccctcagcagcagagccagcaaggccagagacaaggccaaggccagtccca
gagaagcgagcaagaccggcaccagaagatccggcacttcagagagggcgacatcattgctctgccagcc
ggcgtggcccactggtgctacaatgatggcgatagccccgtcgtgaccgtgtctctgctgcacaccaaca
actacgccaaccagctggacgagaaccccagacacttctatctggccggcaaccccgacgacgagcacca
gaggcaagggcagcagcagttcggccagagaagaaggcagcagcagcacagccatggcgagcaaggcgag
caagagcagcaaggcgagggcaacaacgtgttcagcggcttcgacgccgagtttctggccgacgccttca
acgtggacgtggacacagccagacggctgcagtccaaccaagacaagcggcggaacatcgtgaaagtgga
aggccggctccaagtcgtgcggcccgagagatctagacaagagtgggagcggcaagagcggcaagaacgc
gagagcgagcaagagagagagcggcagagaaggcaaggcggcagaggcagagatgtgaacGAATTC

SEQ ID NO:11 Cor a 1-Gly 4-Cor a 9 amino acids

MGVFCYEDEATSVIPPARLFKSFVLDADNLIPKVAPQHFTSAENLEGNGGPGTIKKITFAEGNEFKYMKH

Figure 4

For the constructs, the sequences are highlighted as follows: *hLAMP Signal peptide*-hLAMP Luminal domain –CTCGAG-Antigen-GAATTC-hLAMP TM and Cyto domain KVEEIDHANFKYCYSIIEGGPLGHTLEKISYEIKMAAAPHGGGSILKITSKYHTKGNASINEEEIKAGKE
KAAGLFKAVEAYLLAHPDAYGGGGINVGLRRQQQRYFGECNLDRLNALEPTNRIEAEACQIESWDHNDQQ
FQCAGVAVIRRTIEPNGLLLPQYSNAPELIYIERGRGITGVLFPGCPETFEDPQQQSQQGQRQGQGQSQR
SEQDRHQKIRHFREGDIIALPAGVAHWCYNDGDSPVVTVSLLHTNNYANQLDENPRHFYLAGNPDDEHQR
QGQQQFGQRRRQQQHSHGEQGEQEQQGEGNNVFSGFDAEFLADAFNVDVDTARRLQSNQDKRRNIVKVEG
RLQVVRPERSRQEWERQERQERESEQERERQRRQGGRGRDVN

Polynucleotide encoding Cor a 1-GLY4-Cor a 9 (SEQ ID NO:10) (XhoI-EcoRI and Gly4 linker uppercase)

CATATGCTCGAGatgggcgtgttctgctacgaggacgaggccacaagcgtgatccctcccgccagactgt
tcaagagcttcgtgctggacgccgacaatctgatccccaaagtggccccccagcacttcaccagcgccga
gaatctggaaggcaatggcggacccggcaccatcaagaagatcacattcgccgagggcaacgagttcaag
tacatgaagcacaaagtggaagagatcgaccacgccaacttcaagtactgctacagcatcatcgaaggcg
gccctctgggccacacactggaaaagatcagctacgagatcaagatggccgctgcccctcacggcggagg
cagcattctgaagatcaccagcaagtaccacaccaagggcaacgccagcatcaacgaggaagaaatcaag
gccggcaaagagaaagccgccggactgtttaaggccgtggaagcctatctgctggcccaccccgatgcct
acGGCGGAGGGGGCatcaacgtgggactgcggagacagcagcagcggtacttcggcgagtgcaatctgga
ccggctgaacgctctggaaccaccaacagaatcgaggccgaggcttgccagatcgagagctgggaccac
aacgaccagcagttccagtgtgctggcgtggccgtgatcagacggaccatcgagcccaacggactgctgc
tgccccagtacagcaatgccccgagctgatctacatcgagcggggcagaggaatcaccggcgtgctgtt
tcccggctgccccgagacattcgaggaccctcagcagcagagccagcaaggccagagacaaggccaaggc
cagtccagagaagcgagcaagaccggcaccagaagatccggcacttcagagagggcgacatcattgctc
tgccagccggcgtggcccactggtgctacaatgatggcgatagccccgtcgtgaccgtgtctctgctgca
caccaacaactacgccaaccagctggacgagaaccccagacacttctatctggccggcaaccccgacgac
gagcaccagaggcaaggcagcagcagttcggccagagaagaaggcagcagcagcacagccatggcgagc
aaggcgagcaagagcagcaaggcgagggcaacaacgtgttcagcggcttcgacgccgagtttctggccga
cgccttcaacgtggacgtggacacagccagacggctgcagtccaaccaagacaagcggcggaacatcgtg
aaagtggaaggccggctccaagtcgtgcggcccgagagatctagacaagagtgggagcggcaagagcggc
aagaacgcgagagcgagcaagagagagagcggcagagaaggcaaggcggcagaggcagagatgtgaacGA
ATTCGTCGAC

SEQ ID NO:13 Pru du 6 amino acids (26-272)

ARQSQLSPQNQCQLNQLQAREPDNRIQAEAGQIETWNFNQEDFQCAGVAASRITIQRNGLHLPSYSNAPQ
LIYIVQGRGVLGAVFSGCPETFEESQQSSQQGRQQEQEQERQQQQQGEQGRQQGQQEQQERQGRQQGRQ
QQEEGRQQEQQQGQQGRPQQQQQFRQFDRHQKTRRIREGDVVAIPAGVAYWSYNDGDQELVAVNLFHVSS
DHNQLDQNPRKFYLAGNPENEFNQQGQSQPRQQGEQGRPGQHQQPFGRPRQQEQQGSGNNVFSGFNTQLL
AQALNVNEETARNLQGQNDNRNQIIRVRGNLDFVQPPRGRQEREHEERQQEQLQQERQQQGGQLMAN

Polynucleotide encoding Pru du 6 (SEQ ID NO:12) (flanking XhoI-EcoRI-uppercase)

CTCGAGgccagacagagccagctgagcccccagaatcagtgccagctgaaccagctgcaagccagagagc
ccgacaaccggattcaagccgaggccggccagatcgagacatggaacttcaaccaagaggacttccagtg
tgccggcgtggccgccagcagaatcaccatccagcggaacggactgcatctgccagctacagcaacgcc

Figure 4 (cont.)

For the constructs, the sequences are highlighted as follows: *hLAMP Signal peptide*-hLAMP Luminal domain –CTCGAG-<u>Antigen</u>-GAATTC-hLAMP TM and Cyto domain ccccagctgatctacatcgtgcaaggcagaggcgtgctgggcgccgtgtttagcggatgccccgagacat
tcgaggaaagccagcagagcagccagcaaggccggcagcaagagcaagaacaagagagacaacagcagca
gcaaggggagcaaggcagacagcaaggacagcaagagcagcagcaagagcgccaaggacggcagcaaggg
cgccagcagcaagaagagggcagacagcaagaacagcagcaaggccagcaagggcggcctcagcagcagc
agcagttccggcagttcgaccggcaccagaaaacccggcggatcagagaaggcgacgtggtggctattcc
agccggggtggcctactggtcctacaacgacggcgaccaagaactggtggccgtgaatctgttccacgtg
tccagcgaccacaaccagctggaccagaaccccggaagttctatctggctggcaacccgagaacgagt
tcaaccagcaagggcagagccagcccagacagcaaggcgaacaaggacggcccggacagcaccagcagcc
tttcggcagaccacggcagcaagagcagcaaggcagcggcaacaacgtgttcagcggcttcaacacccag
ctgctggcccaagctctgaacgtgaacgaggaaaccgccggaatctgcaaggccagaacgacaacagaa
accagatcatcagagtgcggggcaatctggacttcgtgcagcccctagagggcggcaagagagagagca
cgaagagaggcagcaagaacagctgcagcaagagcggcagcagcaaggcggacagctgatggccaacGAA
TTC

SEQ ID NO:15 Ana o 1 amino acids (27-538)

KIDPELKQCKHQCKVQRQYDEQQKEQCVKECEKYYKEKKGREREHEEEEEEWGTGGVDEPSTHEPAEKHL
SQCMRQCERQEGGQQKQLCRFRCQERYKKERGQHNYKREDDEDEDEDEAEEEDENPYVFEDEDFTTKVKT
EQGKVVLLPKFTQKSKLLHALEKYRLAVLVANPQAFVVPSHMDADSIFFVSWGRGTITKILENKRESINV
RQGDIVSISSGTPFYIANNDENEKLYLVQFLRPVNLPGHFEVFHGPGGENPESFYRAFSWEILEAALKTS
KDTLEKLFEKQDQGTIMKASKEQIRAMSRRGEGPKIWPFTEESTGSFKLFKKDPSQSNKYGQLFEAERID
YPPLEKLDMVVSYANITKGGMSVPFYNSRATKIAIVVSGEGCVEIACPHLSSSKSSHPSYKKLRARIRKD
TVFIVPAGHPFATVASGNENLEIVCFEVNAEGNIRYTLAGKKNIIKVMEKEAKELAFKMEGEEVDKVFGK
QDEEFFFQGPEWRKEKEGRADE

Polynucleotide encoding Ana o 1(SEQ ID NO:14) (flanking XhoI-EcoRI uppercase)

CTCGAGaagatcgaccccgagctgaagcagtgcaagcaccagtgcaaagtgcagcggcagtacgacgagc
agcagaaagaacagtgcgtgaaagagtgcgagaagtactacaaagagaagaagggccgcgagcgcgagca
cgaagaggaagaggaagaatggggcaccggcggagtggacgagccttctacacacgagcccgccgagaaa
catctgagccagtgcatgagacagtgcgaacggcaagagggcggccagcagaaacagctgtgccggttcc
ggtgccaagagcggtacaagaaagagcggggccagcacaactacaagagagaggacgacgaggacgaaga
tgaggacgaggctgaggaagaggacgagaaccctacgtgttcgaggatgaggacttcaccaccaaagtg
aaaaccgagcaaggcaaagtggtgctgctgccaagttcacccagaagtccaagctgctgcacgctctgg
aaaagtaccggctggccgttctggtggccaaccctcaagccttcgtggtgcccagccacatggacgccga
cagcatcttcttcgtgtcttggggcagaggcaccatcaccaagattctggaaaacaagcgcgagagcatc
aacgtgcggcaaggcgacatcgtgtccatcagcagcggcacccccttctacattgccaacaacgacgaga
acgagaagctgtatctggtgcagtttctgcggcccgtgaatctgcccggccactttgaagtgttccacgg
acccggcggagagaaccccgagagcttctacagagccttcagctgggaaattctggaagccgctctgaaa
acatccaaggacacactggaaaagctgttcgagaagcaagaccaagggaccatcatgaaggccagcaaag
aacagatccgggccatgagcagaagaggcgagggccccaagatctggccttcaccgagaaagcaccgg
cagcttcaagctgtttaagaaggaccccagccagagcaacaaatacgggcagctgtttgaggccgagcgg

Figure 4 (cont.)

For the constructs, the sequences are highlighted as follows: *hLAMP Signal peptide*-hLAMP Luminal domain –CTCGAG-Antigen-GAATTC-hLAMP TM and Cyto domain

```
atcgactaccccccactggaaaagctggacatggtggtgtcctacgccaatatcaccaagggcggcatga
gcgtgccctttcacaacagcagagccaccaagatcgccatcgtggtgtccggcgagggctgcgtggaaat
cgcttgccctcatctgagcagcagcaagtccagccaccccagctacaagaagctgcgggccagaatccgg aaggacaccgtgttcatcgtgccagccggccacccttttgccacagtggccagcggcaacgagaatctgg
aaatcgtgtgcttcgaagtgaacgccgagggcaacatccggtacacactggccggcaagaagaacatcat
caaagtgatggaaaaggaagccaaagaactggcctttaagatggaaggcgaggaagtggacaaagtgttc
ggcaagcaagatgaagagttcttctttcaaggccccgagtggcgcaaagagaaagagggcagagccgacg
agGAATTC
```

SEQ ID NO:17 Ana o 2 amino acids (1-457)

LSVCFLILFHGCLASRQEWQQQDECQIDRLDALEPDNRVEYEAGTVEAWDPNHEQFRCAGVALVRHTIQP
NGLLLPQYSNAPQLIYVVQGEGMTGISYPGCPETYQAPQQGRQQGQSGRFQDRHQKIRRFRRGDIIAIPA
GVAHWCYNEGNSPVVTVTLLDVSNSQNQLDRTPRKFHLAGNPKDVFQQQQQHQSRGRNLFSGFDTELLAE
AFQVDERLIKQLKSEDNRGGIVKVKDDELRVIRPSRSQSERGSESEEESEDEKRRWGQRDNGIEETICTM
RLKENINDPARADIYTPEVGRLTTLNSLNLPILKWLQLSVEKGVLYKNALVLPHWNLNSHSIIYGCKGKG
QVQVVDNFGNRVFDGEVREGQMLVVPQNFAVVKRAREERFEWISFKTNDRAMTSPLAGRTSVLGGMPEEV
LANAFQISREDARKIKFNNQQTTLTSGESSHHMRDDA

Polynucleotide encoding Ana o 2 (SEQ ID NO:16)(flanking XhoI-EcoRI uppercase)

```
CTCGAGctgagcgtgtgctttctgattctgttccacggctgtctggccagccggcaagaatggcagcagc
aagacgagtgccagatcgaccggctggacgctctggaacccgacaaccgggtggaatacgaggccggcac
agtggaagcttgggaccccaaccacgagcagttcagatgtgccggcgtggcactcgtgcggcacaccatc
cagccaaacggactgctgctgccccagtacagcaacgcccccagctgatctatgtggtgcaaggcgagg
gcatgaccggcatcagctatcccggctgccccgagacatatcaagcccctcagcaaggcagacagcaagg
ccagagcggccggttccaagaccggcaccagaagatccggcggttcagacggggcgacatcattgccatt
ccagccggggtggcccactggtgctacaacgagggcaatagcccgtcgtgaccgtgacactgctggacg
tgtccaacagccagaaccagctggaccggacccccggaagtttcatctggccggcaaccccaaggacgt
gttccagcaacagcagcagcaccagagccggggcagaaatctgttcagcggcttcgacaccgagctgctg
gccgaggcttttcaagtggacgagcggctgatcaagcagctgaagtccgaggacaacagaggcggcatcg
tgaaagtgaaggacgacgagctgagagtgatccggcccagcagaagccagagcgagagaggcagcgagag
cgaggaagagtctgaggacgagaagcggagatggggccagcgggacaacggcatcgaagagacaatctgc
accatgcggctgaaagagaacatcaacgaccccgccagagccgacatctacacccccgaagtgggccggc
tgacaactctgaactctctgaatctgccattctgaagtggctgcagctgtccgtggaaaagggggtgct
gtacaagaacgctctggtgctgcctcactggaatctgaacagccacagcatcatctacggctgcaagggc
aagggccaagtccaagtggtggacaacttcggcaacagagtgttcgacggcgaagtgcgcgagggccaga
tgctcgtggtgccccagaatttcgccgtcgtgaagcgggccagagaagaaagattcgagtggatcagctt
caagaccaacgaccgggccatgaccagccctctggccggaagaacatctgtgctgggcggcatgcccgag
gaagtgctggctaacgccttccagatcagcagagaggacgcccggaagatcaagttcaacaaccagcaga
ccacactgaccagcggcgagagcagccaccacatgagagatgacgccGAATTC
```

Figure 4 (cont.)

For the constructs, the sequences are highlighted as follows: *hLAMP Signal peptide*-hLAMP Luminal domain –CTCGAG-Antigen-GAATTC-hLAMP TM and Cyto domain

SEQ ID NO:19 Ana o 3 amino acids (21-138)

SIYRAIVEVEEDSGREQSCQRQFEEQQRFRNCQRYVKQEVQRGGRYNQRQESLRECCQELQEVDRRCRCQ
NLEQMVRQLQQQEQIKGEEVRELYETASELPRICSISPSQGCQFQSSY

Polynucleotide encoding Ana o 3 (SEQ ID NO:18) (flanking XhoI-EcoRI uppercase)

CTCGAGagcatctaccgggccatcgtggaagtggaagaggacagcggcagagagcagagctgccagcggc
agttcgaggaacagcagcggttcagaaactgccagagatacgtgaagcaagaagtgcagagaggcggcag
atacaaccagagacaagagtctctgagagagtgctgccaagagctgcaagaagtggaccggcgctgccgg
tgccagaatctggaacagatggtgcgccagctgcagcagaagagcagatcaagggcgaggaagtgcgcg
agctgtacgagacagccagcgagctgcctcggatctgcagcatcagcccaagccaaggctgccagttcca
gagcagctacGAATTC

SEQ ID NO:21 Ana o 2-Gly4-Ana o 1-Gly4-Ana o 3 amino acids

LSVCFLILFHGCLASRQEWQQQDECQIDRLDALEPDNRVEYEAGTVEAWDPNHEQFRCAGVALVRHTIQF
NGLLLPQYSNAPQLIYVVQGEGMTGISYPGCPETYQAPQQGRQQGQSGRFQDRHQKIRRFRRGDIIAIPA
GVAHWCYNEGNSPVVTVTLLDVSNSQNQLDRTPRKFHLAGNPKDVFQQQQHQSRGRNLFSGFDTELLAE
AFQVDERLIKQLKSEDNRGGIVKVKDDELRVIRPSRSQSERGSESEEESEDEKRRWGQRDNGIEETICTM
RLKENINDPARADIYTPEVGRLTTLNSLNLPILKWLQLSVEKGVLYKNALVLPHWNLNSHSIIYGCKGKG
QVQVVDNFGNRVFDGEVREGQMLVVPQNFAVVKRAREERFEWISPFKTNDRAMTSPLAGRTSVLGGMPEEV
LANAFQISREDARKIKFNNQQTTLTSGESSHHMRDDA*GGGG*KIDPELKQCKHQCKVQRQYDEQQKEQCV
KECEKYYKEKKGREREHEEEEEEWGTGGVDEPSTHEPAEKHLSQCMRQCERQEGGQQKQLCRFRCQERYK
KERGQHNYKREDDEDEDEDEAEEEDENPYVFEDEDFTTKVKTEQGKVVLLPKFTQKSKLLHALEKYRLAV
LVANPQAFVVPSHMDADSIFFVSWGRGTITKILENKRESINVRQGDIVSISSGTPFYIANNDENEKLYLV
QFLRPVNLPGHFEVEHGPGGENPESFYRAFSWEILEAALKTSKDTLEKLFEKQDQGTIMKASKEQIRAMS
RRGEGPKIWPFTEESTGSFKLFKKDPSQSNKYGQLFEAERIDYPPLEKLDMVVSYANITKGGMSVPFYNS
RATKIAIVVSGEGCVEIACPHLSSSKSSHPSYKKLRARIRKDTVFIVPAGHPFATVASGNENLEIVCFEV
NAEGNIRYTLAGKKNIIKVMEKEAKELAFKMEGEEVDKVFGKQDEEFFFQGPEWRKEKEGRADE*GGGG*s
IYRAIVEVEEDSGREQSCQRQFEEQQRFRNCQRYVKQEVQRGGRYNQRQESLRECCQELQEVDRRCRCQN
LEQMVRQLQQQEQIKGEEVRELYETASELPRICSISPSQGCQFQSSY

Polynucleotide encoding Ana 0 2-Gly4-Ana 0 1-Gly4-Ana 0 3 (SEQ ID NO:20)

CTCGAGctgagcgtgtgctttctgattctgttccacggctgtctggccagccggcaagaatggcagcagc
aagacgagtgccagatcgaccggctggacgctctggaacccgacaacgggtggaatacgaggccggcac
agtggaagcttgggaccccaaccacgagcagttcagatgtgccggcgtggcactcgtgcggcacaccatc
cagccaaacggactgctgctgccccagtacagcaacgcccccagctgatctatgtggtgcaaggcgagg
gcatgaccggcatcagctatcccggctgccccgagacatatcaagcccctcagcaaggcagacagcaagg
ccagagcggccggttccaagaccggcaccagaagatccggcggttcagacggggcgacatcattgccatt
ccagccggggtggcccactggtgctacaacgagggcaatagcccgtcgtgaccgtgacactgctggacg
tgtccaacagccagaaccagctggaccggacccccggaagtttcatctggccggcaaccccaaggacgt
gttccagcaacagcagcagcaccagagccggggcagaaatctgttcagcggcttcgacaccgagctgctg For the constructs, the sequences are highlighted as follows: *hLAMP Signal peptide*-hLAMP Luminal domain –CTCGAG-Antigen-GAATTC-hLAMP TM and Cyto domain

```
gccgaggcttttcaagtggacgagcggctgatcaagcagctgaagtccgaggacaacagaggcggcatcg
tgaaagtgaaggacgacgagctgagagtgatccggcccagcagaagccagagcgagagaggcagcgagag
cgaggaagagtctgaggacgagaagcggagatggggccagcgggacaacggcatcgaagagacaatctgc
accatgcggctgaaagagaacatcaacgaccccgccagagccgacatctacaccccgaagtgggccggc
tgacaactctgaactctctgaatctgcccattctgaagtggctgcagctgtccgtggaaaaggggtgct
gtacaagaacgctctggtgctgcctcactggaatctgaacagccacagcatcatctacggctgcaaggg
aagggccaagtccaagtggtggacaacttcggcaacagagtgttcgacggcgaagtgcgcgagggccaga
tgctcgtggtgccccagaatttcgccgtcgtgaagcgggccagagaagaaagattcgagtggatcagctt
caagaccaacgaccgggccatgaccagccctctggccggaagaacatctgtgctgggcggcatgcccgag
gaagtgctggctaacgccttccagatcagcagagaggacgcccggaagatcaagttcaacaaccagcaga
ccacactgaccagcggcgagagcagccaccacatgagagatgacgccGGCGGAGGGGGCaagatcgaccc
cgagctgaagcagtgcaagcaccagtgcaaagtgcagcggcagtacgacgagcagcagaagaacagtgc
gtgaaagagtgcgagaagtactacaaagagaagaagggccgcgagcgcgagcacgaagaggaagaggaag
aatggggcaccggcggagtggacgagccttctacacacgagcccgccgagaaacatctgagccagtgcat
gagacagtgcgaacggcaagagggcggccagcagaaacagctgtgccggttccggtgccaagagcggtac
aagaaagagcggggccagcacaactacaagagagaggacgacgaggacgaagatgaggacgaggctgagg
aagaggacgagaacccctacgtgttcgaggatgaggacttcaccaccaaagtgaaaaccgagcaaggcaa
agtggtgctgctgcccaagttcacccagaagtccaagctgctgcacgctctggaaaagtaccggctggcc
gttctggtggccaaccctcaagccttcgtggtgcccagccacatgacgccgacagcatcttcttcgtgt
cttggggcagaggcaccatcaccaagattctggaaaacaagcgcgagagcatcaacgtgcggcaaggcga
catcgtgtccatcagcagcggcacccccttctacattgccaacaacgacgagaacgagaagctgtatctg
gtgcagtttctgcggcccgtgaatctgcccggccactttgaagtgttccacggacccggcggagagaacc
ccgagagcttctacagagccttcagctgggaaattctggaagccgctctgaaaacatccaaggacacact
ggaaaagctgttcgagaagcaagaccaagggaccatcatgaaggccagcaagaacagatccggccatg
agcagaagaggcgagggccccaagatctggcccttcaccgaggaaagcaccggcagcttcaagctgttta
agaaggacccagccagagcaacaaatacgggcagctgtttgaggccgagcggatcgactacccccccact
ggaaaagctggacatggtggtgtcctacgccaatatccaccaaggggcggcatgagcgtgccccttttacaac
agcagagccaccaagatcgccatcgtggtgtccggcgagggctgcgtggaaatcgcttgccctcatctga
gcagcagcaagtccagccacccagctacaagaagctgcggggccagaatccggaaggacaccgtgttcat
cgtgccagccggccacccttttgccacagtggccagcggcaacgagaatctggaaatcgtgtgcttcgaa
gtgaacgccgagggcaacatccggtacacactggccggcaagaagaacatcatcaaagtgatggaaaagg
aagccaaagaactggcctttaagatggaaggcgaggaagtggacaaagtgttcgcaagcaagatgaaga
gttcttctttcaaggccccgagtggcgcaaagagaaagagggcagagccgacgagGGCGGAGGGGGCagc
atctaccgggccatcgtggaagtggaagaggacagcggcagagagcagagctgccagcggcagttcgagg
aacagcagcggttcagaaactgccagagatacgtgaagcaagaagtgcagagaggcggcagatacaacca
gagacaagagtctctgagagagtgctgccaagagctgcaagaagtggaccggcgctgccggtgccagaat
ctggaacagatggtgcgccagctgcagcagcaagagcagatcaagggcgaggaagtgcgcgagctgtacg
agacagccagcgagctgcctcggatctgcagcatcagcccaagccaaggctgccagttccagagcagcta
cGAATTC
```

Figure 4 (cont.)

For the constructs, the sequences are highlighted as follows: *hLAMP Signal peptide*-hLAMP Luminal domain –CTCGAG-Antigen-GAATTC-hLAMP TM and Cyto domain

SEQ ID NO:23 Jug n 1 amino acids (39-161)

RTTITTMEIDEDIDNPRRRGEGCQEQIQRQQNLNHCQYYLRQQSRSGGYDEDNQRQHFRQCCQQLSQIEE
QCQCEGLRQAVRRQQQQQGLRGEEMEEMVQSARDLPKECGISSQRCEIRRSWF

Polynucleotide encoding Jug n 1(SEQ ID NO:22) (flanking XhoI-EcoRI uppercase)

CTCGAGcggaccaccatcaccaccatggaaatcgacgaggacatcgacaaccccagaagaagaggcgagg
gctgccaagagcagatccagcggcagcagaatctgaaccactgccagtactatctgaggcagcagagcag
aagcggcggctacgacgaggataaccagagacagcacttcagacagtgctgccagcagctgagccagatc
gaggaacagtgccagtgcgagggactgagacaagccgtgcggagacaacagcagcagcaaggactgcggg
gcgaagagatggaagaaatggtgcagagcgccagagatctgcccaaagagtgcggcatcagcagccagag
atgcgagatccggcggagttggttcGAATTC

SEQ ID NO:25 Jug r 2 amino acids (1-593)

RGRDDDDEENPRDPREQYRQCQEYCRRQGQGQRQQQQCQIRCEERLEEDQRSQEERERRRGRDVDDQNPR
DPEQRYEQCQQQCERQRRGQEQTLCRRRCEQRRQQEERERQRGRDRQDPQQQYHRCQRRCQIQEQSPERQ
RQCQQRCERQYKEQQGRERGPEASPRRESRGREEEQQRHNPYYFHSQSIRSRHESEEGEVKYLERFTERT
ELLRGIENYRVVILDANPNTSMLPHHKDAESVAVVTRGRATLTLVSQETRESFNLECGDVIRVPAGATVY
VINQDSNERLEMVKLLQPVNNPGQFREYYAAGAKSPDQSYLRVFSNDILVAALNTPRDRLERFFDQQEQR
EGVIIRASQEKLRALSQHAMSAGQRPWGRRSSGGPISLKSESPSYSNQFGQFFEACPEEHRQLQEMDVLV
NYAEIKRGAMMVPHYNSKATVVVYVVEGTGRYEMACPHVSSQSYEGQGRREQEEEESTGRFQKVTARLAR
GDIFVIPAGHPIAITASQNENLRLLGFDINGENNQRDFLAGQNNIINQLEREAKELSFNMPREEIEEIFE
SQMESYFVPTERQSRRGQGRDHPLASILDFAFF

Polynucleotide encoding Jug r 2 (SEQ ID NO:24) (flanking XhoI-EcoRI uppercase)

CTCGAGagaggccgggacgacgacgatgaggaaaaccccagagatccccgcgagcagtaccggcagtgcc
aagagtactgcagaaggcaaggccaaggccagagacagcagcagcagtgccagatcagatgcgaggaacg
gctggaagaggaccagcggagccaagaggaacgcgagcggagaagaggcagagatgtggacgaccagaac
ccccgggaccccgagcagagatacgagcagtgtcagcagcagtgtgaacggcagcggagaggccaagagc
agacactgtgtcggcggagatgcgagcagcggcggcagcaagaggaaagagaacgccagcggggcagaga
cagacaagaccccagcagcagtaccaccggtgccagagaagatgccagatccaagaacagagccccgag
cggcagcgccagtgccagcagagatgcgaaagacagtacaaagagcagcaaggcagagagaggggcccag
aggccagccctagaagagagtccagaggacgggaagaagaacagcagcggcacaaccctactacttcca
cagccagagcatcagaagccggcacgagagcgaagagggcgaagtgaagtatctggaacggttcaccgag
cggaccgagctgctgagaggcatcgagaactaccgggtcgtgattctggacgccaaccccaacacatcca
tgctgccccaccacaaggacgccgagtctgtggccgtcgtgacaaggggcagagccacactgacactggt
gtcccaagagactcgcgagagcttcaatctggaatgcggcgacgtgatccgggtgccagctggggctaca
gtgtacgtgatcaaccaagacagcaacgagcggctggaaatggtcaagctgctgcagcccgtgaacaacc
ccggccagttcagagagtactacgccgctggcgccaagtccccgaccagagctatctgcgggtgttcag
caacgacattctggtggccgctctgaataccctcgggacagactggaaagattcttcgatcagcaagag For the constructs, the sequences are highlighted as follows: *hLAMP Signal peptide*-hLAMP Luminal domain –CTCGAG-<u>Antigen</u>-GAATTC-hLAMP TM and Cyto domain

```
cagcgcgagggcgtgatcatcagagccagccaagagaagctgcgggctctgagccagcacgccatgtctg
ctggacagaggccttggggcagaagaagctctggcggccctatctctctgaagtccgagagcccctcta
cagcaaccagtttggccagttcttcgaggcttgccccgaggaacaccggcagctgcaagaaatggacgtg
ctcgtgaactacgccgagatcaagagggcgccatgatggtgccccactacaacagcaaggccaccgtgg
tggtgtacgtggtggaaggcaccggcagatacgagatggcatgcccccacgtgtccagccagtcttacga
gggccaaggacgcagagagcaagaagaggaagagtccaccggacggttccagaaagtgaccgccagactg
gccagaggcgacatcttcgtgatcccagccggacaccctatcgccatcaccgccagccagaacgagaatc
tgcggctgctgggcttcgacatcaacggcgagaacaaccagcgggactttctggccggacagaacaacat
catcaaccagctggaacgggaagccaaagaactgagcttcaacatgccccgcgaggaaatcgaagagatt
ttcgagagccagatggaaagctacttcgtgcccaccgagcgccagagcagaagggggccaagggcgggatc
acccactggcctctattctggatttcgccttcttcGAATTC
```

SEQ ID NO:27 Jug n 1-Gly4-Jug r 2 amino acids

RTTITTMEIDEDIDNPRRRGEGCQEQIQRQQNLNHCQYYLRQQSRSGGYDEDNQRQHFRQCCQQLSQIEE
QCQCEGLRQAVRRQQQQQGLRGEEMEEMVQSARDLPKECGISSQRCEIRRSWF<u>GGGG</u>RGRDDDDEENPRD
PREQYRQCQEYCRRQGQGQRQQQQCQIRCEERLEEDQRSQEERERRRGRDVDDQNPRDPEQRYEQCQQQC
ERQRRGQEQTLCRRRCEQRRQQEERERQRGRDRQDPQQQYHRCQRRCQIQEQSPERQRQCQQRCERQYKE
QQGRERGPEASPRRESRGREEEQQRHNPYYFHSQSIRSRHESEEGEVKYLERFTERTELLRGIENYRVVI
LDANPNTSMLPHHKDAESVAVVTRGRATLTLVSQETRESFNLECGDVIRVPAGATVYVINQDSNERLEMV
KLLQPVNNPGQFREYYAAGAKSPDQSYLRVFSNDILVAALNTPRDRLERFFDQQEQREGVIIRASQEKLR
ALSQHAMSAGQRPWGRRSSGGPISLKSESPSYSNQFGQFFEACPEEHRQLQEMDVLVNYAEIKRGAMMVP
HYNSKATVVVYVVEGTGRYEMACPHVSSQSYEGQGRREQEEEESTGRFQKVTARLARGDIFVIPAGHPIA
ITASQNENLRLLGFDINGENNQRDFLAGQNNIINQLEREAKELSFNMPREEIEEIFESQMESYFVPTERQ
SRRGQGRDHPLASILDFAFF

Polynucleotide encoding Jug n 1-Gly4-Jug r 2 (flanking XhoI-EcoRI uppercase) (SEQ ID NO:26)

CTCGAGcggaccaccatcaccaccatggaaatcgacgaggacatcgacaacccagaagaagaggcgagg
gctgccaagagcagatccagcggcagcagaatctgaaccactgccagtactatctgaggcagcagagcag
aagcggcggctacgacgaggataaccagagacagcacttcagacagtgctgccagcagctgagccagatc
gaggaacagtgccagtgcgagggactgagacaagccgtgcggagacaacagcagcagcaaggactgcggg
gcgaagagatggaagaaatggtgcagagcgccagagatctgcccaaagagtgcggcatcagcagccagag
atgcgagatccggcggagttggttc*GGCGGAGGGGGC*agaggccgggacgacgacgatgaggaaaacccc
agagatccccgcgagcagtaccggcagtgccaagagtactgcagaaggcaaggccaagagcagagacagc
agcagcagtgccagatcagatgcgaggaacggctggaagaggaccagcgagccaagaggaacgcgagcg
gagaagaggcagagatgtggacgaccagaacccgggacccgagcagagatacgagcagtgtcagcag
cagtgtgaacggcagcggagaggccaagagcagacactgtgtcggcggagatgcgagcagcggcggcagc
aagaggaaagagaacgccagcggggcagagacagacaagacccccagcagcagtaccaccggtgccagag
aagatgccagatccaagaacagagcccgagcggcagcgccagtgccagcagagatgcgaagacagtac
aaagagcaaggcagagagagggcccgagcggcagcctagaagagagtccagaggacggaagaag
aacagcagcggcacaacccctactacttccacagccagagcatcagaagcggcacgagagcgaagaggg
cgaagtgaagtatctggaacggttcaccgagcggaccgagctgctgagaggcatcgagaactaccgggtc
gtgattctggacgccaaccccaacacatccatgctgccccaccacaaggacgccgagtctgtggccgtcg

Figure 4 (cont.)

For the constructs, the sequences are highlighted as follows: *hLAMP Signal peptide*-hLAMP Luminal domain –CTCGAG-Antigen-GAATTC-hLAMP TM and Cyto domain

```
tgacaagggcagagccacactgacactggtgtcccaagagactcgcgagagcttcaatctggaatgcgg
cgacgtgatccgggtgccagctggggctacagtgtacgtgatcaaccaagacagcaacgagcggctggaa
atggtcaagctgctgcagcccgtgaacaacccggccagttcagagagtactacgccgctggcgccaagt
ccccgaccagagctatctgcgggtgttcagcaacgacattctggtggccgctctgaataccctcgggga
cagactggaaagattcttcgatcagcaagagcagcgcgagggcgtgatcatcagagccagccaagagaag
ctgcgggctctgagccagcacgccatgtctgctggacagaggccttgggcagaagaagctctggcggcc
ctatctctctgaagtccgagagcccctcctacagcaaccagtttggccagttcttcgaggcttgcccga
ggaacaccggcagctgcaagaaatggacgtgctcgtgaactacgccgagatcaagagggcgccatgatg
gtgccccactacaacagcaaggccaccgtggtggtgtacgtggtggaaggcaccggcagatacgagatgg
catgccccacgtgtccagccagtcttacgagggccaaggacgcagagagcaagaagaggaagagtccac
cggacggttccagaaagtgaccgccagactggccagaggcgacatcttcgtgatcccagccggacaccct
atcgccatcaccgccagccagaacgagaatctgcggctgctgggcttcgacatcaacggcgagaacaacc
agcgggactttctggccggacagaacaacatcatcaaccagctggaacgggaagccaaagaactgagctt
caacatgccccgcgaggaaatcgaagagattttcgagagccagatggaaagctacttcgtgccaccgag
cgccagagcagaagggggccaagggcgggatcacccactggcctctattctggatttcgccttcttc
```
GAAT
TC

SEQ ID NO:29 Amb a 1 amino acids (26-296)

AEDLQEILPVNETRRLTTSGAYNIIDGCWRGKADWAENRKALADCAQGFGKGTVGGKDGDIYTVTSELDD
DVANPKEGTLRFGAAQNRPLWIIFERDMVIRLDKEMVVNSDKTIDGRGAKVEIINAGFTLNGVKNVIIHN
INMHDVKVNPGGLIKSNDGPAAPRAGSDGDAISISGSSQIWIDHCSLSKSVDGLVDAKLGTTRLTVSNSL
FTQHQFVLLFGAGDENIEDRGMLATVAFNTFTDNVDQRMPRCRHGFFQVVNNNYDKWGSYAIGGSASPTI
LSQGNRFCAPDERSKKNVLGRHGEAAAESMKWNWRTNKDVLENGAIFVASGVDPVLTPEQSAGMIPAEPG
ESALSLTSSAGVLSCQPGAPC

SEQ ID NO:33 Bet v 1-A amino acids (2-160)

GVFNYETETTSVIPAARLFKAFILDGDNLFPKVAPQAISSVENIEGNGGPGTIKKISFPEGFPFKYVKDR
VDEVDHTNFKYNYSVIEGGPIGDTLEKISNEIKIVATPDGGSILKISNKYHTKGDHEVKAEQVKASKEMG
ETLLRAVESYLLAHSDAYN

SEQ ID NO:37 Can f 1 amino acids (19-174)

QDTPALGKDTVAVSGKWYLKAMTADQEVPEKPDSVTPMILKAQKGGNLEAKITMLTNGQCQNITVVLHKT
SEPGKYTAYEGQRVVFIQPSPVRDHYILYCEGELHGRQIRMAKLLGRDPEQSQEALEDFREFSRAKGLNQ
EILELAQSETCSPGGQ

SEQ ID NO:41 Cyn d 1 amino acids (1-246)

AIGDKPGPNITATYGSKWLEARATFYGSNPRGAAPDDHGGACYKDVDKPPFDGMTACGNEPIFKDGLGC
RACYEIKCKEPVECSGEPVLVKITDKNYEHIAAYHFDLSGKAFGAMAKKGQEDKLRKAGELTLQFRRVKC
KYPSGTKITFHIEKGSNDHYLALLVKYAAGDGNIVAVDIKPRDSDEFIPMKSSWGAIWRIDPKKPLKGPF
SIRLTSEGGAHLVQDDVIPANWKPDTVYTSKLQFGA

Figure 4 (cont.)

For the constructs, the sequences are highlighted as follows: *hLAMP Signal peptide*-hLAMP Luminal domain –CTCGAG-Antigen-GAATTC-hLAMP TM and Cyto domain

SEQ ID NO:45 Der f 1 amino acids (19-321)

RPASIKTFEEFKKAFNKNYATVEEEEVARKNFLESLKYVEANKGAINHLSDLSLDEFKNRYLMSAEAFEQ
LKTQFDLNAETSACRINSVNVPSELDLRSLRTVTPIRMQGGCGSCWAFSGVAATESAYLAYRNTSLDLSE
QELVDCASQHGCHGDTIPRGIEYIQQNGVVEERSYPYVAREQRCRRPNSQHYGISNYCQIYPPDVKQIRE
ALTQTHTAIAVIIGIKDLRAFQHYDGRTIIQHDNGYQPNYHAVNIVGYGSTQGDDYWIVRNSWDTTWGDS
GYGYFQAGNNLMMIEQYPYVVIM

SEQ ID NO:49 Der f 1 amino acids (99-321)

TSACRINSVNVPSELDLRSLRTVTPIRMQGGCGSCWAFSGVAATESAYLAYRNTSLDLSEQELVDCASQH
GCHGDTIPRGIEYIQQNGVVEERSYPYVAREQRCRRPNSQHYGISNYCQIYPPDVKQIREALTQTHTAIA
VIIGIKDLRAFQHYDGRTIIQHDNGYQPNYHAVNIVGYGSTQGDDYWIVRNSWDTTWGDSGYGYFQAGNN
LMMIEQYPYVVIM

SEQ ID NO:53 Der p 2 amino acids (18-146)

DQVDVKDCANHEIKKVLVPGCHGSEPCIIHRGKPFQLEAVFEANQNTKTAKIEIKASIDGLEVDVPGIDP
NACHYMKCPLVKGQQYDIKYTWNVPKIAPKSENVVVTVKVMGDDGVLACAIATHAKIRD

SEQ ID NO:57 Der f 2 amino acids (18-146)

DQVDVKDCANNEIKKVMVDGCHGSDPCIIHRGKPFTLEALFDANQNTKTAKIEVKASLDGLEIDVPGIDT
NACHFVKCPLVKGQQYDIKYTWNVPKIAPKSENVVVTVKLIGDNGVLACAIATHGKIRD

SEQ ID NO:61 Der p 1 (DEL) amino acids (1-26:38-223)

TNACSINGNAPAEIDLRQMRTVTPIRSGVAATESAYLAYRNQSLDLAEQELVDCASQHNGCHGDTIPRGI
EYIQHNGVVQESYYRYVAREQSCRRPNAQRFGISNYCQIYPQNVNKIREALAQTHSAIAVIIGIKDLDAF
RHYDGRTIIQRDNGYQPNYHAVNIVGYSNAQGVDYWIVRNSWDTNWGDNGYGYFAANIDLMMIEEYPYVV
IL

SEQ ID NO:66 Fel d 1 chain 1-chain 2 amino acids (23-92/18-109 )

EICPAVKRDVDLFLTGTPDEYVEQVAQYKALPVVLENARILKNCVDAKMTEEDKENALSLLDKIYTSPLC
VKMAETCPIFYDVFFAVANGNELLLDLSLTKVNATEPERTAMKKIQDCYVENGLISRVLDGLVMTTISSS
KDCMGEAVQNTVEDLKLNTLGR

SEQ ID NO:65 Fel d 1 chain 1-chain 2 amino acids (23-92/18-109 )

EICPAVKRDVDLFLTGTPDEYVEQVAQYKALPVVLENARILKNCVDAKMTEEDKENALSLLDKIYTSPLC
GGGGSGGGGSGGGGSVKMAETCPIFYDVFFAVANGNELLLDLSLTKVNATEPERTAMKKIQDCYVENGLI
SRVLDGLVMTTISSSKDCMGEAVQNTVEDLKLNTLGR

SEQ ID NO:70 Fel d 2 amino acids (25-608)

EAHQSEIAHRFNDLGEEHFRGLVLVAFSQYLQQCPFEDHVKLVNEVTEFAKGCVADQSAANCEKSLHELL
GDKLCTVASLRDKYGEMADCCEKKEPERNECFLQHKDDNPGFGQLVTPEADAMCTAFHENEQRFLGKYLY
EIARRHPYFYAPELLYYAEEYKGVFTECCEAADKAACLTPKVDALREKVLASSAKERLKCASLQKFGERA
FKAWSVARLSQKFPKAEFAEISKLVTDLAKIHKECCHGDLLECADDRADLAKYICENQDSISTKLKECCG

Figure 4 (cont.)

For the constructs, the sequences are highlighted as follows: ***hLAMP Signal peptide*-hLAMP Luminal domain** –CTCGAG-<u>Antigen</u>-GAATTC-hLAMP TM and Cyto domain KPVLEKSHCISEVERDELPADLPPLAVDFVEDKEVCKNYQEAKDVFLGTFLYEYSRRHPEYSVSLLLRLA
KEYEATLEKCCATDDPPACYAHVFDEFKPLVEEPHNLVKTNCELFEKLGEYGFQNALLVRYTKKVPQVST
PTLVEVSRSLGKVGSKCCTHPEAERLSCAEDYLSVVLNRLCVLHEKTPVSERVTKCCTESLVNRRPCFSA
LQVDETYVPKEFSAETFTFHADLCTLPEAEKQIKKQSALVELLKHKPKATEEQLKTVMGDFGSFVDKCCA
AEDKEACFAEEGPKLVAAAQAALA

SEQ ID NO:74  Fel d 4  amino acids (16-186)

HEEENVVRSNIDISKISGEWYSILLASDVKEKIEENGSMRVFVEHIKALDNSSLSFVFHTKENGKCTEIF
LVADKTKDGVYTVVYDGYNVFSIVETVYDEYILLHLLNFDKTRPFQLVEFYAREPDVSQKLKEKFVKYCQ
EHGIVNILDLTEVDRCLQARGSEVAQDSSVE

SEQ ID NO:78  Lit v 1  amino acids (1-284)

MDAIKKKMQAMKLEKDNAMDRADTLEQQNKEANNRAEKSEEEVHNLQKRMQQLENDLDQVQESLLKANIQ
LVEKDKALSNAEGEVAALNRRIQLLEEDLERSEERLNTATTKLAEASQAADESERMRKVLENRSLSDEER
MDALENQLKEARFLAEEEADRKYDEVARKLAMVEADLERAEERAETGESKIVELEEELRVVGNNLKSLEVS
EEKANQREEAYKEQIKTLTNKLKAAEARAEFAERSVQKLQKEVDRLEDELVNEKEKYKSITDELDQTFSE
LSGY

SEQ ID NO:82  Lol p 5a  amino acids (26-272)

ADAGYTPAAAATPATPAATPAAAGGKATTDEQKLLEDVNAGFKAAVAAAANAPPADKFKIFEAAFSESSK
GLLATSAAKAPGLIPKLDTAYDVAYKAAEATPEAKYDAFVTALTEALRVIAGALEVHAVKPATEEVLAAK
IPTGELQIVDKIDAAFKIAATAANAAPTNDKFTVFESAFNKALNECTGGAYETYKFIPSLEAAVKQAYAA
TVAAAPEVKYAVFEAALTKAITAMTQAQKAGKPAAAA

SEQ ID NO:86  Phl p 1  amino acids (24-263)

IPKVPPGPNITATYGDKWLDAKSTWYGKPTGAGPKDNGGACGYKDVDKPPFSGMTGCGNTPIFKSGRGCG
SCFEIKCTKPEACSGEPVVVHITDDNEEPIAPYHFDLSGHAFGAMAKKGDEQKLRSAGELELQFRRVKCK
YPEGTKVTFHVEKGSNPNYLALLVKYVNGDGDVVAVDIKEKGKDKWIELKESWGAIWRIDTPDKLTGPFT
VRYTTEGGTKTEAEDVIPEGWKADTSYESK

SEQ ID NO:90 Phl p 5 amino acids (25-288)

AADLGYGPATPAAPAAGYTPATPAAPAEAAPAGKATTEEQKLIEKINAGFKAALAAAAGVQPADKYRTFV
ATFGAASNKAFAEGLSGEPKGAAESSSKAALTSKLDAAYKLAYKTAEGATPEAKYDAYVATLSEALRIIA
GTLEVHAVKPAAEEVKVIPAGELQVIEKVDAAFKVAATAANAAPANDKFTVFEAAFNDAIKASTGGAYES
YKFIPALEAAVKQAYAATVATAPEVKYTVFETALKKAITAMSEAQKAAKPAAAA

SEQ ID NO:93  Der f 15  amino acids (20-555)

SIKRDHNDYSKNPMRIVCYVGTWSVYHKVDPYTIEDIDPFKCTHLMYGFAKIDEYKYTIQVFDPYQDDNH
NSWEKRGYERFNNLRLKNPELTTMISLGGWYEGSEKYSDMAANPTYRQQFIQSVLDFLQEYKFDGLDLDW
EYPGSRLGNPKIDKQNYLALVRELKDAFEPHGYLLTAAVSPGKDKIDRAYDIKELNKLFDWMNVMTYDYH
GGWENFYGHNAPLYKRPDETDELHTYFNVNYTMHYYLNNGATRDKLVMGVPFYGRAWSIEDRSKLKLGDP

Figure 4 (cont.)

For the constructs, the sequences are highlighted as follows: hLAMP Signal peptide-hLAMP Luminal domain –CTCGAG-Antigen-GAATTC-hLAMP TM and Cyto domain AKGMSPPGFISGEEGVLSYIELCQLFQKEEWHIQYDEYYNAPYGYNDKIWVGYDDLASISCKLAFLKELG
VSGVMVWSLENDDFKGHCGPKNPLLNKVHNMINGDEKNSFECILGPSTTTPTPTTTPTTPTTTPTTPSPT
TPTTTPSPTTPTTTPSPTTPTTTPSPTTPTPTTPTPAPTTSTPSPTTTEHTSETPKYTTYVDGHLIKCYK
EGDIPHPTNIHKYLVCEFVNGGWWVHIMPCPPGTIWCQEKLTCIGE

SEQ ID NO:94  Der f 18  amino acids (18-462)

SNIRPNVATLEPKTVCYYESWVHWRQGEGKMDPEDIDTSLCTHIVYSYFGIDAATHEIKLLDEYLMKDLH
DMEHFTQHKGNAKAMIAVGGSTMSDQFSKTAAVEHYRETFVVSTVDLMTRYGFDGVMIDWSGMQAKDSDN
FIKLLDKFDENYNIPAISNYVDFMNVLSLDYTGSWAHTVGHASPFPEQLKTLEAYHKRGAPRHKMVMAVP
FYARTWILEKMNKQDIGDKASGPGPRGQFTQTDGFLSYNELCVQIQAETNAFTITRDHDNTAIYAVYVHS
NHAEWISFEDRHTLGEKAKNITQQGYAGMSVYTLSNEDVHGVCGDKNPLLHAIQSNYYHGVVTEPTVVTL
PPVTHTTEHVTDIPGVFHCHEEGFFRDKTYCATYYECKKGDFGLEKTVHHCANHLQAFDEVSRTCIDHTK
IPGC

SEQ ID NO:95  Zen-1  amino acids (23-500)

NPRFKRDNRDDVLKQTEELIKSAQDVLEKLPDSDLKDEIAEKLATMKHYKHELENAKNPIKIAHFELELL
TMFKKFQSLLNEANEIIKSLTTTTEPTTPTPEPTTTTPEPTTKTPEPTTKTPEPTTPTPEPTTKTPEPT
TKTPEPTTPTPEPTTKTPEPTTPTPEPTTKTPEPTTKTPEPSTPTPEPTTKTPEPTTKTPEPSTPTPEPT
TKTPEPSTPTPEPTTKTPEPTTKTPEPSTPTPEPTTKTPEPSTPTPEPTTKTPEPSTTKKPNRDDVLKQA
EELIKRAEDVFEKLPDSDLKNEIAEKLATMKNYKHELENAKNPIKIAHLESELLTMFKMFQSLLNEADEI
IRSLTTTTEPTTLNSTTPEPTTLNSTTPEPTTLNSTTPEPTTLNSTTPEPTTLNSTTPEPTTLNSTTPEP
TTLNSTTPEPTTLNSTTPEPTTSNSTTSEPTNSINRKTSEISFLSDWFHKIRTRFNIF

SEQ ID NO:96  Cte f 1  amino acids (19-176)

EDIWKVNKKCTSGGKNQDRKLDQIIQKGQQVKIQNICKLIRDKPHTNQEKEKCMKFCKKVCKGYRGACDG
NICYCSRPSNLGPDWKVSKECKDPNNKDSRPTEIVPYRQQLAIPNICKLKNSETNEDSKCKKHCKEKCRG
GNDAGCDGNFCYCRPKNK

SEQ ID NO:109:   Der F15 GPGPG Der F18 (GPGPG is one example of a linker that can be used)

SIKRDHNDYSKNPMRIVCYVGTWSVYHKVDPYTIEDIDPFKCTHLMYGFAKIDEYKYTIQVFDPYQDDNHNSWEKRGY
ERFNNLRLKNPELTTMISLGGWYEGSEKYSDMAANPTYRQQFIQSVLDFLQEYKFDGLDLDWEYPGSRLGNPKIDKQN
YLALVRELKDAFEPHGYLLTAAVSPGKDKIDRAYDIKELNKLFDWMNVMTYDYHGGWENFYGHNAPLYKRPDETDEL
HTYFNVNYTMHYYLNNGATRDKLVMGVPFYGRAWSIEDRSKLKLGDPAKGMSPPGFISGEEGVLSYIELCQLFQKEEW
HIQYDEYYNAPYGYNDKIWVGYDDLASISCKLAFLKELGVSGVMVWSLENDDFKGHCGPKNPLLNKVHNMINGDEKN
SFECILGPSTTTPTPTTTPTTPTTTPTTPSPTTPTTTPSPTTPTTTPSPTTPTPTTPTPAPTTSTPSPTTTEHTSET
PKYTTYVDGHLIKCYKEGDIPHPTNIHKYLVCEFVNGGWWVHIMPCPPGTIWCQEKLTCIGEGPGPGSNIRPNVATLEP
KTVCYYESWVHWRQGEGKMDPEDIDTSLCTHIVYSYFGIDAATHEIKLLDEYLMKDLHDMEHFTQHKGNAKAMIAVG
GSTMSDQFSKTAAVEHYRETFVVSTVDLMTRYGFDGVMIDWSGMQAKDSDNFIKLLDKFDENYNIPAISNYVDFMNV
LSLDYTGSWAHTVGHASPFPEQLKTLEAYHKRGAPRHKMVMAVPFYARTWILEKMNKQDIGDKASGPGPRGQFTQT
DGFLSYNELCVQIQAETNAFTITRDHDNTAIYAVYVHSNHAEWISFEDRHTLGEKAKNITQQGYAGMSVYTLSNEDVH

Figure 4 (cont.)

For the constructs, the sequences are highlighted as follows: hLAMP Signal peptide-hLAMP Luminal domain –CTCGAG-*Antigen*-GAATTC-hLAMP TM and Cyto domain GVCGDKNPLLHAIQSNYYHGVVTEPTVVTLPPVTHTTEHVTDIPGVFHCHEEGFFRDKTYCATYYECKKGDFGLEKTVH
HCANHLQAFDEVSRTCIDHTKIPGC Der F1 GPGPG Der F2 (SEQ ID NO:110) (with exemplified GPGPG linker)

SIKRDHNDYSKNPMRIVCYVGTWSVYHKVDPYTIEDIDPFKCTHLMYGFAKIDEYKYTIQVFDPYQDDNHNSWEKRGY
ERFNNLRLKNPELTTMISLGGWYEGSEKYSDMAANPTYRQQFIQSVLDFLQEYKFDGLDLDWEYPGSRLGNPKIDKQN
YLALVRELKDAFEPHGYLLTAAVSPGKDKIDRAYDIKELNKLFDWMNVMTYDYHGGWENFYGHNAPLYKRPDETDEL
HTYFNVNYTMHYYLNNGATRDKLVMGVPFYGRAWSIEDRSKLKLGDPAKGMSPPGFISGEEGVLSYIELCQLFQKEEW
HIQYDEYYNAPYGYNDKIWVGYDDLASISCKLAFLKELGVSGVMVWSLENDDFKGHCGPKNPLLNKVHNMINGDEKN
SFECILGPSTTTPTPTTTPTTPTTTPTTPSPTTPTTTPSPTTPTTTPSPTTPTTTPSPTTPTPTTPTPAPTTSTPSPTTTEHTSET
PKYTTYVDGHLIKCYKEGDIPHPTNIHKYLVCEFVNGGWWVHIMPCPPGTIWCQEKLTCIGEGPGPGSNIRPNVATLEP
KTVCYYESWVHWRQGEGKMDPEDIDTSLCTHIVYSYFGIDAATHEIKLLDEYLMKDLHDMEHFTQHKGNAKAMIAVG
GSTMSDQFSKTAAVEHYRETFVVSTVDLMTRYGFDGVMIDWSGMQAKDSDNFIKLLDKFDENYNIPAISNYVDFMNV
LSLDYTGSWAHTVGHASPFPEQLKTLEAYHKRGAPRHKMVMAVPFYARTWILEKMNKQDIGDKASGPGPRGQFTQT
DGFLSYNELCVQIQAETNAFTITRDHDNTAIYAVYVHSNHAEWISFEDRHTLGEKAKNITQQGYAGMSVYTLSNEDVH
GVCGDKNPLLHAIQSNYYHGVVTEPTVVTLPPVTHTTEHVTDIPGVFHCHEEGFFRDKTYCATYYECKKGDFGLEKTVH
HCANHLQAFDEVSRTCIDHTKIPGC

Allergen X is Amb a 1

*atggcgccccgcagcgcccggcgacccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacacctttttccccaatgcgagct
ccaaagaaatcaagactgtggaatctataactgacatcagggcagatatagataaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgccccctgcgccacccagcccctcgccctcacccgtgcccaagagcccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcggggagctgcggcgcccacctggtgactctggagctgcacagcgagggcaccaccgtcctgctcttccagttcgggatgaatgca
agttctagccggttttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgtttcagtcaatatattcaaagtgtgggtccag
gctttcaaggtggaaggtggccagtttggctctgtggaggagtgtctgctggacgagaacagcCTCGAGgccgaggatctgcaagagattctgccc
gtgaacgagacacggcggctgacaacaagcggcgcctacaacatcatcgacggctgctggcggggcaaggccgattgggccgagaacagaaaggc For the constructs, the sequences are highlighted as follows: hLAMP Signal peptide-hLAMP Luminal domain –CTCGAG-Antigen-GAATTC-hLAMP TM and Cyto domain tctggccgattgcgcccaaggcttcggcaagggaacagtgggcggcaaggacggcgacatctacaccgtgaccagcgagctggacgacgacgtggc
caatcccaaagagggcacactgagattcggagccgcccagaaccggcctctgtggatcatcttcgagcgggacatggtcatccggctggacaaagaa
atggtcgtgaacagcgacaagaccatcgacggaagaggcgccaaagtggaaatcatcaacgccggcttcacactgaacggcgtgaagaacgtgatc
atccacaacatcaacatgcacgacgtgaaagtgaatcccggcggactgatcaagagcaacgatggcccagccgcccctagagccggatctgatggc
gacgccatttccatcagcggcagctctcagatctggatcgaccactgctctctgagcaagagcgtggacggactcgtggacgccaagctgggcaccac
aagactgaccgtgtccaactctctgttcacccagcaccagttcgtgctgctgttcggcgctggcgacgagaacatcgaggatagggcatgctggcca
ccgtggccttcaacacattcaccgacaacgtggaccagcggatgcccagatgccggcacggcttcttccaagtcgtgaacaacaactacgataagtg
gggcagctacgccatcggcggctctgccagccctaccattctgagccaaggcaaccggttctgcgccccagacgagcggagcaagaagaatgtgctg
ggacggcacggcgaagccgccgctgaatccatgaagtggaactggcggaccaacaaggacgtgctggaaaacggcgccatcttcgtggcctctggc
gtggacccagtgctgacaccagaacagagcgccggcatgattccagccgagcccggcgaatctgctctgtctctgacaagctctgccggcgtgctgag
ctgtcagcccggagccacatgtGAATTCacgctgatccccatcgctgtgggtggtgccctggcggggctggtcctcatcgtcctcatcgcctacctcgt
cggcaggaagaggagtcacgcaggctaccagactatctagtaa (SEQ ID NO:30)

Allergen X is Bet v 1-A

*atggcgccccgcagcgcccggcgaccccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgacccagtctcgtgattgcttttggaagaggacatac
actcactctcaatttcacgagaaatgcaacacgttacagcgtccagctcatgagttttgtttataacttgtcagacacacacctttttccccaatgcgagct
ccaaagaaatcaagactgtggaatctataactgacatcaggggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccctgcgccacccagccctcgccctcacccgtgcccaagagccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcggagctgcggcgcccacctggtgactctggagctgcacagcgagggcaccaccgtcctgctcttccagttcgggatgaatgca
agttctagccggttttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGggcgtgttcaactacgagacagagaca
accagcgtgatcccagccgccagactgttcaaggccttcattctggacggcgacaatctgttccccaaagtggcccccaagccatcagcagcgtgga
aaacatcgagggcaatggcggacccggcaccatcaagaagatcagcttccccgagggcttcccattcaaatacgtgaaggaccgggtggacgaagt For the constructs, the sequences are highlighted as follows: *hLAMP Signal peptide*-hLAMP Luminal domain –CTCGAG-Antigen-GAATTC-hLAMP TM and Cyto domain ggaccacaccaacttcaagtacaactactccgtgatcgagggcggacccatcggcgacacactggaaaagatcagcaacgagatcaagatcgtggc
caccccgacggcggcagcattctgaagatctccaacaagtaccacacaaagggcgaccacgaagtgaaggccgaacaagtgaaagccagcaaag
agatggggcgagacactgctgcgggccgtggaaagctatctgctggcccacagcgacgcctacaacGAATTCacgctgatccccatcgctgtggtg
gtgccctggcggggctggtcctcatcgtcctcatcgcctacctcgtcggcaggaagaggagtcacgcaggctaccagactatctagtaa (SEQ ID NO:34)

*atggcgccccgcagcgcccggcgaccccctgctgctgctactgctgttgctgctgctcggcctcatgcattgtgcgtcagcag*caatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacacctttttccccaatgcgagct
ccaaagaaatcaagactgtggaatctataactgacatcagggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccctgcgccacccagccctcgccctcacccgtgcccaagagcccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcggagctgcggcgcccacctggtgactctggagctgcacagcgagggcaccaccgtcctgctcttccagttcgggatgaatgca
agttctagccggttttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGcaagacaccccgctctgggcaaggat
accgtggccgtgtccggcaagtggtatctgaaggccatgaccgccgaccaagaagtgcccgagaagcccgatagcgtgaccccccatgattctgaaag
cccagaagggcggcaatctggaagccaagatcaccatgctgaccaacggccagtgccagaacatcaccgtggtgctgcacaagaccagcgagcccg
gcaagtacacagcctacgagggccagcgggtggtgttcatccagccttctccagtgcgggatcactacattctgtactgcgagggcgagctgcacggc
cggcagatcagaatggccaagctgctgggcagagatcccgagcagagccaagaggctctggaagatttcagagagttcagccgggccaagggactg
aaccaagagattctggaactggctcagagcgagacatgctctcccggcggacaaGAATTCacgctgatccccatcgctgtgggtggtgccctggcg
gggctggtcctcatcgtcctcatcgcctacctcgtcggcaggaagaggagtcacgcaggctaccagactatctagtaa (SEQ ID NO:38)

Allergen X is Cyn d 1

*Atggcgccccgcagcgcccggcgaccccctgctgctgctactgctgttgctgctgctcggcctcatgcattgtgcgtcagcag*caatgtttatggtg
aaaaatggcaacgggaccgcgtgcataatggccaacttctctgctgccttctcagtgaactacgacaccaagagtggccctaagaacatgacccttga

Figure 4 (cont.)

For the constructs, the sequences are highlighted as follows: *hLAMP Signal peptide-*hLAMP Luminal domain* –CTCGAG-Antigen-GAATTC-hLAMP TM and Cyto domain cctgccatcagatgccacagtggtgctcaaccgcagctcctgtggaaaagagaacacttctgaccccagtctcgtgattgcttttggaagaggacatac actcactctcaatttcacgagaaatgcaacacgttacagcgtccagctcatgagttttgtttataacttgtcagacacacaccttttccccaatgcgagct ccaaagaaatcaagactgtggaatctataactgacatcagggcagatatagataaaaaatacagatgtgttagtggcacccaggtccacatgaaca acgtgaccgtaacgctccatgatgccaccatccaggcgtaccttccaacagcagcttcagccggggagagacacgctgtgaacaagacaggccttc cccaaccacagcgcccctgcgccacccagccctcgccctcacccgtgcccaagagcccctctgtggacaagtacaacgtgagcggcaccaacggg acctgcctgctggccagcatggggctgcagctgaacctcacctatgagaggaaggacaacacgacggtgacaaggcttctcaacatcaaccccaaca agacctcggccagcgggagctgcggcgcccacctggtgactctggagctgcacagcgagggcaccaccgtcctgctcttccagttcgggatgaatgca agttctagccggttttttcctacaaggaatccagttgaatacaattcttcctgacgccagagaccctgcctttaaagctgccaacggctccctgcgagcgc tgcaggccacagtcggcaattcctacaagtgcaacgcggaggagcacgtccgtgtcacgaaggcgttttcagtcaatatattcaaagtgtgggtccag gctttcaaggtggaaggtggccagtttggctctgtggaggagtgtctgctggacgagaacagcCTCGAGgccatcggcgataagcccggacccaa catcaccgccacatacggcagcaagtggctggaagccagagccacattctacggctccaaccccagaggcgccgctcccgatgatcatggcggagct tgcggctacaaggacgtggacaagccccccttcgacggcatgaccgcttgcggcaacgagcccatcttcaaggacggactgggctgccgggcttgct acgagatcaagtgcaaagaacccgtggaatgcagcggcgagcccgtgctcgtgaagatcaccgacaagaactacgagcacattgccgcctaccact tcgatctgagcggcaaggcctttggcgccatggccaagaaggccaagaggacaagctgcggaaggccggcgaactgacactgcagtttcggagag tgaagtgcaagtaccccagcggcaccaagatcacattccacatcgagaagggcagcaacgatcactatctggctctgctcgtgaaatacgccgctgg cgacggcaacatcgtggccgtggacatcaagcccagagacagcgacgagttcatccccatgaagtccagctggggcgccatctggcggatcgaccc aaagaagcctctgaagggccccttctccatccggctgacatctgagggcggagcacatctggtgcaagacgacgtgatccccgccaactggaagccc gacaccgtgtacaccagcaagctgcagtttggcgccGAATTCacgctgatccccatcgctgtgggtggtgccctggcggggctggtcctcatcgtcct catcgcctacctcgtcggcaggaagaggagtcacgcaggctaccagactatctagtaa (SEQ ID NO:42)

Allergen X is Der F 1 (19-321)

*Atggcgccccgcagcgcccggcgaccccctgctgctgctactgctgttgctgctgctcggcctcatgcattgtgcgtcagca*gcaatgtttatggtg aaaaatggcaacgggaccgcgtgcataatggccaacttctctgctgccttctcagtgaactacgacaccaagagtggccctaagaacatgacccttga cctgccatcagatgccacagtggtgctcaaccgcagctcctgtggaaaagagaacacttctgaccccagtctcgtgattgcttttggaagaggacatac actcactctcaatttcacgagaaatgcaacacgttacagcgtccagctcatgagttttgtttataacttgtcagacacacaccttttccccaatgcgagct ccaaagaaatcaagactgtggaatctataactgacatcagggcagatatagataaaaaatacagatgtgttagtggcacccaggtccacatgaaca acgtgaccgtaacgctccatgatgccaccatccaggcgtaccttccaacagcagcttcagccggggagagacacgctgtgaacaagacaggccttc cccaaccacagcgcccctgcgccacccagccctcgccctcacccgtgcccaagagcccctctgtggacaagtacaacgtgagcggcaccaacggg

Figure 4 (cont.)

For the constructs, the sequences are highlighted as follows: ***hLAMP Signal peptide*-hLAMP Luminal domain –CTCGAG-Antigen-GAATTC-hLAMP TM and Cyto domain** acctgcctgctggccagcatggggctgcagctgaacctcacctatgagaggaaggacaacacgacggtgacaaggcttctcaacatcaaccccaaca agacctcggccagcgggagctgcggcgcccacctggtgactctggagctgcacagcgagggcaccaccgtcctgctcttccagttcgggatgaatgca agttctagccggttttcctacaaggaatccagttgaatacaattcttcctgacgccagagaccctgcctttaaagctgccaacggctccctgcgagcgc tgcaggccacagtcggcaattcctacaagtgcaacgcggaggagcacgtccgtgtcacgaaggcgttttcagtcaatatattcaaagtgtgggtccag gctttcaaggtggaaggtggccagtttggctctgtggaggagtgtctgctggacgagaacagcCTCGAGaggcccgccagcatcaagacattcgaa gagttcaagaaggccttttaacaagaactacgccaccgtggaagaggaagaagtggcccggaagaactttctggaatctctgaaatacgtggaagcc aacaagggcgccatcaaccatctgagcgatctgtctctggacgagtttaagaaccggtatctgatgagcgccgaggccttcgagcagctgaaaaccc agttcgatctgaacgccgaaaccagcgcttgccggatcaacagcgtgaacgtgcccagcgagctggatctgagatctctgagaaccgtgaccccatc agaatgcaaggcggctgcggcagctgctgggcctttagcggagtggccgccacagagtctgcctatctggcctaccggaacacatctctggatctgtc cgagcaagaactcgtggactgcgccagccagcacggctgtcacggcgatacaatccccagaggcatcgagtacatccagcagaacggcgtcgtgga agaacggtcctaccccttacgtggcccgcgagcagagatgcagaaggcccaactctcagcactacggcatcagcaactactgccagatctaccccccc gacgtgaagcagatcagagaggctctgacccagacccacaccgccattgccgtgatcatcggaatcaaggatctgcgggccttccagcactatgacg gccggaccatcatccagcacgacaacggctaccagcccaactaccacgccgtgaacatcgtgggctacggcagcacacaaggcgacgactactgga tcgtgcggaacagctgggacaccacatggggcgatagcggctacggctacttccaagccggcaacaatctgatgatgatcgagcagtaccctacgt cgtgatcatgGAATTCacgctgatccccatcgctgtgggtggtgccctggcggggctggtcctcatcgtcctcatcgcctacctcgtcggcaggaaga ggagtcacgcaggctaccagactatctagtaa (SEQ ID NO:46)

Allergen X is Der F 1 (99-321)

*Atggcgccccgcagcgcccggcgaccctgctgctgctactgctgttgctgctgctcggcctcatgcattgtgcgtcagca*gcaatgtttatggtg aaaaatggcaacgggaccgcgtgcataatggccaacttctctgctgccttctcagtgaactacgacaccaagagtggccctaagaacatgacccttga cctgccatcagatgccacagtggtgctcaaccgcagctcctgtggaaaagagaacacttctgacccagtctcgtgattgcttttggaagaggacatac actcactctcaatttcacgagaaatgcaacacgttacagcgtccagctcatgagttttgtttataacttgtcagacacacaccttttccccaatgcgagct ccaaagaaatcaagactgtggaatctataactgacatcagggcagatatagataaaaaatacagatgtgttagtggcacccaggtccacatgaaca acgtgaccgtaacgctccatgatgccaccatccaggcgtacctttccaacagcagcttcagccggggagagacacgctgtgaacaagacaggccttc cccaaccacagcgcccctgcgccacccagcccctcgccctcacccgtgcccaagagcccctctgtggacaagtacaacgtgagcggcaccaacggg acctgcctgctggccagcatggggctgcagctgaacctcacctatgagaggaaggacaacacgacggtgacaaggcttctcaacatcaaccccaaca agacctcggccagcgggagctgcggcgcccacctggtgactctggagctgcacagcgagggcaccaccgtcctgctcttccagttcgggatgaatgca agttctagccggttttcctacaaggaatccagttgaatacaattcttcctgacgccagagaccctgcctttaaagctgccaacggctccctgcgagcgc For the constructs, the sequences are highlighted as follows: *hLAMP Signal peptide*-hLAMP Luminal domain –CTCGAG-Antigen-GAATTC-hLAMP TM and Cyto domain tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGaccagcgcttgccggatcaacagcgtg
aacgtgcccagcgagctggatctgagatctctgagaaccgtgacccccatcagaatgcaaggcggctgcggcagctgctgggcctttagcggagtgg
ccgccacagagtctgcctatctggcctaccggaacacatctctggatctgtccgagcaagaactcgtggactgcgccagccagcacggctgtcacggc
gatacaatccccagaggcatcgagtacatccagcagaacggcgtcgtggaagaacggtcctacccttacgtggcccgcgagcagagatgcagaagg
cccaactctcagcactacggcatcagcaactactgccagatctacccccccgacgtgaagcagatcagagaggctctgacccagacccacaccgcca
ttgccgtgatcatcggaatcaaggatctgcgggccttccagcactatgacggccggaccatcatccagcacgacaacggctaccagcccaactaccac
gccgtgaacatcgtgggctacggcagcacacaaggcgacgactactggatcgtgcggaacagctgggacaccacatggggcgatagcggctacggc
tacttccaagccggcaacaatctgatgatgatcgagcagtacccctacgtcgtgatcatgGAATTCacgctgatccccatcgctgtgggtggtgccct
ggcggggctggtcctcatcgtcctcatcgcctacctcgtcggcaggaagaggagtcacgcaggctaccagactatctagtaa (SEQ ID NO:50)

Allergen X is Der P2

*atggcgccccgcagcgcccggcgacccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacaccttttccccaatgcgagct
ccaaagaaatcaagactgtggaatctataactgacatcagggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccccctgcgccacccagcccctcgccctcacccgtgcccaagagcccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcgggagctgcggcgcccacctggtgactctggagctgcacagcgagggcaccaccgtcctgctcttccagttcgggatgaatgca
agttctagccggtttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGgaccaagtggacgtgaaggactgcgc
caaccacgagatcaagaaagtgctggtgcccggctgccacggcagcgagccttgtatcatccaccggggcaagccctttcagctggaagccgtgttcg
aggccaaccagaacaccaagaccgccaagattgagatcaaggccagcatcgacggactggaagtggatgtgcccggcatcgaccccaacgcttgtc
actacatgaagtgccctctcgtgaagggccagcagtacgacatcaagtacacatggaacgtgcccaagatcgcccccaagagcgagaacgtcgtcgt

Figure 4 (cont.)

For the constructs, the sequences are highlighted as follows: *hLAMP Signal peptide-hLAMP Luminal domain* –CTCGAG-*Antigen*-GAATTC-hLAMP TM and Cyto domain gaccgtgaaagtgatgggcgacgacggcgtgctggcttgcgccattgccacacacgccaagatccgggacGAATTCacgctgatccccatcgctgtgggtggtgccctggcggggctggtcctcatcgtcctcatcgcctacctcgtcggcaggaagaggagtcacgcaggctaccagactatctagtaa (SEQ ID NO:54)

Allergen X is DerF2

*atggcgccccgcagcgcccggcgaccccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacaccttttccccaatgcgagct
ccaaagaaatcaagactgtggaatctataactgacatcagggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccctgcgccacccagcccctcgccctcacccgtgcccaagagcccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
gacctcggccagcggggagctgcggcgcccacctggtgactctggagctgcacagcgagggcaccaccgtcctgctcttccagttcgggatgaatgca
agttctagccggttttttcctacaaggaatccagttgaatacaattcttcctgacgccagagaccctgccttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGgatcaggtggatgtcaaggactgtgct
aacaacgaaatcaagaaagtcatggtggacggatgtcacgggagcgaccccttgtattatccaccggggaaagcccttcacactggaggccctgtttg
atgctaaccagaataccaagacagcaaaaatcgaggtcaaagccagcctggacggcctggaaatcgatgtgccagggattgacaccaacgcttgcc
atttcgtcaagtgtccctggtgaaaggccagcagtacgacatcaagtatacttggaacgtccccaagattgccctaaatccgaaaatgtggtcgtga
ccgtgaaactgattggagacaacggcgtcctggcctgtgctatcgcaactcacgggaagattagagacGAATTCacgctgatccccatcgctgtgg
gtggtgccctggcggggctggtcctcatcgtcctcatcgcctacctcgtcggcaggaagaggagtcacgcaggctaccagactatctagtaa (SEQ ID NO:58)

Allergen X is DerP1 (del)

*Atggcgccccgcagcgcccggcgaccccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga

Figure 4 (cont.)

For the constructs, the sequences are highlighted as follows: *hLAMP Signal peptide-hLAMP Luminal domain* –CTCGAG-*Antigen*-GAATTC-hLAMP TM and Cyto domain cctgccatcagatgccacagtggtgctcaaccgcagctcctgtggaaaagagaacacttctgaccccagtctcgtgattgcttttggaagaggacatac actcactctcaatttcacgagaaatgcaacacgttacagcgtccagctcatgagttttgtttataacttgtcagacacacaccttttccccaatgcgagct ccaaagaaatcaagactgtggaatctataactgacatcagggcagatatagataaaaaatacagatgtgttagtggcacccaggtccacatgaaca acgtgaccgtaacgctccatgatgccaccatccaggcgtacctttccaacagcagcttcagccggggagagacacgctgtgaacaagacaggccttc cccaaccacagcgcccctgcgccacccagcccctcgccctcacccgtgcccaagagcccctctgtggacaagtacaacgtgagcggcaccaacggg acctgcctgctggccagcatggggctgcagctgaacctcacctatgagaggaaggacaacacgacggtgacaaggcttctcaacatcaaccccaaca agacctcggccagcggggagctgcggcgcccacctggtgactctggagctgcacagcgagggcaccaccgtcctgctcttccagttcgggatgaatgca agttctagccggttttttcctacaaggaatccagttgaatacaattcttcctgacgccagagaccctgcctttaaagctgccaacggctccctgcgagcgc tgcaggccacagtcggcaattcctacaagtgcaacgcggaggagcacgtccgtgtcacgaaggcgttttcagtcaatatattcaaagtgtgggtccag gctttcaaggtggaaggtggccagtttggctctgtggaggagtgtctgctggacgagaacagcCTCGAG*accaacgcttgctctatcaacggaaac*

*gcccccgccgaaatcgacctgaggcagatgaggactgtcacacccattaggtccggagtggccgctactgagtctgcctacctggcttatcgaaatca*

*gagtctggacctggcagagcaggaactggtggattgcgccagccagcacaatgggtgtcatggagacaccatcccaaggggaatcgaatacattca*

*gcacaacggcgtggtccaggagtcatactatagatatgtggcccgcgaacagagctgccgaagaccaaatgctcagaggttcggcatcagtaactac*

*tgtcagatttatcctcagaacgtgaataagatccgagaggcactggcacagacccactccgctatcgcagtcatcattgggattaaagacctggatgc*

*ctttcgacattacgacgggcggacaatcattcagagagataacggataccagcccaattatcatgctgtgaacatcgtcggctactccaatgcacagg*

*gggtggattattggattgtccggaactcttgggacacaaactggggcgataatggatatggctatttcgccgccaacattgacctgatgatgattgaag*

*agtatccttacgtggtgatcctg*GAATTCacgctgatccccatcgctgtgggtggtgccctggcggggctggtcctcatcgtcctcatcgcctacctcg tcggcaggaagaggagtcacgcaggctaccagactatctagtaa (SEQ ID NO:62)

*atggcgccccgcagcgcccggcgaccccctgctgctgctactgctgttgctgctgctcggcctcatgcattgtgcgtcagca*gcaatgtttatggtg aaaaatggcaacgggaccgcgtgcataatggccaacttctctgctgccttctcagtgaactacgacaccaagagtggccctaagaacatgacccttga cctgccatcagatgccacagtggtgctcaaccgcagctcctgtggaaaagagaacacttctgaccccagtctcgtgattgcttttggaagaggacatac actcactctcaatttcacgagaaatgcaacacgttacagcgtccagctcatgagttttgtttataacttgtcagacacacaccttttccccaatgcgagct ccaaagaaatcaagactgtggaatctataactgacatcagggcagatatagataaaaaatacagatgtgttagtggcacccaggtccacatgaaca acgtgaccgtaacgctccatgatgccaccatccaggcgtacctttccaacagcagcttcagccggggagagacacgctgtgaacaagacaggccttc cccaaccacagcgcccctgcgccacccagcccctcgccctcacccgtgcccaagagcccctctgtggacaagtacaacgtgagcggcaccaacggg acctgcctgctggccagcatggggctgcagctgaacctcacctatgagaggaaggacaacacgacggtgacaaggcttctcaacatcaaccccaaca agacctcggccagcggggagctgcggcgcccacctggtgactctggagctgcacagcgagggcaccaccgtcctgctcttccagttcgggatgaatgca

Figure 4 (cont.)

For the constructs, the sequences are highlighted as follows: *hLAMP Signal peptide-hLAMP Luminal domain –CTCGAG-Antigen-GAATTC-hLAMP TM and Cyto domain* agttctagccggttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGgaaatctgcccagccgtgaagcgggat
gtggatctgtttctgaccggcaccccgacgagtacgtggaacaagtggcccagtacaaggctctgcccgtggtgctggaaaacgcccggattctgaa
gaactgcgtggacgccaagatgaccgaagaggacaaagagaacgctctgtctctgctggacaagatctacaccagccctctgtgtggcggcggagg
atctggcggaggcggaagtggcggaggggctctgtgaagatggccgagacatgccccatcttctacgacgttcttcgccgtggccaacggcaac
gagctgctgctggatctgagtctgaccaaagtgaacgccaccgagcccgagcggaccgccatgaagaagatccaagactgctacgtggaaaacgga
ctgatcagccgggtgctggacggactcgtgatgaccaccatcagcagctccaaggactgcatgggcgaggccgtgcagaacaccgtggaagatctga
agctgaacacactgggccggGAATTCacgctgatccccatcgctgtgggtggtgccctggcggggctggtcctcatcgtcctcatcgcctacctcgtc
ggcaggaagaggagtcacgcaggctaccagactatctagtaa (SEQ ID NO:67)

*atggcgccccgcagcgcccggcgaccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacaccttttcccaatgcgagct
ccaaagaaatcaagactgtggaatctataactgacatcagggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccctgcgccacccagcccctcgccctcacccgtgcccaagagcccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcgggagctgcggcgcccacctggtgactctggagctgcacagcgagggcaccaccgtcctgctcttccagttcgggatgaatgca
agttctagccggttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGgaagcccatcagagcgagatcgccca
ccggttcaacgatctggcgaggaacacttccggggactggttctcgtggccttcagccagtatctgcagcagtgcccttcgaggaccacgtgaagct
cgtgaacgaagtgaccgagttcgccaaggggctgcgtggccgatcagtctgccgccaactgcgagaagtctctgcacgagctgctgggcgacaagctg
tgtaccgtggcctctctgcgggataagtacggcgagatggccgactgttgcgagaagaaagagcccgagcggaacgagtgctttctgcagcacaagg
acgacaaccccggcttcggccagctcgtgacaccagaggccgatgccatgtgcaccgccttccacgagaatgagcagcggtttctgggcaagtatctg
tacgagattgccagacggcaccctacttctacgccccagagctgctgtactacgccgaagagtacaagggcgtgttcaccgagtgctgcgaggccgc
cgataaggccgcttgtctgaccccaaagtggacgcactgcgcgagaaagtgctggcctccagcgccaaagaacggctgaagtgcgcttctctgcag
aagttcggcgagcgggccttcaaggcttggagcgtggcaagactgagccagaagttccccaaggccgagtttgccgagatcagcaagctcgtgaccg
atctggccaagatccacaaagagtgctgccacggcgatctgctggaatgcgccgacgacagagctgatctggctaagtacatctgcgagaatcaaga
cagcatcagcaccaagctgaaagagtgttgcgcaagcccgtgctggaaaagagccactgcatcagcgaagtggaacgggacgagctgccccgctga
tctgcctcctctggccgtggacttcgtgaggacaaagaagtgtgcaagaactaccaagaggccaaggatgtgtttctggggacatttctgtatgagta
ctctcggcggcaccccgagtactccgtgtctctgctgctgccggctggccaaagagtacgaggccacactggaaaagtgctgcgccaccgacgatcccc

Figure 4 (cont.)

For the constructs, the sequences are highlighted as follows: *hLAMP Signal peptide-hLAMP Luminal domain* –CTCGAG-Antigen-GAATTC-hLAMP TM and Cyto domain ccgcttgttatgcccacgtgttcgacgagttcaagccactcgtggaagaaccccacaatctcgtgaaaacaaactgcgagctgttcgagaagctgggc
gagtacggcttccagaacgcactgctcgtgcggtacaccaagaaagtgccccaagtgtccaccccccacactcgtggaagtgtccagatctctgggcaa
agtgggcagcaagtgctgcacccaccccgaggccgagagactgtcttgcgccgaggactatctgagcgtggtgctgaaccggctgtgcgtgctgcac
gagaaaaccccgtgtccgagcgcgtgaccaagtgctgtaccgagtctctcgtgaacagacggccttgcttcagcgctctgcaagtggacgagacata
cgtgcccaaagagttcagcgccgagacattcacattccacgccgatctgtgcacactgcccgaagccgagaagcagatcaagaaacagtccgctctc
gtggaactgctgaagcacaagcccaaggccaccgaggaacagctgaaaaccgtgatgggcgacttcggcagcttcgtggataagtgctgtgccgctg
aggacaaagaggcttgcttcgccgaagagggcccaaactcgtggctgctgctcaagctgctctggccGAATTCacgctgatccccatcgctgtgg
gtggtgccctggcggggctggtcctcatcgtcctcatcgcctacctcgtcggcaggaagaggagtcacgcaggctaccagactatctagtaa (SEQ
ID NO:71)

*atggcgccccgcagcgcccggcgaccccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacaccttttccccaatgcgagct
ccaaagaaatcaagactgtggaatctataactgacatcagggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccctgcgccacccagcccctcgccctcacccgtgcccaagagcccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcggagctgcggcgcccacctggtgactctggagctgcacagcgagggcaccaccgtcctgctcttccagttcgggatgaatgca
agttctagccggtttttcctacaaggaatccagttgaatacaattcttcctgacgccagagaccctgccttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAGcacgaggaagagaacgtcgtgcggag
caacatcgacatcagcaagatcagcggcgagtggtacagcattctgctggcctccgacgtgaaagagaagatcgaagaaaacggcagcatgcgggt
gttcgtggaacacatcaaggctctggacaacagctctctgagcttcgtgttccacaccaaagaaatggcaagtgcaccgagatctttctcgtggccga
caagaccaaggacggcgtgtacaccgtggtgtacgacggctacaacgtgttcagcatcgtggaaaccgtgtacgatgagtacattctgctgcatctgc
tgaacttcgacaagacacggcccttccaactcgtggagttctacgccagagaaccccgacgtgtcccagaagctgaaagaaaagttcgtgaagtactg
ccaagagcacggcatcgtgaacattctggatctgaccgaagtggaccggtgtctgcaagccagaggcagcgaagtggcccaagacagcagcgtgga
aGAATTCacgctgatccccatcgctgtgggtggtgccctggcggggctggtcctcatcgtcctcatcgcctacctcgtcggcaggaagaggagtcac
gcaggctaccagactatctagtaa (SEQ ID NO:75)

*atggcgccccgcagcgcccggcgaccccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga

Figure 4 (cont.)

For the constructs, the sequences are highlighted as follows: *hLAMP Signal peptide*-hLAMP Luminal domain –CTCGAG-<u>Antigen</u>-GAATTC-hLAMP TM and Cyto domain cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacaccttttccccaatgcgagct
ccaaagaaatcaagactgtggaatctataactgacatcagggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccctgcgccacccagccctcgccctcacccgtgcccaagagccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcggggagctgcggcgcccacctggtgactctggagctgcacagcgagggcaccaccgtcctgctcttccagttcgggatgaatgca
agttctagccggttttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag
gctttcaaggtggaaggtggccagtttggctctgtggaggagtgtctgctggacgagaacagcCTCGAG<u>atggacgccatcaagaagaaaatgca
agccatgaagctggaaaaggacaacgccatggaccgggccgacacactggaacagcagaacaaagaggccaacaatcggccgagaagtccgag
gaagaagtgcacaatctgcagaaacggatgcagcagctggaaaacgatctggaccaagtgcaagagtctctgctgaaggccaacatccaactcgtg
gaaaaggataaggctctgagcaacgccgagggcgaagtggccgctctgaacagacggattcagctgctggaagaggatctggaaagaagcgagga
acggctgaacaccgccacaacaaagctggccgaagccagccaagccgccgacgagagcgagcggatgcggaaagtgctggaaaaccgctctctga
gcgacgaggaaagaatggacgctctggaaaatcagctgaaagaggcccggtttctggccgaggaagccgaccggaagtacgatgaagtggcccgg
aagctggccatggtcgaggctgatctggaacgggccgaagagagagccgaaaccggcgagagcaagatcgtggaactggaagaggaactgcgggt
cgtgggcaacaatctgaagtctctggaagtgtccgaagagaaggccaatcagagagaggaagcctacaaagagcagatcaagacactgaccaaca
agctgaaggctgccgaggccagagccgagttcgccgagagaagcgtgcagaaactgcagaaagaagtggaccggctggaagatgagctcgtgaac
gagaaagagaagtacaagagcatcaccgacgagctggaccagacattcagcgagctgagcggctac</u>GAATTCacgctgatccccatcgctgtgg
gtggtgccctggcggggctggtcctcatcgtcctcatcgcctacctcgtcggcaggaagaggagtcacgcaggctaccagactatctagtaa (SEQ
ID NO:79)

Allergen X is Lol p 5a

*Atggcgccccgcagcgcccggcgaccccctgctgctgctactgctgttgctgctgctcggcctcatgcattgtgcgtcagca*gcaatgtttatggtg
aaaaatggcaacgggaccgcgtgcataatggccaacttctctgctgccttctcagtgaactacgacaccaagagtggccctaagaacatgacccttga
cctgccatcagatgccacagtggtgctcaaccgcagctcctgtggaaaagagaacacttctgaccccagtctcgtgattgcttttggaagaggacatac
actcactctcaatttcacgagaaatgcaacacgttacagcgtccagctcatgagttttgtttataacttgtcagacacacaccttttccccaatgcgagct
ccaaagaaatcaagactgtggaatctataactgacatcagggcagatatagataaaaaatacagatgtgttagtggcacccaggtccacatgaaca
acgtgaccgtaacgctccatgatgccaccatccaggcgtacctttccaacagcagcttcagccggggagagacacgctgtgaacaagacaggccttc
cccaaccacagcgcccctgcgccacccagccctcgccctcacccgtgcccaagagccctctgtggacaagtacaacgtgagcggcaccaacggg
acctgcctgctggccagcatggggctgcagctgaacctcacctatgagaggaaggacaacacgacggtgacaaggcttctcaacatcaaccccaaca
agacctcggccagcggggagctgcggcgcccacctggtgactctggagctgcacagcgagggcaccaccgtcctgctcttccagttcgggatgaatgca
agttctagccggttttttcctacaaggaatccagttgaatacaattcttcctgacgccagagaccctgcctttaaagctgccaacggctccctgcgagcgc
tgcaggccacagtcggcaattcctacaagtgcaacgcggaggagcacgtccgtgtcacgaaggcgttttcagtcaatatattcaaagtgtgggtccag

Figure 4 (cont.)

For the constructs, the sequences are highlighted as follows: *hLAMP Signal peptide*-hLAMP Luminal domain –CTCGAG-<u>Antigen</u>-GAATTC-hLAMP TM and Cyto domain

*gctttcaaggtggaaggtggccagtttggctctgtggaggagtgtctgctggacgagaacagc*CTCGAGgccgatgccggctacacaccagccgct gctgctacaccagccactccagcagcaacaccagcagccgctggcggcaaggccacaaccgatgagcagaaactgctggaagatgtgaacgccgg cttcaaggccgccgtggctgctgctgcaaatgcccctcccgccgacaagttcaagatcttcgaggccgccttcagcgagagcagcaagggactgctgg ccacatctgccgccaaagcccccggactgatccccaagctggacaccgcctacgacgtggcctacaaagccgccgaggccaccccagaggccaaat acgatgccttcgtgaccgctctgaccgaggctctgagagtgattgccggcgctctggaagtgcacgccgtgaagccagccaccgaagaagtgctggcc gccaagattcctaccggcgagctgcagatcgtggacaagatcgacgccgcctttaagatcgccgccaccgccgcaaatgccgcccctaccaacgata agttcaccgtgttcgagagcgccttcaacaaggctctgaacgagtgcaccggcggagcctacgagacatacaagttcatcccatctctggaagccgct gtgaagcaagcctacgccgccacagtggccgctgcccccgaagtgaagtacgccgtgtttgaggccgcactgaccaaggccatcaccgccatgacac aagcccagaaggccggcaaaccagctgctgcagctGAATTCacgctgatccccatcgctgtgggtggtgccctggcggggctggtcctcatcgtcct catcgcctacctcgtcggcaggaagaggagtcacgcaggctaccagactatctag*taa* (SEQ ID NO:83)

Allergen X is Phl p 1

*atggcgccccgcagcgcccggcgaccccctgctgctgctactgctgttgctgctgctcggcctcatgcattgtgcgtcagcag*caatgtttatggtg aaaaatggcaacgggaccgcgtgcataatggccaacttctctgctgccttctcagtgaactacgacaccaagagtggccctaagaacatgacccttga cctgccatcagatgccacagtggtgctcaaccgcagctcctgtggaaaagagaacacttctgaccccagtctcgtgattgcttttggaagaggacatac actcactctcaatttcacgagaaatgcaacacgttacagcgtccagctcatgagttttgtttataacttgtcagacacacaccttttcccaatgcgagct ccaaagaaatcaagactgtggaatctataactgacatcagggcagatatagataaaaaatacagatgtgttagtggcacccaggtccacatgaaca acgtgaccgtaacgctccatgatgccaccatccaggcgtacctttccaacagcagcttcagccggggagagacacgctgtgaacaagacaggccttc cccaaccacagcgcccctgcgccacccagcccctcgccctcacccgtgcccaagagcccctctgtggacaagtacaacgtgagcggcaccaacggg acctgcctgctggccagcatggggctgcagctgaacctcacctatgagaggaaggacaacacgacggtgacaaggcttctcaacatcaaccccaaca agacctcggccagcggagctgcggcgcccacctggtgactctggagctgcacagcgagggcaccaccgtcctgctcttccagttcgggatgaatgca agttctagccggttttttcctacaaggaatccagttgaatacaattcttcctgacgccagagaccctgcctttaaagctgccaacggctccctgcgagcgc tgcaggccacagtcggcaattcctacaagtgcaacgcggaggagcacgtccgtgtcacgaaggcgttttcagtcaatatattcaaagtgtgggtccag *gctttcaaggtggaaggtggccagtttggctctgtggaggagtgtctgctggacgagaacagc*CTCGAGatccccaaagtgcctcccggcccaaac atcaccgccacatacggcgacaagtggctggacgccaagagcacttggtacggcaagcctactggcgccggacccaaggacaatggcggcgcttgt ggctacaaggacgtggacaagccccccttctctggcatgaccggctgcggcaacaccccatcttcaagagcggcagaggctgtggcagctgcttcga gatcaagtgcaccaagcccgaggcttgcagcggcgaaccagtcgtggtgcacatcaccgacgacaacgaggaacccattgcccctaccacttcgat ctgagcggccacgcctttggcgccatggccaagaaaggcgacgagcagaagctgagatctgccggcgagctggaactgcagtttcggagagtgaag tgcaagtaccccgagggcaccaaagtgacatttcacgtggaaaagggcagcaaccccaactatctggctctgctcgtgaaatacgtgaacggcgacg For the constructs, the sequences are highlighted as follows: ***hLAMP Signal peptide*-hLAMP Luminal domain** –CTCGAG-*Antigen*-GAATTC-hLAMP TM and Cyto domain gcgacgtcgtggccgtggacatcaaagagaagggcaaggacaagtggatcgagctgaaagagagctggggcgccatctggcggatcgacacccca gataagctgaccggccctttcaccgtgcggtacacaacagagggcggcaccaagacagaggccgaggatgtgatcccagagggctggaaggccga caccagctacgagagcaaaGAATTCacgctgatccccatcgctgtgggtggtgccctggcggggctggtcctcatcgtcctcatcgcctacctcgtcggcaggaagaggagtcacgcaggctaccagactatctagtaa (SEQ ID No:87)

Allergen X is Phl p 5

*atggcgccccgcagcgcccggcgaccctgctgctgctactgctgttgctgctgctcggcctcatgcattgtgcgtcagca*gcaatgtttatggtgaaaaatggcaacgggaccgcgtgcataatggccaacttctctgctgccttctcagtgaactacgacaccaagagtggccctaagaacatgacccttgacctgccatcagatgccacagtggtgctcaaccgcagctcctgtggaaaagagaacacttctgacccagtctcgtgattgcttttggaagaggacatacactcactctcaatttcacgagaaatgcaacacgttacagcgtccagctcatgagttttgtttataacttgtcagacacacacctttccccaatgcgagctccaaagaaatcaagactgtggaatctataactgacatcagggcagatatagataaaaaatacagatgtgttagtggcacccaggtccacatgaacacgtgaccgtaacgctccatgatgccaccatccaggcgtacctttccaacagcagcttcagccggggagagacacgctgtgaacaagacaggccttccccaaccacagcgcccctgcgccacccagcccctcgccctcacccgtgcccaagagccctctgtggacaagtacaacgtgagcggcaccaacgggacctgcctgctggccagcatggggctgcagctgaacctcacctatgagaggaaggacaacacgacggtgacaaggcttctcaacatcaaccccaacagacctcggccagcggagctgcggcgcccacctggtgactctggagctgcacagcgagggcaccaccgtcctgctcttccagttcgggatgaatgcaagttctagccggttttttcctacaaggaatccagttgaatacaattcttcctgacgccagagaccctgcctttaaagctgccaacggctccctgcgagcgctgcaggccacagtcggcaattcctacaagtgcaacgcggaggagcacgtccgtgtcacgaaggcgttttcagtcaatatattcaaagtgtgggtccaggctttcaaggtggaaggtggccagtttggctctgtggaggagtgtctgctggacgagaacagcCTCGAGgccgccgatctgggctatggcccagctacaccagctgccccagccgccggatacacaccagcaactccagccgctccagctgaagcagccccagctggaaaggccacaaccgaggaacagaagctgatcgagaagatcaacgccggcttcaaggccgctctggctgcagctgctggggtgcagccagccgacaagtacagaacattcgtggccacattcggagccgccagcaacaaggccttgccgagggactgagcggcgagcctaaaggcgccgctgagtctagcagcaaggccgcactgaccagcaagctggacgccgcctacaagctggcctacaagacagccgaaggcgccaccccgaggccaaatacgatgcctacgtggccactctgagcgaggctctgagaatcattgccggcacactggaagtgcacgccgtgaagccagccgctgaggaagtgaaagtgatcccagccggcgagctccaagtgattgagaaagtggatgccgccttcaaagtggccgccaccgctgccaatgccgccccagccaatgacaagttcaccgtgtttgaggccgccttaacgacgccatcaaggcctctaccggcggagcctacgagagctacaagttcatccccgctctggaagccgccgtgaaacaagcctatgccgccacagtggccacagccccgaagtgaagtacacagtgttcgagacagctctgaagaaagccatcaccgccatgtccgaggcccagaaggccgccaaaccagctgctgctgctGAATTCacgctgatccccatcgctgtgggtggtgccctggcggggctggtcctcatcgtcctcatcgcctacctcgtcggcaggaagaggagtcacgcaggctaccagactatctagtaa (SEQ ID NO:91)

Figure 4 (cont.)

NUCLEIC ACIDS FOR TREATMENT OF ALLERGIES

BACKGROUND OF THE INVENTION

Field of the Invention

The present invention relates to the fields of molecular biology and medicine. More specifically, the invention relates to nucleic acids for use as DNA vaccines, and methods of using them to treat subjects suffering from or susceptible to allergic reactions. Prime boost protocols utilizing the LAMP Constructs described herein are also described.

Discussion of the Related Art

Allergic reactions occur when the immune system reacts to harmless foreign substances, called allergens. For example, food allergies are an important public health issue due to the high risk of anaphylaxis, a potentially deadly systemic shock (Sampson et al. (1992) N. Engl. J. Med. 327:380-384; Bock et al. (2001) J. Allergy Clin. Immunol. 107:191-193). Young children are at greater risk of developing food allergies than the general public (Lack et al. (2003) N. Engl. J. Med 348:977-985; Zimmerman et al. (1989) J. Allergy Clin. Immunol. 83:764-770; Green et al. (2007) Pediatrics 120:1304-1310). During the first three years of life, 6-8% of children experience an allergic reaction caused by food (Bock (1987) Allergy 45:587-596; Burks and Sampson (1993) Curr. Prob. Pediatr. 23:230-252; Jansen et al. (1994) J. Allergy Clin. Immunol. 93; 2:446-456; Sampson (1999) J. Allergy Clin. Immunol. 103; 5:717-728). Nut allergies, e.g., peanut and nut allergies, affect up to 1-2% of the population, and the rate of occurrence of this food allergy is thought to be increasing in the general population, disproportionately affecting those of Asian ethnicity.

Anaphylaxis caused by exposure to an allergen, e.g., tree nuts or peanuts, results in a severe immune reaction characterized by overproduction of histamine and is responsible for half of U.S. anaphylaxis emergency room visits annually. For example, extreme reactions to nuts result in over 30,000 incidents of anaphylaxis and between 100-200 deaths in the U.S. each year. Nuts in trace amounts are commonly found in thousands of individually branded, but not labeled, packaged food items. More than one and a half million Americans suffer symptoms from nut allergy and symptoms often persist throughout life. Many experience dangerous reactions on exposure to trace amounts.

There is no treatment for relieving nut allergy symptoms. Over the last ten years, the prevalence of nut allergies has doubled to affect 2% of adult Americans (Sampson (1999) J. Allergy Clin. Immunol. 103; 5:717-728; Sicherer et al. (2003) J. Allergy Clin. Immunol. 112:1203-1207). While the symptoms for many other allergies like hay fever and short ragweed pollen are not life threatening, for a nut allergic individual, the ingestion of as little as 1/1000th of a nut can induce anaphylactic shock and death (Taylor et al. (2002) J. Allergy Clin. Immunol. 109 (1):24-30; Wensing et al. (2002) J. Allergy Clin. Immunol. 110(6):915-920). In the event that accidental ingestion triggers anaphylaxis, injections of epinephrine are used to open up airway passages (Stark and Sullivan (1986) J. Allergy Clin. Immunol. 78:76-83; Sampson (2003) Pediatrics 111(6):1601-1608).

Food allergies occur when an individual fails to develop oral tolerance and instead becomes sensitized to subsequent allergen exposure (Till et al. (2004) J. Allergy Clin. Immunol. 113(6):1025-1034). In allergic patients, allergens preferentially activate type 2 helper CD4+ T lymphocytes (Th2), which produce the pro-allergic cytokines interleukin IL-4, IL-5, and IL-13 that help orchestrate inflammation underlying most allergic symptoms (Woodfolk (2007) J. Allergy Clin. Immunol. 118(2):260-294). IL-4 instructs antibody-producing B cells to secrete allergen-specific Immunoglobulin (Ig) E (Del Prete et al. (1988) J. Immunol. 140:4193-4198; Swain et al. (1990) J. Immunol. 145:3796-3806). Unlike neutralizing IgG, IgE binds to its high affinity receptor Fc-εR1 expressed by mast cells and eosinophils (Blank et al. (1989) Nature 337:187-190; Benhamou et al. (1990) J. Immunol. 144:3071-3077), thus sensitizing these cells. Upon subsequent exposure, IgE binds the offending allergen, cross-links, and transduces a signal instructing mast cells to degranulate and release the volatile chemicals that trigger the allergic reaction.

Beside food allergies, other environmental agents can also generate an allergic response as described above in an individual. Examples of such environmental agents include, but are not limited to, pollen, dog dander, cat saliva, or dust mites.

Immunotherapy, the administration of increasing doses of an allergen to bring about tolerance, is a standard treatment for allergic diseases, but has not been approved for treating nut allergies due to frequent anaphylactic reactions (Nelson et al. (1997) J. Allergy Clin. Immunol 99; 6:744-751; Oppenheimer et al. (1992) J. Allergy Clin. Immunol 90:256-262). In addition, the utility of immunotherapy is limited by the length of treatment, which requires up to 36 months of weekly or bi-weekly injections and results in varying degrees of success and compliance (Bousquet et al. (1998) J. Allergy Clin. Immunol 102:558-562; Rank and Li (2007) Mayo Clin. Proc. 82(9):1119-1123; Ciprandi et al. (2007) Allergy Asthma Proc. 28:40-43).

DNA vaccines have been proposed as a treatment of allergic disease (Raz et al., 1996; Hartl et al., 2004; Hsu et al., 1996; Crameri 2007; Weiss et al., 2006). The underlying rationale is that allergen protein encoded by a DNA vaccine will preferentially activate the allergen-specific Th1 cellular response with the production of interferons by APCs, natural killer (NK), and T cells, rather than the characteristic Th2-type response, such as secretion of IL-4, IL-5, and IL-13, and the formation of IgE by B lymphocytes and the maturation and recruitment of eosinophils in late-phase reactions. However, the mechanisms underlying the differential induction of the Th1 and Th2 T-cell phenotypes appear to involve a large number of factors, such as unique properties of the bacterial DNA of vaccine preparations, e.g., unmethylated and CpG DNA residues, the cytokine milieu elicited by innate immunity, and the cellular trafficking properties of the allergens (Chen et al., 2001; Kaech et al., 2002).

Generally speaking, DNA vaccines are engineered nucleic acids that include sequences encoding one or more epitopes. The nucleic acids are delivered to cells, typically antigen presenting cells (APCs), the nucleic acids are expressed, and the epitopes present on the expressed proteins are processed in the endosomal/lysosomal compartment, and ultimately presented on the surface of the cell. For example, U.S. Pat. No. 5,633,234 to August et al. discloses and characterizes the endosomal/lysosomal targeting sequence of the lysosomal-associated membrane protein (LAMP), identifying critical residues in the C-terminal region of the protein necessary for targeting of the protein to the endosomal/lysosomal compartment. In addition, U.S. patent application publication number 2004/0157307 to Harris et al. discloses the use of the LAMP lumenal domain as a "trafficking domain" to direct chimeric proteins expressed from DNA vaccines through one or more cellular compartments/organelles, such as through the lysosomal vesicular pathway. The chimeric proteins include the lumenal domain of a LAMP polypeptide, an antigenic domain comprising a peptide epitope sequence previously identified and selected from an antigen protein, a transmembrane domain, and an endosomal/lysosomal targeting sequence.

Although numerous LAMP chimeric vaccines have been proposed, their ability to function as effective vaccines has been inconsistent once tested in vivo. For example, in Godinho et al., PLoS ONE 9(6): 9(6): e99887. doi:10.1371/journal.pone.0099887, the authors reported that an intact lumenal domain was necessary to target an antigen to the lysosomes and exosomes secretory pathway and that fragments of the lumenal domain did not always work. See, id. at page 6. Moreover, the authors acknowledged that the ability to raise an immune response is dependent upon the particular antigen and the epitopes used. For example, on page 9, column 2, the authors state "accordingly, previous studies demonstrated that DNA vaccines that generate Gag secreted as VLP, or in a soluble form, induce different levels of T and B cell activation, which were also different from the response induced by cytoplasmic Gag."

Thus, even with the presence of both LAMP domains, it has increasingly been found that the efficacy of a particular antigen to raise an immune response is highly dependent on the particular sequence used. In fact, different antigenic fragments of the same protein when inserted into the identical LAMP vaccine vectors have been found to not elicit the same immune response. Sometimes the antigen fragment generates an immune response and other times it does not. These observations make the ability to predict ahead of time which particular antigenic sequence from a protein of interest will raise an immune response difficult. Instead, in the case of LAMP vaccines, immune response activity needs to be determined by in vivo testing.

Therefore, there is a need to identify new and improved LAMP chimeric vaccines that can be used to effectively treat susceptibility to allergic reactions.

SUMMARY OF THE INVENTION

It is an object of this invention to provide vaccines comprising specific antigens(s) with enhanced immunogenicity, particularly, genetic vaccines such as DNA or RNA vaccines.

It is a further object of this invention to provide more effective methods of vaccination, through the use of the disclosed antigens which are directed to the lysosomal/endosomal compartment and related organelles (e.g., such as MIIC, CIIV, melanosomes, secretory granules, Birbeck granules, and the like) where they are processed and presented to major histocompatibility complex (MHC) class II molecules so that helper T cells are preferentially stimulated.

The nucleic acids, and thus the encoded proteins, polypeptides, and peptides of the invention can be used in methods of treating subjects, and in particular subjects suffering from or potentially developing allergies. In general, a method of treating according to the present invention comprises administering a nucleic acid of the invention to a subject in an amount sufficient to deliver the nucleic acid to one or more immune cells, and preferably to one or more antigen presenting cells (APC) of the immune system. Once delivered, the nucleic acid is expressed, the encoded protein processed inside the cell, and the epitope(s) displayed on the surface of the cell. The method of treating can be considered a method of using the nucleic acids and proteins to provide a therapeutic or prophylactic immune response in subjects suffering from or potentially developing allergies.

In one aspect, the invention provides a chimeric protein, comprising: a N-terminal domain comprising at least one Allergen X; and a trafficking domain; wherein the trafficking domain directs Allergen X to an endosomal compartment (e.g., a lysosome) in a cell. Preferably, the trafficking domain comprises the lumenal domain of a LAMP polypeptide, such as a LAMP-1 or LAMP-2 polypeptide.

In another aspect, the chimeric protein comprises a targeting sequence that directs at least one Allergen X to an endosomal/lysosomal compartment or a related organelle for protein processing and peptide epitope binding to MHC II, such as the tetrapeptide sequence Tyr-Xaa-Xaa-Xbb, wherein Xaa is any amino acid and Xbb is a hydrophobic amino acid. In still another aspect, the targeting sequence comprises a dileucine sequence. In a further aspect, the targeting sequence comprises a cytosolic protein targeting domain from an endocytic receptor. Suitable domains, include, but are not limited to the targeting domain of a C-type lectin receptor, a DEC-205 polypeptide, gp200-MR6 protein, or homolog, ortholog, variant, or modified form thereof.

In one particularly preferred aspect, the protein comprises the lumenal domain of a LAMP polypeptide and a cytoplasmic domain comprising the tetrapeptide sequence Tyr-Xaa-Xaa-Xbb, wherein Xaa is any amino acid and Xbb is a hydrophobic amino acid. The chimeric protein, preferably, further comprises a transmembrane protein. Still more preferably, the chimeric protein also comprises a signaling domain.

Allergen X can be used to generate chimeric proteins. In one aspect, preferred allergens comprise the amino acid sequence of Allergen X of any one of SEQ ID NO:Y as shown in Table 1. Representative examples of polynucleotides that can encode Allergen X (SEQ ID NO:Y) are shown as SEQ ID NO:Z in Table 1. These polynucleotides are inserted between a trafficking domain and a targeting domain. Insertion may be facilitated by the use of cloning sequences that flank the amino acid sequence of SEQ ID NO:Y, such as, for example, polynucleotides that encode "Leu-Glu" and "Glu-Phe" (e.g., "CTCGAG" and "GAATTC.")

The invention further provides a nucleic acid molecule encoding any of the Allergen X of Table 1. The invention also provides a vector comprising the nucleic acid encoding Allergen X, such as, for example, SEQ ID NO:Z and SEQ ID NO:W, wherein the nucleic acid molecule is operably linked to an expression control sequence. In one preferred aspect, the vector is a vaccine vector, suitable for vaccinating a patient against Allergen X. In another aspect, the invention provides a delivery vehicle comprising the nucleic acid molecule for facilitating the introduction of the nucleic acid molecule into a cell. The delivery vehicle may be lipid-based (e.g., a liposome formulation), viral-based (e.g., comprising viral proteins encapsulating the nucleic acid molecule), or cell-based. In one preferred aspect, the vector is a vaccine vector.

The invention also provides a cell comprising any of the vectors described above. In one aspect, the cell is an antigen presenting cell. The antigen presenting cell may be a professional antigen presenting cell (e.g., a dendritic cell, macrophage, B cell, and the like) or an engineered antigen presenting cell (e.g., a non-professional antigen presenting cell engineered to express molecules required for antigen presentation, such as MHC class II molecules). The molecules required for antigen presentation may be derived from other cells, e.g., naturally occurring, or may themselves be engineered (e.g. mutated or modified to express desired properties, such as higher or lower affinity for an antigenic epitope). In one aspect, the antigen presenting cell does not express any co-stimulatory signals and the antigen is an auto-antigen.

The invention additionally provides a kit comprising a plurality of cells comprising any of the vectors described above. At least two of the cells express different MHC class II molecules, and each cell comprises the same vector. In one aspect, a kit is provided comprising a vector and a cell for receiving the vector.

The invention also provides a transgenic animal comprising at least one of the cells described above.

The invention further provides a method for generating an immune response in an animal to Allergen X, comprising: administering to the animal a cell or a polynucleotide comprising a nucleic acid sequence encoding Allergen X (such as, for example, SEQ ID NO:Z or SEQ ID NO:W) as described above, wherein the cell expresses, or can be induced to express the chimeric protein in the animal. In one aspect, the cell comprises an MHC class II molecule compatible with MHC proteins of the animal, such that the animal does not generate an immune response against the MHC class II molecule. In one preferred aspect, the animal is a human.

In one aspect, the invention provides a method of treating subjects suffering from or potentially developing allergies to Allergen X, comprising administering to an animal, any of the vectors, host cells, polynucleotides, or polypeptides described above. In one embodiment, the vector is infectious for a cell of the animal. For example, the vector may be a viral vector, such as a vaccinia vector. Preferred chimeric vaccines administered to the animal include polynucleotides that encode any one of the amino acid sequences of SEQ ID NO:Y as shown in Table 1.

Prime boost protocols are also contemplated. For example, the invention further provides a method for generating an immune response in a subject to Allergen X, comprising priming the subject with a LAMP Construct as described herein followed by at least one boosting of the subject with Allergen X or a related antigen (e.g., a second Allergen derived from the same or highly similar protein sequence). Mixtures of allergens can be used in either or both the priming and the boosting step. Use of a LAMP Construct for the prime step followed by a boost step has been shown to significantly produce higher titers, indicating the power of LAMP in enhancing antibody response.

In a further aspect, a cell is obtained from a patient, the vector is introduced into the cell and the cell or progeny of the cell is reintroduced into the patient. In one aspect, the cell is a stem cell-capable of differentiating into an antigen presenting cell.

BRIEF DESCRIPTION OF THE FIGURES

The objects and features of the invention can be better understood with reference to the following detailed description and accompanying drawings.

FIG. 1 provides the different portions of Human LAMP-1 sequences used to generate constructs described herein.

FIG. 2 provides the known structural domains and amino acid sequence for Human Lamp-1 Protein (SEQ ID NO:4).

FIG. 3 provides the known structural domains and amino acid sequence of Mouse Lamp-1 Protein (SEQ ID NO:5)

FIG. 4 is a schematic representation of the different constructs described herein as provided as Table 1.

DETAILED DESCRIPTION

The invention provides chimeric proteins and nucleic acids encoding these proteins which can be used to generate vaccines against Allergen X. In one aspect, a chimeric protein comprises Allergen X and a domain for trafficking the protein to an endosomal/lysosomal compartment or related organelle. In one preferred aspect, the trafficking domain comprises a lumenal domain of a LAMP polypeptide. Alternatively, or additionally, the chimeric protein comprises a trafficking domain of an endocytic receptor (e.g., such as C-type lectin, DEC-205 or gp200-MR6). The vaccines can be used to modulate an immune response. In one preferred aspect, the invention provides a method of treating or prevention an allergic response in a patient by providing a chimeric protein comprising Allergen X or a nucleic acid encoding Allergen X to the patient.

Definitions

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a nucleic acid molecule" includes a plurality of nucleic acid molecules.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, "the lysosomal/endosomal compartment" refers to membrane-bound acidic vacuoles containing LAMP molecules in the membrane, hydrolytic enzymes that function in antigen processing, and MHC class II molecules for antigen recognition and presentation. This compartment functions as a site for degradation of foreign materials internalized from the cell surface by any of a variety of mechanisms including endocytosis, phagocytosis and pinocytosis, and of intracellular material delivered to this compartment by specialized autolytic phenomena (de Duve, Eur. J. Biochem. 137: 391, 1983). The term "endosome" as used herein and in the claims encompasses a lysosome.

As used herein, a "lysosome-related organelle" refers to any organelle which comprises lysosomes and includes, but is not limited to, MIIC, CIIV, melanosomes, secretory granules, lytic granules, platelet-dense granules, basophil granules, Birbeck granules, phagolysosomes, secretory lysosomes, and the like. Preferably, such an organelle lacks mannose 6-phosphate receptors and comprises LAMP, but may or may not comprise an MHC class II molecule. For reviews, see, e.g., Blott and Griffiths, Nature Reviews, Molecular Cell Biology, 2002; Dell'Angelica, et al., The FASEB Journal 14:1265-1278, 2000.

As used herein, the terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, antisense molecules, cDNA, recombinant polynucleotides, branched polynucleotides, aptamers, plasmids, vectors, isolated DNA of any sequence, isolated RNA of any sequence, nucleic acid probes, and primers. A nucleic acid molecule may also comprise modified nucleic acid molecules (e.g., comprising modified bases, sugars, and/or internucleotide linkers).

As used herein, the term "peptide" refers to a compound of two or more subunit amino acids, amino acid analogs, or peptidomimetics. The subunits may be linked by peptide bonds or by other bonds (e.g., as esters, ethers, and the like).

As used herein, the term "amino acid" refers to either natural and/or unnatural or synthetic amino acids, including glycine and both D or L optical isomers, and amino acid analogs and peptidomimetics. A peptide of three or more amino acids is commonly called an oligopeptide if the peptide chain is short. If the peptide chain is long (e.g., greater than about 10 amino acids), the peptide is commonly called a polypeptide or a protein. While the term "protein" encompasses the term "polypeptide", a "polypeptide" may be a less than full-length protein.

As used herein, the term "Allergen X" refers to the specific genes/proteins listed in the following Table 1, fragments thereof, or mixtures of the listed proteins that are known to induce allergies, i.e., IgE mediated reactions upon their repeated exposure to an individual. Generally, an allergen is any compound, substance, or material that is capable of evoking an allergic reaction. Allergens are usually understood as a subcategory of antigens, which are compounds, substances, or materials capable of evoking an immune response. For carrying out the invention, Allergen X may be selected, among other things, from natural or native allergens, modified natural allergens, synthetic allergens, recombinant allergens, allergoids, and mixtures or combinations thereof. Of particular interest is Allergen X that is capable of causing an IgE-mediated immediate type hypersensitivity.

TABLE 1

| Allergen X | Amino Acid Sequence of Allergen X (SEQ ID NO: Y) | Representative Polynucleotide Sequences Encoding SEQ ID NO: Y (SEQ ID NO: Z) | Amino Acid Sequence of Full Length Construct (SEQ ID NO: V) | Representative Polynucleotide Sequence Encoding SEQ ID NO: V (SEQ ID NO: W) |
|---|---|---|---|---|
| Cor a 1 | SEQ ID NO: 7 | SEQ ID NO: 6 | | |
| Cor a 9 | SEQ ID NO: 9 | SEQ ID NO: 8 | | |
| Cor a 1 - Gly4 - Cor a 9 | SEQ ID NO: 11 | SEQ ID NO: 10 | | |
| Pru du 6 | SEQ ID NO: 13 | SEQ ID NO: 12 | | |
| Ana 0 1 | SEQ ID NO: 15 | SEQ ID NO: 14 | | |
| Ana 0 2 | SEQ ID NO: 17 | SEQ ID NO: 16 | | |
| Ana 0 3 | SEQ ID NO: 19 | SEQ ID NO: 18 | | |
| Ana 0 2 -Gly4- Ana 0 1 - Gly4- Ana 0 3 | SEQ ID NO: 21 | SEQ ID NO: 20 | | |
| Jug n 1 | SEQ ID NO: 23 | SEQ ID NO: 22 | | |
| Jug r 2 | SEQ ID NO: 25 | SEQ ID NO: 24 | | |
| Jug n 1 - Gly4 - Jug r 2 | SEQ ID NO: 27 | SEQ ID NO: 26 | | |
| Amb a 1 | SEQ ID NO: 29 | SEQ ID NO: 28 | SEQ ID NO: 31 | SEQ ID NO: 30 |
| Bet v 1-A | SEQ ID NO: 33 | SEQ ID NO: 32 | SEQ ID NO: 35 | SEQ ID NO: 34 |
| Can f 1 | SEQ ID NO: 37 | SEQ ID NO: 36 | SEQ ID NO: 39 | SEQ ID NO: 38 |
| Cyn d 1 | SEQ ID NO: 41 | SEQ ID NO: 40 | SEQ ID NO: 43 | SEQ ID NO: 42 |
| Der F 1 (19-321) | SEQ ID NO: 45 | SEQ ID NO: 44 | SEQ ID NO: 47 | SEQ ID NO: 46 |
| Der F 1 (99-321) | SEQ ID NO: 49 | SEQ ID NO: 48 | SEQ ID NO: 51 | SEQ ID NO: 50 |
| Der P2 | SEQ ID NO: 53 | SEQ ID NO: 52 | SEQ ID NO: 55 | SEQ ID NO: 54 |
| DerF2 | SEQ ID NO: 57 | SEQ ID NO: 56 | SEQ ID NO: 59 | SEQ ID NO: 58 |
| DerP1 (del) | SEQ ID NO: 61 | SEQ ID NO: 60 | SEQ ID NO: 63 | SEQ ID NO: 62 |
| Fel D 1 | SEQ ID NO: 65 SEQ ID NO: 66 | SEQ ID NO: 64 | SEQ ID NO: 68 | SEQ ID NO: 67 |
| Fel d 2 | SEQ ID NO: 70 | SEQ ID NO: 69 | SEQ ID NO: 72 | SEQ ID NO: 71 |
| Fel d 4 | SEQ ID NO: 74 | SEQ ID NO: 73 | SEQ ID NO: 76 | SEQ ID NO: 75 |
| Lit v 1 | SEQ ID NO: 78 | SEQ ID NO: 77 | SEQ ID NO: 80 | SEQ ID NO: 79 |
| Lol p 5a | SEQ ID NO: 82 | SEQ ID NO: 81 | SEQ ID NO: 84 | SEQ ID NO: 83 |
| Phl p 1 | SEQ ID NO: 86 | SEQ ID NO: 85 | SEQ ID NO: 88 | SEQ ID NO: 87 |
| Phl p 5 | SEQ ID NO: 90 | SEQ ID NO: 89 | SEQ ID NO: 92 | SEQ ID NO: 91 |
| Der f 15 | SEQ ID NO: 93 | | | |
| Der f 18 | SEQ ID NO: 94 | | | |
| Zen-1 | SEQ ID NO: 95 | | | |
| Cte f 1 | SEQ ID NO: 96 | | | |
| Der F15-Der F18 | SEQ ID NO: 109 | | | |
| Der F1-Der F2 | SEQ ID NO: 110 | | | |

As used herein, the amino acid sequence of Allergen X comprises any one of SEQ ID NO:Y. Preferred representative examples of polynucleotides that can encode Allergen X are shown as SEQ ID NO:Z in Table 1. Polynucleotides encoding Allergen X polypeptides are specifically contemplated.

As used herein, "Allergen X" also encompasses variants of Allergen X. For example, preferred embodiments include Allergen X polypeptide variants that have at least about 60%, at least about 70%, at least about 75%, at least about 80%, at least about 85%, at least about 90%, at least about 95%, 96%, 97%, 98% or 99% identity to SEQ ID NO: Y. These variants retain either (a) the ability to raise an antibody that cross-reacts with the Allergen X from which it was derived and/or (b) Allergen X biological activity. Polynucleotides that encode these variant Allergen X polypeptides are specifically contemplated.

Additionally, more than one Allergen X can be combined and administered as a vaccine as described herein. When cloned, the order of the combination of Allergen X can vary within a construct. Moreover, it is specifically envisioned that the combinations of Allergen X can be cloned within a single vaccine construct, or can be delivered in a composition comprising multiple vaccine constructs or Allergen X. Specifically, Allergen X as described in Table 1 can be cloned into the LAMP Constructs described herein either individually, or in combination with one another. As used herein in this paragraph, the names Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and Ctef1 refer to the Allergen X described in Table 1. Specifically, the combinations of Allergen X can be cloned into the LAMP Constructs described herein as follows: (a) Cora1 and at least one of Cora9, Prudu6, Anao1, Anao2, Anao3, Jugn1, Jugr2, Amba1, Betv1-A, Canf1, Cynd1, DerF1(19-321), DerF1 (99-321), DerP2, DerF2, DerP1(del), FelD1, FelD2, FelD4, Litv1, Lolp5a, Phlp1, Phlp5, Derf15, Derf18, Zen-1, and/or Ctef1; (b) Cora9 and at least one of Cora1, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (c) Prudu6 and at least one of Cora1, Cora9, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (d) Anao1 and at least one of Cora1, Cora9, Prudu6, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (e) Anao2 and at least one of Cora1, Cora9, Prudu6, Anao1, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (f) Anao3 and at least one of Cora1, Cora9, Prudu6, Anao1, Anao2, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (g) Jugn1 and at least one of Cora1, Cora9, Prudu6, Anao1, Anao2, Anao3, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (h) Jugr2 and at least one of Cora1, Cora9, Prudu6, Anao1, Anao2, Anao3, Jugn1, Amba1, Betv1-A, Canf1, Cynd1, DerF1(19-321), DerF1 (99-321), DerP2, DerF2, DerP1(del), FelD1, FelD2, FelD4, Litv1, Lolp5a, Phlp1, Phlp5, Derf15, Derf18, Zen-1, and/or Ctef1; (i) Betv1-A and at least one of Cora1, Cora9, Prudu6, Anao1, Anao2, Anao3, Jugn1, Jugr2, Amba1, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (j) Canf1 and at least one of Cora9, Prudu6, Anao1, Anao2, Anao3, Jugn1, Jugr2, Amba1, Betv1-A, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (k) Cynd1 and at least one of Cora9, Prudu6, Anao1, Anao2, Anao3, Jugn1, Jugr2, Amba1, Betv1-A, Canf1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (l) DerF1(19-321) and at least one of Cora9, Prudu6, Anao1, Anao2, Anao3, Jugn1, Jugr2, Amba1, Betv1-A, Canf1, Cynd1, DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (m) DerF1(99-321) and at least one of Cora1, Cora9, Prudu6, Anao1, Anao2, Anao3, Jugn1, Jugr2, Amba1, Betv1-A, Canf1, Cynd1, DerF1(19-321), DerP2, DerF2, DerP1(del), FelD1, FelD2, FelD4, Litv1, Lolp5a, Phlp1, Phlp5, Derf15, Derf18, Zen-1, and/or Ctef1; (n) DerP2 and at least one of Cora1, Cora9, Prudu6, Anao1, Anao2, Anao3, Jugn1, Jugr2, Amba1, Betv1-A, Canf1, Cynd1, DerF1(19-321), DerF1 (99-321), DerF2, DerP1(del), FelD1, FelD2, FelD4, Litv1, Lolp5a, Phlp1, Phlp5, Derf15, Derf18, Zen-1, and/or Ctef1; (o) DerF2 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerP1(del), FelD1, FelD2, FelD4, Litv1, Lolp5a, Phlp1, Phlp5, Derf15, Derf18, Zen-1, and/or Ctef1; (p) DerP1(del) and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, FelD1, FelD2, FelD4, Litv1, Lolp5a, Phlp1, Phlp5, Derf15, Derf18, Zen-1, and/or Ctef1; (q) FelD1 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD2, FelD4, Litv1, Lolp5a, Phlp1, Phlp5, Derf15, Derf18, Zen-1, and/or Ctef1; (r) FelD2 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD4, Litv1, Lolp5a, Phlp1, Phlp5, Derf15, Derf18, Zen-1, and/or Ctef1; (s) FelD4 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, Litv1, Lolp5a, Phlp1, Phlp5, Derf15, Derf18, Zen-1, and/or Ctef1; (t) Litv1 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Lolp5a, Phlp1, Phlp5, Derf15, Derf18, Zen-1, and/or Ctef1; (u) Lolp5a and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Phlp1, Phlp5, Derf15, Derf18, Zen-1, and/or Ctef1; (v) Phlp1 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp5, Derf15, Derf18, Zen-1, and/or Ctef1; (w) Amba1 and at least one of Cora1, Cora9, Prudu6, Anao1, Anao2, Anao3, Jugn1, Jugr2, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, Zen-1, and/or Ctef1; (x) Phlp5 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Derf15, Derf18, Zen-1, and/or Ctef1; (y) Derf15 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf18, Zen-1, and/or Ctef1; (z) Derf18 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Zen-1, and/or Ctef1; (aa) Zen-1 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, and/or Ctef1; and/or (bb) Ctef1 and at least one of Cora1, Cora9, Prudu6, Anao1, Anao2, Anao3, Jugn1, Jugr2, Amba1, Betv1-A, Canf1, Cynd1, DerF1(19-321), DerF1(99-321), DerP2, DerF2, DerP1(del), FelD1, FelD2, FelD4, Litv1, Lolp5a, Phlp1, Phlp5, Derf15, Derf18, and/or Zen-1.

The order of the combination of antigens as described above in a particular LAMP construct can vary as this list describes what a LAMP Construct comprises and not necessarily to describe the arrangement of the antigens within a particular construct. Moreover, it is specifically envisioned that these antigens can be combined within a single LAMP Construct, or can be delivered in a composition comprising multiple LAMP Constructs.

As used herein a "LAMP polypeptide" refers to LAMP-1, LAMP-2, CD63/LAMP-3, DC-LAMP, or any lysosomal associated membrane protein, or homologs, orthologs, variants (e.g., allelic variants) and modified forms (e.g., comprising one or more mutations, either naturally occurring or engineered). In one aspect, a LAMP polypeptide is a mammalian lysosomal associated membrane protein, e.g., such as a human or mouse lysosomal associated membrane protein. More generally, a "lysosomal associated membrane protein" refers to any protein comprising a domain found in the membrane of an endosomal/lysosomal compartment or lysosome-related organelle and which further comprises a lumenal domain. Representative examples of LAMP-1 polypeptide include SEQ ID NO:4 (human LAMP-1), SEQ ID NO:5 (mouse LAMP-1), or canine LAMP (XP_534193) and any of these sequences can be used to generated DNA vaccines as described herein.

As used herein, "an endocytic receptor" refers to a transmembrane protein with either its C-terminal or N-terminal end facing the cytoplasm and which comprises a trafficking domain (e.g., a lumenal domain) for transporting a polypeptide or peptide conjugated to it (e.g., via a chemical bond) to an MHC class II molecule or to an intracellular compartment for subsequent association with an MHC class II molecule. Examples of endocytic receptors include, but are not limited to, Fc-receptors, complement receptors, scavenger receptors, integrins, lectins (e.g., C-type lectins), DEC-205 polypeptides, gp200-MR6 polypeptides, Toll-like receptors, heat shock protein receptors (e.g., CD 91), apoptotic body or necrotic body receptors (e.g., such as CD 14), or homologs, orthologs, variants (e.g., allelic variants) and modified forms thereof (e.g., comprising one or more mutations, either naturally occurring or engineered).

As used herein, "expression" refers to the process by which polynucleotides are transcribed into mRNA and/or translated into peptides, polypeptides, or proteins. If the polynucleotide is derived from genomic DNA, expression may include splicing of the mRNA transcribed from the genomic DNA.

As used herein, "under transcriptional control" or "operably linked" refers to expression (e.g., transcription or translation) of a polynucleotide sequence which is controlled by an appropriate juxtaposition of an expression control element and a coding sequence. In one aspect, a DNA sequence is "operatively linked" to an expression control sequence when the expression control sequence controls and regulates the transcription of that DNA sequence.

As used herein, "coding sequence" is a sequence which is transcribed and translated into a polypeptide when placed under the control of appropriate expression control sequences. The boundaries of a coding sequence are determined by a start codon at the 5' (amino) terminus and a translation stop codon at the 3' (carboxyl) terminus. A coding sequence can include, but is not limited to, a prokaryotic sequence, cDNA from eukaryotic mRNA, a genomic DNA sequence from eukaryotic (e.g., mammalian) DNA, and even synthetic DNA sequences. A polyadenylation signal and transcription termination sequence will usually be located 3' to the coding sequence.

As used herein, two coding sequences "correspond" to each other if the sequences or their complementary sequences encode the same amino acid sequences.

As used herein, "signal sequence" denotes the endoplasmic reticulum translocation sequence. This sequence encodes a signal peptide that communicates to a cell to direct a polypeptide to which it is linked (e.g., via a chemical bond) to an endoplasmic reticulum vesicular compartment, to enter an exocytic/endocytic organelle, to be delivered either to a cellular vesicular compartment, the cell surface or to secrete the polypeptide. This signal sequence is sometimes clipped off by the cell in the maturation of a protein. Signal sequences can be found associated with a variety of proteins native to prokaryotes and eukaryotes.

As used herein, "trafficking" denotes movement or progression of the Allergen X polypeptide through all of the cellular organelles or compartments in the pathway from the rough endoplasmic reticulum to the endosomal/lysosomal compartment or related organelles where antigen processing and binding to MHC II occurs. "Transport" refers to delivery of a chimeric protein to one particular type of cellular compartment.

As used herein, a "trafficking sequence" which is substantially homologous to another trafficking sequence is one which shares substantial homology to the other trafficking sequence; however, the ultimate test for substantial homology is a functional assay in which a polypeptide comprising a sequence substantially homologous to a trafficking sequence is able to co-localize to the same endosomal compartment as the trafficking sequence.

As used herein, "a trafficking domain" refers to a series of continuous or discontinuous amino acids in a protein which are required for vesicular flow of the protein through one or more cellular compartments/organelles. A trafficking domain preferably comprises necessary sequences for proper protein folding to mediate this flow. In one aspect, a trafficking domain comprises a lumenal sequence; preferably, such a sequence comprises one or more binding sites for interactions with a cellular folding protein such as a chaperone.

As used herein, "targeting" denotes the polypeptide sequence that directs the trafficking of Allergen X to the preferred site or cellular organelles or compartment where antigen processing and binding to MHC II occurs.

In contrast, as used herein, a "targeting domain" refers to a series of amino acids which are required for delivery to a cellular compartment/organelle. Preferably, a targeting domain is a sequence which binds to an adaptor or AP protein (e.g., such as an AP1, AP2, or AP3 protein). Exemplary targeting domain sequences are described in Dell'Angelica, 2000, supra.

A "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. Allelic variations or naturally occurring mutational events do not give rise to a chimeric DNA as defined herein.

Short stretches of polynucleotides that encode amino acids may be included at the ends of the polynucleotides that encode Allergen X to facilitate cloning into any of the vectors described herein. For example, use of cloning sequences that flank the amino acid sequence of SEQ ID NO:Y, such as, for example, polynucleotides that encode "Leu-Glu" and "Glu-Phe" (e.g., "CTCGAG" and "GAATTC") may be included in the construct design.

As used herein, a "nucleic acid delivery vector" is a nucleic acid molecule which can transport a polynucleotide of interest into a cell. Preferably, such a vector comprises a coding sequence operably linked to an expression control sequence. However, a polynucleotide sequence of interest may not necessarily comprise a coding sequence. For example, in one aspect a polynucleotide sequence of interest is an aptamer which binds to a target molecule. In another aspect, the sequence of interest is a complementary sequence of a regulatory sequence which binds to a regulatory sequence to inhibit regulation of the regulatory sequence. In still another aspect, the sequence of interest is itself a regulatory sequence (e.g., for titrating out regulatory factors in a cell).

As used herein, a "nucleic acid delivery vehicle" is defined as any molecule or group of molecules or macromolecules that can carry polynucleotides into a host cell (e.g., such as genes or gene fragments, antisense molecules, ribozymes, aptamers, and the like) and which occurs in association with a nucleic acid vector as described above.

As used herein, "nucleic acid delivery," or "nucleic acid transfer," refers to the introduction of an exogenous polynucleotide (e.g., such as a "transgene") into a host cell, irrespective of the method used for the introduction. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome.

As used herein, a "viral vector" refers to a virus or viral particle that comprises a polynucleotide to be delivered into a host cell, either in vivo, ex vivo or in vitro. Examples of viral vectors include, but are not limited to, adenovirus vectors, adeno-associated virus vectors, retroviral vectors, and the like. In aspects where gene transfer is mediated by an adenoviral vector, a vector construct refers to the polynucleotide comprising the adenovirus genome or part thereof, and a selected, non-adenoviral gene, in association with adenoviral capsid proteins.

As used herein, "adenoviral-mediated gene transfer" or "adenoviral transduction" refers to the process by which a gene or nucleic acid sequences are transferred into a host cell by virtue of the adenovirus entering the cell. Preferably, the virus is able to replicate and/or integrate and be transcribed within the cell.

As used herein, "adenovirus particles" are individual adenovirus virions comprised of an external capsid and internal nucleic acid material, where the capsid is further comprised of adenovirus envelope proteins. The adenovirus envelope proteins may be modified to comprise a fusion polypeptide which contains a polypeptide ligand covalently attached to the viral protein, e.g., for targeting the adenoviral particle to a particular cell and/or tissue type.

As used herein, the term "administering a molecule to a cell" (e.g., an expression vector, nucleic acid, an accessory factor, a delivery vehicle, agent, and the like) refers to transducing, transfecting, microinjecting, electroporating, or shooting the cell with the molecule. In some aspects, molecules are introduced into a target cell by contacting the target cell with a delivery cell (e.g., by cell fusion or by lysing the delivery cell when it is in proximity to the target cell).

As used herein, the phrase "prime boost" describes the use of a LAMP Construct described herein used to prime a T-cell response followed by the use of a second LAMP Construct comprising an Allergen, a DNA vaccine comprising an Allergen or a recombinant Allergen to boost the response. These heterologous prime-boost immunizations elicit immune responses of greater height and breadth than can be achieved by priming and boosting with the same vector. The priming with a LAMP Construct comprising an Allergen X memory cells; the boost step expands the memory response. Preferably, use of the two different agents do not raise responses against each other and thus do not interfere with each other's activity. Mixtures of allergens are specifically contemplated in the prime and/or boost step. Boosting can occur one or multiple times.

As used herein, "hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

As used herein, a polynucleotide or polynucleotide region (or a polypeptide or polypeptide region) which has a certain percentage (for example, at least about 50%, at least about 60%, at least about 70%, at least about 80%, at least about 85%, at least about 90%, at least about 95%, at least about 99%) of "sequence identity" to another sequence means that, when maximally aligned, using software programs routine in the art, that percentage of bases (or amino acids) are the same in comparing the two sequences.

Two sequences are "substantially homologous" or "substantially similar" when at least about 50%, at least about 60%, at least about 70%, at least about 75%, and preferably at least about 80%, and most preferably at least about 90 or 95% of the nucleotides match over the defined length of the DNA sequences. Similarly, two polypeptide sequences are "substantially homologous" or "substantially similar" when at least about 50%, at least about 60%, at least about 65%, at least about 70%, at least about 75%, and preferably at least about 80%, and most preferably at least about 90 or 95% of the amino acid residues of the polypeptide match over a defined length of the polypeptide sequence. Sequences that are substantially homologous can be identified by comparing the sequences using standard software available in sequence data banks. Substantially homologous nucleic acid sequences also can be identified in a Southern hybridization experiment under, for example, stringent conditions as defined for that particular system. Defining appropriate hybridization conditions is within the skill of the art. For example, stringent conditions can be: hybridization at 5×SSC and 50% formamide at 42° C., and washing at 0.1×SSC and 0.1% sodium dodecyl sulfate at 60° C.

The terms "percent (%) sequence similarity", "percent (%) sequence identity", and the like, generally refer to the degree of identity or correspondence between different nucleotide sequences of nucleic acid molecules or amino acid sequences of polypeptides that may or may not share a common evolutionary origin (see Reeck et al., supra). Sequence identity can be determined using any of a number of publicly available sequence comparison algorithms, such as BLAST, FASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al, J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al, Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/ on the WorldWideWeb.

Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWSgapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

Statistical analysis of the properties described herein may be carried out by standard tests, for example, t-tests, ANOVA, or Chi squared tests. Typically, statistical significance will be measured to a level of $p=0.05$ (5%), more preferably $p=0.01$, $p=0.001$, $p=0.0001$, $p=0.000001$ "Conservatively modified variants" of domain sequences also can be provided. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, Nucleic Acid Res. 19: 5081; Ohtsuka, et al., 1985, J. Biol. Chem. 260: 2605-2608; Rossolini et al., 1994, Mol. Cell. Probes 8: 91-98).

The term "biologically active fragment", "biologically active form", "biologically active equivalent" of and "functional derivative" of a wild-type protein, possesses a biological activity that is at least substantially equal (e.g., not significantly different from) the biological activity of the wild type protein as measured using an assay suitable for detecting the activity. For example, a biologically active fragment comprising a trafficking domain is one which can co-localize to the same compartment as a full-length polypeptide comprising the trafficking domain.

As used herein, "in vivo" nucleic acid delivery, nucleic acid transfer, nucleic acid therapy" and the like, refer to the introduction of a vector comprising an exogenous polynucleotide directly into the body of an organism, such as a human or non-human mammal, whereby the exogenous polynucleotide is introduced into a cell of such organism in vivo.

As used herein, the term "in situ" refers to a type of in vivo nucleic acid delivery in which the nucleic acid is brought into proximity with a target cell (e.g., the nucleic acid is not administered systemically). For example, in situ delivery methods include, but are not limited to, injecting a nucleic acid directly at a site (e.g., into a tissue, such as a tumor or heart muscle), contacting the nucleic acid with cell(s) or tissue through an open surgical field, or delivering the nucleic acid to a site using a medical access device such as a catheter.

As used herein, the term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart.

As used herein, a "target cell" or "recipient cell" refers to an individual cell or cell which is desired to be, or has been, a recipient of exogenous nucleic acid molecules, polynucleotides and/or proteins. The term is also intended to include progeny of a single cell, and the progeny may not necessarily be completely identical (in morphology or in genomic or total DNA complement) to the original parent cell due to natural, accidental, or deliberate mutation. A target cell may be in contact with other cells (e.g., as in a tissue) or may be found circulating within the body of an organism.

As used herein, a "subject" is a vertebrate, preferably a mammal, more preferably a human. Mammals include, but are not limited to, murines, simians, humans, farm animals, sport animals, and pets. In other preferred embodiments, the "subject" is a rodent (e.g., a guinea pig, a hamster, a rat, a mouse), murine (e.g., a mouse), canine (e.g., a dog), feline (e.g., a cat), equine (e.g., a horse), a primate, simian (e.g., a monkey or ape), a monkey (e.g., marmoset, baboon), or an ape (e.g., gorilla, chimpanzee, orangutan, gibbon). In other embodiments, non-human mammals, especially mammals that are conventionally used as models for demonstrating therapeutic efficacy in humans (e.g., murine, primate, porcine, canine, or rabbit animals) may be employed.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin Remington's Pharm. Sci., 15th Ed. (Mack Publ. Co., Easton (1975)).

A cell has been "transformed", "transduced", or "transfected" by exogenous or heterologous nucleic acids when such nucleic acids have been introduced inside the cell. Transforming DNA may or may not be integrated (covalently linked) with chromosomal DNA making up the genome of the cell. In prokaryotes, yeast, and mammalian cells for example, the transforming DNA may be maintained on an episomal element, such as a plasmid. In a eukaryotic cell, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations (e.g., at least about 10).

As used herein, an "effective amount" is an amount sufficient to affect beneficial or desired results, e.g., such as an effective amount of nucleic acid transfer and/or expression, and/or the attainment of a desired therapeutic endpoint. An effective amount can be administered in one or more administrations, applications or dosages. In one aspect, an effective amount of a nucleic acid delivery vector is an amount sufficient to transform/transduce/transfect at least one cell in a population of cells comprising at least two cells.

As used herein, a "therapeutically effective amount" is used herein to mean an amount sufficient to prevent, correct and/or normalize an abnormal physiological response. In one aspect, a "therapeutically effective amount" is an amount sufficient to reduce by at least about 30 percent, more preferably by at least 50 percent, most preferably by at least 90 percent, a clinically significant feature of pathology, such as for example, a clinically significant feature of pathology, such as for example, antibody production, cytokine production, fever or white cell count, or level of histamine.

As used herein, the term "prevent" or "prevents" in the context of allergy immunotherapy, allergy treatment, or other terms that describe an intervention designed for an allergy patient, means the prevention of an IgE response in at least 20% of all patients. The term "prevent" does not mean total prevention from developing an IgE mediated disease in all patients, and such a definition is outside the scope of the present invention for treating allergy through a mechanism that reduces allergy symptoms, and is inconsistent with the use of the term in the art. It is well known to those skilled in the art of allergy immunotherapy that allergy treatments are not 100% effective in 100% of patients, and as such an absolute definition of "prevent" does not apply within the context of the present invention. The art-recognized concept of prevention is contemplated by the present invention.

The term "oromucosal administration" refers to a route of administration where the dosage form is placed under the tongue or anywhere else in the oral cavity to allow the active ingredient to come in contact with the mucosa of the oral cavity or the pharynx of the patient in order to obtain a local or systemic effect of the active ingredient. An example of an oromucosal administration route is sublingual administration. The term "sublingual administration" refers to a route of administration where a dosage form is placed underneath the tongue in order to obtain a local or systemic effect of the active ingredient. As used herein, the term "intradermal delivery" means delivery of the vaccine to the dermis in the skin. However, the vaccine will not necessarily be located exclusively in the dermis. The dermis is the layer in the skin located between about 1.0 and about 2.0 mm from the surface in human skin, but there is a certain amount of variation between individuals and in different parts of the body. In general, it can be expected to reach the dermis by going 1.5 mm below the surface of the skin. The dermis is located between the stratum corneum and the epidermis at the surface and the subcutaneous layer below. Depending on the mode of delivery, the vaccine may ultimately be located solely or primarily within the dermis, or it may ultimately be distributed within the epidermis and the dermis.

An "antibody" is any immunoglobulin, including antibodies and fragments thereof, that binds a specific epitope. The term encompasses polyclonal, monoclonal, and chimeric antibodies (e.g., bispecific antibodies). An "antibody combining site" is that structural portion of an antibody molecule comprised of heavy and light chain variable and hypervariable regions that specifically binds antigen. Exemplary antibody molecules are intact immunoglobulin molecules, substantially intact immunoglobulin molecules, and those portions of an immunoglobulin molecule that contains the paratope, including Fab, Fab', F(ab')$_2$ and F(v) portions, which portions are preferred for use in the therapeutic methods described herein.

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two epitopes correspond to each other if both are capable of binding to the same B cell receptor or to the same T cell receptor, and binding of one antibody to its epitope substantially prevents binding by the other epitope (e.g., less than about 30%, preferably, less than about 20%, and more preferably, less than about 10%, 5%, 1%, or about 0.1% of the other epitope binds). In the present invention, multiple Allergen X can be combined to make up an Allergen X antigen (see, for example, SEQ ID NOs: 11, 21, 27, 109 and 110).

The term "antigenic material" as used herein covers any substance that will elicit an innate or adaptive immune response.

The term "antigen presenting cell" as used herein includes any cell which presents on its surface an antigen in association with a major histocompatibility complex molecule, or portion thereof, or, alternatively, one or more non-classical MHC molecules, or a portion thereof. Examples of suitable APCs are discussed in detail below and include, but are not limited to, whole cells such as macrophages, dendritic cells, B cells, hybrid APCs, and foster antigen presenting cells.

As used herein an "engineered antigen-presenting cell" refers to an antigen-presenting cell that has a non-natural molecular moiety on its surface. For example, such a cell may not naturally have a costimulator on its surface or may have an additional artificial costimulator in addition to a natural costimulator on its surface, or may express a non-natural class II molecule on its surface. In preferred embodiments, the engineered antigen-presenting cells have one or more Allergen X on its surface.

As used herein, "immune effector cells" refers to cells capable of binding an antigen and which mediate an immune response. These cells include, but are not limited to, T cells, B cells, monocytes, macrophages, NK cells and cytotoxic T lymphocytes (CTLs), for example CTL lines, CTL clones, and CTLs from tumor, inflammatory, or other infiltrates.

An "isolated" or "purified" population of cells is substantially free of cells and materials with which it is associated in nature. By substantially free or substantially purified APCs it is meant at least 50% of the population are APCs, preferably at least 70%, more preferably at least 80%, and even more preferably at least 90%, are free of non-APCs cells with which they are associated in nature.

As used herein, a "genetic modification" refers to any addition, deletion or disruption to a cell's normal nucleotides. Any method which can achieve the genetic modification of APCs are within the spirit and scope of this invention. Art recognized methods include viral mediated gene transfer, liposome mediated transfer, transformation, transfection and transduction, e.g., viral-mediated gene transfer such as the use of vectors based on DNA viruses such as adenovirus, adeno-associated virus and herpes virus, as well as retroviral based vectors.

The practice of the present invention employs, unless otherwise indicated, conventional molecular biology, microbiology, and recombinant DNA techniques within the skill of the art. Such techniques are explained fully in the literature. See, e.g., Maniatis, Fritsch & Sambrook, In Molecular Cloning: A Laboratory Manual (1982); DNA Cloning: A Practical Approach, Volumes I and II (D. N. Glover, ed., 1985); Oligonucleotide Synthesis (M. J. Gait, ed., 1984); Nucleic Acid Hybridization (B. D. Hames & S. J. Higgins, eds., 1985); Transcription and Translation (B. D. Hames & S. I. Higgins, eds., 1984); Animal Cell Culture (R. I. Freshney, ed., 1986); Immobilized Cells and Enzymes (IRL Press, 1986); B. Perbal, A Practical Guide to Molecular Cloning (1984).

Allergen X Antigen Sequences

The present invention provides polynucleic acids, polyaminoacids, host cells, vectors directed to Allergen X and methods of treating subjects in need of such polynucleic acids, polyaminoacids, host cells, or vectors. Broadly speaking, the polynucleic acids can be thought of as nucleic acid (e.g., DNA, RNA) vaccines for the intracellular production of allergenic sequences (polyaminoacids) that elicit a protective immune response within the body of the subject to whom the polynucleic acid is administered. The polynucleic acids, when administered, preferentially evoke a cell-mediated immune response via the MHC-II pathway and production of IgG antibodies by activating an allergen-specific T-helper type 1 (Th1) cellular response with the production of interferons by APCs, NK cells, and T cells rather than a Th2-type response, which involves production of IgE antibodies, granulocytes (e.g., eosinophils), and other substances. To an extent, both an MHC-II and an MHC-I response can be generated; however, the invention provides a response that is primarily or substantially an MHC-II response. Preferably, the nucleic acids do not encode an antibiotic resistance gene.

The invention is based, at least in part, on the recognition that a combination of certain structural, and thus functional, elements provides advantageous properties to the nucleic acid vaccines and the encoded allergens, and allows for allergy treatment methods that satisfy unmet needs in the art. In the various embodiments of the invention, which are intended to be understood as standing alone as independent embodiments and as embodiments that combine two or more features of the independent embodiments, the combinations include the use of a lysosomal trafficking domain to direct Allergen X to lysosomes with MHC II proteins. Doing so allows for predominantly an IgG response as opposed to an IgE response to the Allergen X. Yet further, independent embodiments or combinations of embodiments provide constructs containing a sufficient length of a nucleic acid sequence (e.g., the full length nucleic acid sequence or a fragment thereof, a variant of the full length nucleic acid sequence or a fragment thereof, etc.) to encode an amino acid sequence that provides a naturally-occurring three-dimensional structure of an epitope. In preferred embodiments, the nucleic acid sequence encodes Allergen X (SEQ ID NO:Y). In other embodiments, the nucleic acid sequence encodes at least one Allergen X. Although it is recognized in the art that an immune response can be generated against the primary sequence of an epitope, the present invention recognizes that nucleic acid vaccines for the production of an MHC-II immune response to encoded epitopes preferably uses nucleic acid constructs that encode enough sequence data to produce a correct three-dimensional peptide structure in the region comprising Allergen X, at least at the time when Allergen X is delivered to a lysosome for processing. While not being limited to any particular molecular theory, it is believed that delivery of a properly three-dimensionally folded protein, polypeptide, or peptide to an endosome improves processing and presentation of allergenic epitopes for an immune response.

Thus, the invention provides chimeras which comprise Allergen X and lumenal sequences of a polypeptide that result in trafficking of the chimera to the endosomal/lysosomal compartment for antigen processing and antigen epitope association with MHC II. In one aspect, the chimeric protein additionally comprises cytoplasmic targeting sequences that direct the chimera to endosomal/lysosomal compartments. Additionally, the chimeric protein also may comprise a signal sequence and/or a transmembrane sequence. Suitable trafficking domains are provided by LAMP-1, LAMP-2, DC-LAMP, Trp-1, DEC-205, gp200-MR6, and other polypeptides, as discussed below. The signal sequence and transmembrane sequence may, but do not have to be, from these polypeptides. However, in one aspect, an antigen/LAMP chimera comprises a full-length LAMP polypeptide.

Allergen X can be used to generate chimeric proteins. In one aspect, preferred compositions comprise the amino acid sequence of Allergen X of any one of SEQ ID NO:Y as shown in Table 1 or polynucleotides that encode any one of the SEQ ID NO:Y. Preferred representative examples of polynucleotides that can encode Allergen X are shown as SEQ ID NO:Z in Table 1. Further preferred representative embodiments are constructs comprising Allergen X along with either human, murine, or canine LAMP sequences (see, for example, SEQ ID NO:W and SEQ ID NO:V). As described in Table 3 in the Examples, it was surprisingly found that the chimeric LAMP vaccines comprising the specific Allergen X amino acid sequences corresponding to SEQ ID NOs: Y generated an unexpectedly robust immune response as compared to other constructs tested.

Allergen X can also include Allergen X variants. For example, preferred embodiments include Allergen X polypeptide variants that have at least about 60%, at least about 70%, at least about 75%, at least about 80%, at least about 85%, at least about 90%, at least about 95%, 96%, 97%, 98% or 99% identity to SEQ ID NO:Y. These variants retain either (a) the ability to raise an antibody that cross-reacts with the Allergen X from which it was derived and/or (b) Allergen X biological activity. Polynucleotides that encode these polypeptides are specifically contemplated.

Synthetic Allergen X antigens and altered Allergen X antigens also can be used in the methods described herein. Synthetic antigenic Allergen X peptide epitopes have modified amino acid sequences relative to the natural Allergen X sequence. Further encompassed by the term "synthetic Allergen X antigenic peptides" are multimers (concatemers) of synthetic antigenic Allergen X peptides, optionally including intervening amino acid sequences. For example, synthetic Allergen X antigenic peptide epitopes of the present invention can be designed based on known amino acid sequences of antigenic Allergen X peptide epitopes.

Also included within the scope of the invention are antigenic Allergen X peptides that are differentially modified during or after translation, e.g., by phosphorylation, glycosylation, crosslinking, acylation, proteolytic cleavage, linkage to an antibody molecule, membrane molecule or other ligand (Ferguson et al., Ann. Rev. Biochem. 57: 285-320, 1998).

Isolated Allergen X peptides can be synthesized using an appropriate solid state synthetic procedure (Steward and Young, Solid Phase Peptide Synthesis, Freemantle, San Francisco, Calif. 1968). A preferred method is the Merrifield process (Merrifield, Recent Progress in Hormone Res. 23: 451, 1967). The Allergen X antigenic activity of these peptides may conveniently be tested using, for example, the assays as described herein.

Once an isolated Allergen X peptide is obtained, it may be purified by standard methods including chromatography (e.g., ion exchange, affinity, and sizing column chromatography), centrifugation, differential solubility, or by any other standard technique for protein purification. For immunoaffinity chromatography, an Allergen X epitope may be isolated by binding it to an affinity column comprising antibodies that were raised against that peptide, or a related peptide, and were affixed to a stationary support. Alternatively, affinity tags such as hexa-His (Invitrogen), Maltose binding domain (New England Biolabs), influenza coat sequence (Kolodziej, et al., Methods Enzymol. 194: 508-509, 1991), and glutathione-S-transferase can be attached to the peptides to allow easy purification by passage over an appropriate affinity column. Isolated Allergen X peptides also can be physically characterized using such techniques as proteolysis, nuclear magnetic resonance, and x-ray crystallography.

Having isolated and identified the Allergen X peptide sequence of a desired epitope, nucleic acids comprising sequences encoding these epitopes can be sequenced readily.

Endocytic Trafficking Sequences

The available data suggest the following sequence of events in the intracellular transport of MHC class II molecules: MHC class II molecules with the invariant chain are assembled in the endoplasmic reticulum and transported through the Golgi with other membrane proteins including MHC class I. The molecules are then targeted to specific endosomal/lysosomal organelles by an unknown mechanism, segregating from the MHC class I molecules which follow a constitutive route to the cell surface. In the endocytic/lysosomal route, the invariant chain is removed from MHC class II by proteases acting in an acidic environment. At the same time, antigenic fragments of proteins that have entered the endocytic/lysosomal pathway are generated by these proteases and the resulting peptides bind to the class II molecules and are carried to the cell surface.

The biosynthesis and vacuolar targeting mechanisms of the hydrolytic enzymes present in the lysosomal/endosomal compartment have been extensively studied (Kornfeld and Mellman, Ann. Rev. Cell Biol. 5: 483, 1989). Newly synthesized hydrolases in the Golgi apparatus acquire mannose 6-phosphate groups that serve as specific recognition markers for the binding of these enzymes to mannose 6-phosphate receptors which are then targeted in some unknown manner to a prelysosomal vacuole. There the receptor-enzyme complex is dissociated by low pH, and the receptors recycle to the Golgi apparatus, while the enzyme-containing vacuole matures into a lysosome.

The localization of the lysosomal membrane glycoproteins is controlled by a targeting mechanism independent of the well-defined mannose 6-phosphate receptor (MPR) pathway for hydrolytic lysosomal enzymes (Kornfeld and Mellman, 1989, supra). Recent studies describe a distinct vesicular compartment with lysosomal properties and characterized by high concentration of lysosomal-associated membrane protein (LAMP-1) and MHC class II molecules (Peters, et al., EMBO J. 9: 3497, 1990). Lysosomal/Endosomal Compartment Kinetic analysis of intracellular transport and targeting of newly synthesized LAMP-1 and other similar proteins indicate that the molecule is synthesized in the endoplasmic reticulum, processed in the Golgi cisternae and transported to lysosomes within one hour of its biosynthesis, without detectable accumulation in the plasma membrane (Barriocanal, et al., J Biol. Chem. 15: 261(35): 16755-63, 1986; D'Sousa, et al., Arch. Biochem. Biophys. 249: 522, 1986; Green, et al., J. Cell Biol., 105: 1227, 1987).

Studies of the structure and function of the lysosomal membrane were initiated in 1981 by August and colleagues with the discovery of major cellular glycoproteins that were subsequently termed lysosomal-associated membrane proteins one and two (LAMP-1 and LAMP-2) due to their predominant localization in the lysosomal membrane (Hughes, et al., J. Biol. Chem. 256: 664, 1981; Chen, et al., J. Cell Biol. 101:85, 1985). Analogous proteins were subsequently identified in rat, chicken and human cells (Barriocanal, et al., 1986, supra; Lewis, et al., J. Cell Biol. 100:1839, 1985; Fambourgh, et al., J. Cell Biol. 106: 61, 1988; Mane, et al., Arch. Biochem. Biophys. 268: 360, 1989).

Typically, LAMP-1, as deduced from a cDNA clone (Chen, et al., J. Biol. Chem. 263: 8754, 1988) consists of a polypeptide core of about 382 amino acids with a large (346-residue) lumenal amino-terminal domain followed by a 24-residue hydrophobic transmembrane region and short (12-residue) carboxyl-terminal cytoplasmic tail. See, FIGS. 2 and 3. The lumenal domain is highly glycosylated, being substituted with about 20 asparagine linked complex-type oligosaccharides and consists of two to about 160-residue homology units that are separated by a proline/serine-rich region. Each of these homologous domains contains 4 uniformly spaced cysteine residues, disulfide bonded to form four 36-38-residue loops symmetrically placed within the two halves of the lumenal domain (Arterburn, et al., J. Biol. Chem. 265: 7419, 1990; see, also Chen, et al., J. Biol. Chem. 25: 263(18): 8754-8, 1988). The LAMP-2 molecule is highly similar to LAMP-1 in overall amino acid sequence (Cha, et al., J. Biol. Chem. 265: 5008, 1990).

LAMP-1 and LAMP-2 are not specifically found in antigen presenting cells (dendritic cells). Their precise function is unknown, but they presumably are involved in some manner with lysosome function. Their colocalization with MHC II in the multilaminar MIIC vesicular compartment of APCs has no known functional association to antigen processing or presentation; however, chimeric antigens comprising LAMP cytoplasmic domains, as discussed above, show enhanced immunogenicity (see, U.S. Pat. No. 5,633,234).

The invention provides chimeric Allergen X proteins comprising the lumenal domain of a lysosomal associated membrane protein, such as a LAMP polypeptide, or a bioactive fragment or modified form thereof (collectively referred to as "a LAMP-lumenal domain"). In one aspect, the LAMP lumenal domain comprises at least two homology units. Preferably, each homology unit is separated by a proline/serine-rich region. More preferably, each homology domain comprises 4 cysteine residues capable of forming four 36-38-residue loops symmetrically placed within the two halves of the lumenal domain when disulfide bonded together. Most preferably, the lumenal domain comprises sequences necessary to target and traffic a polypeptide to which it is linked (e.g., via a chemical bond) to an endosomal/lysosomal compartment or lysosome-related organelle for binding to an MHC class II molecule or for delivery to another compartment/organelle where it will bind to an MHC class II molecule.

In a preferred embodiment, the portion of the lumenal domain of LAMP-1 that can be used in the present invention, includes, but is not limited to SEQ ID NOs:2 or 3 or amino acids 29-381 of SEQ ID NO:4 (or the corresponding sequence of SEQ ID NO:5). In further preferred embodiments, the transmembrane domain/cytoplasmic tail of LAMP-1 can be used in the present invention. For example, SEQ ID NO:1 or amino acids 382-417 of SEQ ID NO:4 (or the corresponding sequence of SEQ ID NO:5) can be used in the chimeric vaccines as described herein. Moreover, any combination of the lumenal domain fragments with the transmembrane domain/cytoplasmic tail fragments can be used.

In another aspect, the chimeric protein additionally, or alternatively, comprises a dileucine-based signal comprising at least one leucine-leucine pair or at least one leucine/isoleucine pair. Preferably, the protein further comprises an acidic residue 4-5 residues upstream of the pair. More preferably, this signal domain binds to an AP complex polypeptide (see, e.g., Bonafacino and Dell'Angelica, J. Cell Biol. 145: 923-926, 1999). Suitable dileucine-based domains can be found in tyrosinase (TM-$X_{10}$-EKQPLL-$X_5$-YHSL-$X_5$) (SEQ ID NO:97); TRP-2 (TM-$X_7$-EANQPLL-$X_{12}$) (SEQ ID NO:98); and Pmel7 (TM-$X_{34}$-ENSPLL-$X_5$) (SEQ ID NO:99) and P-protein (see, e.g., Dell'Angelica, 2000, supra), for example.

In a preferred aspect, the chimeric protein also comprises a cytoplasmic domain for targeting and/or trafficking a chimeric Allergen X protein to an endosomal/lysosomal compartment or lysosome-related organelle. In one aspect, the cytoplasmic domain comprises the tail of a LAMP polypeptide. The eleven amino-acid sequence of the cytoplasmic tail of LAMP-1 and other similar lysosomal membrane glycoproteins has the following sequence: Arg-Lys-Arg-Ser-His-Ala-Gly-Tyr-Gln-Thr-Ile-COOH (Chen, et al., 1988, supra)(Residues 25-35 of SEQ ID NO:1). In LAMP-1, these sequences are from amino acids 372-382 of the full-length polypeptide.

The known cytoplasmic tail sequences of lysosomal membrane proteins, LAMP-1 (Chen, et al., 1988, supra), LAMP-2 (Cha, et al., 1990, supra) and CD63 (Hotta, et al., Cancer Res. 48: 2955, 1988), have been aligned with the Tyr-containing internalization signal in the cytoplasmic tail of LAP (Pohlman, et al., EMBO J. 7: 2343, 1988) in Table 2. The Tyr residue is known to be required for endosomal/lysosomal targeting, and it was demonstrated in U.S. Pat. No. 5,633,234 that the complete sequence required to target other molecules to lysosomes requires the Tyr-X-X-hyd sequence (i.e., a "Tyr motif"), a Tyr followed by two amino acids followed by a hydrophobic residue.

TABLE 2

Cytoplasmic Tail Sequences of the Major Lysosomal Membrane Proteins*

| | |
|---|---|
| LAMP-1 | RKRSHA GYQTI (Residues 25-25 of SEQ ID NO: 1) |
| LAMP-2 | KHHHA GYEQF (SEQ ID NO: 100) |
| CD63 | KSIRS GYEVM (SEQ ID NO: 101) |
| LAP | RMEAPP GYRHVADGEDHA (SEQ ID NO: 102) |

*The conserved Gly-Tyr-X-X-hydrophobic residue motif in the cytoplasmic domain of the described lysosomal membrane proteins is underlined, where X is any amino acid. The complete cytoplasmic tail sequence of the listed proteins is shown from the transmembrane region to the carboxyl terminus.

The importance of a hydrophobic residue at or near the carboxyl-terminal position is shown by results obtained from modification of the Tyr-Gln-Thr-Ile sequence of LAMP-1 (Residues 32-35 of SEQ ID NO:1). Mutant cDNA molecules in which Ile was substituted with two other hydrophobic residues, Leu or Phe, and a polar residue, Thr. Substituting Leu (Tyr-Gln-Thr-Leu) (SEQ ID NO:103) and Phe (Tyr-Gln-Thr-Phe) (SEQ ID NO:104) does not affect lysosomal targeting, whereas the Thr-containing mutant protein (Tyr-Gln-Thr-Thr) (SEQ ID NO:105) accumulates at the cell surface. Mutants containing Ala substituted for Gln (Tyr-Ala-Thr-Ile) (SEQ ID NO: 106), Thr (Tyr-Gln-Ala-Ile) (SEQ ID NO:107), and both residues (Tyr-Ala-Ala-Ile) (SEQ ID NO:108) have no effect on targeting to the lysosomal membrane, indicating that these positions may be occupied by charged, polar, or nonpolar residues.

The preferred targeting signal to the lysosomal/endosomal compartment, therefore, includes a tetrapeptide sequence located in the cytoplasmic domain, near the transmembrane domain and also near the C-terminus. The cytoplasmic domain is preferably a short amino acid sequence (less than 70 amino acids, preferably less than 30 amino acids, most preferably less than 20 amino acids) ending in a free carboxyl group. In a more preferred embodiment, the tetrapeptide is at the C-terminal end of a short cytoplasmic tail that contains the targeting signal, or is in a context similar to LAMP-1.

A suitable four amino acid sequence for the tetrapeptide may be obtained by amino acid substitutions, so long as the motif consists of Tyr-X-X-Hyd (where X may be any amino acid and Hyd denotes a hydrophobic amino acid), and the ability to confer lysosomal/endosomal targeting is conserved. A particularly preferred tetrapeptide has the sequence Tyr-Gln-Thr-Ile (Residues 32-35 of SEQ ID NO:1). In the most preferred embodiment, the entire LAMP cytoplasmic tail in conjunction with its transmembrane domain, and most preferably, its luminal domain is coupled to the primary sequence of the antigenic domain for highly efficient MHC class II processing and presentation. However, the cytoplasmic domain is not necessary to facilitate trafficking so long as a lumenal domain of a LAMP polypeptide is provided.

In another aspect, the endosomal targeting domain comprises a transmembrane sequence. Many proteins that will serve as the source of the antigenic domain for particular immune stimulatory constructs will be surface antigens that include a transmembrane domain in their primary sequence. Such a transmembrane domain can be retained, and the cytoplasmic domain replaced with a lysosomal/endosomal targeting domain as taught herein (e.g., a domain comprising a LAMP lumenal domain).

In one preferred aspect, the transmembrane domain of LAMP (see, Chen, et al., J. Biol. Chem. 263: 8754, 1988) is coupled to the primary sequence of the Allergen X derived polypeptide and the sequence of the lumenal domain. The structure of a transmembrane domain in a polypeptide is well known in the art (see, e.g., Bangham, Anal. Biochem. 174: 142, 1988; Klein, et al., Biochem. Biophys. Acta 815: 468, 1985; Kyle & Doolittle, J. Mol. Biol. 157: 105, 1982). Usually the transmembrane region appears in the primary sequence as a sequence of 20-25 hydrophobic amino acid residues flanked by hydrophilic regions. Such sequences can be found, for example, in most cell surface antigen sequences listed by Genbank as well as many other membrane proteins. The particular transmembrane sequence is not critical, so long as it serves to connect the antigenic domain to the lumenal domain and cytoplasmic tail and anchors the construct in the membranous compartment.

Additional, or alternative sorting motifs, can include, but are not limited to, one or more of: a targeting domain, a tyrosine motif domain as described above; a di-leucine and tyrosine-based domain; a proline rich domain; and S-V-V domain (see, e.g., Blott and Grifitts, Nature 3: 122-131, 2002).

Endocytic Receptor Sequences

Antigen access to the MHC II vesicular compartment of antigen presenting cells, such as dendritic cells, is normally by endocytosis of foreign antigens. The trafficking domains of endocytic receptors can be used to generate chimeric polypeptides to carry Allergen X to endosomal/lysosomal compartments or to lysosome-related organelles for association with class II MHC molecules and subsequent processing.

In one aspect, therefore, the invention provides at least one Allergen X linked to a trafficking domain of an endocytic receptor (e.g., via in-frame fusion of nucleic acid sequences encoding the trafficking domain and antigen). The trafficking domain localizes Allergen X to an endosomal/lysosomal compartment or to a lysosome-related organelle for association with an MHC class II molecule in the compartment/organelle or in a subsequent compartment to which Allergen X is delivered.

Endocytic receptors according to the invention, include, but are not limited to receptors for microorganisms, Fc receptors (e.g., CD64, CD32, CD16, CD23, and CD89); complement receptors (e.g., CR1 or CD35, CR3, CR4); scavenger receptors or receptors which bind to acetylated or modified lipoproteins, polyribonucleotides, lipopolysaccharides and silica particles (e.g., such as SRA, MARCO), integrins (CD49e/CD29; CD49d/CD29; CD51/CD61); lectins (e.g., such as dectin-1, C-type lectins, and the like), and Toll-like receptors (e.g., TLRs). For a review of such receptors, see Underhill and Ozinsky, Annu. Rev. Immunol. 20: 825-52, 2002, for example.

In one aspect, the endocytic receptor is obtained from a professional antigen presenting cell such as a dendritic cell. A number of endocytic receptors of dendritic cells have been identified, including the macrophage mannose receptor (MMR), phospholipaseA2-receptor, Endo 180, and DEC-205 and its human homologue, gp200-MR6 (McKay, et al., 1998). DEC-205 is reported to differ from the MMR, at least, in that it targets antigenic material to an endosomal/lysosomal compartment co-localized with LAMP and MHC II, whereas MMR is found in peripheral endosomes lacking LAMP and MHC II (Mahnke, et al., J. Cell Biol. 151(3): 673-684, 2000).

DEC-205 also demonstrates a greatly enhanced presentation of endocytosed antigen to CD4+ T-cells, as compared to that by the MMR. This difference in trafficking and antigen delivery to MHC II between the two molecules is reported to result from the presence in the cytosolic tail of DEC-205, in addition to the coated pit uptake sequence, of an EDE triad that is lacking in the MMR. The distal portion of the cytosolic tail containing the EDE sequence was shown to be required for the targeting to the deeper endosome/lysosome compartment containing LAMP and MHC II, and EDE was not replaced by an AAA sequence. Mahnke et al., 2000, supra, have also shown that these cytoplasmic tail trafficking signals are sufficient to traffic and recycle a CD 16 chimera to the MHC II/LAMP site and to mediate a 100-fold increase in antigen presentation.

The sequence similarity between DEC-205 and gp200-MR6, particularly, in the cytoplasmic domain, makes this sequence a suitable trafficking sequence as well. Further, gp200-MR6 has been shown to have the further important property of IL-4 regulation. McKay et al., Eur J Immunol. 28(12): 4071-83, 1998, have shown that ligation of gp200-MR6 can mimic IL-4 and have an antiproliferative, promaturational influence within the immune system, causing up-regulation of costimulatory molecules on B lymphocytes.

However, DEC-205 fusions with LAMP do not traffic to the endosomal compartment but rather localize to the cell surface. Chimeric proteins which combine LAMP domains and at least one Allergen X, and endocytic receptor domains such as DEC-205 domains, however, are able to traffic to endosomal compartments, co-localizing with endogenous LAMP.

Therefore, in a preferred aspect, a chimeric Allergen X protein of the invention comprises a lumenal domain of a lysosomal membrane polypeptide (e.g., such as a LAMP lumenal domain) and the targeting domain of an endocytic receptor (e.g., such as DEC-205 or gp 200-MR6 polypeptide). Such constructs may not only show correct targeting but improved antigenicity as well. In a further aspect, both the targeting and trafficking domain of an endocytic receptor is provided along with at least one Allergen X. Chimeric Allergen X proteins may additionally, or alternatively, comprise the lumenal domain of an endocytic receptor. In still a further aspect, a chimeric protein may comprise a full-length endocytic receptor polypeptide along with at least one Allergen X.

In one aspect, the targeting domain of the endocytic receptor comprises the 31 amino acid cytoplasmic domain of a DEC polypeptide (see, e.g., Manhke, et al., 2000, supra). In another aspect, the targeting domain comprises residues 7-9 of the DEC-205 cytoplasmic tail. Preferably, the domain comprises a Tyr motif. More preferably, the targeting domain also comprises residues 18-27 of the DEC-205 cytoplasmic tail. In a further aspect, the targeting domain comprises an EDE domain. The sequence of DEC-205 is provided in Kato, et al., Immunogenetics 47(6): 442-50, 1998, while that of gp200-MR6 is provided in McKay, et al., 1998, supra, for example.

The chimeric Allergen X protein may additionally comprise a cytoplasmic targeting domain for targeting at least one Allergen X to an endosomal/lysosomal compartment or a lysosome-related organelle (e.g., such as a cytoplasmic LAMP domain) as well as one or more of the other domains described above (e.g., signal sequence, transmembrane sequence, etc.). As above, additional, or alternative sorting motifs, can include, but are not limited to, one or more of the M6P domain; a tyrosine motif domain; a di-leucine and tyrosine-based domain; a proline rich domain; and S-V-V domain (see, e.g., Blott and Grifitts, Nature 3: 122-131, 2002).

Vaccine Compositions

Although a number of antigens have been hypothesized to be capable of combination with LAMP to produce novel chimeric vaccines; in actuality when tested, these vaccines do not always work.

Thus, this invention provides a vaccine composition for eliciting an immune response in a mammal to Allergen X. The composition comprises a vaccine vector which comprises a chimeric DNA segment comprising a sequence encoding at least one Allergen X (SEQ ID NO:Y). Preferably, the DNA segment further includes a sequence encoding a lumenal domain of a lysosome associated membrane polypeptide (e.g., such as a LAMP polypeptide (e.g., SEQ ID NOs:2, 3, 4 or 5), homolog, ortholog, variant, or modified form thereof) or the trafficking domain of an endocytic receptor. Preferably, the lumenal domain or trafficking domain traffics the antigen to an endosomal/lysosomal compartment or to a lysosome-related organelle of a cell, where it binds to an MHC class II molecule or is processed for delivery to another compartment/organelle where it will subsequently bind to an MHC class II molecule. More preferably, Allergen X is processed within the compartment/organelle (or subsequent compartment to which it is delivered) to generate an Allergen X epitope which is presented on the surface of the cell and which is bound to the MHC class II molecule.

The vector also may encode one or more of a transmembrane domain, a cytoplasmic domain containing an endosomal/lysosomal targeting signal directing the protein to an endosomal/lysosomal compartment or lysosome-related organelle, and a dileucine domain, a Tyr motif, a proline rich domain, and/or S-V-V domain.

The domains may be provided in sequence or separated by nucleic acids encoding linker polypeptides or which encode other amino acid sequences with desired functionalities (e.g., protein stabilizing sequences, and the like). Generally, where linker sequences are included, these encode linker polypeptides which range from about one to about 50 amino acids. The minimal requirement of the vector is that it encode a chimeric Allergen X protein with the desired trafficking properties. Such properties can be readily tested using assays routine in the art.

For example, immunofluorescence microscopy can be used to confirm the trafficking of an Allergen X chimeric protein to an appropriate compartment/organelle. 35S methionine pulse-chase labeling analysis can be used to monitor the synthesis and degradation of the Allergen X chimeric protein to demonstrate that the rates of synthesis of the Allergen X chimeric protein vs. the endogenous Allergen X protein are essentially equal and/or that the processing of the Allergen X chimeric protein occurs properly.

In particular embodiments, the protein encoded by the chimeric DNA segment contains an intralumenal domain comprising at least one Allergen X epitope which is a peptide that complexes with major histocompatibility complex (MHC) class II molecules, an endosomal/lysosomal trafficking sequence as described above, and a cytoplasmic domain which contains an endosomal/lysosomal targeting sequence. Preferably, the targeting sequence comprises the tetrapeptide sequence Tyr-Xaa-Xaa-Xbb, wherein Xbb is a hydrophobic amino acid.

In another aspect, the protein encoded by the chimeric DNA segment comprises a full length lysosomal membrane associated polypeptide, such as a LAMP polypeptide, homolog, ortholog, variant or modified form thereof, which comprises sequences for targeting and trafficking both membrane-bound and non-membrane bound antigenic material to an endosomal/lysosomal compartment.

In preferred embodiments, the chimeric vaccines comprise (a) any one of the polynucleotides of SEQ ID NO:Z or SEQ ID NO:W as shown in Table 1; (b) a polynucleotide encoding a polypeptide encoded by any one of the polynucleotide identified as SEQ ID NO:Z or SEQ ID NO:W as shown in Table 1; (c) a polynucleotide that encodes a polypeptide comprising the amino acid sequence of SEQ ID NO: Y or SEQ ID NO:V as shown in Table 1; (d) a polynucleotide encoding a lumenal domain (such as, for example, SEQ ID NOs: 2 or 3 or as shown in SEQ ID Nos: 4 or 5), one or more of SEQ ID NO:Y as shown in Table 1, and a trafficking domain (such as SEQ ID NO:1, or as shown in SEQ ID Nos: 4 or 5); (e) a polynucleotide encoding a lumenal domain (such as, for example, SEQ ID NOs: 2 or 3 or as shown in SEQ ID Nos: 4 or 5) and one or more of SEQ ID NO:Y as shown in Table 1; (f) a polynucleotide encoding one or more of SEQ ID NO:Y as shown in Table 1 and a trafficking domain (such as SEQ ID NO:1, or as shown in SEQ ID Nos: 4 or 5) or (g) a polynucleotide at least about 60%, at least about 70%, at least about 75%, at least about 80%, at least about 85%, at least about 90%, at least about 95%, 96%, 97%, 98% or 99% identity to any one of the polynucleotides of (a)-(f).

Assembly of Sequences Encoding Allergen X Chimeric Proteins

Procedures for construction of chimeric proteins are well known in the art (see e.g., Williams, et al., J. Cell Biol. 111: 955, 1990). DNA sequences encoding the desired segments can be obtained from readily available recombinant DNA materials such as those available from the American Type Culture Collection, 12301 Parklawn Drive, Rockville, Md. 20852, U.S.A., or from DNA libraries that contain the desired DNA.

Such DNA segments minimally include: sequences encoding an antigenic domain from the Allergen X protein and a lumenal domain of a lysosomal membrane associated polypeptide for trafficking a polypeptide linked to the lumenal domain to an endosomal/lysosomal compartment or lysosome-related organelle and/or a trafficking domain of an endocytic receptor for trafficking to an endosomal/lysosomal compartment and or lysosome-related organelle. Additional DNA segments may include, but are not limited to, sequences encoding: cytoplasmic targeting sequences for targeting the chimeric protein to an endosomal/lysosomal compartment or lysosome-related organelle, transmembrane sequences, signal sequences, di-leucine sequences, Tyr motifs, proline rich domains, M6P sequences, Ser-Val-Val sequences and as well as cloning sequences and the like.

The DNA segments corresponding to the desired domain sequences are then assembled with appropriate control and signal sequences using routine procedures of recombinant DNA methodology. See, e.g., as described in U.S. Pat. No. 4,593,002, and Langford, et al., Molec. Cell. Biol. 6: 3191, 1986.

A DNA sequence encoding a protein or polypeptide can be synthesized chemically or isolated by one of several approaches. The DNA sequence to be synthesized can be designed with the appropriate codons for the desired amino acid sequence. In general, one will select preferred codons for the intended host in which the sequence will be used for expression. The complete sequence may be assembled from overlapping oligonucleotides prepared by standard methods and assembled into a complete coding sequence. See, e.g., Edge, Nature 292: 756, 1981; Nambair, et al. Science 223: 1299, 1984; Jay, et al., J. Biol. Chem. 259: 6311, 1984.

In one aspect, one or more of the nucleic acids encoding the domain sequences of the chimeric protein are isolated individually using the polymerase chain reaction (M. A. Innis, et al., In PCR Protocols: A Guide to Methods and Applications, Academic Press, 1990). The domains are preferably isolated from publicly available clones known to contain them, but they may also be isolated from genomic DNA or cDNA libraries. Preferably, isolated fragments are bordered by compatible restriction endonuclease sites which allow a chimeric DNA encoding the immunogenic protein sequence to be constructed. This technique is well known to those of skill in the art. Domain sequences may be fused directly to each other (e.g., with no intervening sequences), or inserted into one another (e.g., where domain sequences are discontinuous), or may be separated by intervening sequences (e.g., such as linker sequences).

The basic strategies for preparing oligonucleotide primers, probes and DNA libraries, as well as their screening by nucleic acid hybridization, are well known to those of ordinary skill in the art. See, e.g., Sambrook, et al., 1989, supra; Perbal, 1984, supra. The construction of an appropriate genomic DNA or cDNA library is within the skill of the art. See, e.g., Perbal, 1984, supra. Alternatively, suitable DNA libraries or publicly available clones are available from suppliers of biological research materials, such as Clonetech and Stratagene, as well as from public depositories such as the American Type Culture Collection.

Selection may be accomplished by expressing sequences from an expression library of DNA and detecting the expressed peptides immunologically. Clones which express peptides that bind to MHC II molecules and to the desired antibodies/T cell receptors are selected. These selection procedures are well known to those of ordinary skill in the art (see, e.g., Sambrook, et al., 1989, supra).

Once a clone containing the coding sequence for the desired polypeptide sequence has been prepared or isolated, the sequence can be cloned into any suitable vector, preferably comprising an origin of replication for maintaining the sequence in a host cell.

In preferred embodiments, the chimeric proteins are encoded by (a) any one of the polynucleotides of SEQ ID NO:Z or SEQ ID NO:W as shown in Table 1; (b) a polynucleotide encoding a polypeptide encoded by any one of the polynucleotides of SEQ ID NO:Z or SEQ ID NO:W as shown in Table 1; (c) a polynucleotide that encodes a polypeptide comprising the amino acid sequence of SEQ ID NO: Y or SEQ ID NO:V as shown in Table 1; (d) a polynucleotide encoding a lumenal domain (such as, for example, SEQ ID NOs: 2 or 3 or as shown in SEQ ID Nos: 4 or 5), one or more of SEQ ID NO:Y as shown in Table 1, and a trafficking domain (such as SEQ ID NO:1 or as shown in SEQ ID Nos: 4 or 5); (e) a polynucleotide encoding a lumenal domain (such as, for example, SEQ ID NOs:2 or 3 or as shown in SEQ ID Nos: 4 or 5) and one or more of SEQ ID NO:Y as shown in Table 1; (f) a polynucleotide encoding one or more of SEQ ID NO:Y as shown in Table 1 and a trafficking domain (such as SEQ ID NO:1, or as shown in SEQ ID Nos: 4 or 5); or (g) polynucleotides with at least about 60%, at least about 70%, at least about 75%, at least about 80%, at least about 85%, at least about 90%, at least about 95%, 96%, 97%, 98% or 99% identity to any one of the polynucleotides of (a)-(f). Polypeptides encoded by these polynucleotides are additional preferred embodiments.

Nucleic Acid Delivery Vehicles

In one aspect, a nucleic acid vector encoding a chimeric vaccine is introduced into a cell. The cell may be a host cell for replicating the nucleic acid or for expressing the chimeric vaccine. Preferably, the host cell for expressing the chimeric vaccine is an antigen presenting cell (described further below).

The nucleic acid vector minimally comprises a polynucleotide sequence for insertion into a target cell and an expression control sequence operably linked thereto to control expression of the polynucleotide sequence (e.g., transcription and/or translation) in the cell. Examples include plasmids, phages, autonomously replicating sequences (ARS), centromeres, and other sequences which are able to replicate or be replicated in vitro or in a host cell (e.g., such as a bacterial, yeast, or insect cell) and/or target cell (e.g., such as a mammalian cell, preferably an antigen presenting cell) and/or to convey the sequences encoding the chimeric vaccine to a desired location within the target cell.

In preferred embodiments, the vectors/vehicles described herein comprise (a) any one of the polynucleotides of SEQ ID NO:Z or SEQ ID NO:W as shown in Table 1; (b) a polynucleotide encoding a polypeptide encoded by any one of the polynucleotides of SEQ ID NO:Z or SEQ ID NO:W as shown in Table 1; (c) a polynucleotide that encodes a polypeptide comprising the amino acid sequence of SEQ ID NO: Y or SEQ ID NO:V as shown in Table 1; (d) a polynucleotide encoding a lumenal domain (such as, for example, SEQ ID NOs:2 or 3 or as shown in SEQ ID Nos: 4 or 5), one or more of SEQ ID NO:Y as shown in Table 1, and a trafficking domain (such as SEQ ID NO:1, or as shown in SEQ ID Nos: 4 or 5); (e) a polynucleotide encoding a lumenal domain (such as, for example, SEQ ID NOs:2 or 3 or as shown in SEQ ID Nos: 4 or 5) and one or more of SEQ ID NO:Y as shown in Table 1; (f) a polynucleotide encoding one or more of SEQ ID NO:Y as shown in Table 1 and a trafficking domain (such as SEQ ID NO:1, or as shown in SEQ ID Nos: 4 or 5); or (g) polynucleotides with at least about 60%, at least about 70%, at least about 75%, at least about 80%, at least about 85%, at least about 90%, at least about 95%, 96%, 97%, 98% or 99% identity to any one of the polynucleotides of (a)-(f).

Recombinant expression vectors may be derived from micro-organisms which readily infect animals, including man, horses, cows, pigs, llamas, giraffes, dogs, cats or chickens. Preferred vectors include those which have already been used as live vaccines, such as vaccinia. These recombinants can be directly inoculated into a host, conferring immunity not only to the microbial vector, but also to express foreign antigens. Preferred vectors contemplated herein as live recombinant vaccines include RNA viruses, adenovirus, herpesviruses, poliovirus, and vaccinia and other pox viruses, as taught in Flexner, Adv. Pharmacol. 21: 51, 1990, for example.

Expression control sequences include, but are not limited to, promoter sequences to bind RNA polymerase, enhancer sequences or negative regulatory elements to bind to transcriptional activators and repressors, respectively, and/or translation initiation sequences for ribosome binding. For example, a bacterial expression vector can include a promoter such as the lac promoter and for transcription initiation, the Shine-Dalgarno sequence and the start codon AUG (Sambrook, et al., 1989, supra). Similarly, a eukaryotic expression vector preferably includes a heterologous, homologous, or chimeric promoter for RNA polymerase II, a downstream polyadenylation signal, the start codon AUG, and a termination codon for detachment of a ribosome.

Expression control sequences may be obtained from naturally occurring genes or may be designed. Designed expression control sequences include, but are not limited to, mutated and/or chimeric expression control sequences or synthetic or cloned consensus sequences. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.).

In order to optimize expression and/or transcription, it may be necessary to remove, add or alter 5' and/or 3' untranslated portions of the vectors to eliminate extra, or alternative translation initiation codons or other sequences that may interfere with, or reduce, expression, either at the level of transcription or translation. Alternatively, consensus ribosome binding sites can be inserted immediately 5' of the start codon to enhance expression. A wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma, adenovirus, herpes virus and other sequences known to control the expression of genes of mammalian cells, and various combinations thereof.

In one aspect, the nucleic acid delivery vector comprises an origin of replication for replicating the vector. Preferably, the origin functions in at least one type of host cell which can be used to generate sufficient numbers of copies of the sequence for use in delivery to a target cell. Suitable origins therefore include, but are not limited to, those which function in bacterial cells (e.g., such as *Escherichia* sp., *Salmonella* sp., *Proteus* sp., *Clostridium* sp., *Klebsiella* sp., *Bacillus* sp., *Streptomyces* sp., and *Pseudomonas* sp.), yeast (e.g., such as *Saccharamyces* sp. or *Pichia* sp.), insect cells, and mammalian cells. In one preferred aspect, an origin of replication is provided which functions in the target cell into which the nucleic acid delivery vehicle is introduced (e.g., a mammalian cell, such as a human cell). In another aspect, at least two origins of replication are provided, one that functions in a host cell and one that functions in a target cell.

The nucleic acid delivery vector may alternatively, or additionally, comprise sequences to facilitate integration of at least a portion of the nucleic acid delivery vector into a target cell chromosome. For example, the nucleic acid delivery vector may comprise regions of homology to target cell chromosomal DNA. In one aspect, the delivery vector comprises two or more recombination sites which flank a nucleic acid sequence encoding the chimeric vaccine.

The vector may additionally comprise a detectable and/or selectable marker to verify that the vector has been successfully introduced in a target cell and/or can be expressed by the target cell. These markers can encode an activity, such as, but not limited to, production of RNA, peptide, or protein, or can provide a binding site for RNA, peptides, proteins, inorganic and organic compounds or compositions and the like.

Examples of detectable/selectable markers genes include, but are not limited to: DNA segments that encode products which provide resistance against otherwise toxic compounds (e.g., antibiotics); DNA segments that encode products which are otherwise lacking in the recipient cell (e.g., tRNA genes, auxotrophic markers); DNA segments that encode products which suppress the activity of a gene product; DNA segments that encode products which can be readily identified (e.g., phenotypic markers such as beta-galactosidase, a fluorescent protein (GFP, CFP, YFG, BFP, RFP, EGFP, EYFP, EBFP, dsRed, mutated, modified, or enhanced forms thereof, and the like), and cell surface proteins); DNA segments that bind products which are otherwise detrimental to cell survival and/or function; DNA segments that otherwise inhibit the activity of other nucleic acid segments (e.g., antisense oligonucleotides); DNA segments that bind products that modify a substrate (e.g., restriction endonucleases); DNA segments that can be used to isolate or identify a desired molecule (e.g., segments encoding specific protein binding sites); primer sequences; DNA segments, which when absent, directly or indirectly confer resistance or sensitivity to particular compounds; and/or DNA segments that encode products which are toxic in recipient cells.

The marker gene can be used as a marker for conformation of successful gene transfer and/or to isolate cells expressing transferred genes and/or to recover transferred genes from a cell. For example, in one aspect, the marker gene is used to isolate and purify antigen presenting cells expressing the chimeric vaccines.

As discussed above, homologs, variants, and modified forms of any of the domain sequences can be used so long as they retain the ability to function with their respective domain function. For example, a modified lumenal sequence must retain the ability to traffic both membrane and non-membrane antigenic materials to an endosomal compartment with at least about 50%, at least about 60%, at least 70%, at least about 80%, at least about 90%, or at least about 100% efficacy as compared to the original domain sequence, i.e., an efficacy that results in sufficient antigen presentation by a cell comprising the chimeric sequence for it to mount an immune response. In one aspect, sequences containing a suitable trafficking signal may be identified by constructing a chimeric DNA containing the well-characterized antigenic domain of ovalbumin, a transmembrane domain, and the cytoplasmic domain of a protein containing a putative lysosomal/endosomal targeting signal. Efficiency of targeting can be measured by determining the ability of antigen presenting cells, expressing the chimeric protein, to stimulate HA epitope-specific, MHC class II restricted T-cells (see, e.g., Example 5 of U.S. Pat. No. 5,633,234).

Substantially similar genes may be provided, e.g., genes with greater than about 50%, greater than about 60%, greater than about 70%, greater than 80%, greater than about 90%, and preferably, greater than about 95% identity to a known gene. Percent identity can be determined using software programs known in the art, for example those described in Current Protocols In Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Description=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: www.ncbi.nlm.nih.gov/cgi-bin/BLAST.

"Conservatively modified variants" of genes also can be provided. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed-base and/or deoxyinosine residues (Batzer, et al., 1991, Nucleic Acid Res. 19: 5081; Ohtsuka, et al., 1985, J. Biol. Chem. 260: 2605-2608; Rossolini et al., 1994, Mol. Cell. Probes 8: 91-98).

Substantially similar domain sequences may initially be identified by selecting a sequence which specifically hybridizes to a domain sequence of interest under stringent hybridization conditions. Examples of stringent hybridization conditions include: incubation temperatures of about 25 degrees C. to about 37 degrees C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40 degrees C. to about 50 degrees C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55 degrees C. to about 68 degrees C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed. Similarity can be verified by sequencing, but preferably, is also or alternatively, verified by function (e.g., ability to traffic to an endosomal compartment, and the like), using assays suitable for the particular domain in question.

Performing assays to determine the suitability of homologous, variant, or modified domain sequences is merely a matter of screening for sequences which express the appropriate activity. Such screening is routine in the art.

The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides, polysaccharides, lipopolysaccharides, viral formulations (e.g., including viruses, viral particles, artificial viral envelopes and the like), cell delivery vehicles, and the like.

Lipid-Based Formulations

Delivery vehicles designed to facilitate intracellular delivery of biologically active molecules must interact with both non-polar and polar environments (in or on, for example, the plasma membrane, tissue fluids, compartments within the cell, and the like). Therefore, preferably, delivery vehicles are designed to contain both polar and non-polar domains or a translocating sequence for translocating a nucleic acid into a cell.

Compounds having polar and non-polar domains are termed amphiphiles. Cationic amphiphiles have polar groups that are capable of being positively charged at, or around, physiological pH for interacting with negatively charged polynucleotides such as DNA.

The nucleic acid vectors described above can be provided in formulations comprising lipid monolayers or bilayers to facilitate transfer of the vectors across a cell membrane. Liposomes or any form of lipid membrane, such as planar lipid membranes or the cell membrane of an intact cell, e.g., a red blood cell, can be used. Liposomal formulations can be administered by any means, including administration intravenously or orally.

Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. In one aspect, the liposome comprises a targeting molecule for targeting a liposome:nucleic acid vector complex to a particular cell type. In a particularly preferred aspect, a targeting molecule comprises a binding partner (e.g., a ligand or receptor) for a biomolecule (e.g., a receptor or ligand) on the surface of a blood vessel or a cell found in a target tissue.

Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Liposomes with prolonged circulation half-lives are typically desirable for therapeutic and diagnostic uses. For a general discussion of pharmacokinetics, see, e.g., Remington's, Chapters 37-39, Lee, et al., In Pharmacokinetic Analysis: A Practical Approach (Technomic Publishing AG, Basel, Switzerland 1996).

Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028).

Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The nucleic acid delivery vehicles of the invention can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powderlike form. This film is covered with an aqueous solution of the peptide or polypeptide complex and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium preferably comprises the nucleic acid at a concentration which is desired in the interior volume of the liposomes in the final liposome suspension.

Following liposome preparation, the liposomes can be sized to achieve a desired size range and relatively narrow distribution of liposome sizes. One preferred size range is about 0.2 to 0.4 microns, which allows the liposome suspension to be sterilized by filtration through a conventional filter, typically a 0.22 micron filter. Filter sterilization can be carried out on a high throughput basis if the liposomes have been sized down to about 0.2 to 0.4 microns. Several techniques are available for sizing liposome to a desired size (see, e.g., U.S. Pat. No. 4,737,323).

Suitable lipids include, but are not limited to, DOTMA (Felgner, et al., 1987, Proc. Natl. Acad. Sci. USA 84: 7413-7417), DOGS or Transfectain.™. (Behr, et al., 1989, Proc. Natl. Acad. Sci. USA 86: 6982-6986), DNERIE or DORIE (Felgner, et al., Methods 5: 67-75), DC-CHOL (Gao and Huang, 1991, BBRC 179: 280-285), DOTAPTM (McLachlan, et al., 1995, Gene Therapy 2: 674-622), Lipo-fectamine.®. and glycerolipid compounds (see, e.g., EP901463 and WO98/37916).

Other molecules suitable for complexing with nucleic acid delivery vectors include cationic molecules, such as, polyamidoamine (Haensler and Szoka, 1993, Bioconjugate Chem. 4: 372-379), dendritic polysine (WO 95/24221), polyethylene irinine or polypropylene h-nine (WO 96/02655), polylysine (U.S. Pat. No. 5,595,897; FR 2 719 316), chitosan (U.S. Pat. No. 5,744,166), DNA-gelatin coarcervates (see, e.g., U.S. Pat. Nos. 6,207,195; 6,025,337; 5,972,707) or DEAE dextran (Lopata, et al., 1984, Nucleic Acid Res. 12: 5707-5717).

Viral-Based Gene Delivery Vehicles

In one aspect, the nucleic acid delivery vehicle comprises a virus or viral particle. In this aspect, preferably, the nucleic acid vector comprises a viral vector. Viral vectors, such as retroviruses, adenoviruses, adeno-associated viruses and herpes viruses, are often made up of two components, a modified viral genome and a coat structure surrounding it (see, e.g., Smith et al., 1995, Ann. Rev. Microbiol. 49: 807-838), although sometimes viral vectors are introduced in naked form or coated with proteins other than viral proteins. Most current vectors have coat structures similar to a wild-type virus. This structure packages and protects the viral nucleic acid and provides the means to bind and enter target cells.

Preferably, viral vectors are modified from wild-type viral genomes to disable the growth of the virus in a target cell while enabling the virus to grow in a host cell (e.g., such as a packaging or helper cell) used to prepare infectious particles. Vector nucleic acids generally essential cis-acting viral sequences for replication and packaging in a helper line and expression control sequences for regulating the expression of a polynucleotide being delivered to a target cell. Other viral functions are expressed in trans in specific packaging or helper cell lines as are known in the art.

Preferred vectors are viral vectors derived from a virus selected from the group consisting of herpes viruses, cytomegaloviruses, foamy viruses, lentiviruses, Semliki forrest virus, AAV (adeno-associated virus), poxviruses, adenovirases and retroviruses. Such viral vectors are well known in the art.

In one preferred aspect, a viral vector used is an adenoviral vector. The adenoviral genome consists of a linear double-stranded DNA molecule of approximately 36 kb carrying more than about thirty genes necessary to complete the viral replication cycle. The early genes are divided into 4 regions (E1 to E4) that are essential for viral replication with the exception of the E3 region, which is believed to modulate the anti-viral host immune response. The E1 region (EIA and EIB) encodes proteins responsible for the regulation of transcription of the viral genome. Expression of the E2 region genes (E2A and E2B) leads to the synthesis of the polypeptides needed for viral replication. The proteins encoded by the E3 region prevent cytolysis by cytotoxic T cells and tumor necrosis factor (Wold and Gooding, 1991, Virology 184: 1-8). The proteins encoded by the E4 region are involved in DNA replication, late gene expression and splicing and host cell shut off (Halbert, et al., 1985, J. Virol. 56: 250-257). The late genes generally encode structural proteins contributing to the viral capsid. In addition, the adenoviral genome carries at cis-acting 5' and 3' ITRs (Inverted Terminal Repeat) and packaging sequences essential for DNA replication. The ITRs harbor origins of DNA replication while the encapsidation region is required for the packaging of adenoviral DNA into infectious particles.

Adenoviral vectors can be engineered to be conditionally replicative (CRAd vectors) in order to replicate selectively in specific cells (e.g., such as proliferative cells) as described in Heise and Kim (2000, J. Clin. Invest. 105: 847-851). In another aspect, an adenoviral vector is replication-defective for the E1 function (e.g., by total or partial deletion or mutagenesis of E1). The adenoviral backbone of the vector may comprise additional modifications (deletions, insertions or mutations in one or more viral genes). An example of an E2 modification is illustrated by the thermosensitive mutation localized on the DBP (DNA Binding Protein) encoding gene (Ensinger et al., 1972, J. Virol. 10: 328-339). The adenoviral sequence may also be deleted of all or part of the E4 region (see, e.g., EP 974 668; Christ, et al., 2000, Human Gene Ther. 11: 415-427; Lusky, et al., 1999, J. Virol. 73: 8308-8319). Additional deletions within the non-essential E3 region may allow the size of the polynucleotide being delivered to be increased (Yeh, et al., 1997, FASEB Journal 11: 615 623). However, it may be advantageous to retain all or part of the E3 sequences coding for polypeptides (e.g., such as gp19k) allowing the virus to escape the immune system (Gooding, et al., 1990, Critical Review of Immunology 10: 53-71) or inflammatory reactions (EP 00440267.3).

Second generation vectors retaining the ITRs and packaging sequences and comprising substantial genetic modifications to abolish the residual synthesis of the viral antigens also may be used in order to improve long-term expression of the expressed gene in the transduced cells (see, e.g., WO 94/28152; Lusky, et al., 1998, J. Virol 72: 2022-2032).

The polynucleotide being introduced into the cell may be inserted in any location of the viral genome, with the exception of the cis-acting sequences. Preferably, it is inserted in replacement of a deleted region (E1, E3 and/or E4), preferably, within a deleted E1 region.

Adenoviruses can be derived from any human or animal source, in particular canine (e.g. CAV-1 or CAV-2 Genbank ref. CAVIGENOM and CAV77082, respectively), avian (Genbank ref. AAVEDSDNA), bovine (such as BAV3; Reddy, et al., 1998, J. Virol. 72: 1394 1402), murine (Genbank ref. ADRMUSMAV1), ovine, feline, porcine or simian sources or alternatively, may be a hybrid virus. Any serotype can be employed. However, the human adenoviruses of the C sub-group are preferred, especially adenoviruses 2 (Ad2) and 5 (Ad5). Such viruses are available, for example, from the ATCC.

Adenoviral particles or empty adenoviral capsids also can be used to transfer nucleic acid delivery vectors by a virus-mediated cointernalization process as described in U.S. Pat. No. 5,928,944. This process can be accomplished in the presence of cationic agent(s) such as polycarbenes or lipid vesicles comprising one or more lipid layers.

Adenoviral particles may be prepared and propagated according to any conventional technique in the field of the art (e.g., WO 96/17070) using a complementation cell line or a helper virus, which supplies in trans the missing viral genes necessary for viral replication. The cell lines 293 (Graham et al., 1977, J. Gen. Virol. 36: 59-72) and PERC6 (Fallaux et al., 1998, Human Gene Therapy 9: 1909-1917) are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and WO 97/04119). The adenoviral particles can be recovered from the culture supernatant but also from the cells after lysis and optionally further purified according to standard techniques (e.g., chromatography, ultracentrifugation, as described in WO 96/27677, WO 98/00524 WO 98/26048 and WO 00/50573).

Cell-type specific targeting may be achieved with vectors derived from adenoviruses having a broad host range by the modification of viral surface proteins. For example, the specificity of infection of adenoviruses is determined by the attachment to cellular receptors present at the surface of permissive cells. In this regard, the fiber and penton present at the surface of the adenoviral capsid play a critical role in cellular attachment (Defer, et al., 1990, J. Virol. 64: 3661-3673). Thus, cell targeting of adenoviruses can be carried out by genetic modification of the viral gene encoding fiber and/or penton, to generate modified fiber and/or penton capable of specific interaction with unique cell surface receptors. Examples of such modifications are described in Wickarn, et al., 1997, J. Virol. 71: 8221-8229; Arriberg, et al., 1997, Virol. Chem 268: 6866-6869; Roux, et al., 1989, Proc. Natl. Acad. Sci. USA 86: 9079-9083; Miller and Vile, 1995, FASEB J. 9: 190-199; WO 93/09221, and in WO 95/28494.

In a particularly preferred aspect, adeno-associated viral sequences are used as vectors. Vectors derived from the human parvovirus AAV-2 (adeno-associated virus type 2) are among the most promising gene delivery vehicles currently being developed. Several of the features of this system for packaging a single-stranded DNA suggest it as a possible alternative to naked DNA for delivery of genetic vaccines. A primary attractive feature, in contrast to other viral vectors such as vaccinia or adenovirus, is that AAV vectors do not express any viral genes. The only viral DNA sequences included in the vaccine construct are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{11}$ particles or copies of DNA in contrast to naked DNA doses of 50 ug or about $10^{15}$ copies.

In one aspect, AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ads. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay). AAV titer may be determined by quantitative PCR with virus DNA samples prepared after digestion with proteinase K. Preferably, vector titers produced by such a method are approximately $5 \times 10^{12}$ to $1 \times 10^{13}$ DNase resistant particles per ml.

In other aspects, retroviral vectors are used. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (WO 95/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323). Preferably, the polynucleotide of interest is inserted downstream of the encapsidation sequence, preferably in opposite direction relative to the retroviral genome. Cell specific targeting may be achieved by the conjugation of antibodies or antibody fragments to the retroviral envelope protein as is known in the art.

Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. In the context of the invention, it is advantageous to use a packaging cell line, such as the PA317 cells (ATCC CRL 9078) or 293EI6 (WO97/35996) containing an amphotropic envelope protein, to allow infection of human and other species' target cells. The retroviral particles are preferably recovered from the culture supernatant and may optionally be further purified according to standard techniques (e.g. chromatography, ultracentrifugation).

Other suitable viruses include poxviruses. The genome of several members of poxyiridae has been mapped and sequenced. A poxyiral vector may be obtained from any member of the poxyiridae, in particular canarypox, fowlpox and vaccinia virus. Suitable vaccinia viruses include, but are not limited to, the Copenhagen strain (Goebel, et al., 1990, Virol. 179: 247-266; Johnson, et al., 1993, Virol. 196: 381-401), the Wyeth strain and the modified Ankara (MVA) strain (Antoine, et al., 1998, Virol. 244: 365-396). The general conditions for constructing a vaccinia virus vector are known in the art (see, e.g., EP 83 286 and EP 206 920; Mayr et al., 1975, Infection 3: 6-14; Sutter and Moss, 1992, Proc. Natl. Acad. Sci. USA 89: 10847-10851). Preferably, the polynucleotide of interest is inserted within a nonessential locus such as the nOD7coding intergenic regions or any gene for which inactivation or deletion does not significantly impair viral growth and replication.

Poxyiral particles are prepared as described in the art (Piccini, et al., 1987, Methods of Enzymology 153: 545-563; U.S. Pat. Nos. 4,769,330; 4,772,848; 4,603,112; 5,100,587 and 5,179,993). Generally, a donor plasmid is constructed, amplified by growth in *E. coli* and isolated by conventional procedures. Then, it is introduced into a suitable cell culture (e.g. chicken embryo fibroblasts) together with a poxvirus genome, to produce, by homologous recombination, poxyiral particles. These can be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

The use of vaccinia as a live virus vaccine in the global campaign to eradicate smallpox made vaccinia an obvious choice for development as a live recombinant vaccine vector. Live recombinant vaccinia viruses expressing close to 100 different foreign proteins have been reported, and a number of these are effective experimental vaccines (reviewed by Moss and Flexner, 1987). Vaccinia is particularly versatile as an expression vector because of its large genomic size, capability of accepting at least 25,000 base pairs of foreign DNA, and its ability to infect most eukaryotic cell types, including insect cells (ibid.). Unlike other DNA viruses, poxviruses replicate exclusively in the cytoplasm of infected cells, reducing the possibility of genetic exchange of recombinant viral DNA with the host chromosome. Recombinant vaccinia vectors have been shown to properly process and express proteins from a variety of sources including man, other mammals, parasites, RNA and DNA viruses, bacteria and bacteriophage.

The virus is capable of infecting most mammals, making it a useful vector for studying a broad range of human and animal diseases. The expression of DNA encoding a foreign protein is controlled by host virus regulatory elements, including upstream promoter sequences and, where necessary, RNA processing signals. Insertion of foreign DNA into nonessential regions of the vaccinia virus genome has been carried out by homologous recombination (Panicali, et al., Proc. Nat'l. Acad. Sci, USA, 79: 4927, 1982; Mackett, et al., Proc. Nat'l. Acad. Sci. USA, 79: 7415, 1982).

Expression of foreign genes by the DNA may occur because of transcriptional regulatory elements at or near the site of insertion or by more precise genetic engineering. Plasmid vectors that greatly facilitate insertion and expression of foreign genes have been constructed (Mackett, et al., J. Virol, 49: 857, 1982). These vectors contain an expression site, composed of a vaccinia transcriptional promoter and one or more unique restriction endonuclease sites for insertion of the foreign coding sequence flanked by DNA from a nonessential region of the vaccinia genome. The choice of promoter determines both the time (e.g., early or late) and level of expression, whereas the flanking DNA sequence determines the site of homologous recombination.

Only about one in a thousand virus particles produced by this procedure is a recombinant. Although recombinant virus plaques can be identified by DNA hybridization, efficient selection procedures have been developed. By using segments of nonessential vaccinia virus thymidine kinase (TK) gene as flanking sequences, the foreign gene recombines into the TK locus and by insertion inactivates the TK gene. Selection of TK virus is achieved by carrying out the virus plaque assay in TK cells in the presents of 5-bromodeoxyuridine. Phosphorylation of the nucleoside analogue and consequent lethal incorporation into viral DNA occurs only in cells infected with TK+ parental virus. Depending on the efficiency of the transfection and recombination, up to 80 of the plaques are desired recombinants, and the rest are spontaneous TK mutants.

Plasmid vectors that contain the *E. coli* beta-galactosidase gene, as well as an expression site for a second gene, permit an alternative method of distinguishing recombinant from parental virus (Chakrabarti, et al., Mol. Cell. Biol., 5: 3403, 1985). Plaques formed by such recombinants can be positively identified by the blue color that forms upon addition of an appropriate indicator. By combining both TK selection and beta-galactosidase expression, recombinant virus is readily and quickly isolated. The recombinants are then amplified by propagation in suitable cell lines and expression of the inserted gene is checked by appropriate enzymological, immunological or physical procedures.

An upper limit to the amount of genetic information that can be added to the vaccinia virus genome is not yet known. However, the addition of nearly 25,000 base pairs of foreign DNA had no apparent deleterious effect on virus yield (Smith, et al., Gene, 25:21, 1983). Were it necessary, large segments of the vaccinia virus genome could be deleted to provide additional capacity (Moss, et al., J. Virol. 40: 387, 1981).

Viral capsid molecules may include targeting moieties to facilitate targeting and/or entry into cells. Suitable targeting molecules, include, but are not limited to: chemical conjugates, lipids, glycolipids, hormones, sugars, polymers (e.g. PEG, polylysine, PEI and the like), peptides, polypeptides (see, e.g., WO 94/40958), vitamins, antigens, lectins, antibodies and fragments thereof. Preferably, such targeting molecules recognize and bind to cell-specific markers, tissue-specific markers, cellular receptors, viral antigens, antigenic epitopes or tumor-associated markers.

A composition based on viral particles may be formulated in the form of doses of between 10 and $10^{14}$ i.u. (infectious units), and preferably, between 10 and $10^{11}$ i.u. The titer may be determined by conventional techniques. The doses of nucleic acid delivery vector are preferably comprised between 0.01 and 10 mg/kg, more especially between 0.1 and 2 mg/kg.

Cell-Based Delivery Vehicles

The nucleic acid vectors according to the invention can be delivered to target cells by means of other cells ("delivery cells") which comprise the vectors. Methods for introducing vectors into cells are known in the art and include microinjection of DNA into the nucleus of a cell (Capechi, et al., 1980, Cell 22: 479-488); transfection with $CaPo_4$ (Chen and Okayama, 1987, Mol. Cell Biol. 7: 2745 2752), electroporation (Chu, et al., 1987, Nucleic Acid Res. 15: 1311-1326); lipofection/liposome fusion (Feigner, et al., 1987, Proc. Natl. Acad. Sci. USA 84: 7413-7417) and particle bombardment (Yang, et al., 1990, Proc. Natl. Acad. Sci. USA 87: 9568-9572). Suitable cells include autologous and non-autologous cells, and may include xenogenic cells. Delivery cells may be induced to deliver their contents to the target cells by inducing their death (e.g., by providing inducible suicide genes to these cells).

Accessory Molecules

The compositions according to the invention may comprise one or more accessory molecules for facilitating the introduction of a nucleic acid delivery vector into a cell and/or for enhancing a particular therapeutic effect.

In addition, the composition according to the present invention may include one or more stabilizing substance(s), such as lipids, nuclease inhibitors, hydrogels, hyaluronidase (WO 98/53853), collagenase, polymers, chelating agents (EP 890362), in order to inhibit degradation within the animal/human body and/or improve transfection/infection of the vector into a target cell. Such substances may be used alone or in combination (e.g., cationic and neutral lipids).

It has also been shown that adenovirus proteins are capable of destabilizing endosomes and enhancing the uptake of DNA into cells. The mixture of adenoviruses to solutions containing a lipid-complexed DNA vector or the binding of DNA to polylysine covalently attached to adenoviruses using protein cross-linking agents may substantially improve the uptake and expression of a nucleic acid delivery vector (see, e.g., Curiel, et al., 1992, Am. I. Respir. Cell. Mol. Biol. 6: 247-252).

Host Cells

Nucleic acid vectors according to the invention can be expressed in a variety of host cell, including, but not limited to: prokaryotic cells (e.g., *E. coli, Staphylococcus* sp., *Bacillus* sp.); yeast cells (e.g., *Saccharomyces* sp.); insect cells; nematode cells; plant cells; amphibian cells (e.g., *Xenopus*); avian cells; and mammalian cells (e.g., human cells, mouse cells, mammalian cell lines, primary cultured mammalian cells, such as from dissected tissues).

The molecules can be expressed in host cells isolated from an organism, host cells which are part of an organism, or host cells which are introduced into an organism. In one aspect, fusion molecules are expressed in host cells in vitro, e.g., in culture. In another aspect, fusion molecules are expressed in a transgenic organism (e.g., a transgenic mouse, rat, rabbit, pig, primate, etc.) that comprises somatic and/or germline cells comprising nucleic acids encoding the fusion molecules. Methods for constructing transgenic animals are well known in the art and are routine.

Nucleic acid vectors also can be introduced into cells in vitro, and the cells (e.g., such as stem cells, hematopoietic cells, lymphocytes, and the like) can be introduced into the host organism. The cells may be heterologous or autologous with respect to the host organism. For example, cells can be obtained from the host organism, nucleic acid vectors introduced into the cells in vitro, and then reintroduced into the host organism.

Antigen Presenting Cells

In a preferred aspect of the invention, a nucleic acid delivery vehicle such as described above is introduced into a natural or engineered antigen presenting cell.

The term "antigen presenting cell" (APC) as used herein includes any cell which presents on its surface an antigen in association with a major histocompatibility complex molecule, preferably a class II molecule, or portion thereof. Examples of suitable APCs are discussed in detail below and include, but are not limited to, whole cells such as macrophages, dendritic cells, B cells, hybrid APCs, and foster antigen presenting cells. Methods of making hybrid APCs are described and known in the art.

Dendritic cells (DCs) are potent antigen-presenting cells. It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC" defined above) class I or II protein on the surface of APCs. This interaction is necessary, but not sufficient, for T cell activation to occur. In fact, without the second type of signals, the first type of signals can result in T cell anergy. The second type of signals, called co-stimulatory signals, is neither antigen-specific nor MHC-restricted, and can lead to a full proliferation response of T cells and induction of T cell effector functions in the presence of the first type of signals.

Several molecules have been shown to enhance co-stimulatory activity. These include, but are not limited to, heat stable antigen (HSA), chondroitin sulfate-modified MHC invariant chain (Ii-CS), intracellular adhesion molecule I (ICAM-1), and B7 co-stimulatory molecule on the surface of APCs and its counter-receptor CD28 or CTLA-4 on T cells.

Other important co-stimulatory molecules are CD40, CD54, CD80, CD86. As used herein, the term "co-stimulatory molecule" encompasses any single molecule or combination of molecules which, when acting together with a peptide/MHC complex bound by a TCR on the surface of a T cell, provides a co-stimulatory effect which achieves activation of the T cell that binds the peptide. The term thus encompasses B7, or other co-stimulatory molecule(s) on an APC, fragments thereof (alone, complexed with another molecule(s), or as part of a fusion protein) which, together with peptide/MHC complex, binds to a cognate ligand and results in activation of the T cell when the TCR on the surface of the T cell specifically binds the peptide. Co-stimulatory molecules are commercially available from a variety of sources, including, for example, Beckman Coulter.

In one aspect of the invention, the method described in Romani et al., J. Immunol. Methods 196: 135-151, 1996, and Bender et al, J. Immunol. Methods 196: 121-135, 1996, are used to generate both immature and mature dendritic cells from the peripheral blood mononuclear cells (PBMCs) of a mammal, such as a murine, simian or human. Briefly, isolated PBMCs are pre-treated to deplete T- and B-cells by means of an immunomagnetic technique. Lymphocyte-depleted PBMC are then cultured for in RPMI medium 9 e.g., about 7 days), supplemented with human plasma (preferably autologous plasma) and GM-CSF/IL-4, to generate dendritic cells. Dendritic cells are nonadherent when compared to their monocyte progenitors. Thus, on approximately day 7, non-adherent cells are harvested for further processing.

The dendritic cells derived from PBMC in the presence of GM-CSF and IL-4 are immature, in that they can lose their nonadherence property and revert back to macrophage cell fate if the cytokine stimuli are removed from the culture. The dendritic cells in an immature state are very effective in processing native protein antigens for the MHC class II restricted pathway (Romani, et al., J. Exp. Med. 169:1169, 1989). Further maturation of cultured dendritic cells is accomplished by culturing for 3 days in a macrophage-conditioned medium (CM), which contains the necessary maturation factors. Mature dendritic cells are less able to capture new proteins for presentation but are much better at stimulating resting T cells (both CD4 and CD8) to grow and differentiate.

Mature dendritic cells can be identified by their change in morphology, such as by the formation of more motile cytoplasmic processes; by their nonadherence; by the presence of at least one of the following markers: CD83, CD68, HLA-DR or CD86; or by the loss of Fc receptors such as CD 115 (reviewed in Steinman, Annu. Rev. Immunol. 9: 271, 1991). Mature dendritic cells can be collected and analyzed using typical cytofluorography and cell sorting techniques and devices, such as FACScan and FACStar. Primary antibodies used for flow cytometry are those specific to cell surface antigens of mature dendritic cells and are commercially available. Secondary antibodies can be biotinylated Igs followed by FITC- or PE-conjugated streptavidin.

Alternatively, others have reported that a method for upregulating (activating) dendritic cells and converting monocytes to an activated dendritic cell phenotype. This method involves the addition of calcium ionophore to the culture media convert monocytes into activated dendritic cells. Adding the calcium 21 ionophore A23187, for example, at the beginning of a 24-48 hour culture period resulted in uniform activation and dendritic cell phenotypic conversion of the pooled "monocyte plus DC" fractions: characteristically, the activated population becomes uniformly CD 14 (Leu M3) negative, and upregulates HLA-DR, HLA-DQ, ICAM-1, 137.1, and 137.2. Furthermore, this activated bulk population functions as well on a small numbers basis as a further purified. Specific combination(s) of cytokines have been used successfully to amplify (or partially substitute) for the activation/conversion achieved with calcium ionophore: these cytokines include but are not limited to G-CSF, GM-CSF, IL-2, and IL-4. Each cytokine when given alone is inadequate for optimal upregulation.

The second approach for isolating APCs is to collect the relatively large numbers of precommitted APCs already circulating in the blood. Previous techniques for isolating committed APCs from human peripheral blood have involved combinations of physical procedures such as metrizamide gradients and adherence/nonadherence steps (Freudenthal et al. PNAS 87: 7698-7702, 1990); Percoll gradient separations (Mehta-Damani, et al., J. Immunol. 153: 996-1003, 1994); and fluorescence activated cell sorting techniques (Thomas et al., J. Immunol. 151: 6840-52, 1993).

It should be obvious to those of skill in the art that there are many methods routine in the art for isolating professional antigen presenting cells (or their precursors) and that such methods and others which may be developed are not limiting and are encompassed within the scope of the invention.

In one embodiment, the APCs and therefore the cells presenting one or more antigens are autologous. In another embodiment, the APCs presenting the antigen are allogeneic, i.e., derived from a different subject.

As discussed above, nucleic acids encoding chimeric molecules can be introduced into APCs using the methods described above or others known in the art, including, but not limited to, transfection, electroporation, fusion, microinjection, viral-based delivery, or cell based delivery. Arthur et al., Cancer Gene Therapy 4(1): 17-25, 1997, reports a comparison of gene transfer methods in human dendritic cells.

Known, partial and putative human leukocyte antigen (HLA), the genetic designation for the human MHC, amino acid and nucleotide sequences, including the consensus sequence, are published (see, e.g., Zemmour and Parham, Immunogenetics 33: 310-320, 1991), and cell lines expressing HLA variants are known and generally available as well, many from the American Type Culture Collection ("ATCC"). Therefore, using PCR, MHC class II-encoding nucleotide sequences are readily operatively linked to an expression vector of this invention that is then used to transform an appropriate cell for expression therein.

Professional APCs can be used, such as macrophages, B cells, monocytes, dendritic cells, and Langerhans cells. These are collected from the blood or tissue of 1) an autologous donor; 2) a heterologous donor having a different HLA specificity than the host to be treated; or 3) from a xenogeneic donor of a different species using standard procedures (Coligan, et. al., Current Protocols in Immunology, sections 3 and 14, 1994). The cells may be isolated from a normal host or a patient having an infectious disease, cancer, autoimmune disease, or allergy.

Professional APCs may be obtained from the peripheral blood using leukopheresis and "FICOLL/HYPAQUE" density gradient centrifugation (stepwise centrifugation through Ficoll and discontinuous Percoll density gradients). Procedures are utilized which avoid the exposure of the APCs to antigens which could be internalized by the APCs, leading to activation of T cells not specific for the antigens of interest.

Cells which are not naturally antigen presenting can be engineered to be antigen presenting by introducing sequences encoding appropriate molecules. For example, nucleic acid sequences encoding MHC class II molecules, accessory molecules, co-stimulatory molecules and antigen processing assisting molecules can be introduced after direct synthesis, cloning, purification of DNA from cells containing such genes, and the like. One expedient means to obtain genes for encoding the molecules used in the compositions and methods described herein is by polymerase chain reaction (PCR) amplification on selected nucleic acid templates with selected oligonucleotide primer pairs. For example, epithelial cells, endothelial cells, tumor cells, fibroblasts, activated T cells, eosinophils, keratinocytes, astrocytes, microglial cells, thymic cortical epithelial cells, Schwann cells, retinal pigment epithelial cells, myoblasts, vascular smooth muscle cells, chondrocytes, enterocytes, thyrocytes and kidney tubule cells can be used. These may be primary cells recently explanted from a host and not extensively passaged in cell culture to form an established cell line, or established cell lines that are relatively homogeneous and capable of proliferating for many generations or indefinitely.

Cells that are not professional APCs are isolated from any tissue of an autologous donor; a heterologous donor or a xenogeneic donor, where they reside using a variety of known separation methods (Darling, Animal Cells: Culture and Media. J. Wiley, New York, 1994; Freshney, Culture of Animal Cells. Alan R. Liss, Inc., New York, 1987). Non-autologous cells, e.g., heterologous or xenogeneic cells, can be engineered ex vivo to express HLA class I and class II molecules that match known human HLA specificities. These cells can then be introduced into a human subject matching the HLA specificity of the engineered cells. The cells are further engineered ex vivo to express one or more chimeric vaccines according to the invention.

The engineered cells are maintained in cell culture by standard cell culture methods (Darling, Animal Cells: Culture and Media". J. Wiley, New York, 1994; Freshney, Culture of Animal Cells". Alan R. Liss, Inc., New York, 1987). Cell lines for use in the present invention are obtained from a variety of sources (e.g., ATCC Catalogue of Cell Lines & Hybidomas, American Type Culture Collection, 8th edition, 1995), or are produced using standard methods (Freshney, Culture of Immortalized Cells, Wiley-Liss, New York, 1996). Non-transformed cell lines are preferred for use in human subjects.

In one aspect, CD34+ precursors that are differentiating under the influence of GM-CSF into dendritic cells are obtained from the body of a subject and nucleic acids encoding chimeric vaccines according to the invention are introduced into the cells, which are then re-injected into the subject. Utilizing the construct containing antigenic sequences linked to an endosomal/lysosomal targeting signal (and preferably comprising a LAMP-like lumenal polypeptide) will enhance the association of peptides derived from a particular antigen with MHC class II molecules on the transduced antigen presenting cells, resulting in significantly more potent systemic T cell dependent immune responses. While the antigen presenting cells transfected in this strategy are preferably autologous cells, any MHC class II cells that effectively present antigen in the host may be used as described above.

Peptide Vaccines

Also within the scope of this invention are vaccines containing cell-free peptide immunogens, where the immunogen contains at least one Allergen X fused to sequences of a lysosomal membrane polypeptide (e.g., such as a LAMP polypeptide or a homolog, ortholog, variant, or modified version thereof) or sequences of an endocytic receptor for targeting and trafficking Allergen X to an endosomal/lysosomal compartment or lysosome-related organelle for binding to an MHC class II molecule or for delivery to another compartment/organelle for binding to an MHC class II molecule. Preferably, Allergen X is processed within the compartment/organelle (or subsequent compartment/organelle to which it is delivered) to generate an Allergen X epitope bound to an MHC class II molecule capable of modulating an immune response.

The chimeric vaccine may also comprise a transmembrane region and/or cytoplasmic tail with lysosomal targeting region (preferably from a LAMP polypeptide), and/or di-leucine domain, Tyr motif, MR6 domain, proline rich domain, and/or Ser-Val-Val domain. The chimeric vaccine also may be bound in a membranous structure to facilitate its administration to the body of an organism. For example, the chimeric vaccine may be incorporated into liposomes, as described in U.S. Pat. No. 4,448,765.

In preferred embodiments, a peptide vaccine of the present invention comprises: (a) a polypeptide encoded by any one of the polynucleotides of SEQ ID NO:Z or SEQ ID NO:W as shown in Table 1; (b) a polypeptide comprising the amino acid sequence of SEQ ID NO: Y or SEQ ID NO:V as shown in Table 1; (c) a polypeptide comprising a lumenal domain (such as, for example, SEQ ID NOs:2 or 3 or as shown in SEQ ID Nos: 4 or 5), one or more of SEQ ID NO:Y as shown in Table 1, and a trafficking domain (such as SEQ ID NO:1, or as shown in SEQ ID Nos: 4 or 5); (d) a polypeptide comprising a lumenal domain (such as, for example, SEQ ID NOs:2 or 3 or as shown in SEQ ID Nos: 4 or 5) and one or more of SEQ ID NO:Y as shown in Table 1; (e) a polypeptide comprising one or more of SEQ ID NO:Y as shown in Table 1 and a trafficking domain (such as SEQ ID NO:1, or as shown in SEQ ID Nos: 4 or 5); or (f) polypeptides with at least about 60%, at least about 70%, at least about 75%, at least about 80%, at least about 85%, at least about 90%, at least about 95%, 96%, 97%, 98% or 99% identity to any one of the polynucleotides of (a)-(e).

When a protein or polypeptide is to be used as an immunogen, it may be produced by expression of any one or more of the DNA constructs described above in a recombinant cell or it may be prepared by chemical synthesis. For example, the Merrifield technique (Journal of American Chemical Society, vol. 85, pp. 2149-2154, 1968), can be used.

Priming with the LAMP Constructs as polynucleotides, the encoded proteins of the LAMP Constructs, and/or cells (such as antigen presenting cells which express the LAMP Constructs described herein) followed by boosting with Allergen X is a preferred embodiment of the invention. In further preferred embodiments, priming with a LAMP Construct as described herein followed by boosting with an allergen, and preferably an allergen derived from the protein by which Allergen X is derived, is specifically contemplated and can be used to generate an even more robust immune response, especially in view of antibody repertoire diversity and titer.

Administration

Vaccine material according to this invention may contain the immune stimulatory constructs described above or may be recombinant microorganisms, or antigen presenting cells which express the immune stimulatory constructs. Preparation of compositions containing vaccine material according to this invention and administration of such compositions for immunization of individuals are accomplished according to principles of immunization that are well known to those skilled in the art.

Large quantities of these materials may be obtained by culturing recombinant or transformed cells containing replicons that express the chimeric Allergen X proteins described herein. Culturing methods are well-known to those skilled in the art and are taught in one or more of the documents cited above. The vaccine material is generally produced by culture of recombinant or transformed cells and formulated in a pharmacologically acceptable solution or suspension, which is usually a physiologically-compatible aqueous solution, or in coated tablets, tablets, capsules, suppositories or ampules, as described in the art, for example in U.S. Pat. No. 4,446,128, incorporated herein by reference. Administration may be any suitable route, including oral, rectal, intranasal or by injection where injection may be, for example, transdermal, subcutaneous, intramuscular or intravenous.

The vaccine composition is administered to a mammal in an amount sufficient to induce an immune response in the mammal. A minimum preferred amount for administration is the amount required to elicit antibody formation to a concentration at least 4 times that which existed prior to administration. A typical initial dose for administration would be 10-5000 micrograms when administered intravenously, intramuscularly or subcutaneously, or $10^5$ to $10^{11}$ plaque forming units of a recombinant vector, although this amount may be adjusted by a clinician doing the administration as commonly occurs in the administration of vaccines and other agents which induce immune responses. A single administration may usually be sufficient to induce immunity, but multiple administrations may be carried out to assure or boost the response (such as with a recombinantly produced derived from the same protein from which Allergen X is derived).

Vaccines may be tested initially in a non-human mammal (e.g., a mouse or primate). For example, assays of the immune responses of inoculated mice can be used to demonstrate greater antibody, T cell proliferation, and cytotoxic T cell responses to the lysosome-targeted chimeric proteins than to wild type antigen. Chimeric proteins can be evaluated in Rhesus monkeys to determine whether a DNA vaccine formulation that is highly effective in mice will also elicit an appropriate monkey immune response. In one aspect, each monkey receives a total of 5 mg DNA per immunization, delivered IM and divided between 2 sites, with immunizations at day 0 and at weeks 4, 8, and 20, with additional doses optional. Antibody responses, ADCC, CD4+ and CD8+ T-cell cytokine production, CD4+ and CD8+ T-cell antigen-specific cytokine staining can be measured to monitor immune responses to the vaccine.

Further description of suitable methods of formulation and administration according to this invention may be found in U.S. Pat. No. 4,454,116 (constructs), U.S. Pat. No. 4,681,762 (recombinant bacteria), and U.S. Pat. Nos. 4,592,002 and 4,920,209 (recombinant viruses).

Treatment of Allergies

This invention provides a formulation useful for the treatment of pollinosis correlated with Allergen X. It has previously been determined that delivering a DNA plasmid encoding the protein coding sequence of an allergen to an animal can increase IFN-gamma production and lower IL-4 production, which is useful in treating animals allergic to the specific allergen. The present invention provides an improved vaccine composition for treating patients with an allergy correlated to Allergen X. The fusion protein of the invention has a specific intracellular trafficking pattern that intersects with MHC class II vesicles, and results in enhanced presentation of Allergen X to the immune system, specifically resulting in an enhanced antibody response. Nucleic acids and compositions provided by the present invention are useful for conducting allergy immunotherapy.

The present invention provides a formulation that when administered to a cell results in an increased specific antibody response. The increased antibody response to Allergen X is useful for treating an IgE-mediated allergic disease. IgE has certain properties related to its cellular restriction and the resulting intracellular signaling upon binding cognate allergen. IgE is generated against an allergen when B cells receive IL-4 secreted by Th2 cells. This helps instruct B cells to produce IgE class antibodies. Upon secretion by B cells, IgE binds to Fc-εRI, its high affinity receptor expressed by mast cells and eosinophils, resulting in these cells and the animal becoming sensitized to future allergen exposure. Consequently, the symptoms of allergy can be triggered upon the ingestion, inhalation, or mucosal contact with an allergen. Due to the binding properties of antibodies, it has been proposed that one way of reducing allergy symptoms is to chelate free allergen available for binding by IgE through competition with other antibody classes. In particular, an allergy formulation that increases IgG has been proposed to be a pathway for reducing allergic disease. The invention described herein induces enhanced IgG production, thus causing a decrease in the ratio of IgE to IgG in a clinically significant manner.

In a particularly preferred embodiment, the invention provides a method of treatment or prevention of an allergy to Allergen X. In one preferred method, polynucleotides encoding Allergen X described herein and a lumenal trafficking domain of a lysosome associated membrane polypeptide (e.g., LAMP polypeptide, homolog, ortholog, variant, or modified form thereof) or the lumenal trafficking domain of an endocytic receptor, and a cytoplasmic targeting domain of a LAMP polypeptide, homolog, ortholog, variant, or modified form thereof, or of an endocytic receptor for targeting the Allergen X antigen to an endosomal/lysosomal compartment or lysosome-related organelle and for association with an MHC class II molecule either within the compartment/organelle or within another compartment/organelle to which the antigen is delivered. Such chimeric DNA molecules can encode additional domain sequences as described above (e.g., sequences encoding transmembrane domains, signal sequences, cytoplasmic domains for targeting to an endosomal/lysosomal compartment or lysosome-related organelles, di-leucine domains, Tyr motif domains, proline rich domains, Ser-Val-Val domains, and the like).

More generally, in one embodiment, this invention provides a vaccine composition for modulating an immune response in a mammal to Allergen X (i.e., stimulating, enhancing, or reducing such a response). Preferably, the composition comprises a vaccine vector, wherein the vector contains a chimeric DNA segment which encodes a protein containing Allergen X and a lumenal trafficking domain of a lysosome associated membrane polypeptide (e.g., LAMP polypeptide, homolog, ortholog, variant, or modified form thereof) or the lumenal trafficking domain of an endocytic receptor, and a targeting domain, such as the cytoplasmic targeting domain of a LAMP polypeptide, homolog, ortholog, variant, or modified form thereof, or of an endocytic receptor, for targeting the antigen to an endosomal/lysosomal compartment or lysosome-related organelle and for association with an MHC class II molecule either within the compartment/organelle or within another compartment/organelle to which the antigen is delivered. Such chimeric DNA molecules can encode additional domain sequences as described above (e.g., sequences encoding transmembrane domains, signal sequences, cytoplasmic domains for targeting to an endosomal/lysosomal compartment or lysosome-related organelles, di-leucine domains, Tyr motif domains, proline rich domains, Ser-Val-Val domains, and the like).

Kits

The invention further comprises kits to facilitate performing the methods described herein. In one aspect, a kit comprises a nucleic acid vector as described above and a cell for receiving the vector. The kit may additionally comprise one or more nucleic acids for engineering the cell into a professional APC. In one aspect, however, the cell is a professional APC. The cell may or may not express co-stimulatory molecules. In a preferred aspect, when the cell does not express co-stimulatory molecules, the antigen encoded by the vector is an autoantigen. In another aspect, a panel of cells is provided expressing different MHC molecules (e.g., known to be expressed in human beings). In a further aspect, the kit comprises reagents to facilitate entry of the vectors into a cell (e.g., lipid-based formulations, viral packaging materials, cells, and the like). In still a further aspect, one or more T cell lines specific for the antigen encoded by the vector is provided, to verify the ability of the vector to elicit, modulate, or enhance an immune response.

EXAMPLES

The invention will now be further illustrated with reference to the following examples. It will be appreciated that what follows is by way of example only and that modifications to detail may be made while still falling within the scope of the invention.

Example 1

Construction of Allergen X Constructs

A number of different nucleic acid constructs were constructed encoding chimeric Allergen X vaccines as described in Table 1. Plasmids comprising the polynucleotides of SEQ ID NO:Z were designed using techniques well known in the art. Specifically, a plasmids comprising polynucleotides encoding gene fusions comprising a portion of the LAMP-1 lumenal domain (SEQ ID NO:2) to Allergen X (SEQ ID NO:Y) and then to a portion of the LAMP-1 Transmembrane/Cytoplasmic Tail (SEQ ID NO:1) were inserted into the NTC 8382 vector. Representative examples of such constructed polynucleotides are provided as SEQ ID NO:W. The resulting constructs were sequence confirmed and protein expression was confirmed.

Example 2

Evaluation of the Immune Response of Mice to Plasmids Encoding Allergen X

Allergen X antigen constructs as described in Example 1 were tested for their ability to modulate an immune response using the assay described in Su, Yan, Michael Connolly, Anthony Marketon, and Teri Heiland. "CryJ-LAMP DNA Vaccines for Japanese Red Cedar Allergy Induce Robust Th1-Type Immune Responses in Murine Model." *Journal of Immunology Research* 2016 (2016): 1-15.

Results for each construct is are reported in Table 3. Unless otherwise indicated, the "control" construct is the vector backbone lacking allergen sequence.

TABLE 3

| Active | Weakly/Non-Active |
|---|---|
| Cor a 1 (SEQ ID NO: 7)<br>IgG1: Vaccinated group: $4 \times 10^5$ endpoint titer<br>IgG2a: Vaccinated group: $3.5 \times 10^6$ endpoint titer | IgG1: Control group: $2.1 \times 10^4$ endpoint titer<br>IgG2a: Control group: Not detected |
| After removal of amino acids 319-480aa of full length Cor a 9 to generate<br>SEQ ID NO: 9:<br>IgG1 Vaccinated group: $5.7 \times 10^5$ endpoint titer<br>Control group: Not detected<br>IgG2a Vaccinated group: $6.2 \times 10^5$ endpoint titer<br>Control group: Not detected<br>Removal specifically enhanced the IgG2a:IgG1 ratio | Before Removal (full length Cor a 9 sequence that includes amino acids 319-480aa)<br>IgG1 Vaccinated group: $1.2 \times 10^6$ endpoint titer<br>Control group: $2.7 \times 10^4$ endpoint titer<br>IgG2a Vaccinated group: $7.5 \times 10^5$ endpoint titer<br>Control group: Not detected |
| Cor a 1 - Gly4 - Cor a 9 (SEQ ID NO: 11)<br>IgG1: Vaccinated group: $1 \times 10^5$ endpoint titer<br>IgG2a: Vaccinated group: $3.3 \times 10^5$ endpoint titer | IgG1: Control group: $2.2 \times 10^3$ endpoint titer<br>IgG2a: Control group: $2.7 \times 10^3$ endpoint titer |
| Removal of aa 368-551 of Pru du 6 sequence to generate<br>SEQ ID NO: 13:<br>After removal:<br>IgG1 Vaccinated group: $1.6 \times 10^5$ endpoint titer<br>Control group: $1.3 \times 10^4$ endpoint titer<br>IgG2a Vaccinated group: $5.5 \times 10^5$ endpoint titer<br>Control group: Not detected<br>Removal of the basic chain (368-551 aa) improved the antibody responses and specifically enhanced the IgG2a:IgG1 ratio | Full length Pru du 6 sequence with aa 368-551.<br>Before removal:<br>IgG1 Vaccinated group: $9.9 \times 10^5$ endpoint titer<br>Control group: $1.3 \times 10^4$ endpoint titer<br>IgG2a Vaccinated group: $2.8 \times 10^5$ endpoint titer<br>Control group: Not detected |
| Ana 0 1 (SEQ ID NO: 15)<br>IgG1: Vaccinated group: $1.2 \times 10^6$ endpoint titer<br>IgG2a: Vaccinated group: $6 \times 10^6$ endpoint titer | IgG1: Control group: 4.9 × 104 endpoint titer<br>IgG2a: Control group: Not detected |
| Ana 0 2 (SEQ ID NO: 17)<br>IgG1: Vaccinated group: 8.1 × 105 endpoint titer<br>IgG2a: Vaccinated group: 4 × 106 endpoint titer | IgG1: Control group: $1.6 \times 10^4$ endpoint titer<br>IgG2a: Control group: Not detected |
| Ana 0 3 (SEQ ID NO: 19)<br>IgG1: Vaccinated group: $2 \times 10^5$ endpoint titer<br>IgG2a: Vaccinated group: $1.4 \times 10^6$ endpoint titer | IgG1: Control group: $5.4 \times 10^3$ endpoint titer<br>IgG2a: Control group: Not detected |
| Ana 0 2 -Gly4- Ana 0 1 - Gly4- Ana 0 3 (SEQ ID NO: 21)<br>IgG1: Vaccinated group: $5.5 \times 10^5$ endpoint titer<br>IgG2a: Vaccinated group: $3.4 \times 10^6$ endpoint titer | IgG1: Control group: $3.7 \times 10^4$ endpoint titer<br>IgG2a: Control group: Not detected |
| Jug n 1 (SEQ ID NO: 23) | IgG1: Control group: $7 \times 10^4$ endpoint titer |

TABLE 3-continued

| Active | Weakly/Non-Active |
|---|---|
| IgG1: Vaccinated group: $6 \times 10^5$ endpoint titer<br>IgG2a: Vaccinated group: $1.7 \times 10^6$ endpoint titer | IgG2a: Control group: $1 \times 10^3$ endpoint titer |
| Jug r 2 (SEQ ID NO: 25)<br>IgG1: Vaccinated group: $9.9 \times 10^5$ endpoint titer<br>IgG2a: Vaccinated group: $4.2 \times 10^6$ endpoint titer | IgG1: Control group: $7 \times 10^4$ endpoint titer<br>IgG2a: Control group: $2 \times 10^3$ endpoint titer |
| Jug n 1 - Gly4 - Jug r 2 (SEQ ID NO: 27)<br>IgG1: Vaccinated group: $2 \times 10^5$ endpoint titer<br>IgG2a: Vaccinated group: $1.7 \times 10^5$ endpoint titer | IgG1: Control group: $1 \times 10^4$ endpoint titer<br>IgG2a: Control group: Not detected |
| Amb a 1 (SEQ ID NO: 29)<br>IgG1: Vaccinated group: $4 \times 10^5$ endpoint titer<br>IgG2a: Vaccinated group: $3.5 \times 10^6$ endpoint titer | IgG1: Control group: $2.1 \times 10^4$ endpoint titer<br>IgG2a: Control group: Not detected |
| Bet v 1-A (SEQ ID NO: 33)<br>IgG1: Vaccinated group: $4 \times 10^5$ endpoint titer<br>IgG2a: Vaccinated group: $2 \times 10^6$ endpoint titer | IgG1: Control group: $5 \times 10^3$ endpoint titer<br>IgG2a: Control group: $5 \times 10^3$ endpoint titer |
| Can f 1 (SEQ ID NO: 37)<br>IgG1: Vaccinated group: $4 \times 10^5$ endpoint titer<br>IgG2a: Vaccinated group: $2 \times 10^6$ endpoint titer | IgG1: Control group: $1.8 \times 10^4$ endpoint titer<br>IgG2a: Control group: $5 \times 10^3$ endpoint titer |
| Cyn d 1 (SEQ ID NO: 41)<br>IgG1: Vaccinated group: $5 \times 10^5$ endpoint titer<br>IgG2a: Vaccinated group: $6 \times 10^6$ endpoint titer | IgG1: Control group: $4 \times 104$ endpoint titer<br>IgG2a: Control group: $5 \times 103$ endpoint titer |
| Der F 1 (19-321) (SEQ ID NO: 45)<br>IgG1: Vaccinated group: $1.5 \times 10^5$ endpoint titer<br>IgG2a: Vaccinated group: $2 \times 10^6$ endpoint titer | IgG1: Vaccinated group with Der F 1 (99-321)<br>(SEQ ID NO: 49): $5 \times 10^4$ endpoint titer<br>Control group: Not detected<br>IgG2a Vaccinated group with Der F 1 (99-321)<br>(SEQ ID NO: 49): $1 \times 10^6$ endpoint titer<br>Control group: Not detected |
| Der P2 (SEQ ID NO: 53)<br>IgG1: Vaccinated group: $1 \times 10^5$ endpoint titer<br>IgG2a: Vaccinated group: $1 \times 10^6$ endpoint titer | IgG1: Control group: $8 \times 10^3$ endpoint titer<br>IgG2a: Control group: Not detectable |
| DerF2 (SEQ ID NO: 57)<br>IgG1: Vaccinated group: $6 \times 10^5$ endpoint titer<br>IgG2a: Vaccinated group: $1.2 \times 10^6$ endpoint titer | IgG1: Control group: Not detectable<br>IgG2a: Control group: Not detectable |
| After deletion of amino acids 27-50 of DerP1 sequence<br>(SEQ ID NO: 61):<br>IgG1 Vaccinated group: $3.5 \times 10^3$ endpoint titer<br>Control group: Not detectable<br>IgG2a Vaccinated group: $4 \times 10^5$ endpoint titer<br>Control group: Not detectable<br>Removal sequence improved the antibody responses and specifically<br>enhanced the IgG2a:IgG1 ratio | Before deletion of amino acids 27-50 of<br>DerP1 sequence:<br>IgG1 Vaccinated group: $2.3 \times 105$ endpoint titer<br>Control group: $1.1 \times 104$<br>IgG2a Vaccinated group: $9.3 \times 104$ endpoint titer<br>Control group: Not detectable |
| Fel D 1 (SEQ ID NO: 66)<br>IgG1: Vaccinated group: $4 \times 10^5$ endpoint titer<br>IgG2a: Vaccinated group: $2 \times 10^6$ endpoint titer | IgG1: Control group: $1.4 \times 103$ endpoint titer<br>IgG2a: Control group: Not detectable |
| Fel d 4 (SEQ ID NO: 74)<br>IgG1: Vaccinated group: $2.5 \times 10^4$ endpoint titer<br>IgG2a: Vaccinated group: $7 \times 10^4$ endpoint titer | IgG1: Control group: Not detectable<br>IgG2a: Control group: Not detectable |
| Lit v 1 (SEQ ID NO: 78)<br>IgG1: Vaccinated group: $6 \times 10^5$ endpoint titer<br>IgG2a: Vaccinated group: $1.1 \times 10^6$ endpoint titer | IgG1: Control group: $4.2 \times 10^4$ endpoint titer<br>IgG2a: Control group: $1.9 \times 10^4$ endpoint titer |
| Lol p 5a (SEQ ID NO: 82)<br>IgG1: Vaccinated group: $1 \times 10^6$ endpoint titer<br>IgG2a: Vaccinated group: $1.5 \times 10^6$ endpoint titer | IgG1: Control group: $1.8 \times 105$ endpoint titer<br>IgG2a: Control group: Not detected |
| Phl p 1 (SEQ ID NO: 86)<br>IgG1: Vaccinated group: $5 \times 10^5$ endpoint titer<br>IgG2a: Vaccinated group: $1.5 \times 10^6$ endpoint titer | IgG1: Control group: No detected<br>IgG2a: Control group: Not detected |
| Phl p 5 (SEQ ID NO: 90)<br>IgG1: Vaccinated group: $1 \times 10^6$ endpoint titer<br>IgG2a: Vaccinated group: $3 \times 10^6$ endpoint titer | IgG1: Control group: $5 \times 104$ endpoint titer<br>IgG2a: Control group: Not detected |
| Der f 15 (SEQ ID NO: 93)<br>IgG1: Vaccinated group: $1.2 \times 10^6$ endpoint titer<br>IgG2a: Vaccinated group: $4.4 \times 10^6$ endpoint titer | IgG1: Control group: $1 \times 10^5$ endpoint titer<br>IgG2a: Control group: $2.7 \times 10^3$ endpoint titer |
| Der f 18 (SEQ ID NO: 94)<br>IgG1: Vaccinated group: $1.2 \times 10^6$ endpoint titer<br>IgG2a: Vaccinated group: $4.4 \times 106$ endpoint titer | IgG1: Control group: $1 \times 10^5$ endpoint titer<br>IgG2a: Control group: $2.7 \times 10^3$ endpoint titer |
| Cte f 1 (SEQ ID NO: 96)<br>IgG1: Vaccinated group: $1.3 \times 10^6$ endpoint titer<br>IgG2a: Vaccinated group: $2.9 \times 10^6$ endpoint titer | IgG1: Control group: $1 \times 10^5$ endpoint titer<br>IgG2a: Control group: $2.3 \times 105$ endpoint titer |
| Der F1-Der F2 (SEQ ID NO: 110)<br>F1<br>IgG1: Vaccinated group: $1.8 \times 10^5$ endpoint titer<br>IgG2: Vaccinated group: $1.0 \times 10^6$ endpoint titer<br>F2<br>IgG1: Vaccinated group: $9.4 \times 10^3$ endpoint titer<br>IgG2: Vaccinated group: $6.0 \times 10^5$ endpoint titer<br>Der F15 - Der F18 (SEQ ID NO: 109) | |

TABLE 3-continued

| Active | Weakly/Non-Active |
|---|---|
| F15 IgG1: Vaccinated group: $3.8 \times 10^4$ endpoint titer IgG2: Vaccinated group: $4.0 \times 10^5$ endpoint titer F18 IgG1: Vaccinated group: $1.2 \times 10^5$ endpoint titer IgG2: Vaccinated group: $1.1 \times 10^6$ endpoint titer | |

Six to eight week old female Balb/c mice were treated with either control vector or vaccines and immunized by Bioject intradermal delivery at days 0, 7, and 14. Mice were boosted with recombinant allergen (5 μg/mouse) in the presence of Alum adjuvant on day 42 and bled on day 21, 35, and 56.

Serum samples were diluted 1:100 (day 21), 1:2000 (day 35) or 1:5000 (day 56) fold in 1% BSA in PBS. Day 56 samples were further diluted by a 7 point 1:3 serial dilution to measure the endpoint antibody titers. To detect IgE, sera were treated with Agarose-Protein G (Thermo Fisher Scientific, Rockford, Ill.) 50 minutes and then 1:20 diluted samples were loaded to ELISA plates. Samples were detected with goat anti-mouse IgG1-HRP, goat anti-mouse IgG2a-HRP (Southern Biotech, Birmingham, Ala.), or rat anti-mouse-IgE-biotin (R35-118, BD Pharmingen, San Jose, Calif.) followed Pierce Streptavidin-HRP (Thermo Fisher Scientific, Rockford, Ill.). Reaction was developed with SureBlue TMB Substrate and stopped with TMB Stop Solution. Plates were read (OD450) by using Epoch ELISA reader (BioTek, Winooski, Vt.). Endpoint titers were determined by subtracting twice above the the background average (PBS) reading. The means and standard errors of endpoint titers or OD450 values per group were analyzed by using Excel statistic function. IgE data were analyzed by using Student T test. Tests were two tailed, and p values≤0.05 were considered significant.

Variations, modifications, and other implementations of what is described herein will occur to those of ordinary skill in the art without departing from the spirit and scope of the invention and the claims. All of the patents, patent applications, international applications, and references identified are expressly incorporated herein by reference in their entireties.

What is claimed:

1. An isolated nucleic acid encoding a polypeptide comprising:
   (a) a lysosomal associated membrane protein (LAMP) lumenal domain;
   (b) at least one allergen comprising the amino acid sequence of SEQ ID NO: 45, 49, 53, 57, and/or 61 and
   (c) a LAMP transmembrane domain/cytoplasmic tail.

2. The nucleic acid of claim 1, wherein LAMP is selected from LAMP polypeptide (LAMP-1), DC-LAMP, LAMP-2, LAMP-3, LIMP II, or ENDOLYN.

3. The nucleic acid of claim 2, wherein the LAMP lumenal domain is derived from LAMP-1.

4. The nucleic acid of claim 3, wherein the LAMP lumenal domain comprises an amino acid sequence chosen from:
   (a) SEQ ID NO:2;
   (b) SEQ ID NO:3;
   (c) amino acids 29-381 of SEQ ID NO:4 or 25-370 of SEQ ID NO:5; or
   (d) a variant of any one of (a)-(c), wherein the variant comprises an amino acid sequence that is at least about 90%, at least about 95%, 96%, 97%, 98% or 99% identical to an amino acid sequence of any one of (a)-(c).

5. The nucleic acid of claim 1, wherein the LAMP transmembrane domain/cytoplasmic tail comprises an amino acid sequence chosen from:

(a) SEQ ID NO:1;
(b) amino acids 382-417 of SEQ ID NO:4 or 371-406 of SEQ ID NO:5; or
(c) a variant of (a) or (b), wherein the variant comprises an amino acid sequence that is at least about 90%, at least about 95%, 96%, 97%, 98% or 99% identical to an amino acid sequence of (a) or (b).

6. The nucleic acid of claim 1, wherein the nucleic acid comprises:
(a) any one of the polynucleotide sequences of SEQ ID NO: 44, 48, 52, 56 or 60;
(b) a polynucleotide encoding a polypeptide encoded by any one of the polynucleotide sequences of SEQ ID NO: 44, 48, 52, 56 or 60;
(c) a polynucleotide that encodes a polypeptide comprising the amino acid sequence of SEQ ID NO: 45, 49, 53, 57 and/or 61;
(d) a polynucleotide encoding a LAMP lumenal domain one or more of SEQ ID NO: 45, 49, 53, 57, and/or 61, and a LAMP transmembrane domain/cytoplasmic tail;
(e) a polynucleotide encoding a LAMP lumenal domain and one or more of SEQ ID NO: 45, 49, 53, 57, and/or 61; or
(f) a polynucleotide encoding one or more of SEQ ID NO: 45, 49, 53, 57, and/or 61 and a trafficking domain LAMP transmembrane domain/cytoplasmic tail.

7. The nucleic acid of claim 6,
wherein the LAMP lumenal domain comprises:
(a) SEQ ID NO:2;
(b) SEQ ID NO:3;
(c) SEQ ID NO:4 or SEQ ID NO:5; or
(d) a variant of any one of (a)-(c), wherein the variant comprises an amino acid sequence that is at least about 90%, at least about 95%, 96%, 97%, 98% or 99% identical to any one of the sequences shown in (a)-(c);
and wherein the LAMP transmembrane domain/cytoplasmic tail comprises:
(a) SEQ ID NO:1;
(b) SEQ ID NO:4 or SEQ ID NO:5; or
(c) a variant of (a) or (b), wherein the variant comprises an amino acid sequence that is at least about 90%, at least about 95%, 96%, 97%, 98% or 99% identical to an amino acid sequence of (a) or (b).

8. The nucleic acid of claim 1, wherein the nucleic acid encodes the amino acid sequence of SEQ ID No: 45.

9. The nucleic acid of claim 3, wherein the LAMP lumenal domain comprises:
(a) SEQ ID NO:2 or
(b) a variant of (a), wherein the variant comprises an amino acid sequence that is at least about 90%, at least about 95%, 96%, 97%, 98% or 99% identical to (a).

10. The nucleic acid of claim 3, wherein the LAMP transmembrane domain/cytoplasmic tail comprises:
(a) SEQ ID NO:1; or
(b) a variant of (a), wherein the variant comprises an amino acid sequence that is at least about 90%, at least about 95%, 96%, 97%, 98% or 99% identical to (a).

11. A vector comprising the nucleic acid of claim 1.

12. A host cell comprising the nucleic acid of claim 1 or comprising a vector comprising the nucleic acid.

13. A vaccine comprising (a) the nucleic acid of claim 1, (b) a vector comprising the nucleic acid, or (c) a host cell comprising either the nucleic acid or the vector.

14. A method of treating or preventing an allergic response, wherein the method comprises administering to a subject the vaccine of claim 13 in an effective amount sufficient to reduce, inhibit or prevent an allergic response.

15. The method of claim 14, wherein the vaccine is administered therapeutically.

16. The method of claim 14, wherein the vaccine is administered prophylactically.

17. The method of claim 14, wherein the method comprises a priming step and at least one boosting step.

18. The method of claim 17, wherein:
(a) nucleic acid, vector, or host cell is administered to the subject in the priming step; and/or
(b) the nucleic acid, vector, or host cell is administered to the subject in the boosting step.

19. The method of claim 17, wherein the allergen used to prime is the same that is used to boost.

20. The method of claim 17, wherein the allergen used to prime is derived from the same protein as the allergen used to boost.

21. The method of claim 17, wherein more than one allergen is used to prime and/or boost.

\* \* \* \* \*

UNITED STATES PATENT AND TRADEMARK OFFICE
CERTIFICATE OF CORRECTION

| | |
|---|---|
| PATENT NO. | : 11,826,423 B2 |
| APPLICATION NO. | : 16/461185 |
| DATED | : November 28, 2023 |
| INVENTOR(S) | : Teri Heiland |

It is certified that error appears in the above-identified patent and that said Letters Patent is hereby corrected as shown below:

In the Claims

In Claim 6, Lines 24-26 should read:
-- (f) a polynucleotide encoding one or more of SEQ ID NO: 45, 49, 53, 57, and/or 61 and a LAMP transmembrane domain/cytoplasmic tail. --

Signed and Sealed this
Ninth Day of January, 2024

Katherine Kelly Vidal
*Director of the United States Patent and Trademark Office*

SEQUENCE LISTING

```
<160> NUMBER OF SEQ ID NOS: 110

<210> SEQ ID NO 1
<211> LENGTH: 35
<212> TYPE: PRT
<213> ORGANISM: Homo sapiens

<400> SEQUENCE: 1

Leu Ile Pro Ile Ala Val Gly Gly Ala Leu Ala Gly Leu Val Leu Ile
1               5                   10                  15

Val Leu Ile Ala Tyr Leu Val Gly Arg Lys Arg Ser His Ala Gly Tyr
            20                  25                  30

Gln Thr Ile
        35

<210> SEQ ID NO 2
<211> LENGTH: 379
<212> TYPE: PRT
<213> ORGANISM: Homo sapiens

<400> SEQUENCE: 2

Ala Pro Arg Ser Ala Arg Arg Pro Leu Leu Leu Leu Leu Leu Leu Leu
1               5                   10                  15

Leu Leu Gly Leu Met His Cys Ala Ser Ala Ala Met Phe Met Val Lys
            20                  25                  30

Asn Gly Asn Gly Thr Ala Cys Ile Met Ala Asn Phe Ser Ala Ala Phe
        35                  40                  45

Ser Val Asn Tyr Asp Thr Lys Ser Gly Pro Lys Asn Met Thr Leu Asp
    50                  55                  60

Leu Pro Ser Asp Ala Thr Val Val Leu Asn Arg Ser Ser Cys Gly Lys
65                  70                  75                  80

Glu Asn Thr Ser Asp Pro Ser Leu Val Ile Ala Phe Gly Arg Gly His
            85                  90                  95
```

```
Thr Leu Thr Leu Asn Phe Thr Arg Asn Ala Thr Arg Tyr Ser Val Gln
            100                 105                 110

Leu Met Ser Phe Val Tyr Asn Leu Ser Asp Thr His Leu Phe Pro Asn
        115                 120                 125

Ala Ser Ser Lys Glu Ile Lys Thr Val Glu Ser Ile Thr Asp Ile Arg
130                 135                 140

Ala Asp Ile Asp Lys Lys Tyr Arg Cys Val Ser Gly Thr Gln Val His
145                 150                 155                 160

Met Asn Asn Val Thr Val Thr Leu His Asp Ala Thr Ile Gln Ala Tyr
                165                 170                 175

Leu Ser Asn Ser Ser Phe Ser Arg Gly Glu Thr Arg Cys Glu Gln Asp
            180                 185                 190

Arg Pro Ser Pro Thr Thr Ala Pro Pro Ala Pro Pro Ser Pro Ser Pro
        195                 200                 205

Ser Pro Val Pro Lys Ser Pro Ser Val Asp Lys Tyr Asn Val Ser Gly
    210                 215                 220

Thr Asn Gly Thr Cys Leu Leu Ala Ser Met Gly Leu Gln Leu Asn Leu
225                 230                 235                 240

Thr Tyr Glu Arg Lys Asp Asn Thr Thr Val Thr Arg Leu Leu Asn Ile
                245                 250                 255

Asn Pro Asn Lys Thr Ser Ala Ser Gly Ser Cys Gly Ala His Leu Val
            260                 265                 270

Thr Leu Glu Leu His Ser Glu Gly Thr Thr Val Leu Leu Phe Gln Phe
        275                 280                 285

Gly Met Asn Ala Ser Ser Ser Arg Phe Phe Leu Gln Gly Ile Gln Leu
    290                 295                 300

Asn Thr Ile Leu Pro Asp Ala Arg Asp Pro Ala Phe Lys Ala Ala Asn
305                 310                 315                 320

Gly Ser Leu Arg Ala Leu Gln Ala Thr Val Gly Asn Ser Tyr Lys Cys
                325                 330                 335

Asn Ala Glu Glu His Val Arg Val Thr Lys Ala Phe Ser Val Asn Ile
            340                 345                 350

Phe Lys Val Trp Val Gln Ala Phe Lys Val Glu Gly Gly Gln Phe Gly
        355                 360                 365

Ser Val Glu Glu Cys Leu Leu Asp Glu Asn Ser
    370                 375

<210> SEQ ID NO 3
<211> LENGTH: 382
<212> TYPE: PRT
<213> ORGANISM: Homo sapiens

<400> SEQUENCE: 3

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
```

```
                 85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Arg Phe Phe Leu Gln Gly Ile Gln
290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu
370                 375                 380

<210> SEQ ID NO 4
<211> LENGTH: 417
<212> TYPE: PRT
<213> ORGANISM: Homo sapiens

<400> SEQUENCE: 4

Met Ala Ala Pro Gly Ser Ala Arg Arg Pro Leu Leu Leu Leu Leu Leu
1               5                   10                  15

Leu Leu Leu Leu Gly Leu Met His Cys Ala Ser Ala Ala Met Phe Met
            20                  25                  30

Val Lys Asn Gly Asn Gly Thr Ala Cys Ile Met Ala Asn Phe Ser Ala
        35                  40                  45

Ala Phe Ser Val Asn Tyr Asp Thr Lys Ser Gly Pro Lys Asn Met Thr
    50                  55                  60

Phe Asp Leu Pro Ser Asp Ala Thr Val Val Leu Asn Arg Ser Ser Cys
65                  70                  75                  80
```

```
Gly Lys Glu Asn Thr Ser Asp Pro Ser Leu Val Ile Ala Phe Gly Arg
                85                  90                  95
Gly His Thr Leu Thr Leu Asn Phe Thr Arg Asn Ala Thr Arg Tyr Ser
            100                 105                 110
Val Gln Leu Met Ser Phe Val Tyr Asn Leu Ser Asp Thr His Leu Phe
        115                 120                 125
Pro Asn Ala Ser Ser Lys Glu Ile Lys Thr Val Glu Ser Ile Thr Asp
    130                 135                 140
Ile Arg Ala Asp Ile Asp Lys Lys Tyr Arg Cys Val Ser Gly Thr Gln
145                 150                 155                 160
Val His Met Asn Asn Val Thr Val Thr Leu His Asp Ala Thr Ile Gln
                165                 170                 175
Ala Tyr Leu Ser Asn Ser Ser Phe Ser Arg Gly Glu Thr Arg Cys Glu
            180                 185                 190
Gln Asp Arg Pro Ser Pro Thr Thr Ala Pro Ala Pro Pro Ser Pro
        195                 200                 205
Ser Pro Ser Pro Val Pro Lys Ser Pro Ser Val Asp Lys Tyr Asn Val
    210                 215                 220
Ser Gly Thr Asn Gly Thr Cys Leu Leu Ala Ser Met Gly Leu Gln Leu
225                 230                 235                 240
Asn Leu Thr Tyr Glu Arg Lys Asp Asn Thr Thr Val Thr Arg Leu Leu
                245                 250                 255
Asn Ile Asn Pro Asn Lys Thr Ser Ala Ser Gly Ser Cys Gly Ala His
            260                 265                 270
Leu Val Thr Leu Glu Leu His Ser Glu Gly Thr Thr Val Leu Leu Phe
        275                 280                 285
Gln Phe Gly Met Asn Ala Ser Ser Ser Arg Phe Phe Leu Gln Gly Ile
    290                 295                 300
Gln Leu Asn Thr Ile Leu Pro Asp Ala Arg Asp Pro Ala Phe Lys Ala
305                 310                 315                 320
Ala Asn Gly Ser Leu Arg Ala Leu Gln Ala Thr Val Gly Asn Ser Tyr
                325                 330                 335
Lys Cys Asn Ala Glu Glu His Val Arg Val Thr Lys Ala Phe Ser Val
            340                 345                 350
Asn Ile Phe Lys Val Trp Val Gln Ala Phe Lys Val Glu Gly Gly Gln
        355                 360                 365
Phe Gly Ser Val Glu Glu Cys Leu Leu Asp Glu Asn Ser Met Leu Ile
    370                 375                 380
Pro Ile Ala Val Gly Gly Ala Leu Ala Gly Leu Val Leu Ile Val Leu
385                 390                 395                 400
Ile Ala Tyr Leu Val Gly Arg Lys Arg Ser His Ala Gly Tyr Gln Thr
                405                 410                 415
Ile

<210> SEQ ID NO 5
<211> LENGTH: 406
<212> TYPE: PRT
<213> ORGANISM: Mus musculus

<400> SEQUENCE: 5

Met Ala Ala Pro Gly Ala Arg Arg Pro Leu Leu Leu Leu Leu Leu Ala
1               5                   10                  15
Gly Leu Ala His Gly Ala Ser Ala Leu Phe Glu Val Lys Asn Asn Gly
            20                  25                  30
```

Thr Thr Cys Ile Met Ala Ser Phe Ser Ala Ser Phe Leu Thr Thr Tyr
            35                  40                  45

Glu Thr Ala Asn Gly Ser Gln Ile Val Asn Ile Ser Leu Pro Ala Ser
 50                  55                  60

Ala Glu Val Leu Lys Asn Gly Ser Ser Cys Gly Lys Glu Asn Val Ser
 65                  70                  75                  80

Asp Pro Ser Leu Thr Ile Thr Phe Gly Arg Gly Tyr Leu Leu Thr Leu
                85                  90                  95

Asn Phe Thr Lys Asn Thr Thr Arg Tyr Ser Val Gln His Met Tyr Phe
                100                 105                 110

Thr Tyr Asn Leu Ser Asp Thr Glu His Phe Pro Asn Ala Ile Ser Lys
            115                 120                 125

Glu Ile Tyr Thr Met Asp Ser Thr Thr Asp Ile Lys Ala Asp Ile Asn
130                 135                 140

Lys Ala Tyr Arg Cys Val Ser Asp Ile Arg Val Tyr Met Lys Asn Val
145                 150                 155                 160

Thr Val Val Leu Arg Asp Ala Thr Ile Gln Ala Tyr Leu Ser Ser Gly
                165                 170                 175

Asn Phe Ser Lys Glu Glu Thr His Cys Thr Gln Asp Gly Pro Ser Pro
                180                 185                 190

Thr Thr Gly Pro Pro Ser Pro Pro Leu Val Pro Thr Asn Pro
            195                 200                 205

Thr Val Ser Lys Tyr Asn Val Thr Gly Asn Asn Gly Thr Cys Leu Leu
            210                 215                 220

Ala Ser Met Ala Leu Gln Leu Asn Ile Thr Tyr Leu Lys Lys Asp Asn
225                 230                 235                 240

Lys Thr Val Thr Arg Ala Phe Asn Ile Ser Pro Asn Asp Thr Ser Ser
                245                 250                 255

Gly Ser Cys Gly Ile Asn Leu Val Thr Leu Lys Val Glu Asn Lys Asn
                260                 265                 270

Arg Ala Leu Glu Leu Gln Phe Gly Met Asn Ala Ser Ser Ser Leu Phe
            275                 280                 285

Phe Leu Gln Gly Val Arg Leu Asn Met Thr Leu Pro Asp Ala Leu Val
290                 295                 300

Pro Thr Phe Ser Ile Ser Asn His Ser Leu Lys Ala Leu Gln Ala Thr
305                 310                 315                 320

Val Gly Asn Ser Tyr Lys Cys Asn Thr Glu Glu His Ile Phe Val Ser
                325                 330                 335

Lys Met Leu Ser Leu Asn Val Phe Ser Val Gln Val Gln Ala Phe Lys
            340                 345                 350

Val Asp Ser Asp Arg Phe Gly Ser Val Glu Glu Cys Val Gln Asp Gly
            355                 360                 365

Asn Asn Met Leu Ile Pro Ile Ala Val Gly Gly Ala Leu Ala Gly Leu
            370                 375                 380

Val Leu Ile Val Leu Ile Ala Tyr Leu Ile Gly Arg Lys Arg Ser His
385                 390                 395                 400

Ala Gly Tyr Gln Thr Ile
            405

<210> SEQ ID NO 6
<211> LENGTH: 492
<212> TYPE: DNA
<213> ORGANISM: Corylus avellana
<220> FEATURE:
<221> NAME/KEY: CDS

<222> LOCATION: (7)..(486)

<400> SEQUENCE: 6

```
ctcgag atg ggc gtg ttc tgc tac gag gac gag gcc aca agc gtg atc          48
       Met Gly Val Phe Cys Tyr Glu Asp Glu Ala Thr Ser Val Ile
         1               5                  10 cct ccc gcc aga ctg ttc aag agc ttc gtg ctg gac gcc gac aat ctg          96
Pro Pro Ala Arg Leu Phe Lys Ser Phe Val Leu Asp Ala Asp Asn Leu
 15              20                  25                  30 atc ccc aaa gtg gcc ccc cag cac ttc acc agc gcc gag aat ctg gaa         144
Ile Pro Lys Val Ala Pro Gln His Phe Thr Ser Ala Glu Asn Leu Glu
                 35                  40                  45 ggc aat ggc gga ccc ggc acc atc aag aag atc aca ttc gcc gag ggc         192
Gly Asn Gly Gly Pro Gly Thr Ile Lys Lys Ile Thr Phe Ala Glu Gly
             50                  55                  60 aac gag ttc aag tac atg aag cac aaa gtg gaa gag atc gac cac gcc         240
Asn Glu Phe Lys Tyr Met Lys His Lys Val Glu Glu Ile Asp His Ala
         65                  70                  75 aac ttc aag tac tgc tac agc atc atc gaa ggc ggc cct ctg ggc cac         288
Asn Phe Lys Tyr Cys Tyr Ser Ile Ile Glu Gly Gly Pro Leu Gly His
     80                  85                  90 aca ctg gaa aag atc agc tac gag atc aag atg gcc gct gcc cct cac         336
Thr Leu Glu Lys Ile Ser Tyr Glu Ile Lys Met Ala Ala Ala Pro His
 95                 100                 105                 110 ggc gga ggc agc att ctg aag atc acc agc aag tac cac acc aag ggc         384
Gly Gly Gly Ser Ile Leu Lys Ile Thr Ser Lys Tyr His Thr Lys Gly
                115                 120                 125 aac gcc agc atc aac gag gaa gaa atc aag gcc ggc aaa gag aaa gcc         432
Asn Ala Ser Ile Asn Glu Glu Glu Ile Lys Ala Gly Lys Glu Lys Ala
            130                 135                 140 gcc gga ctg ttt aag gcc gtg gaa gcc tat ctg ctg gcc cac ccc gat         480
Ala Gly Leu Phe Lys Ala Val Glu Ala Tyr Leu Leu Ala His Pro Asp
        145                 150                 155 gcc tac gaattc                                                          492
Ala Tyr
    160
```

<210> SEQ ID NO 7
<211> LENGTH: 160
<212> TYPE: PRT
<213> ORGANISM: Corylus avellana

<400> SEQUENCE: 7

```
Met Gly Val Phe Cys Tyr Glu Asp Glu Ala Thr Ser Val Ile Pro Pro
  1               5                  10                  15

Ala Arg Leu Phe Lys Ser Phe Val Leu Asp Ala Asp Asn Leu Ile Pro
                 20                  25                  30

Lys Val Ala Pro Gln His Phe Thr Ser Ala Glu Asn Leu Glu Gly Asn
             35                  40                  45

Gly Gly Pro Gly Thr Ile Lys Lys Ile Thr Phe Ala Glu Gly Asn Glu
         50                  55                  60

Phe Lys Tyr Met Lys His Lys Val Glu Glu Ile Asp His Ala Asn Phe
 65                  70                  75                  80

Lys Tyr Cys Tyr Ser Ile Ile Glu Gly Gly Pro Leu Gly His Thr Leu
                 85                  90                  95

Glu Lys Ile Ser Tyr Glu Ile Lys Met Ala Ala Ala Pro His Gly Gly
            100                 105                 110

Gly Ser Ile Leu Lys Ile Thr Ser Lys Tyr His Thr Lys Gly Asn Ala
        115                 120                 125
```

```
Ser Ile Asn Glu Glu Ile Lys Ala Gly Lys Glu Lys Ala Ala Gly
            130                 135                 140

Leu Phe Lys Ala Val Glu Ala Tyr Leu Leu Ala His Pro Asp Ala Tyr
145                 150                 155                 160

<210> SEQ ID NO 8
<211> LENGTH: 905
<212> TYPE: DNA
<213> ORGANISM: Corylus avellana
<220> FEATURE:
<221> NAME/KEY: CDS
<222> LOCATION: (7)..(900)

<400> SEQUENCE: 8 ctcgag atc aac gtg gga ctg cgg aga cag cag cag cgg tac ttc ggc         48
       Ile Asn Val Gly Leu Arg Arg Gln Gln Gln Arg Tyr Phe Gly
         1               5                  10 gag tgc aat ctg gac cgg ctg aac gct ctg gaa ccc acc aac aga atc        96
Glu Cys Asn Leu Asp Arg Leu Asn Ala Leu Glu Pro Thr Asn Arg Ile
 15                  20                  25                  30 gag gcc gag gct tgc cag atc gag agc tgg gac cac aac gac cag cag       144
Glu Ala Glu Ala Cys Gln Ile Glu Ser Trp Asp His Asn Asp Gln Gln
                 35                  40                  45 ttc cag tgt gct ggc gtg gcc gtg atc aga cgg acc atc gag ccc aac       192
Phe Gln Cys Ala Gly Val Ala Val Ile Arg Arg Thr Ile Glu Pro Asn
             50                  55                  60 gga ctg ctg ctc ccc cag tac agc aat gcc ccc gag ctg atc tac atc       240
Gly Leu Leu Leu Pro Gln Tyr Ser Asn Ala Pro Glu Leu Ile Tyr Ile
         65                  70                  75 gag cgg ggc aga gga atc acc ggc gtg ctg ttt ccc ggc tgc ccc gag       288
Glu Arg Gly Arg Gly Ile Thr Gly Val Leu Phe Pro Gly Cys Pro Glu
     80                  85                  90 aca ttc gag gac cct cag cag cag agc cag caa ggc cag aga caa ggc       336
Thr Phe Glu Asp Pro Gln Gln Gln Ser Gln Gln Gly Gln Arg Gln Gly
 95                 100                 105                 110 caa ggc cag tcc cag aga agc gag caa gac cgg cac cag aag atc cgg       384
Gln Gly Gln Ser Gln Arg Ser Glu Gln Asp Arg His Gln Lys Ile Arg
                115                 120                 125 cac ttc aga gag ggc gac atc att gct ctg cca gcc ggc gtg gcc cac       432
His Phe Arg Glu Gly Asp Ile Ile Ala Leu Pro Ala Gly Val Ala His
            130                 135                 140 tgg tgc tac aat gat ggc gat agc ccc gtc gtg acc gtg tct ctg ctg       480
Trp Cys Tyr Asn Asp Gly Asp Ser Pro Val Val Thr Val Ser Leu Leu
            145                 150                 155 cac acc aac aac tac gcc aac cag ctg gac gag aac ccc aga cac ttc       528
His Thr Asn Asn Tyr Ala Asn Gln Leu Asp Glu Asn Pro Arg His Phe
        160                 165                 170 tat ctg gcc ggc aac ccc gac gac gag cac cag agg caa ggg cag cag       576
Tyr Leu Ala Gly Asn Pro Asp Asp Glu His Gln Arg Gln Gly Gln Gln
175                 180                 185                 190 cag ttc ggc cag aga aga agg cag cag cag cac agc cat ggc gag caa       624
Gln Phe Gly Gln Arg Arg Arg Gln Gln Gln His Ser His Gly Glu Gln
                195                 200                 205 ggc gag caa gag cag caa ggc gag ggc aac aac gtg ttc agc ggc ttc       672
Gly Glu Gln Glu Gln Gln Gly Glu Gly Asn Asn Val Phe Ser Gly Phe
            210                 215                 220 gac gcc gag ttt ctg gcc gac gcc ttc aac gtg gac gtg gac aca gcc       720
Asp Ala Glu Phe Leu Ala Asp Ala Phe Asn Val Asp Val Asp Thr Ala
                    225                 230                 235 aga cgg ctg cag tcc aac caa gac aag cgg cgg aac atc gtg aaa gtg       768
```

```
Arg Arg Leu Gln Ser Asn Gln Asp Lys Arg Arg Asn Ile Val Lys Val
        240                 245                 250 gaa ggc cgg ctc caa gtc gtg cgg ccc gag aga tct aga caa gag tgg      816
Glu Gly Arg Leu Gln Val Val Arg Pro Glu Arg Ser Arg Gln Glu Trp
255                 260                 265                 270 gag cgg caa gag cgg caa gaa cgc gag agc gag caa gag aga gag cgg      864
Glu Arg Gln Glu Arg Gln Glu Arg Glu Ser Glu Gln Glu Arg Glu Arg
                275                 280                 285 cag aga agg caa ggc ggc aga ggc aga gat gtg aac gaatt                905
Gln Arg Arg Gln Gly Gly Arg Gly Arg Asp Val Asn
                290                 295

<210> SEQ ID NO 9
<211> LENGTH: 298
<212> TYPE: PRT
<213> ORGANISM: Corylus avellana

<400> SEQUENCE: 9
```

Ile Asn Val Gly Leu Arg Arg Gln Gln Gln Arg Tyr Phe Gly Glu Cys
1               5                   10                  15

Asn Leu Asp Arg Leu Asn Ala Leu Glu Pro Thr Asn Arg Ile Glu Ala
            20                  25                  30

Glu Ala Cys Gln Ile Glu Ser Trp Asp His Asn Asp Gln Gln Phe Gln
        35                  40                  45

Cys Ala Gly Val Ala Val Ile Arg Arg Thr Ile Glu Pro Asn Gly Leu
    50                  55                  60

Leu Leu Pro Gln Tyr Ser Asn Ala Pro Glu Leu Ile Tyr Ile Glu Arg
65                  70                  75                  80

Gly Arg Gly Ile Thr Gly Val Leu Phe Pro Gly Cys Pro Glu Thr Phe
                85                  90                  95

Glu Asp Pro Gln Gln Ser Gln Gly Gln Arg Gln Gly Gln Gly
            100                 105                 110

Gln Ser Gln Arg Ser Glu Gln Asp Arg His Gln Lys Ile Arg His Phe
        115                 120                 125

Arg Glu Gly Asp Ile Ile Ala Leu Pro Ala Gly Val Ala His Trp Cys
    130                 135                 140

Tyr Asn Asp Gly Asp Ser Pro Val Val Thr Val Ser Leu Leu His Thr
145                 150                 155                 160

Asn Asn Tyr Ala Asn Gln Leu Asp Glu Asn Pro Arg His Phe Tyr Leu
                165                 170                 175

Ala Gly Asn Pro Asp Asp Glu His Gln Arg Gln Gly Gln Gln Gln Phe
            180                 185                 190

Gly Gln Arg Arg Arg Gln Gln His Ser His Gly Glu Gln Gly Glu
        195                 200                 205

Gln Glu Gln Gln Gly Glu Gly Asn Asn Val Phe Ser Gly Phe Asp Ala
    210                 215                 220

Glu Phe Leu Ala Asp Ala Phe Asn Val Asp Val Asp Thr Ala Arg Arg
225                 230                 235                 240

Leu Gln Ser Asn Gln Asp Lys Arg Arg Asn Ile Val Lys Val Glu Gly
                245                 250                 255

Arg Leu Gln Val Val Arg Pro Glu Arg Ser Arg Gln Glu Trp Glu Arg
            260                 265                 270

Gln Glu Arg Gln Glu Arg Glu Ser Glu Gln Glu Arg Glu Arg Gln Arg
        275                 280                 285

Arg Gln Gly Gly Arg Gly Arg Asp Val Asn
    290                 295

<210> SEQ ID NO 10
<211> LENGTH: 1410
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (13)..(1398)

<400> SEQUENCE: 10

```
catatgctcg ag atg ggc gtg ttc tgc tac gag gac gag gcc aca agc gtg      51
          Met Gly Val Phe Cys Tyr Glu Asp Glu Ala Thr Ser Val
          1               5                  10 atc cct ccc gcc aga ctg ttc aag agc ttc gtg ctg gac gcc gac aat         99
Ile Pro Pro Ala Arg Leu Phe Lys Ser Phe Val Leu Asp Ala Asp Asn
 15                  20                  25 ctg atc ccc aaa gtg gcc ccc cag cac ttc acc agc gcc gag aat ctg        147
Leu Ile Pro Lys Val Ala Pro Gln His Phe Thr Ser Ala Glu Asn Leu
 30                  35                  40                  45 gaa ggc aat ggc gga ccc ggc acc atc aag aag atc aca ttc gcc gag        195
Glu Gly Asn Gly Gly Pro Gly Thr Ile Lys Lys Ile Thr Phe Ala Glu
                 50                  55                  60 ggc aac gag ttc aag tac atg aag cac aaa gtg gaa gag atc gac cac        243
Gly Asn Glu Phe Lys Tyr Met Lys His Lys Val Glu Glu Ile Asp His
             65                  70                  75 gcc aac ttc aag tac tgc tac agc atc atc gaa ggc ggc cct ctg ggc        291
Ala Asn Phe Lys Tyr Cys Tyr Ser Ile Ile Glu Gly Gly Pro Leu Gly
         80                  85                  90 cac aca ctg gaa aag atc agc tac gag atc aag atg gcc gct gcc cct        339
His Thr Leu Glu Lys Ile Ser Tyr Glu Ile Lys Met Ala Ala Ala Pro
     95                 100                 105 cac ggc gga ggc agc att ctg aag atc acc agc aag tac cac acc aag        387
His Gly Gly Gly Ser Ile Leu Lys Ile Thr Ser Lys Tyr His Thr Lys
110                 115                 120                 125 ggc aac gcc agc atc aac gag gaa gaa atc aag gcc ggc aaa gag aaa        435
Gly Asn Ala Ser Ile Asn Glu Glu Glu Ile Lys Ala Gly Lys Glu Lys
                130                 135                 140 gcc gcc gga ctg ttt aag gcc gtg gaa gcc tat ctg ctg gcc cac ccc        483
Ala Ala Gly Leu Phe Lys Ala Val Glu Ala Tyr Leu Leu Ala His Pro
            145                 150                 155 gat gcc tac ggc gga ggg ggc atc aac gtg gga ctg cgg aga cag cag        531
Asp Ala Tyr Gly Gly Gly Gly Ile Asn Val Gly Leu Arg Arg Gln Gln
        160                 165                 170 cag cgg tac ttc ggc gag tgc aat ctg gac cgg ctg aac gct ctg gaa        579
Gln Arg Tyr Phe Gly Glu Cys Asn Leu Asp Arg Leu Asn Ala Leu Glu
    175                 180                 185 ccc acc aac aga atc gag gcc gag gct tgc cag atc gag agc tgg gac        627
Pro Thr Asn Arg Ile Glu Ala Glu Ala Cys Gln Ile Glu Ser Trp Asp
190                 195                 200                 205 cac aac gac cag cag ttc cag tgt gct ggc gtg gcc gtg atc aga cgg        675
His Asn Asp Gln Gln Phe Gln Cys Ala Gly Val Ala Val Ile Arg Arg
                210                 215                 220 acc atc gag ccc aac gga ctg ctg ctg ccc cag tac agc aat gcc ccc        723
Thr Ile Glu Pro Asn Gly Leu Leu Leu Pro Gln Tyr Ser Asn Ala Pro
            225                 230                 235 gag ctg atc tac atc gag cgg ggc aga gga atc acc ggc gtg ctg ttt        771
Glu Leu Ile Tyr Ile Glu Arg Gly Arg Gly Ile Thr Gly Val Leu Phe
        240                 245                 250 ccc ggc tgc ccc gag aca ttc gag gac cct cag cag cag agc cag caa        819
Pro Gly Cys Pro Glu Thr Phe Glu Asp Pro Gln Gln Gln Ser Gln Gln
```

```
Pro Gly Cys Pro Glu Thr Phe Glu Asp Pro Gln Gln Ser Gln Gln
    255                 260                 265 ggc cag aga caa ggc caa ggc cag tcc cag aga agc gag caa gac cgg        867
Gly Gln Arg Gln Gly Gln Gly Gln Ser Gln Arg Ser Glu Gln Asp Arg
270                 275                 280                 285 cac cag aag atc cgg cac ttc aga gag ggc gac atc att gct ctg cca        915
His Gln Lys Ile Arg His Phe Arg Glu Gly Asp Ile Ile Ala Leu Pro
                290                 295                 300 gcc ggc gtg gcc cac tgg tgc tac aat gat ggc gat agc ccc gtc gtg        963
Ala Gly Val Ala His Trp Cys Tyr Asn Asp Gly Asp Ser Pro Val Val
            305                 310                 315 acc gtg tct ctg ctg cac acc aac aac tac gcc aac cag ctg gac gag       1011
Thr Val Ser Leu Leu His Thr Asn Asn Tyr Ala Asn Gln Leu Asp Glu
        320                 325                 330 aac ccc aga cac ttc tat ctg gcc ggc aac ccc gac gac gag cac cag       1059
Asn Pro Arg His Phe Tyr Leu Ala Gly Asn Pro Asp Asp Glu His Gln
    335                 340                 345 agg caa ggg cag cag cag ttc ggc cag aga aga agg cag cag cag cac       1107
Arg Gln Gly Gln Gln Gln Phe Gly Gln Arg Arg Arg Gln Gln Gln His
350                 355                 360                 365 agc cat ggc gag caa ggc gag caa gag cag caa ggc gag ggc aac aac       1155
Ser His Gly Glu Gln Gly Glu Gln Glu Gln Gln Gly Glu Gly Asn Asn
                370                 375                 380 gtg ttc agc ggc ttc gac gcc gag ttt ctg gcc gac gcc ttc aac gtg       1203
Val Phe Ser Gly Phe Asp Ala Glu Phe Leu Ala Asp Ala Phe Asn Val
            385                 390                 395 gac gtg gac aca gcc aga cgg ctg cag tcc aac caa gac aag cgg cgg       1251
Asp Val Asp Thr Ala Arg Arg Leu Gln Ser Asn Gln Asp Lys Arg Arg
        400                 405                 410 aac atc gtg aaa gtg gaa ggc cgg ctc caa gtc gtg cgg ccc gag aga       1299
Asn Ile Val Lys Val Glu Gly Arg Leu Gln Val Val Arg Pro Glu Arg
    415                 420                 425 tct aga caa gag tgg gag cgg caa gag cgg caa gaa cgc gag agc gag       1347
Ser Arg Gln Glu Trp Glu Arg Gln Glu Arg Gln Glu Arg Glu Ser Glu
430                 435                 440                 445 caa gag aga gag cgg cag aga agg caa ggc ggc aga ggc aga gat gtg       1395
Gln Glu Arg Glu Arg Gln Arg Arg Gln Gly Gly Arg Gly Arg Asp Val
                450                 455                 460 aac gaattcgtcg ac                                                     1410
Asn

<210> SEQ ID NO 11
<211> LENGTH: 462
<212> TYPE: PRT
<213> ORGANISM: Artificial sequence
<220> FEATURE:
<223> OTHER INFORMATION: Synthetic Construct

<400> SEQUENCE: 11

Met Gly Val Phe Cys Tyr Glu Asp Glu Ala Thr Ser Val Ile Pro Pro
1               5                   10                  15

Ala Arg Leu Phe Lys Ser Phe Val Leu Asp Ala Asp Asn Leu Ile Pro
            20                  25                  30

Lys Val Ala Pro Gln His Phe Thr Ser Ala Glu Asn Leu Glu Gly Asn
        35                  40                  45

Gly Gly Pro Gly Thr Ile Lys Lys Ile Thr Phe Ala Glu Gly Asn Glu
    50                  55                  60

Phe Lys Tyr Met Lys His Lys Val Glu Glu Ile Asp His Ala Asn Phe
65                  70                  75                  80
```

```
Lys Tyr Cys Tyr Ser Ile Ile Glu Gly Gly Pro Leu Gly His Thr Leu
                85                  90                  95

Glu Lys Ile Ser Tyr Glu Ile Lys Met Ala Ala Pro His Gly Gly
            100                 105                 110

Gly Ser Ile Leu Lys Ile Thr Ser Lys Tyr His Thr Lys Gly Asn Ala
            115                 120                 125

Ser Ile Asn Glu Glu Ile Lys Ala Gly Lys Glu Lys Ala Ala Gly
130                 135                 140

Leu Phe Lys Ala Val Glu Ala Tyr Leu Leu Ala His Pro Asp Ala Tyr
145                 150                 155                 160

Gly Gly Gly Gly Ile Asn Val Gly Leu Arg Arg Gln Gln Gln Arg Tyr
                165                 170                 175

Phe Gly Glu Cys Asn Leu Asp Arg Leu Asn Ala Leu Glu Pro Thr Asn
                180                 185                 190

Arg Ile Glu Ala Glu Ala Cys Gln Ile Glu Ser Trp Asp His Asn Asp
            195                 200                 205

Gln Gln Phe Gln Cys Ala Gly Val Ala Val Ile Arg Arg Thr Ile Glu
            210                 215                 220

Pro Asn Gly Leu Leu Leu Pro Gln Tyr Ser Asn Ala Pro Glu Leu Ile
225                 230                 235                 240

Tyr Ile Glu Arg Gly Arg Gly Ile Thr Gly Val Leu Phe Pro Gly Cys
                245                 250                 255

Pro Glu Thr Phe Glu Asp Pro Gln Gln Ser Gln Gly Gln Arg
            260                 265                 270

Gln Gly Gln Gly Gln Ser Gln Arg Ser Glu Gln Asp Arg His Gln Lys
            275                 280                 285

Ile Arg His Phe Arg Glu Gly Asp Ile Ile Ala Leu Pro Ala Gly Val
            290                 295                 300

Ala His Trp Cys Tyr Asn Asp Gly Asp Ser Pro Val Val Thr Val Ser
305                 310                 315                 320

Leu Leu His Thr Asn Asn Tyr Ala Asn Gln Leu Asp Glu Asn Pro Arg
                325                 330                 335

His Phe Tyr Leu Ala Gly Asn Pro Asp Asp Glu His Gln Arg Gln Gly
                340                 345                 350

Gln Gln Gln Phe Gly Gln Arg Arg Gln Gln Gln His Ser His Gly
            355                 360                 365

Glu Gln Gly Glu Gln Glu Gln Gly Glu Gly Asn Asn Val Phe Ser
            370                 375                 380

Gly Phe Asp Ala Glu Phe Leu Ala Asp Ala Phe Asn Val Asp Val Asp
385                 390                 395                 400

Thr Ala Arg Arg Leu Gln Ser Asn Gln Asp Lys Arg Arg Asn Ile Val
                405                 410                 415

Lys Val Glu Gly Arg Leu Gln Val Val Arg Pro Glu Arg Ser Arg Gln
            420                 425                 430

Glu Trp Glu Arg Gln Glu Arg Gln Glu Arg Glu Ser Glu Gln Glu Arg
            435                 440                 445

Glu Arg Gln Arg Arg Gln Gly Gly Arg Gly Arg Asp Val Asn
450                 455                 460

<210> SEQ ID NO 12
<211> LENGTH: 1053
<212> TYPE: DNA
<213> ORGANISM: Prunus dulcis
<220> FEATURE:
<221> NAME/KEY: CDS
```

<222> LOCATION: (7)..(1047)

<400> SEQUENCE: 12

```
ctcgag gcc aga cag agc cag ctg agc ccc cag aat cag tgc cag ctg       48
       Ala Arg Gln Ser Gln Leu Ser Pro Gln Asn Gln Cys Gln Leu
        1               5                  10 aac cag ctg caa gcc aga gag ccc gac aac cgg att caa gcc gag gcc       96
Asn Gln Leu Gln Ala Arg Glu Pro Asp Asn Arg Ile Gln Ala Glu Ala
 15              20                  25                  30 ggc cag atc gag aca tgg aac ttc aac caa gag gac ttc cag tgt gcc      144
Gly Gln Ile Glu Thr Trp Asn Phe Asn Gln Glu Asp Phe Gln Cys Ala
                 35                  40                  45 ggc gtg gcc gcc agc aga atc acc atc cag cgg aac gga ctg cat ctg      192
Gly Val Ala Ala Ser Arg Ile Thr Ile Gln Arg Asn Gly Leu His Leu
             50                  55                  60 ccc agc tac agc aac gcc ccc cag ctg atc tac atc gtg caa ggc aga      240
Pro Ser Tyr Ser Asn Ala Pro Gln Leu Ile Tyr Ile Val Gln Gly Arg
         65                  70                  75 ggc gtg ctg ggc gcc gtg ttt agc gga tgc ccc gag aca ttc gag gaa      288
Gly Val Leu Gly Ala Val Phe Ser Gly Cys Pro Glu Thr Phe Glu Glu
     80                  85                  90 agc cag cag agc agc cag caa ggc cgg cag caa gag caa gaa caa gag      336
Ser Gln Gln Ser Ser Gln Gln Gly Arg Gln Gln Glu Gln Glu Gln Glu
 95                 100                 105                 110 aga caa cag cag cag caa ggg gag caa ggc aga cag caa gga cag caa      384
Arg Gln Gln Gln Gln Gln Gly Glu Gln Gly Arg Gln Gln Gly Gln Gln
                115                 120                 125 gag cag cag caa gag cgc caa gga cgg cag caa ggg cgc cag cag caa      432
Glu Gln Gln Gln Glu Arg Gln Gly Arg Gln Gln Gly Arg Gln Gln Gln
            130                 135                 140 gaa gag ggc aga cag caa gaa cag cag caa ggc cag caa ggg cgg cct      480
Glu Glu Gly Arg Gln Gln Glu Gln Gln Gln Gly Gln Gln Gly Arg Pro
145                 150                 155 cag cag cag cag cag ttc cgg cag ttc gac cgg cac cag aaa acc cgg      528
Gln Gln Gln Gln Gln Phe Arg Gln Phe Asp Arg His Gln Lys Thr Arg
        160                 165                 170 cgg atc aga gaa ggc gac gtg gtg gct att cca gcc ggg gtg gcc tac      576
Arg Ile Arg Glu Gly Asp Val Val Ala Ile Pro Ala Gly Val Ala Tyr
175                 180                 185                 190 tgg tcc tac aac gac ggc gac caa gaa ctg gtg gcc gtg aat ctg ttc      624
Trp Ser Tyr Asn Asp Gly Asp Gln Glu Leu Val Ala Val Asn Leu Phe
                195                 200                 205 cac gtg tcc agc gac cac aac cag ctg gac cag aac ccc cgg aag ttc      672
His Val Ser Ser Asp His Asn Gln Leu Asp Gln Asn Pro Arg Lys Phe
            210                 215                 220 tat ctg gct ggc aac ccc gag aac gag ttc aac cag caa ggg cag agc      720
Tyr Leu Ala Gly Asn Pro Glu Asn Glu Phe Asn Gln Gln Gly Gln Ser
        225                 230                 235 cag ccc aga cag caa ggc gaa caa gga cgg ccc gga cag cac cag cag      768
Gln Pro Arg Gln Gln Gly Glu Gln Gly Arg Pro Gly Gln His Gln Gln
    240                 245                 250 cct ttc ggc aga cca cgg cag caa gag cag caa ggc agc ggc aac aac      816
Pro Phe Gly Arg Pro Arg Gln Gln Glu Gln Gln Gly Ser Gly Asn Asn
255                 260                 265                 270 gtg ttc agc ggc ttc aac acc cag ctg ctg gcc caa gct ctg aac gtg      864
Val Phe Ser Gly Phe Asn Thr Gln Leu Leu Ala Gln Ala Leu Asn Val
                275                 280                 285 aac gag gaa acc gcc cgg aat ctg caa ggc cag aac gac aac aga aac      912
Asn Glu Glu Thr Ala Arg Asn Leu Gln Gly Gln Asn Asp Asn Arg Asn
            290                 295                 300
```

```
cag atc atc aga gtg cgg ggc aat ctg gac ttc gtg cag ccc cct aga     960
Gln Ile Ile Arg Val Arg Gly Asn Leu Asp Phe Val Gln Pro Pro Arg
        305                 310                 315 ggg cgg caa gag aga gag cac gaa gag agg cag caa gaa cag ctg cag    1008
Gly Arg Gln Glu Arg Glu His Glu Glu Arg Gln Gln Glu Gln Leu Gln
320                 325                 330 caa gag cgg cag cag caa ggc gga cag ctg atg gcc aac gaattc         1053
Gln Glu Arg Gln Gln Gln Gly Gly Gln Leu Met Ala Asn
335                 340                 345
```

<210> SEQ ID NO 13
<211> LENGTH: 347
<212> TYPE: PRT
<213> ORGANISM: Prunus dulcis

<400> SEQUENCE: 13

```
Ala Arg Gln Ser Gln Leu Ser Pro Gln Asn Gln Cys Gln Leu Asn Gln
1               5                   10                  15

Leu Gln Ala Arg Glu Pro Asp Asn Arg Ile Gln Ala Glu Ala Gly Gln
            20                  25                  30

Ile Glu Thr Trp Asn Phe Asn Gln Glu Asp Phe Gln Cys Ala Gly Val
        35                  40                  45

Ala Ala Ser Arg Ile Thr Ile Gln Arg Asn Gly Leu His Leu Pro Ser
    50                  55                  60

Tyr Ser Asn Ala Pro Gln Leu Ile Tyr Ile Val Gln Gly Arg Gly Val
65                  70                  75                  80

Leu Gly Ala Val Phe Ser Gly Cys Pro Glu Thr Phe Glu Glu Ser Gln
                85                  90                  95

Gln Ser Ser Gln Gln Gly Arg Gln Gln Glu Gln Glu Gln Glu Arg Gln
            100                 105                 110

Gln Gln Gln Gln Gly Glu Gln Gly Arg Gln Gly Gln Gln Glu Gln
        115                 120                 125

Gln Gln Glu Arg Gln Gly Arg Gln Gln Gly Arg Gln Gln Glu Glu
    130                 135                 140

Gly Arg Gln Gln Glu Gln Gln Gln Gly Gln Gln Gly Arg Pro Gln Gln
145                 150                 155                 160

Gln Gln Gln Phe Arg Gln Phe Asp Arg His Gln Lys Thr Arg Arg Ile
                165                 170                 175

Arg Glu Gly Asp Val Val Ala Ile Pro Ala Gly Val Ala Tyr Trp Ser
            180                 185                 190

Tyr Asn Asp Gly Asp Gln Glu Leu Val Ala Val Asn Leu Phe His Val
        195                 200                 205

Ser Ser Asp His Asn Gln Leu Asp Gln Asn Pro Arg Lys Phe Tyr Leu
    210                 215                 220

Ala Gly Asn Pro Glu Asn Glu Phe Asn Gln Gln Gly Gln Ser Gln Pro
225                 230                 235                 240

Arg Gln Gln Gly Glu Gln Gly Arg Pro Gly Gln His Gln Gln Pro Phe
                245                 250                 255

Gly Arg Pro Arg Gln Gln Glu Gln Gln Gly Ser Gly Asn Asn Val Phe
            260                 265                 270

Ser Gly Phe Asn Thr Gln Leu Leu Ala Gln Ala Leu Asn Val Asn Glu
        275                 280                 285

Glu Thr Ala Arg Asn Leu Gln Gly Gln Asn Asp Asn Arg Asn Gln Ile
    290                 295                 300

Ile Arg Val Arg Gly Asn Leu Asp Phe Val Gln Pro Pro Arg Gly Arg
```

```
                305                 310                 315                 320
Gln Glu Arg Glu His Glu Glu Arg Gln Gln Glu Gln Leu Gln Gln Glu
                    325                 330                 335

Arg Gln Gln Gln Gly Gly Gln Leu Met Ala Asn
            340                 345

<210> SEQ ID NO 14
<211> LENGTH: 1548
<212> TYPE: DNA
<213> ORGANISM: Anacardium occidentale
<220> FEATURE:
<221> NAME/KEY: CDS
<222> LOCATION: (7)..(1542)

<400> SEQUENCE: 14 ctcgag aag atc gac ccc gag ctg aag cag tgc aag cac cag tgc aaa         48
       Lys Ile Asp Pro Glu Leu Lys Gln Cys Lys His Gln Cys Lys
        1               5                  10 gtg cag cgg cag tac gac gag cag cag aaa gaa cag tgc gtg aaa gag        96
Val Gln Arg Gln Tyr Asp Glu Gln Gln Lys Glu Gln Cys Val Lys Glu
 15              20                  25                  30 tgc gag aag tac tac aaa gag aag aag ggc cgc gag cgc gag cac gaa       144
Cys Glu Lys Tyr Tyr Lys Glu Lys Lys Gly Arg Glu Arg Glu His Glu
                 35                  40                  45 gag gaa gag gaa gaa tgg ggc acc ggc gga gtg gac gag cct tct aca       192
Glu Glu Glu Glu Glu Trp Gly Thr Gly Gly Val Asp Glu Pro Ser Thr
             50                  55                  60 cac gag ccc gcc gag aaa cat ctg agc cag tgc atg aga cag tgc gaa       240
His Glu Pro Ala Glu Lys His Leu Ser Gln Cys Met Arg Gln Cys Glu
         65                  70                  75 cgg caa gag ggc ggc cag cag aaa cag ctg tgc cgg ttc cgg tgc caa       288
Arg Gln Glu Gly Gly Gln Gln Lys Gln Leu Cys Arg Phe Arg Cys Gln
     80                  85                  90 gag cgg tac aag aaa gag cgg ggc cag cac aac tac aag aga gag gac       336
Glu Arg Tyr Lys Lys Glu Arg Gly Gln His Asn Tyr Lys Arg Glu Asp
 95                 100                 105                 110 gac gag gac gaa gat gag gac gag gct gag gaa gag gac gag aac ccc       384
Asp Glu Asp Glu Asp Glu Asp Glu Ala Glu Glu Asp Glu Asn Pro
                115                 120                 125 tac gtg ttc gag gat gag gac ttc acc acc aaa gtg aaa acc gag caa       432
Tyr Val Phe Glu Asp Glu Asp Phe Thr Thr Lys Val Lys Thr Glu Gln
            130                 135                 140 ggc aaa gtg gtg ctg ctg ccc aag ttc acc cag aag tcc aag ctg ctg       480
Gly Lys Val Val Leu Leu Pro Lys Phe Thr Gln Lys Ser Lys Leu Leu
        145                 150                 155 cac gct ctg gaa aag tac cgg ctg gcc gtt ctg gtg gcc aac cct caa       528
His Ala Leu Glu Lys Tyr Arg Leu Ala Val Leu Val Ala Asn Pro Gln
    160                 165                 170 gcc ttc gtg gtg ccc agc cac atg gac gcc gac agc atc ttc ttc gtg       576
Ala Phe Val Val Pro Ser His Met Asp Ala Asp Ser Ile Phe Phe Val
175                 180                 185                 190 tct tgg ggc aga ggc acc atc acc aag att ctg gaa aac aag cgc gag       624
Ser Trp Gly Arg Gly Thr Ile Thr Lys Ile Leu Glu Asn Lys Arg Glu
                195                 200                 205 agc atc aac gtg cgg caa ggc gac atc gtg tcc atc agc agc ggc acc       672
Ser Ile Asn Val Arg Gln Gly Asp Ile Val Ser Ile Ser Ser Gly Thr
            210                 215                 220 ccc ttc tac att gcc aac aac gac gag aac gag aag ctg tat ctg gtg       720
Pro Phe Tyr Ile Ala Asn Asn Asp Glu Asn Glu Lys Leu Tyr Leu Val
        225                 230                 235
```

| | | | | | | | | | | | | | | | | |
|---|---|---|---|---|---|---|---|---|---|---|---|---|---|---|---|---|
| cag | ttt | ctg | cgg | ccc | gtg | aat | ctg | ccc | ggc | cac | ttt | gaa | gtg | ttc | cac | 768 |
| Gln | Phe | Leu | Arg | Pro | Val | Asn | Leu | Pro | Gly | His | Phe | Glu | Val | Phe | His | |
| | 240 | | | | 245 | | | | | 250 | | | | | | |

| | | | | | | | | | | | | | | | | |
|---|---|---|---|---|---|---|---|---|---|---|---|---|---|---|---|---|
| gga | ccc | ggc | gga | gag | aac | ccc | gag | agc | ttc | tac | aga | gcc | ttc | agc | tgg | 816 |
| Gly | Pro | Gly | Gly | Glu | Asn | Pro | Glu | Ser | Phe | Tyr | Arg | Ala | Phe | Ser | Trp | |
| 255 | | | | | 260 | | | | | 265 | | | | | 270 | |

| | | | | | | | | | | | | | | | | |
|---|---|---|---|---|---|---|---|---|---|---|---|---|---|---|---|---|
| gaa | att | ctg | gaa | gcc | gct | ctg | aaa | aca | tcc | aag | gac | aca | ctg | gaa | aag | 864 |
| Glu | Ile | Leu | Glu | Ala | Ala | Leu | Lys | Thr | Ser | Lys | Asp | Thr | Leu | Glu | Lys | |
| | | | | 275 | | | | | 280 | | | | | 285 | | |

| | | | | | | | | | | | | | | | | |
|---|---|---|---|---|---|---|---|---|---|---|---|---|---|---|---|---|
| ctg | ttc | gag | aag | caa | gac | caa | ggg | acc | atc | atg | aag | gcc | agc | aaa | gaa | 912 |
| Leu | Phe | Glu | Lys | Gln | Asp | Gln | Gly | Thr | Ile | Met | Lys | Ala | Ser | Lys | Glu | |
| | | | 290 | | | | | 295 | | | | | 300 | | | |

| | | | | | | | | | | | | | | | | |
|---|---|---|---|---|---|---|---|---|---|---|---|---|---|---|---|---|
| cag | atc | cgg | gcc | atg | agc | aga | aga | ggc | gag | ggc | ccc | aag | atc | tgg | ccc | 960 |
| Gln | Ile | Arg | Ala | Met | Ser | Arg | Arg | Gly | Glu | Gly | Pro | Lys | Ile | Trp | Pro | |
| | | 305 | | | | | 310 | | | | | 315 | | | | |

| | | | | | | | | | | | | | | | | |
|---|---|---|---|---|---|---|---|---|---|---|---|---|---|---|---|---|
| ttc | acc | gag | gaa | agc | acc | ggc | agc | ttc | aag | ctg | ttt | aag | aag | gac | ccc | 1008 |
| Phe | Thr | Glu | Glu | Ser | Thr | Gly | Ser | Phe | Lys | Leu | Phe | Lys | Lys | Asp | Pro | |
| | 320 | | | | | 325 | | | | | 330 | | | | | |

| | | | | | | | | | | | | | | | | |
|---|---|---|---|---|---|---|---|---|---|---|---|---|---|---|---|---|
| agc | cag | agc | aac | aaa | tac | ggg | cag | ctg | ttt | gag | gcc | gag | cgg | atc | gac | 1056 |
| Ser | Gln | Ser | Asn | Lys | Tyr | Gly | Gln | Leu | Phe | Glu | Ala | Glu | Arg | Ile | Asp | |
| 335 | | | | | 340 | | | | | 345 | | | | | 350 | |

| | | | | | | | | | | | | | | | | |
|---|---|---|---|---|---|---|---|---|---|---|---|---|---|---|---|---|
| tac | ccc | cca | ctg | gaa | aag | ctg | gac | atg | gtg | gtg | tcc | tac | gcc | aat | atc | 1104 |
| Tyr | Pro | Pro | Leu | Glu | Lys | Leu | Asp | Met | Val | Val | Ser | Tyr | Ala | Asn | Ile | |
| | | | | 355 | | | | | 360 | | | | | 365 | | |

| | | | | | | | | | | | | | | | | |
|---|---|---|---|---|---|---|---|---|---|---|---|---|---|---|---|---|
| acc | aag | ggc | ggc | atg | agc | gtg | ccc | ttt | tac | aac | agc | aga | gcc | acc | aag | 1152 |
| Thr | Lys | Gly | Gly | Met | Ser | Val | Pro | Phe | Tyr | Asn | Ser | Arg | Ala | Thr | Lys | |
| | | | 370 | | | | | 375 | | | | | 380 | | | |

| | | | | | | | | | | | | | | | | |
|---|---|---|---|---|---|---|---|---|---|---|---|---|---|---|---|---|
| atc | gcc | atc | gtg | gtg | tcc | ggc | gag | ggc | tgc | gtg | gaa | atc | gct | tgc | cct | 1200 |
| Ile | Ala | Ile | Val | Val | Ser | Gly | Glu | Gly | Cys | Val | Glu | Ile | Ala | Cys | Pro | |
| | | 385 | | | | | 390 | | | | | 395 | | | | |

| | | | | | | | | | | | | | | | | |
|---|---|---|---|---|---|---|---|---|---|---|---|---|---|---|---|---|
| cat | ctg | agc | agc | agc | aag | tcc | agc | cac | ccc | agc | tac | aag | aag | ctg | cgg | 1248 |
| His | Leu | Ser | Ser | Ser | Lys | Ser | Ser | His | Pro | Ser | Tyr | Lys | Lys | Leu | Arg | |
| | 400 | | | | | 405 | | | | | 410 | | | | | |

| | | | | | | | | | | | | | | | | |
|---|---|---|---|---|---|---|---|---|---|---|---|---|---|---|---|---|
| gcc | aga | atc | cgg | aag | gac | acc | gtg | ttc | atc | gtg | cca | gcc | ggc | cac | cct | 1296 |
| Ala | Arg | Ile | Arg | Lys | Asp | Thr | Val | Phe | Ile | Val | Pro | Ala | Gly | His | Pro | |
| 415 | | | | | 420 | | | | | 425 | | | | | 430 | |

| | | | | | | | | | | | | | | | | |
|---|---|---|---|---|---|---|---|---|---|---|---|---|---|---|---|---|
| ttt | gcc | aca | gtg | gcc | agc | ggc | aac | gag | aat | ctg | gaa | atc | gtg | tgc | ttc | 1344 |
| Phe | Ala | Thr | Val | Ala | Ser | Gly | Asn | Glu | Asn | Leu | Glu | Ile | Val | Cys | Phe | |
| | | | | 435 | | | | | 440 | | | | | 445 | | |

| | | | | | | | | | | | | | | | | |
|---|---|---|---|---|---|---|---|---|---|---|---|---|---|---|---|---|
| gaa | gtg | aac | gcc | gag | ggc | aac | atc | cgg | tac | aca | ctg | gcc | ggc | aag | aag | 1392 |
| Glu | Val | Asn | Ala | Glu | Gly | Asn | Ile | Arg | Tyr | Thr | Leu | Ala | Gly | Lys | Lys | |
| | | | 450 | | | | | 455 | | | | | 460 | | | |

| | | | | | | | | | | | | | | | | |
|---|---|---|---|---|---|---|---|---|---|---|---|---|---|---|---|---|
| aac | atc | atc | aaa | gtg | atg | gaa | aag | gaa | gcc | aaa | gaa | ctg | gcc | ttt | aag | 1440 |
| Asn | Ile | Ile | Lys | Val | Met | Glu | Lys | Glu | Ala | Lys | Glu | Leu | Ala | Phe | Lys | |
| | | 465 | | | | | 470 | | | | | 475 | | | | |

| | | | | | | | | | | | | | | | | |
|---|---|---|---|---|---|---|---|---|---|---|---|---|---|---|---|---|
| atg | gaa | ggc | gag | gaa | gtg | gac | aaa | gtg | ttc | ggc | aag | caa | gat | gaa | gag | 1488 |
| Met | Glu | Gly | Glu | Glu | Val | Asp | Lys | Val | Phe | Gly | Lys | Gln | Asp | Glu | Glu | |
| | 480 | | | | | 485 | | | | | 490 | | | | | |

| | | | | | | | | | | | | | | | | |
|---|---|---|---|---|---|---|---|---|---|---|---|---|---|---|---|---|
| ttc | ttc | ttt | caa | ggc | ccc | gag | tgg | cgc | aaa | gag | aaa | gag | ggc | aga | gcc | 1536 |
| Phe | Phe | Phe | Gln | Gly | Pro | Glu | Trp | Arg | Lys | Glu | Lys | Glu | Gly | Arg | Ala | |
| 495 | | | | 500 | | | | | 505 | | | | | 510 | | |

| | | | | |
|---|---|---|---|---|
| gac | gag | gaattc | | 1548 |
| Asp | Glu | | | |

```
<210> SEQ ID NO 15
<211> LENGTH: 512
<212> TYPE: PRT
<213> ORGANISM: Anacardium occidentale

<400> SEQUENCE: 15
```

-continued

```
Lys Ile Asp Pro Glu Leu Lys Gln Cys Lys His Gln Cys Lys Val Gln
1               5                   10                  15

Arg Gln Tyr Asp Glu Gln Gln Lys Glu Gln Cys Val Lys Glu Cys Glu
            20                  25                  30

Lys Tyr Tyr Lys Glu Lys Lys Gly Arg Glu Arg Glu His Glu Glu Glu
        35                  40                  45

Glu Glu Glu Trp Gly Thr Gly Gly Val Asp Glu Pro Ser Thr His Glu
50                  55                  60

Pro Ala Glu Lys His Leu Ser Gln Cys Met Arg Gln Cys Glu Arg Gln
65                  70                  75                  80

Glu Gly Gly Gln Gln Lys Gln Leu Cys Arg Phe Arg Cys Gln Glu Arg
                85                  90                  95

Tyr Lys Lys Glu Arg Gly Gln His Asn Tyr Lys Arg Glu Asp Asp Glu
            100                 105                 110

Asp Glu Asp Glu Asp Glu Ala Glu Glu Asp Glu Asn Pro Tyr Val
        115                 120                 125

Phe Glu Asp Glu Asp Phe Thr Thr Lys Val Lys Thr Glu Gln Gly Lys
130                 135                 140

Val Val Leu Leu Pro Lys Phe Thr Gln Lys Ser Lys Leu Leu His Ala
145                 150                 155                 160

Leu Glu Lys Tyr Arg Leu Ala Val Leu Val Ala Asn Pro Gln Ala Phe
            165                 170                 175

Val Val Pro Ser His Met Asp Ala Asp Ser Ile Phe Phe Val Ser Trp
            180                 185                 190

Gly Arg Gly Thr Ile Thr Lys Ile Leu Glu Asn Lys Arg Glu Ser Ile
        195                 200                 205

Asn Val Arg Gln Gly Asp Ile Val Ser Ile Ser Ser Gly Thr Pro Phe
210                 215                 220

Tyr Ile Ala Asn Asn Asp Glu Asn Glu Lys Leu Tyr Leu Val Gln Phe
225                 230                 235                 240

Leu Arg Pro Val Asn Leu Pro Gly His Phe Glu Val Phe His Gly Pro
            245                 250                 255

Gly Gly Glu Asn Pro Glu Ser Phe Tyr Arg Ala Phe Ser Trp Glu Ile
            260                 265                 270

Leu Glu Ala Ala Leu Lys Thr Ser Lys Asp Thr Leu Glu Lys Leu Phe
275                 280                 285

Glu Lys Gln Asp Gln Gly Thr Ile Met Lys Ala Ser Lys Glu Gln Ile
290                 295                 300

Arg Ala Met Ser Arg Arg Gly Glu Gly Pro Lys Ile Trp Pro Phe Thr
305                 310                 315                 320

Glu Glu Ser Thr Gly Ser Phe Lys Leu Phe Lys Lys Asp Pro Ser Gln
            325                 330                 335

Ser Asn Lys Tyr Gly Gln Leu Phe Glu Ala Glu Arg Ile Asp Tyr Pro
            340                 345                 350

Pro Leu Glu Lys Leu Asp Met Val Val Ser Tyr Ala Asn Ile Thr Lys
        355                 360                 365

Gly Gly Met Ser Val Pro Phe Tyr Asn Ser Arg Ala Thr Lys Ile Ala
        370                 375                 380

Ile Val Val Ser Gly Glu Gly Cys Val Glu Ile Ala Cys Pro His Leu
385                 390                 395                 400

Ser Ser Ser Lys Ser Ser His Pro Ser Tyr Lys Lys Leu Arg Ala Arg
            405                 410                 415

Ile Arg Lys Asp Thr Val Phe Ile Val Pro Ala Gly His Pro Phe Ala
```

```
                420                 425                 430
Thr Val Ala Ser Gly Asn Glu Asn Leu Glu Ile Val Cys Phe Glu Val
            435                 440                 445

Asn Ala Glu Gly Asn Ile Arg Tyr Thr Leu Ala Gly Lys Lys Asn Ile
450                 455                 460

Ile Lys Val Met Glu Lys Ala Lys Glu Leu Ala Phe Lys Met Glu
465                 470                 475                 480

Gly Glu Glu Val Asp Lys Val Phe Gly Lys Gln Asp Glu Glu Phe Phe
                485                 490                 495

Phe Gln Gly Pro Glu Trp Arg Lys Glu Lys Glu Gly Arg Ala Asp Glu
            500                 505                 510

<210> SEQ ID NO 16
<211> LENGTH: 1383
<212> TYPE: DNA
<213> ORGANISM: Anacardium occidentale
<220> FEATURE:
<221> NAME/KEY: CDS
<222> LOCATION: (7)..(1377)

<400> SEQUENCE: 16 ctcgag ctg agc gtg tgc ttt ctg att ctg ttc cac ggc tgt ctg gcc      48
       Leu Ser Val Cys Phe Leu Ile Leu Phe His Gly Cys Leu Ala
       1               5                   10 agc cgg caa gaa tgg cag cag caa gac gag tgc cag atc gac cgg ctg     96
Ser Arg Gln Glu Trp Gln Gln Gln Asp Glu Cys Gln Ile Asp Arg Leu
15                  20                  25                  30 gac gct ctg gaa ccc gac aac cgg gtg gaa tac gag gcc ggc aca gtg    144
Asp Ala Leu Glu Pro Asp Asn Arg Val Glu Tyr Glu Ala Gly Thr Val
                35                  40                  45 gaa gct tgg gac ccc aac cac gag cag ttc aga tgt gcc ggc gtg gca    192
Glu Ala Trp Asp Pro Asn His Glu Gln Phe Arg Cys Ala Gly Val Ala
            50                  55                  60 ctc gtg cgg cac acc atc cag cca aac gga ctg ctg ctg ccc cag tac    240
Leu Val Arg His Thr Ile Gln Pro Asn Gly Leu Leu Leu Pro Gln Tyr
65                  70                  75 agc aac gcc ccc cag ctg atc tat gtg gtg caa ggc gag ggc atg acc    288
Ser Asn Ala Pro Gln Leu Ile Tyr Val Val Gln Gly Glu Gly Met Thr
                80                  85                  90 ggc atc agc tat ccc ggc tgc ccc gag aca tat caa gcc cct cag caa    336
Gly Ile Ser Tyr Pro Gly Cys Pro Glu Thr Tyr Gln Ala Pro Gln Gln
95                  100                 105                 110 ggc aga cag caa ggc cag agc ggc cgg ttc caa gac cgg cac cag aag    384
Gly Arg Gln Gln Gly Gln Ser Gly Arg Phe Gln Asp Arg His Gln Lys
            115                 120                 125 atc cgg cgg ttc aga cgg ggc gac atc att gcc att cca gcc ggg gtg    432
Ile Arg Arg Phe Arg Arg Gly Asp Ile Ile Ala Ile Pro Ala Gly Val
                130                 135                 140 gcc cac tgg tgc tac aac gag ggc aat agc ccc gtc gtg acc gtg aca    480
Ala His Trp Cys Tyr Asn Glu Gly Asn Ser Pro Val Val Thr Val Thr
145                 150                 155 ctg ctg gac gtg tcc aac agc cag aac cag ctg gac cgg acc ccc cgg    528
Leu Leu Asp Val Ser Asn Ser Gln Asn Gln Leu Asp Arg Thr Pro Arg
                160                 165                 170 aag ttt cat ctg gcc ggc aac ccc aag gac gtg ttc cag caa cag cag    576
Lys Phe His Leu Ala Gly Asn Pro Lys Asp Val Phe Gln Gln Gln Gln
175                 180                 185                 190 cag cac cag agc cgg ggc aga aat ctg ttc agc ggc ttc gac acc gag    624
Gln His Gln Ser Arg Gly Arg Asn Leu Phe Ser Gly Phe Asp Thr Glu
            195                 200                 205
```

| | |
|---|---|
| ctg ctg gcc gag gct ttt caa gtg gac gag cgg ctg atc aag cag ctg<br>Leu Leu Ala Glu Ala Phe Gln Val Asp Glu Arg Leu Ile Lys Gln Leu<br>210                      215                    220 | 672 |
| aag tcc gag gac aac aga ggc ggc atc gtg aaa gtg aag gac gac gag<br>Lys Ser Glu Asp Asn Arg Gly Gly Ile Val Lys Val Lys Asp Asp Glu<br>225                      230                    235 | 720 |
| ctg aga gtg atc cgg ccc agc aga agc cag agc gag aga ggc agc gag<br>Leu Arg Val Ile Arg Pro Ser Arg Ser Gln Ser Glu Arg Gly Ser Glu<br>240                      245                    250 | 768 |
| agc gag gaa gag tct gag gac gag aag cgg aga tgg ggc cag cgg gac<br>Ser Glu Glu Glu Ser Glu Asp Glu Lys Arg Arg Trp Gly Gln Arg Asp<br>255                  260                    265                    270 | 816 |
| aac ggc atc gaa gag aca atc tgc acc atg cgg ctg aaa gag aac atc<br>Asn Gly Ile Glu Glu Thr Ile Cys Thr Met Arg Leu Lys Glu Asn Ile<br>                      275                    280                    285 | 864 |
| aac gac ccc gcc aga gcc gac atc tac acc ccc gaa gtg ggc cgg ctg<br>Asn Asp Pro Ala Arg Ala Asp Ile Tyr Thr Pro Glu Val Gly Arg Leu<br>290                      295                    300 | 912 |
| aca act ctg aac tct ctg aat ctg ccc att ctg aag tgg ctg cag ctg<br>Thr Thr Leu Asn Ser Leu Asn Leu Pro Ile Leu Lys Trp Leu Gln Leu<br>                      305                    310                    315 | 960 |
| tcc gtg gaa aag ggg gtg ctg tac aag aac gct ctg gtg ctg cct cac<br>Ser Val Glu Lys Gly Val Leu Tyr Lys Asn Ala Leu Val Leu Pro His<br>320                      325                    330 | 1008 |
| tgg aat ctg aac agc cac agc atc atc tac ggc tgc aag ggc aag ggc<br>Trp Asn Leu Asn Ser His Ser Ile Ile Tyr Gly Cys Lys Gly Lys Gly<br>335                  340                    345                    350 | 1056 |
| caa gtc caa gtg gtg gac aac ttc ggc aac aga gtg ttc gac ggc gaa<br>Gln Val Gln Val Val Asp Asn Phe Gly Asn Arg Val Phe Asp Gly Glu<br>                      355                    360                    365 | 1104 |
| gtg cgc gag ggc cag atg ctc gtg gtg ccc cag aat ttc gcc gtc gtg<br>Val Arg Glu Gly Gln Met Leu Val Val Pro Gln Asn Phe Ala Val Val<br>370                      375                    380 | 1152 |
| aag cgg gcc aga gaa gaa aga ttc gag tgg atc agc ttc aag acc aac<br>Lys Arg Ala Arg Glu Glu Arg Phe Glu Trp Ile Ser Phe Lys Thr Asn<br>385                  390                    395 | 1200 |
| gac cgg gcc atg acc agc cct ctg gcc gga aga aca tct gtg ctg ggc<br>Asp Arg Ala Met Thr Ser Pro Leu Ala Gly Arg Thr Ser Val Leu Gly<br>400                      405                    410 | 1248 |
| ggc atg ccc gag gaa gtg ctg gct aac gcc ttc cag atc agc aga gag<br>Gly Met Pro Glu Glu Val Leu Ala Asn Ala Phe Gln Ile Ser Arg Glu<br>415                  420                    425                    430 | 1296 |
| gac gcc cgg aag atc aag ttc aac aac cag cag acc aca ctg acc agc<br>Asp Ala Arg Lys Ile Lys Phe Asn Asn Gln Gln Thr Thr Leu Thr Ser<br>                      435                    440                    445 | 1344 |
| ggc gag agc agc cac cac atg aga gat gac gcc gaattc<br>Gly Glu Ser Ser His His Met Arg Asp Asp Ala<br>450                      455 | 1383 |

```
<210> SEQ ID NO 17
<211> LENGTH: 457
<212> TYPE: PRT
<213> ORGANISM: Anacardium occidentale

<400> SEQUENCE: 17

Leu Ser Val Cys Phe Leu Ile Leu Phe His Gly Cys Leu Ala Ser Arg
1               5                   10                  15

Gln Glu Trp Gln Gln Gln Asp Glu Cys Gln Ile Asp Arg Leu Asp Ala
            20                  25                  30
```

```
Leu Glu Pro Asp Asn Arg Val Glu Tyr Glu Ala Gly Thr Val Glu Ala
             35                  40                  45

Trp Asp Pro Asn His Glu Gln Phe Arg Cys Ala Gly Val Ala Leu Val
 50                  55                  60

Arg His Thr Ile Gln Pro Asn Gly Leu Leu Pro Gln Tyr Ser Asn
 65                  70                  75                  80

Ala Pro Gln Leu Ile Tyr Val Val Gln Gly Glu Gly Met Thr Gly Ile
                 85                  90                  95

Ser Tyr Pro Gly Cys Pro Glu Thr Tyr Gln Ala Pro Gln Gly Arg
                100                 105                 110

Gln Gln Gly Gln Ser Gly Arg Phe Gln Asp Arg His Gln Lys Ile Arg
             115                 120                 125

Arg Phe Arg Arg Gly Asp Ile Ile Ala Ile Pro Ala Gly Val Ala His
    130                 135                 140

Trp Cys Tyr Asn Glu Gly Asn Ser Pro Val Val Thr Val Thr Leu Leu
145                 150                 155                 160

Asp Val Ser Asn Ser Gln Asn Gln Leu Asp Arg Thr Pro Arg Lys Phe
                165                 170                 175

His Leu Ala Gly Asn Pro Lys Asp Val Phe Gln Gln Gln Gln His
                180                 185                 190

Gln Ser Arg Gly Arg Asn Leu Phe Ser Gly Phe Asp Thr Glu Leu Leu
    195                 200                 205

Ala Glu Ala Phe Gln Val Asp Glu Arg Leu Ile Lys Gln Leu Lys Ser
    210                 215                 220

Glu Asp Asn Arg Gly Gly Ile Val Lys Val Lys Asp Glu Leu Arg
225                 230                 235                 240

Val Ile Arg Pro Ser Arg Ser Gln Ser Glu Arg Gly Ser Glu Ser Glu
                245                 250                 255

Glu Glu Ser Glu Asp Glu Lys Arg Arg Trp Gly Gln Arg Asp Asn Gly
        260                 265                 270

Ile Glu Glu Thr Ile Cys Thr Met Arg Leu Lys Glu Asn Ile Asn Asp
            275                 280                 285

Pro Ala Arg Ala Asp Ile Tyr Thr Pro Glu Val Gly Arg Leu Thr Thr
    290                 295                 300

Leu Asn Ser Leu Asn Leu Pro Ile Leu Lys Trp Leu Gln Leu Ser Val
305                 310                 315                 320

Glu Lys Gly Val Leu Tyr Lys Asn Ala Leu Val Leu Pro His Trp Asn
                325                 330                 335

Leu Asn Ser His Ser Ile Ile Tyr Gly Cys Lys Gly Lys Gly Gln Val
            340                 345                 350

Gln Val Val Asp Asn Phe Gly Asn Arg Val Phe Asp Gly Glu Val Arg
    355                 360                 365

Glu Gly Gln Met Leu Val Val Pro Gln Asn Phe Ala Val Val Lys Arg
    370                 375                 380

Ala Arg Glu Glu Arg Phe Glu Trp Ile Ser Phe Lys Thr Asn Asp Arg
385                 390                 395                 400

Ala Met Thr Ser Pro Leu Ala Gly Arg Thr Ser Val Leu Gly Gly Met
                405                 410                 415

Pro Glu Glu Val Leu Ala Asn Ala Phe Gln Ile Ser Arg Glu Asp Ala
                420                 425                 430

Arg Lys Ile Lys Phe Asn Asn Gln Gln Thr Thr Leu Thr Ser Gly Glu
    435                 440                 445

Ser Ser His His Met Arg Asp Asp Ala
```

```
<210> SEQ ID NO 18
<211> LENGTH: 366
<212> TYPE: DNA
<213> ORGANISM: Anacardium occidentale
<220> FEATURE:
<221> NAME/KEY: CDS
<222> LOCATION: (7)..(360)

<400> SEQUENCE: 18 ctcgag agc atc tac cgg gcc atc gtg gaa gtg gaa gag gac agc ggc        48
       Ser Ile Tyr Arg Ala Ile Val Glu Val Glu Glu Asp Ser Gly
       1               5                   10 aga gag cag agc tgc cag cgg cag ttc gag gaa cag cag cgg ttc aga       96
Arg Glu Gln Ser Cys Gln Arg Gln Phe Glu Glu Gln Gln Arg Phe Arg
15                  20                  25                  30 aac tgc cag aga tac gtg aag caa gaa gtg cag aga ggc ggc aga tac      144
Asn Cys Gln Arg Tyr Val Lys Gln Glu Val Gln Arg Gly Gly Arg Tyr
                35                  40                  45 aac cag aga caa gag tct ctg aga gag tgc tgc caa gag ctg caa gaa      192
Asn Gln Arg Gln Glu Ser Leu Arg Glu Cys Cys Gln Glu Leu Gln Glu
        50                  55                  60 gtg gac cgg cgc tgc cgg tgc cag aat ctg gaa cag atg gtg cgc cag      240
Val Asp Arg Arg Cys Arg Cys Gln Asn Leu Glu Gln Met Val Arg Gln
65                  70                  75 ctg cag cag caa gag cag atc aag ggc gag gaa gtg cgc gag ctg tac      288
Leu Gln Gln Gln Glu Gln Ile Lys Gly Glu Glu Val Arg Glu Leu Tyr
            80                  85                  90 gag aca gcc agc gag ctg cct cgg atc tgc agc atc agc cca agc caa      336
Glu Thr Ala Ser Glu Leu Pro Arg Ile Cys Ser Ile Ser Pro Ser Gln
95                  100                 105                 110 ggc tgc cag ttc cag agc agc tac gaattc                               366
Gly Cys Gln Phe Gln Ser Ser Tyr
                115

<210> SEQ ID NO 19
<211> LENGTH: 118
<212> TYPE: PRT
<213> ORGANISM: Anacardium occidentale

<400> SEQUENCE: 19

Ser Ile Tyr Arg Ala Ile Val Glu Val Glu Glu Asp Ser Gly Arg Glu
1               5                   10                  15

Gln Ser Cys Gln Arg Gln Phe Glu Glu Gln Gln Arg Phe Arg Asn Cys
            20                  25                  30

Gln Arg Tyr Val Lys Gln Glu Val Gln Arg Gly Gly Arg Tyr Asn Gln
        35                  40                  45

Arg Gln Glu Ser Leu Arg Glu Cys Cys Gln Glu Leu Gln Glu Val Asp
    50                  55                  60

Arg Arg Cys Arg Cys Gln Asn Leu Glu Gln Met Val Arg Gln Leu Gln
65                  70                  75                  80

Gln Gln Glu Gln Ile Lys Gly Glu Glu Val Arg Glu Leu Tyr Glu Thr
                85                  90                  95

Ala Ser Glu Leu Pro Arg Ile Cys Ser Ile Ser Pro Gln Gly Cys
            100                 105                 110

Gln Phe Gln Ser Ser Tyr
        115

<210> SEQ ID NO 20
```

```
<211> LENGTH: 3297
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (7)..(3291)

<400> SEQUENCE: 20
```

```
ctcgag ctg agc gtg tgc ttt ctg att ctg ttc cac ggc tgt ctg gcc          48
       Leu Ser Val Cys Phe Leu Ile Leu Phe His Gly Cys Leu Ala
       1               5                  10 agc cgg caa gaa tgg cag cag caa gac gag tgc cag atc gac cgg ctg          96
Ser Arg Gln Glu Trp Gln Gln Gln Asp Glu Cys Gln Ile Asp Arg Leu
15              20                  25                  30 gac gct ctg gaa ccc gac aac cgg gtg gaa tac gag gcc ggc aca gtg         144
Asp Ala Leu Glu Pro Asp Asn Arg Val Glu Tyr Glu Ala Gly Thr Val
                35                  40                  45 gaa gct tgg gac ccc aac cac gag cag ttc aga tgt gcc ggc gtg gca         192
Glu Ala Trp Asp Pro Asn His Glu Gln Phe Arg Cys Ala Gly Val Ala
        50                  55                  60 ctc gtg cgg cac acc atc cag cca aac gga ctg ctg ctg ccc cag tac         240
Leu Val Arg His Thr Ile Gln Pro Asn Gly Leu Leu Leu Pro Gln Tyr
65                  70                  75 agc aac gcc ccc cag ctg atc tat gtg gtg caa ggc gag ggc atg acc         288
Ser Asn Ala Pro Gln Leu Ile Tyr Val Val Gln Gly Glu Gly Met Thr
                80                  85                  90 ggc atc agc tat ccc ggc tgc ccc gag aca tat caa gcc cct cag caa         336
Gly Ile Ser Tyr Pro Gly Cys Pro Glu Thr Tyr Gln Ala Pro Gln Gln
95                  100                 105                 110 ggc aga cag caa ggc cag agc ggc cgg ttc caa gac cgg cac cag aag         384
Gly Arg Gln Gln Gly Gln Ser Gly Arg Phe Gln Asp Arg His Gln Lys
                115                 120                 125 atc cgg cgg ttc aga cgg ggc gac atc att gcc att cca gcc ggg gtg         432
Ile Arg Arg Phe Arg Arg Gly Asp Ile Ile Ala Ile Pro Ala Gly Val
            130                 135                 140 gcc cac tgg tgc tac aac gag ggc aat agc ccc gtc gtg acc gtg aca         480
Ala His Trp Cys Tyr Asn Glu Gly Asn Ser Pro Val Val Thr Val Thr
        145                 150                 155 ctg ctg gac gtg tcc aac agc cag aac cag ctg gac cgg acc ccc cgg         528
Leu Leu Asp Val Ser Asn Ser Gln Asn Gln Leu Asp Arg Thr Pro Arg
160                 165                 170 aag ttt cat ctg gcc ggc aac ccc aag gac gtg ttc cag caa cag cag         576
Lys Phe His Leu Ala Gly Asn Pro Lys Asp Val Phe Gln Gln Gln Gln
175             180                 185                 190 cag cac cag agc cgg ggc aga aat ctg ttc agc ggc ttc gac acc gag         624
Gln His Gln Ser Arg Gly Arg Asn Leu Phe Ser Gly Phe Asp Thr Glu
                195                 200                 205 ctg ctg gcc gag gct ttt caa gtg gac gag cgg ctg atc aag cag ctg         672
Leu Leu Ala Glu Ala Phe Gln Val Asp Glu Arg Leu Ile Lys Gln Leu
            210                 215                 220 aag tcc gag gac aac aga ggc ggc atc gtg aaa gtg aag gac gac gag         720
Lys Ser Glu Asp Asn Arg Gly Gly Ile Val Lys Val Lys Asp Asp Glu
225                 230                 235 ctg aga gtg atc cgg ccc agc aga agc cag agc gag aga ggc agc gag         768
Leu Arg Val Ile Arg Pro Ser Arg Ser Gln Ser Glu Arg Gly Ser Glu
        240                 245                 250 agc gag gaa gag tct gag gac gag aag cgg aga tgg ggc cag cgg gac         816
Ser Glu Glu Glu Ser Glu Asp Glu Lys Arg Arg Trp Gly Gln Arg Asp
255                 260                 265                 270
```

```
aac ggc atc gaa gag aca atc tgc acc atg cgg ctg aaa gag aac atc         864
Asn Gly Ile Glu Glu Thr Ile Cys Thr Met Arg Leu Lys Glu Asn Ile
            275                 280                 285 aac gac ccc gcc aga gcc gac atc tac acc ccc gaa gtg ggc cgg ctg         912
Asn Asp Pro Ala Arg Ala Asp Ile Tyr Thr Pro Glu Val Gly Arg Leu
            290                 295                 300 aca act ctg aac tct ctg aat ctg ccc att ctg aag tgg ctg cag ctg         960
Thr Thr Leu Asn Ser Leu Asn Leu Pro Ile Leu Lys Trp Leu Gln Leu
            305                 310                 315 tcc gtg gaa aag ggg gtg ctg tac aag aac gct ctg gtg ctg cct cac        1008
Ser Val Glu Lys Gly Val Leu Tyr Lys Asn Ala Leu Val Leu Pro His
            320                 325                 330 tgg aat ctg aac agc cac agc atc atc tac ggc tgc aag ggc aag ggc        1056
Trp Asn Leu Asn Ser His Ser Ile Ile Tyr Gly Cys Lys Gly Lys Gly
335                 340                 345                 350 caa gtc caa gtg gtg gac aac ttc ggc aac aga gtg ttc gac ggc gaa        1104
Gln Val Gln Val Val Asp Asn Phe Gly Asn Arg Val Phe Asp Gly Glu
            355                 360                 365 gtg cgc gag ggc cag atg ctc gtg gtg ccc cag aat ttc gcc gtc gtg        1152
Val Arg Glu Gly Gln Met Leu Val Val Pro Gln Asn Phe Ala Val Val
            370                 375                 380 aag cgg gcc aga gaa gaa aga ttc gag tgg atc agc ttc aag acc aac        1200
Lys Arg Ala Arg Glu Glu Arg Phe Glu Trp Ile Ser Phe Lys Thr Asn
            385                 390                 395 gac cgg gcc atg acc agc cct ctg gcc gga aga aca tct gtg ctg ggc        1248
Asp Arg Ala Met Thr Ser Pro Leu Ala Gly Arg Thr Ser Val Leu Gly
            400                 405                 410 ggc atg ccc gag gaa gtg ctg gct aac gcc ttc cag atc agc aga gag        1296
Gly Met Pro Glu Glu Val Leu Ala Asn Ala Phe Gln Ile Ser Arg Glu
415                 420                 425                 430 gac gcc cgg aag atc aag ttc aac aac cag cag acc aca ctg acc agc        1344
Asp Ala Arg Lys Ile Lys Phe Asn Asn Gln Gln Thr Thr Leu Thr Ser
            435                 440                 445 ggc gag agc agc cac cac atg aga gat gac gcc ggc gga ggg ggc aag        1392
Gly Glu Ser Ser His His Met Arg Asp Asp Ala Gly Gly Gly Gly Lys
            450                 455                 460 atc gac ccc gag ctg aag cag tgc aag cac cag tgc aaa gtg cag cgg        1440
Ile Asp Pro Glu Leu Lys Gln Cys Lys His Gln Cys Lys Val Gln Arg
            465                 470                 475 cag tac gac gag cag cag aaa gaa cag tgc gtg aaa gag tgc gag aag        1488
Gln Tyr Asp Glu Gln Gln Lys Glu Gln Cys Val Lys Glu Cys Glu Lys
            480                 485                 490 tac tac aaa gag aag aag ggc cgc gag cgc gag cac gaa gag gaa gag        1536
Tyr Tyr Lys Glu Lys Lys Gly Arg Glu Arg Glu His Glu Glu Glu Glu
495                 500                 505                 510 gaa gaa tgg ggc acc ggc gga gtg gac gag cct tct aca cac gag ccc        1584
Glu Glu Trp Gly Thr Gly Gly Val Asp Glu Pro Ser Thr His Glu Pro
            515                 520                 525 gcc gag aaa cat ctg agc cag tgc atg aga cag tgc gaa cgg caa gag        1632
Ala Glu Lys His Leu Ser Gln Cys Met Arg Gln Cys Glu Arg Gln Glu
            530                 535                 540 ggc ggc cag cag aaa cag ctg tgc cgg ttc cgg tgc caa gag cgg tac        1680
Gly Gly Gln Gln Lys Gln Leu Cys Arg Phe Arg Cys Gln Glu Arg Tyr
            545                 550                 555 aag aaa gag cgg ggc cag cac aac tac aag aga gag gac gac gag gac        1728
Lys Lys Glu Arg Gly Gln His Asn Tyr Lys Arg Glu Asp Asp Glu Asp
            560                 565                 570 gaa gat gag gac gag gct gag gaa gag gac gag aac ccc tac gtg ttc        1776
Glu Asp Glu Asp Glu Ala Glu Glu Glu Asp Glu Asn Pro Tyr Val Phe
575                 580                 585                 590
```

```
gag gat gag gac ttc acc acc aaa gtg aaa acc gag caa ggc aaa gtg         1824
Glu Asp Glu Asp Phe Thr Thr Lys Val Lys Thr Glu Gln Gly Lys Val
            595                 600                 605 gtg ctg ctg ccc aag ttc acc cag aag tcc aag ctg ctg cac gct ctg         1872
Val Leu Leu Pro Lys Phe Thr Gln Lys Ser Lys Leu Leu His Ala Leu
    610                 615                 620 gaa aag tac cgg ctg gcc gtt ctg gtg gcc aac cct caa gcc ttc gtg         1920
Glu Lys Tyr Arg Leu Ala Val Leu Val Ala Asn Pro Gln Ala Phe Val
625                 630                 635 gtg ccc agc cac atg gac gcc gac agc atc ttc ttc gtg tct tgg ggc         1968
Val Pro Ser His Met Asp Ala Asp Ser Ile Phe Phe Val Ser Trp Gly
            640                 645                 650 aga ggc acc atc acc aag att ctg gaa aac aag cgc gag agc atc aac         2016
Arg Gly Thr Ile Thr Lys Ile Leu Glu Asn Lys Arg Glu Ser Ile Asn
655                 660                 665                 670 gtg cgg caa ggc gac atc gtg tcc atc agc agc ggc acc ccc ttc tac         2064
Val Arg Gln Gly Asp Ile Val Ser Ile Ser Ser Gly Thr Pro Phe Tyr
            675                 680                 685 att gcc aac aac gac gag aac gag aag ctg tat ctg gtg cag ttt ctg         2112
Ile Ala Asn Asn Asp Glu Asn Glu Lys Leu Tyr Leu Val Gln Phe Leu
        690                 695                 700 cgg ccc gtg aat ctg ccc ggc cac ttt gaa gtg ttc cac gga ccc ggc         2160
Arg Pro Val Asn Leu Pro Gly His Phe Glu Val Phe His Gly Pro Gly
    705                 710                 715 gga gag aac ccc gag agc ttc tac aga gcc ttc agc tgg gaa att ctg         2208
Gly Glu Asn Pro Glu Ser Phe Tyr Arg Ala Phe Ser Trp Glu Ile Leu
720                 725                 730 gaa gcc gct ctg aaa aca tcc aag gac aca ctg gaa aag ctg ttc gag         2256
Glu Ala Ala Leu Lys Thr Ser Lys Asp Thr Leu Glu Lys Leu Phe Glu
735                 740                 745                 750 aag caa gac caa ggg acc atc atg aag gcc agc aaa gaa cag atc cgg         2304
Lys Gln Asp Gln Gly Thr Ile Met Lys Ala Ser Lys Glu Gln Ile Arg
            755                 760                 765 gcc atg agc aga aga ggc gag ggc ccc aag atc tgg ccc ttc acc gag         2352
Ala Met Ser Arg Arg Gly Glu Gly Pro Lys Ile Trp Pro Phe Thr Glu
        770                 775                 780 gaa agc acc ggc agc ttc aag ctg ttt aag aag gac ccc agc cag agc         2400
Glu Ser Thr Gly Ser Phe Lys Leu Phe Lys Lys Asp Pro Ser Gln Ser
    785                 790                 795 aac aaa tac ggg cag ctg ttt gag gcc gag cgg atc gac tac ccc cca         2448
Asn Lys Tyr Gly Gln Leu Phe Glu Ala Glu Arg Ile Asp Tyr Pro Pro
800                 805                 810 ctg gaa aag ctg gac atg gtg gtg tcc tac gcc aat atc acc aag ggc         2496
Leu Glu Lys Leu Asp Met Val Val Ser Tyr Ala Asn Ile Thr Lys Gly
815                 820                 825                 830 ggc atg agc gtg ccc ttt tac aac agc aga gcc acc aag atc gcc atc         2544
Gly Met Ser Val Pro Phe Tyr Asn Ser Arg Ala Thr Lys Ile Ala Ile
            835                 840                 845 gtg gtg tcc ggc gag ggc tgc gtg gaa atc gct tgc cct cat ctg agc         2592
Val Val Ser Gly Glu Gly Cys Val Glu Ile Ala Cys Pro His Leu Ser
        850                 855                 860 agc agc aag tcc agc cac ccc agc tac aag aag ctg cgg gcc aga atc         2640
Ser Ser Lys Ser Ser His Pro Ser Tyr Lys Lys Leu Arg Ala Arg Ile
    865                 870                 875 cgg aag gac acc gtg ttc atc gtg cca gcc ggc cac cct ttt gcc aca         2688
Arg Lys Asp Thr Val Phe Ile Val Pro Ala Gly His Pro Phe Ala Thr
880                 885                 890 gtg gcc agc ggc aac gag aat ctg gaa atc gtg tgc ttc gaa gtg aac         2736
Val Ala Ser Gly Asn Glu Asn Leu Glu Ile Val Cys Phe Glu Val Asn
```

```
                895                 900                 905                 910
gcc gag ggc aac atc cgg tac aca ctg gcc ggc aag aag aac atc atc          2784
Ala Glu Gly Asn Ile Arg Tyr Thr Leu Ala Gly Lys Lys Asn Ile Ile
                    915                 920                 925 aaa gtg atg gaa aag gaa gcc aaa gaa ctg gcc ttt aag atg gaa ggc          2832
Lys Val Met Glu Lys Glu Ala Lys Glu Leu Ala Phe Lys Met Glu Gly
                930                 935                 940 gag gaa gtg gac aaa gtg ttc ggc aag caa gat gaa gag ttc ttc ttt          2880
Glu Glu Val Asp Lys Val Phe Gly Lys Gln Asp Glu Glu Phe Phe Phe
            945                 950                 955 caa ggc ccc gag tgg cgc aaa gag aaa gag ggc aga gcc gac gag ggc          2928
Gln Gly Pro Glu Trp Arg Lys Glu Lys Glu Gly Arg Ala Asp Glu Gly
        960                 965                 970 gga ggg ggc agc atc tac cgg gcc atc gtg gaa gtg gaa gag gac agc          2976
Gly Gly Gly Ser Ile Tyr Arg Ala Ile Val Glu Val Glu Glu Asp Ser
975                 980                 985                 990 ggc aga gag cag agc tgc cag cgg cag ttc gag gaa cag cag cgg ttc          3024
Gly Arg Glu Gln Ser Cys Gln Arg Gln Phe Glu Glu Gln Gln Arg Phe
                995                 1000                1005 aga aac tgc cag aga tac gtg aag caa gaa gtg cag aga ggc ggc              3069
Arg Asn Cys Gln Arg Tyr Val Lys Gln Glu Val Gln Arg Gly Gly
                1010                1015                1020 aga tac aac cag aga caa gag tct ctg aga gag tgc tgc caa gag              3114
Arg Tyr Asn Gln Arg Gln Glu Ser Leu Arg Glu Cys Cys Gln Glu
                1025                1030                1035 ctg caa gaa gtg gac cgg cgc tgc cgg tgc cag aat ctg gaa cag              3159
Leu Gln Glu Val Asp Arg Arg Cys Arg Cys Gln Asn Leu Glu Gln
                1040                1045                1050 atg gtg cgc cag ctg cag cag caa gag cag atc aag ggc gag gaa              3204
Met Val Arg Gln Leu Gln Gln Gln Glu Gln Ile Lys Gly Glu Glu
                1055                1060                1065 gtg cgc gag ctg tac gag aca gcc agc gag ctg cct cgg atc tgc              3249
Val Arg Glu Leu Tyr Glu Thr Ala Ser Glu Leu Pro Arg Ile Cys
                1070                1075                1080 agc atc agc cca agc caa ggc tgc cag ttc cag agc agc tac gaattc          3297
Ser Ile Ser Pro Ser Gln Gly Cys Gln Phe Gln Ser Ser Tyr
                1085                1090                1095

<210> SEQ ID NO 21
<211> LENGTH: 1095
<212> TYPE: PRT
<213> ORGANISM: Artificial sequence
<220> FEATURE:
<223> OTHER INFORMATION: Synthetic Construct

<400> SEQUENCE: 21

Leu Ser Val Cys Phe Leu Ile Leu Phe His Gly Cys Leu Ala Ser Arg
1               5                   10                  15

Gln Glu Trp Gln Gln Asp Glu Cys Gln Ile Asp Arg Leu Asp Ala
            20                  25                  30

Leu Glu Pro Asp Asn Arg Val Glu Tyr Glu Ala Gly Thr Val Glu Ala
            35                  40                  45

Trp Asp Pro Asn His Glu Gln Phe Arg Cys Ala Gly Val Ala Leu Val
        50                  55                  60

Arg His Thr Ile Gln Pro Asn Gly Leu Leu Pro Gln Tyr Ser Asn
65                  70                  75                  80

Ala Pro Gln Leu Ile Tyr Val Val Gln Gly Glu Gly Met Thr Gly Ile
                85                  90                  95

Ser Tyr Pro Gly Cys Pro Glu Thr Tyr Gln Ala Pro Gln Gln Gly Arg
```

```
              100                 105                 110
Gln Gln Gly Gln Ser Gly Arg Phe Gln Asp Arg His Gln Lys Ile Arg
            115                 120                 125

Arg Phe Arg Arg Gly Asp Ile Ile Ala Ile Pro Ala Gly Val Ala His
130                 135                 140

Trp Cys Tyr Asn Glu Gly Asn Ser Pro Val Val Thr Val Thr Leu Leu
145                 150                 155                 160

Asp Val Ser Asn Ser Gln Asn Gln Leu Asp Arg Thr Pro Arg Lys Phe
                165                 170                 175

His Leu Ala Gly Asn Pro Lys Asp Val Phe Gln Gln Gln Gln Gln His
            180                 185                 190

Gln Ser Arg Gly Arg Asn Leu Phe Ser Gly Phe Asp Thr Glu Leu Leu
        195                 200                 205

Ala Glu Ala Phe Gln Val Asp Glu Arg Leu Ile Lys Gln Leu Lys Ser
    210                 215                 220

Glu Asp Asn Arg Gly Gly Ile Val Lys Val Lys Asp Asp Glu Leu Arg
225                 230                 235                 240

Val Ile Arg Pro Ser Arg Ser Gln Ser Glu Arg Gly Ser Glu Ser Glu
                245                 250                 255

Glu Glu Ser Glu Asp Glu Lys Arg Arg Trp Gly Gln Arg Asp Asn Gly
            260                 265                 270

Ile Glu Glu Thr Ile Cys Thr Met Arg Leu Lys Glu Asn Ile Asn Asp
        275                 280                 285

Pro Ala Arg Ala Asp Ile Tyr Thr Pro Glu Val Gly Arg Leu Thr Thr
    290                 295                 300

Leu Asn Ser Leu Asn Leu Pro Ile Leu Lys Trp Leu Gln Leu Ser Val
305                 310                 315                 320

Glu Lys Gly Val Leu Tyr Lys Asn Ala Leu Val Leu Pro His Trp Asn
                325                 330                 335

Leu Asn Ser His Ser Ile Ile Tyr Gly Cys Lys Gly Lys Gly Gln Val
            340                 345                 350

Gln Val Val Asp Asn Phe Gly Asn Arg Val Phe Asp Gly Glu Val Arg
        355                 360                 365

Glu Gly Gln Met Leu Val Val Pro Gln Asn Phe Ala Val Val Lys Arg
    370                 375                 380

Ala Arg Glu Glu Arg Phe Glu Trp Ile Ser Phe Lys Thr Asn Asp Arg
385                 390                 395                 400

Ala Met Thr Ser Pro Leu Ala Gly Arg Thr Ser Val Leu Gly Gly Met
                405                 410                 415

Pro Glu Glu Val Leu Ala Asn Ala Phe Gln Ile Ser Arg Glu Asp Ala
            420                 425                 430

Arg Lys Ile Lys Phe Asn Asn Gln Gln Thr Thr Leu Thr Ser Gly Glu
        435                 440                 445

Ser Ser His His Met Arg Asp Asp Ala Gly Gly Gly Lys Ile Asp
    450                 455                 460

Pro Glu Leu Lys Gln Cys Lys His Gln Cys Lys Val Gln Arg Gln Tyr
465                 470                 475                 480

Asp Glu Gln Gln Lys Glu Gln Cys Val Lys Glu Cys Glu Lys Tyr Tyr
                485                 490                 495

Lys Glu Lys Lys Gly Arg Glu Arg Glu His Glu Glu Glu Glu Glu Glu
            500                 505                 510

Trp Gly Thr Gly Gly Val Asp Glu Pro Ser Thr His Glu Pro Ala Glu
        515                 520                 525
```

```
Lys His Leu Ser Gln Cys Met Arg Gln Cys Glu Arg Gln Glu Gly Gly
    530                 535                 540

Gln Gln Lys Gln Leu Cys Arg Phe Arg Cys Gln Glu Arg Tyr Lys Lys
545                 550                 555                 560

Glu Arg Gly Gln His Asn Tyr Lys Arg Glu Asp Asp Glu Asp Glu Asp
                565                 570                 575

Glu Asp Glu Ala Glu Glu Asp Glu Asn Pro Tyr Val Phe Glu Asp
            580                 585                 590

Glu Asp Phe Thr Thr Lys Val Lys Thr Glu Gln Gly Lys Val Val Leu
        595                 600                 605

Leu Pro Lys Phe Thr Gln Lys Ser Lys Leu Leu His Ala Leu Glu Lys
    610                 615                 620

Tyr Arg Leu Ala Val Leu Val Ala Asn Pro Gln Ala Phe Val Val Pro
625                 630                 635                 640

Ser His Met Asp Ala Asp Ser Ile Phe Phe Val Ser Trp Gly Arg Gly
                645                 650                 655

Thr Ile Thr Lys Ile Leu Glu Asn Lys Arg Glu Ser Ile Asn Val Arg
                660                 665                 670

Gln Gly Asp Ile Val Ser Ile Ser Ser Gly Thr Pro Phe Tyr Ile Ala
            675                 680                 685

Asn Asn Asp Glu Asn Glu Lys Leu Tyr Leu Val Gln Phe Leu Arg Pro
690                 695                 700

Val Asn Leu Pro Gly His Phe Glu Val Phe His Gly Pro Gly Gly Glu
705                 710                 715                 720

Asn Pro Glu Ser Phe Tyr Arg Ala Phe Ser Trp Glu Ile Leu Glu Ala
                725                 730                 735

Ala Leu Lys Thr Ser Lys Asp Thr Leu Glu Lys Leu Phe Glu Lys Gln
            740                 745                 750

Asp Gln Gly Thr Ile Met Lys Ala Ser Lys Glu Gln Ile Arg Ala Met
        755                 760                 765

Ser Arg Arg Gly Glu Gly Pro Lys Ile Trp Pro Phe Thr Glu Glu Ser
    770                 775                 780

Thr Gly Ser Phe Lys Leu Phe Lys Lys Asp Pro Ser Gln Ser Asn Lys
785                 790                 795                 800

Tyr Gly Gln Leu Phe Glu Ala Glu Arg Ile Asp Tyr Pro Pro Leu Glu
                805                 810                 815

Lys Leu Asp Met Val Val Ser Tyr Ala Asn Ile Thr Lys Gly Gly Met
            820                 825                 830

Ser Val Pro Phe Tyr Asn Ser Arg Ala Thr Lys Ile Ala Ile Val Val
        835                 840                 845

Ser Gly Glu Gly Cys Val Glu Ile Ala Cys Pro His Leu Ser Ser Ser
    850                 855                 860

Lys Ser Ser His Pro Ser Tyr Lys Lys Leu Arg Ala Arg Ile Arg Lys
865                 870                 875                 880

Asp Thr Val Phe Ile Val Pro Ala Gly His Pro Phe Ala Thr Val Ala
                885                 890                 895

Ser Gly Asn Glu Asn Leu Glu Ile Val Cys Phe Glu Val Asn Ala Glu
            900                 905                 910

Gly Asn Ile Arg Tyr Thr Leu Ala Gly Lys Lys Asn Ile Ile Lys Val
        915                 920                 925

Met Glu Lys Glu Ala Lys Glu Leu Ala Phe Lys Met Glu Gly Glu Glu
    930                 935                 940
```

-continued

```
Val Asp Lys Val Phe Gly Lys Gln Asp Glu Glu Phe Phe Gln Gly
945                 950                 955                 960

Pro Glu Trp Arg Lys Glu Lys Glu Gly Arg Ala Asp Glu Gly Gly
            965                 970                 975

Gly Ser Ile Tyr Arg Ala Ile Val Glu Val Glu Glu Asp Ser Gly Arg
        980                 985                 990

Glu Gln Ser Cys Gln Arg Gln Phe Glu Glu Gln Gln Arg Phe Arg Asn
    995                 1000                    1005

Cys Gln Arg Tyr Val Lys Gln  Glu Val Gln Arg Gly  Gly Arg Tyr
    1010                1015                 1020

Asn Gln Arg Gln Glu Ser Leu  Arg Glu Cys Cys Gln  Glu Leu Gln
    1025                1030                 1035

Glu Val Asp Arg Arg Cys Arg  Cys Gln Asn Leu Glu  Gln Met Val
    1040                1045                 1050

Arg Gln Leu Gln Gln Gln Glu  Gln Ile Lys Gly Glu  Glu Val Arg
    1055                1060                 1065

Glu Leu Tyr Glu Thr Ala Ser  Glu Leu Pro Arg Ile  Cys Ser Ile
    1070                1075                 1080

Ser Pro Ser Gln Gly Cys Gln  Phe Gln Ser Ser Tyr
    1085                1090                 1095
```

<210> SEQ ID NO 22
<211> LENGTH: 381
<212> TYPE: DNA
<213> ORGANISM: Juglans nigra
<220> FEATURE:
<221> NAME/KEY: CDS
<222> LOCATION: (7)..(375)

<400> SEQUENCE: 22

```
ctcgag cgg acc acc atc acc acc atg gaa atc gac gag gac atc gac         48
       Arg Thr Thr Ile Thr Thr Met Glu Ile Asp Glu Asp Ile Asp
       1               5                   10 aac ccc aga aga aga ggc gag ggc tgc caa gag cag atc cag cgg cag        96
Asn Pro Arg Arg Arg Gly Glu Gly Cys Gln Glu Gln Ile Gln Arg Gln
15                  20                  25                  30 cag aat ctg aac cac tgc cag tac tat ctg agg cag cag agc aga agc       144
Gln Asn Leu Asn His Cys Gln Tyr Tyr Leu Arg Gln Gln Ser Arg Ser
                35                  40                  45 ggc ggc tac gac gag gat aac cag aga cag cac ttc aga cag tgc tgc       192
Gly Gly Tyr Asp Glu Asp Asn Gln Arg Gln His Phe Arg Gln Cys Cys
            50                  55                  60 cag cag ctg agc cag atc gag gaa cag tgc cag tgc gag gga ctg aga       240
Gln Gln Leu Ser Gln Ile Glu Glu Gln Cys Gln Cys Glu Gly Leu Arg
        65                  70                  75 caa gcc gtg cgg aga caa cag cag cag caa gga ctg cgg ggc gaa gag       288
Gln Ala Val Arg Arg Gln Gln Gln Gln Gln Gly Leu Arg Gly Glu Glu
80                  85                  90 atg gaa gaa atg gtg cag agc gcc aga gat ctg ccc aaa gag tgc ggc       336
Met Glu Glu Met Val Gln Ser Ala Arg Asp Leu Pro Lys Glu Cys Gly
95                  100                 105                 110 atc agc agc cag aga tgc gag atc cgg cgg agt tgg ttc gaattc            381
Ile Ser Ser Gln Arg Cys Glu Ile Arg Arg Ser Trp Phe
                115                 120
```

<210> SEQ ID NO 23
<211> LENGTH: 123
<212> TYPE: PRT
<213> ORGANISM: Juglans nigra

<400> SEQUENCE: 23

```
Arg Thr Thr Ile Thr Thr Met Glu Ile Asp Glu Asp Ile Asp Asn Pro
1               5                   10                  15

Arg Arg Arg Gly Glu Gly Cys Gln Glu Gln Ile Gln Arg Gln Gln Asn
            20                  25                  30

Leu Asn His Cys Gln Tyr Tyr Leu Arg Gln Gln Ser Arg Ser Gly Gly
        35                  40                  45

Tyr Asp Glu Asp Asn Gln Arg Gln His Phe Arg Gln Cys Cys Gln Gln
    50                  55                  60

Leu Ser Gln Ile Glu Glu Gln Cys Gln Cys Glu Gly Leu Arg Gln Ala
65                  70                  75                  80

Val Arg Arg Gln Gln Gln Gln Gly Leu Arg Gly Glu Glu Met Glu
                85                  90                  95

Glu Met Val Gln Ser Ala Arg Asp Leu Pro Lys Glu Cys Gly Ile Ser
            100                 105                 110

Ser Gln Arg Cys Glu Ile Arg Arg Ser Trp Phe
        115                 120
```

<210> SEQ ID NO 24
<211> LENGTH: 1791
<212> TYPE: DNA
<213> ORGANISM: Juglans regia
<220> FEATURE:
<221> NAME/KEY: CDS
<222> LOCATION: (7)..(1785)

<400> SEQUENCE: 24

```
ctcgag aga ggc cgg gac gac gac gat gag gaa aac ccc aga gat ccc         48
       Arg Gly Arg Asp Asp Asp Asp Glu Glu Asn Pro Arg Asp Pro
       1               5                   10 cgc gag cag tac cgg cag tgc caa gag tac tgc aga agg caa ggc caa         96
Arg Glu Gln Tyr Arg Gln Cys Gln Glu Tyr Cys Arg Arg Gln Gly Gln
15                  20                  25                  30 ggc cag aga cag cag cag cag tgc cag atc aga tgc gag gaa cgg ctg        144
Gly Gln Arg Gln Gln Gln Gln Cys Gln Ile Arg Cys Glu Glu Arg Leu
                35                  40                  45 gaa gag gac cag cgg agc caa gag gaa cgc gag cgg aga aga ggc aga        192
Glu Glu Asp Gln Arg Ser Gln Glu Glu Arg Glu Arg Arg Arg Gly Arg
            50                  55                  60 gat gtg gac gac cag aac ccc cgg gac ccc gag cag aga tac gag cag        240
Asp Val Asp Asp Gln Asn Pro Arg Asp Pro Glu Gln Arg Tyr Glu Gln
65                  70                  75 tgt cag cag cag tgt gaa cgg cag cgg aga ggc caa gag cag aca ctg        288
Cys Gln Gln Gln Cys Glu Arg Gln Arg Arg Gly Gln Glu Gln Thr Leu
        80                  85                  90 tgt cgg cgg aga tgc gag cag cgg cgg cag caa gag gaa aga gaa cgc        336
Cys Arg Arg Arg Cys Glu Gln Arg Arg Gln Gln Glu Glu Arg Glu Arg
95                  100                 105                 110 cag cgg ggc aga gac aga caa gac ccc cag cag cag tac cac cgg tgc        384
Gln Arg Gly Arg Asp Arg Gln Asp Pro Gln Gln Gln Tyr His Arg Cys
                115                 120                 125 cag aga aga tgc cag atc caa gaa cag agc ccc gag cgg cag cgc cag        432
Gln Arg Arg Cys Gln Ile Gln Glu Gln Ser Pro Glu Arg Gln Arg Gln
            130                 135                 140 tgc cag cag aga tgc gaa aga cag tac aaa gag cag caa ggc aga gag        480
Cys Gln Gln Arg Cys Glu Arg Gln Tyr Lys Glu Gln Gln Gly Arg Glu
145                 150                 155 agg ggc cca gag gcc agc cct aga aga gag tcc aga gga cgg gaa gaa        528
Arg Gly Pro Glu Ala Ser Pro Arg Arg Glu Ser Arg Gly Arg Glu Glu
```

-continued

```
                160                 165                 170
gaa cag cag cgg cac aac ccc tac tac ttc cac agc cag agc atc aga        576
Glu Gln Gln Arg His Asn Pro Tyr Tyr Phe His Ser Gln Ser Ile Arg
175                 180                 185                 190 agc cgg cac gag agc gaa gag ggc gaa gtg aag tat ctg gaa cgg ttc        624
Ser Arg His Glu Ser Glu Glu Gly Glu Val Lys Tyr Leu Glu Arg Phe
                    195                 200                 205 acc gag cgg acc gag ctg ctg aga ggc atc gag aac tac cgg gtc gtg        672
Thr Glu Arg Thr Glu Leu Leu Arg Gly Ile Glu Asn Tyr Arg Val Val
            210                 215                 220 att ctg gac gcc aac ccc aac aca tcc atg ctg ccc cac cac aag gac        720
Ile Leu Asp Ala Asn Pro Asn Thr Ser Met Leu Pro His His Lys Asp
                225                 230                 235 gcc gag tct gtg gcc gtc gtg aca agg ggc aga gcc aca ctg aca ctg        768
Ala Glu Ser Val Ala Val Val Thr Arg Gly Arg Ala Thr Leu Thr Leu
240                 245                 250 gtg tcc caa gag act cgc gag agc ttc aat ctg gaa tgc ggc gac gtg        816
Val Ser Gln Glu Thr Arg Glu Ser Phe Asn Leu Glu Cys Gly Asp Val
255                 260                 265                 270 atc cgg gtg cca gct ggg gct aca gtg tac gtg atc aac caa gac agc        864
Ile Arg Val Pro Ala Gly Ala Thr Val Tyr Val Ile Asn Gln Asp Ser
                    275                 280                 285 aac gag cgg ctg gaa atg gtc aag ctg ctg cag ccc gtg aac aac ccc        912
Asn Glu Arg Leu Glu Met Val Lys Leu Leu Gln Pro Val Asn Asn Pro
            290                 295                 300 ggc cag ttc aga gag tac tac gcc gct ggc gcc aag tcc ccc gac cag        960
Gly Gln Phe Arg Glu Tyr Tyr Ala Ala Gly Ala Lys Ser Pro Asp Gln
                305                 310                 315 agc tat ctg cgg gtg ttc agc aac gac att ctg gtg gcc gct ctg aat       1008
Ser Tyr Leu Arg Val Phe Ser Asn Asp Ile Leu Val Ala Ala Leu Asn
320                 325                 330 acc cct cgg gac aga ctg gaa aga ttc ttc gat cag caa gag cag cgc       1056
Thr Pro Arg Asp Arg Leu Glu Arg Phe Phe Asp Gln Gln Glu Gln Arg
335                 340                 345                 350 gag ggc gtg atc atc aga gcc agc caa gag aag ctg cgg gct ctg agc       1104
Glu Gly Val Ile Ile Arg Ala Ser Gln Glu Lys Leu Arg Ala Leu Ser
                    355                 360                 365 cag cac gcc atg tct gct gga cag agg cct tgg ggc aga aga agc tct       1152
Gln His Ala Met Ser Ala Gly Gln Arg Pro Trp Gly Arg Arg Ser Ser
            370                 375                 380 ggc ggc cct atc tct ctg aag tcc gag agc ccc tcc tac agc aac cag       1200
Gly Gly Pro Ile Ser Leu Lys Ser Glu Ser Pro Ser Tyr Ser Asn Gln
                385                 390                 395 ttt ggc cag ttc ttc gag gct tgc ccc gag gaa cac cgg cag ctg caa       1248
Phe Gly Gln Phe Phe Glu Ala Cys Pro Glu Glu His Arg Gln Leu Gln
            400                 405                 410 gaa atg gac gtg ctc gtg aac tac gcc gag atc aag agg ggc gcc atg       1296
Glu Met Asp Val Leu Val Asn Tyr Ala Glu Ile Lys Arg Gly Ala Met
415                 420                 425                 430 atg gtg ccc cac tac aac agc aag gcc acc gtg gtg tac gtg gtg            1344
Met Val Pro His Tyr Asn Ser Lys Ala Thr Val Val Tyr Val Val
                    435                 440                 445 gaa ggc acc ggc aga tac gag atg gca tgc ccc cac gtg tcc agc cag       1392
Glu Gly Thr Gly Arg Tyr Glu Met Ala Cys Pro His Val Ser Ser Gln
            450                 455                 460 tct tac gag ggc caa gga cgc aga gag caa gaa gag gaa gag tcc acc       1440
Ser Tyr Glu Gly Gln Gly Arg Arg Glu Gln Glu Glu Glu Glu Ser Thr
                465                 470                 475 gga cgg ttc cag aaa gtg acc gcc aga ctg gcc aga ggc gac atc ttc       1488
```

-continued

```
Gly Arg Phe Gln Lys Val Thr Ala Arg Leu Ala Arg Gly Asp Ile Phe
            480                 485                 490 gtg atc cca gcc gga cac cct atc gcc atc acc gcc agc cag aac gag      1536
Val Ile Pro Ala Gly His Pro Ile Ala Ile Thr Ala Ser Gln Asn Glu
495                 500                 505                 510 aat ctg cgg ctg ctg ggc ttc gac atc aac ggc gag aac aac cag cgg      1584
Asn Leu Arg Leu Leu Gly Phe Asp Ile Asn Gly Glu Asn Asn Gln Arg
                515                 520                 525 gac ttt ctg gcc gga cag aac aac atc atc aac cag ctg gaa cgg gaa      1632
Asp Phe Leu Ala Gly Gln Asn Asn Ile Ile Asn Gln Leu Glu Arg Glu
            530                 535                 540 gcc aaa gaa ctg agc ttc aac atg ccc cgc gag gaa atc gaa gag att      1680
Ala Lys Glu Leu Ser Phe Asn Met Pro Arg Glu Glu Ile Glu Glu Ile
545                 550                 555 ttc gag agc cag atg gaa agc tac ttc gtg ccc acc gag cgc cag agc      1728
Phe Glu Ser Gln Met Glu Ser Tyr Phe Val Pro Thr Glu Arg Gln Ser
        560                 565                 570 aga agg ggc caa ggg cgg gat cac cca ctg gcc tct att ctg gat ttc      1776
Arg Arg Gly Gln Gly Arg Asp His Pro Leu Ala Ser Ile Leu Asp Phe
575                 580                 585                 590 gcc ttc ttc gaattc                                                   1791
Ala Phe Phe <210> SEQ ID NO 25
<211> LENGTH: 593
<212> TYPE: PRT
<213> ORGANISM: Juglans regia

<400> SEQUENCE: 25

Arg Gly Arg Asp Asp Asp Glu Glu Asn Pro Arg Asp Pro Arg Glu
1               5                   10                  15

Gln Tyr Arg Gln Cys Gln Glu Tyr Cys Arg Arg Gln Gly Gln Gly Gln
                20                  25                  30

Arg Gln Gln Gln Cys Gln Ile Arg Cys Glu Glu Arg Leu Glu Glu
        35                  40                  45

Asp Gln Arg Ser Gln Glu Glu Arg Glu Arg Arg Gly Arg Asp Val
    50                  55                  60

Asp Asp Gln Asn Pro Arg Asp Pro Glu Gln Arg Tyr Glu Gln Cys Gln
65                  70                  75                  80

Gln Gln Cys Glu Arg Gln Arg Gly Gln Glu Gln Thr Leu Cys Arg
                85                  90                  95

Arg Arg Cys Glu Gln Arg Gln Gln Glu Glu Arg Glu Arg Gln Arg
            100                 105                 110

Gly Arg Asp Arg Gln Asp Pro Gln Gln Gln Tyr His Arg Cys Gln Arg
        115                 120                 125

Arg Cys Gln Ile Gln Glu Gln Ser Pro Glu Arg Gln Arg Gln Cys Gln
    130                 135                 140

Gln Arg Cys Glu Arg Gln Tyr Lys Glu Gln Gln Gly Arg Glu Arg Gly
145                 150                 155                 160

Pro Glu Ala Ser Pro Arg Arg Glu Ser Arg Gly Arg Glu Glu Gln
                165                 170                 175

Gln Arg His Asn Pro Tyr Tyr Phe His Ser Gln Ser Ile Arg Ser Arg
            180                 185                 190

His Glu Ser Glu Glu Gly Glu Val Lys Tyr Leu Glu Arg Phe Thr Glu
        195                 200                 205

Arg Thr Glu Leu Leu Arg Gly Ile Glu Asn Tyr Arg Val Val Ile Leu
    210                 215                 220
```

Asp Ala Asn Pro Asn Thr Ser Met Leu Pro His His Lys Asp Ala Glu
225                 230                 235                 240

Ser Val Ala Val Val Thr Arg Gly Arg Ala Thr Leu Thr Leu Val Ser
            245                 250                 255

Gln Glu Thr Arg Glu Ser Phe Asn Leu Glu Cys Gly Asp Val Ile Arg
        260                 265                 270

Val Pro Ala Gly Ala Thr Val Tyr Val Ile Asn Gln Asp Ser Asn Glu
    275                 280                 285

Arg Leu Glu Met Val Lys Leu Leu Gln Pro Val Asn Asn Pro Gly Gln
290                 295                 300

Phe Arg Glu Tyr Tyr Ala Ala Gly Ala Lys Ser Pro Asp Gln Ser Tyr
305                 310                 315                 320

Leu Arg Val Phe Ser Asn Asp Ile Leu Val Ala Ala Leu Asn Thr Pro
            325                 330                 335

Arg Asp Arg Leu Glu Arg Phe Phe Asp Gln Gln Glu Gln Arg Glu Gly
        340                 345                 350

Val Ile Ile Arg Ala Ser Gln Glu Lys Leu Arg Ala Leu Ser Gln His
    355                 360                 365

Ala Met Ser Ala Gly Gln Arg Pro Trp Gly Arg Ser Ser Gly Gly
370                 375                 380

Pro Ile Ser Leu Lys Ser Glu Ser Pro Ser Tyr Ser Asn Gln Phe Gly
385                 390                 395                 400

Gln Phe Phe Glu Ala Cys Pro Glu Glu His Arg Gln Leu Gln Glu Met
            405                 410                 415

Asp Val Leu Val Asn Tyr Ala Glu Ile Lys Arg Gly Ala Met Met Val
        420                 425                 430

Pro His Tyr Asn Ser Lys Ala Thr Val Val Tyr Val Val Glu Gly
    435                 440                 445

Thr Gly Arg Tyr Glu Met Ala Cys Pro His Val Ser Ser Gln Ser Tyr
450                 455                 460

Glu Gly Gln Gly Arg Arg Glu Gln Glu Glu Glu Ser Thr Gly Arg
465                 470                 475                 480

Phe Gln Lys Val Thr Ala Arg Leu Ala Arg Gly Asp Ile Phe Val Ile
            485                 490                 495

Pro Ala Gly His Pro Ile Ala Ile Thr Ala Ser Gln Asn Glu Asn Leu
        500                 505                 510

Arg Leu Leu Gly Phe Asp Ile Asn Gly Glu Asn Asn Gln Arg Asp Phe
    515                 520                 525

Leu Ala Gly Gln Asn Asn Ile Ile Asn Gln Leu Glu Arg Glu Ala Lys
530                 535                 540

Glu Leu Ser Phe Asn Met Pro Arg Glu Ile Glu Glu Ile Phe Glu
545                 550                 555                 560

Ser Gln Met Glu Ser Tyr Phe Val Pro Thr Glu Arg Gln Ser Arg Arg
            565                 570                 575

Gly Gln Gly Arg Asp His Pro Leu Ala Ser Ile Leu Asp Phe Ala Phe
        580                 585                 590

Phe

<210> SEQ ID NO 26
<211> LENGTH: 2172
<212> TYPE: DNA
<213> ORGANISM: Artificial sequence
<220> FEATURE:
<223> OTHER INFORMATION: Synthetic Construct -continued

```
<220> FEATURE:
<221> NAME/KEY: CDS
<222> LOCATION: (7)..(2166)

<400> SEQUENCE: 26
```

| | | | | | | | | | | | | | | |
|---|---|---|---|---|---|---|---|---|---|---|---|---|---|---|
| ctcgag | cgg | acc | acc | atc | acc | acc | atg | gaa | atc | gac | gag | gac | atc | gac | 48 |
| | Arg | Thr | Thr | Ile | Thr | Thr | Met | Glu | Ile | Asp | Glu | Asp | Ile | Asp | |
| | 1 | | | | 5 | | | | | 10 | | | | | |

| aac | ccc | aga | aga | aga | ggc | gag | ggc | tgc | caa | gag | cag | atc | cag | cgg | cag | 96 |
|---|---|---|---|---|---|---|---|---|---|---|---|---|---|---|---|---|
| Asn | Pro | Arg | Arg | Arg | Gly | Glu | Gly | Cys | Gln | Glu | Gln | Ile | Gln | Arg | Gln | |
| 15 | | | | | 20 | | | | | 25 | | | | | 30 | |

| cag | aat | ctg | aac | cac | tgc | cag | tac | tat | ctg | agg | cag | cag | agc | aga | agc | 144 |
|---|---|---|---|---|---|---|---|---|---|---|---|---|---|---|---|---|
| Gln | Asn | Leu | Asn | His | Cys | Gln | Tyr | Tyr | Leu | Arg | Gln | Gln | Ser | Arg | Ser | |
| | | | | 35 | | | | | 40 | | | | | 45 | | |

| ggc | ggc | tac | gac | gag | gat | aac | cag | aga | cag | cac | ttc | aga | cag | tgc | tgc | 192 |
|---|---|---|---|---|---|---|---|---|---|---|---|---|---|---|---|---|
| Gly | Gly | Tyr | Asp | Glu | Asp | Asn | Gln | Arg | Gln | His | Phe | Arg | Gln | Cys | Cys | |
| | | 50 | | | | | 55 | | | | | 60 | | | | |

| cag | cag | ctg | agc | cag | atc | gag | gaa | cag | tgc | cag | tgc | gag | gga | ctg | aga | 240 |
|---|---|---|---|---|---|---|---|---|---|---|---|---|---|---|---|---|
| Gln | Gln | Leu | Ser | Gln | Ile | Glu | Glu | Gln | Cys | Gln | Cys | Glu | Gly | Leu | Arg | |
| 65 | | | | | 70 | | | | | 75 | | | | | | |

| caa | gcc | gtg | cgg | aga | caa | cag | cag | caa | gga | ctg | cgg | ggc | gaa | gag | | 288 |
|---|---|---|---|---|---|---|---|---|---|---|---|---|---|---|---|---|
| Gln | Ala | Val | Arg | Arg | Gln | Gln | Gln | Gln | Gly | Leu | Arg | Gly | Glu | Glu | | |
| 80 | | | | | 85 | | | | | 90 | | | | | | |

| atg | gaa | gaa | atg | gtg | cag | agc | gcc | aga | gat | ctg | ccc | aaa | gag | tgc | ggc | 336 |
|---|---|---|---|---|---|---|---|---|---|---|---|---|---|---|---|---|
| Met | Glu | Glu | Met | Val | Gln | Ser | Ala | Arg | Asp | Leu | Pro | Lys | Glu | Cys | Gly | |
| 95 | | | | 100 | | | | | 105 | | | | | 110 | | |

| atc | agc | agc | cag | aga | tgc | gag | atc | cgg | cgg | agt | tgg | ttc | ggc | gga | ggg | 384 |
|---|---|---|---|---|---|---|---|---|---|---|---|---|---|---|---|---|
| Ile | Ser | Ser | Gln | Arg | Cys | Glu | Ile | Arg | Arg | Ser | Trp | Phe | Gly | Gly | Gly | |
| | | | | 115 | | | | | 120 | | | | | 125 | | |

| ggc | aga | ggc | cgg | gac | gac | gac | gat | gag | gaa | aac | ccc | aga | gat | ccc | cgc | 432 |
|---|---|---|---|---|---|---|---|---|---|---|---|---|---|---|---|---|
| Gly | Arg | Gly | Arg | Asp | Asp | Asp | Asp | Glu | Glu | Asn | Pro | Arg | Asp | Pro | Arg | |
| | | 130 | | | | | 135 | | | | | 140 | | | | |

| gag | cag | tac | cgg | cag | tgc | caa | gag | tac | tgc | aga | agg | caa | ggc | caa | ggc | 480 |
|---|---|---|---|---|---|---|---|---|---|---|---|---|---|---|---|---|
| Glu | Gln | Tyr | Arg | Gln | Cys | Gln | Glu | Tyr | Cys | Arg | Arg | Gln | Gly | Gln | Gly | |
| | | | 145 | | | | | 150 | | | | | 155 | | | |

| cag | aga | cag | cag | cag | cag | tgc | cag | atc | aga | tgc | gag | gaa | cgg | ctg | gaa | 528 |
|---|---|---|---|---|---|---|---|---|---|---|---|---|---|---|---|---|
| Gln | Arg | Gln | Gln | Gln | Gln | Cys | Gln | Ile | Arg | Cys | Glu | Glu | Arg | Leu | Glu | |
| | 160 | | | | | 165 | | | | | 170 | | | | | |

| gag | gac | cag | cgg | agc | caa | gag | gaa | cgc | gag | cgg | aga | aga | ggc | aga | gat | 576 |
|---|---|---|---|---|---|---|---|---|---|---|---|---|---|---|---|---|
| Glu | Asp | Gln | Arg | Ser | Gln | Glu | Glu | Arg | Glu | Arg | Arg | Arg | Gly | Arg | Asp | |
| 175 | | | | | 180 | | | | | 185 | | | | | 190 | |

| gtg | gac | gac | cag | aac | ccc | cgg | gac | ccc | gag | cag | aga | tac | gag | cag | tgt | 624 |
|---|---|---|---|---|---|---|---|---|---|---|---|---|---|---|---|---|
| Val | Asp | Asp | Gln | Asn | Pro | Arg | Asp | Pro | Glu | Gln | Arg | Tyr | Glu | Gln | Cys | |
| | | | | 195 | | | | | 200 | | | | | 205 | | |

| cag | cag | cag | tgt | gaa | cgg | cag | cgg | aga | ggc | caa | gag | cag | aca | ctg | tgt | 672 |
|---|---|---|---|---|---|---|---|---|---|---|---|---|---|---|---|---|
| Gln | Gln | Gln | Cys | Glu | Arg | Gln | Arg | Arg | Gly | Gln | Glu | Gln | Thr | Leu | Cys | |
| | | | 210 | | | | | 215 | | | | | 220 | | | |

| cgg | cgg | aga | tgc | gag | cag | cgg | cgg | cag | caa | gag | gaa | aga | gaa | cgc | cag | 720 |
|---|---|---|---|---|---|---|---|---|---|---|---|---|---|---|---|---|
| Arg | Arg | Arg | Cys | Glu | Gln | Arg | Arg | Gln | Gln | Glu | Glu | Arg | Glu | Arg | Gln | |
| | 225 | | | | | 230 | | | | | 235 | | | | | |

| cgg | ggc | aga | gac | aga | caa | gac | ccc | cag | cag | cag | tac | cac | cgg | tgc | cag | 768 |
|---|---|---|---|---|---|---|---|---|---|---|---|---|---|---|---|---|
| Arg | Gly | Arg | Asp | Arg | Gln | Asp | Pro | Gln | Gln | Gln | Tyr | His | Arg | Cys | Gln | |
| 240 | | | | | 245 | | | | | 250 | | | | | | |

| aga | aga | tgc | cag | atc | caa | gaa | cag | agc | ccc | gag | cgg | cag | cgc | cag | tgc | 816 |
|---|---|---|---|---|---|---|---|---|---|---|---|---|---|---|---|---|
| Arg | Arg | Cys | Gln | Ile | Gln | Glu | Gln | Ser | Pro | Glu | Arg | Gln | Arg | Gln | Cys | |
| 255 | | | | | 260 | | | | | 265 | | | | | 270 | |

| cag | cag | aga | tgc | gaa | aga | cag | tac | aaa | gag | cag | caa | ggc | aga | gag | agg | 864 |
|---|---|---|---|---|---|---|---|---|---|---|---|---|---|---|---|---|
| Gln | Gln | Arg | Cys | Glu | Arg | Gln | Tyr | Lys | Glu | Gln | Gln | Gly | Arg | Glu | Arg | |
| | | | | 275 | | | | | 280 | | | | | 285 | | |

| ggc | cca | gag | gcc | agc | cct | aga | aga | gag | tcc | aga | gga | cgg | gaa | gaa | gaa | 912 |
|---|---|---|---|---|---|---|---|---|---|---|---|---|---|---|---|---|

```
                Gly Pro Glu Ala Ser Pro Arg Arg Glu Ser Arg Gly Arg Glu Glu
                                290                 295                 300 cag cag cgg cac aac ccc tac tac ttc cac agc cag agc atc aga agc            960
Gln Gln Arg His Asn Pro Tyr Tyr Phe His Ser Gln Ser Ile Arg Ser
            305                 310                 315 cgg cac gag agc gaa gag ggc gaa gtg aag tat ctg gaa cgg ttc acc           1008
Arg His Glu Ser Glu Glu Gly Glu Val Lys Tyr Leu Glu Arg Phe Thr
        320                 325                 330 gag cgg acc gag ctg ctg aga ggc atc gag aac tac cgg gtc gtg att           1056
Glu Arg Thr Glu Leu Leu Arg Gly Ile Glu Asn Tyr Arg Val Val Ile
335                 340                 345                 350 ctg gac gcc aac ccc aac aca tcc atg ctg ccc cac cac aag gac gcc           1104
Leu Asp Ala Asn Pro Asn Thr Ser Met Leu Pro His His Lys Asp Ala
                355                 360                 365 gag tct gtg gcc gtc gtg aca agg ggc aga gcc aca ctg aca ctg gtg           1152
Glu Ser Val Ala Val Val Thr Arg Gly Arg Ala Thr Leu Thr Leu Val
            370                 375                 380 tcc caa gag act cgc gag agc ttc aat ctg gaa tgc ggc gac gtg atc           1200
Ser Gln Glu Thr Arg Glu Ser Phe Asn Leu Glu Cys Gly Asp Val Ile
        385                 390                 395 cgg gtg cca gct ggg gct aca gtg tac gtg atc aac caa gac agc aac           1248
Arg Val Pro Ala Gly Ala Thr Val Tyr Val Ile Asn Gln Asp Ser Asn
400                 405                 410 gag cgg ctg gaa atg gtc aag ctg ctg cag ccc gtg aac aac ccc ggc           1296
Glu Arg Leu Glu Met Val Lys Leu Leu Gln Pro Val Asn Asn Pro Gly
415                 420                 425                 430 cag ttc aga gag tac tac gcc gct ggc gcc aag tcc ccc gac cag agc           1344
Gln Phe Arg Glu Tyr Tyr Ala Ala Gly Ala Lys Ser Pro Asp Gln Ser
                435                 440                 445 tat ctg cgg gtg ttc agc aac gac att ctg gtg gcc gct ctg aat acc           1392
Tyr Leu Arg Val Phe Ser Asn Asp Ile Leu Val Ala Ala Leu Asn Thr
            450                 455                 460 cct cgg gac aga ctg gaa aga ttc ttc gat cag caa gag cag cgc gag           1440
Pro Arg Asp Arg Leu Glu Arg Phe Phe Asp Gln Gln Glu Gln Arg Glu
        465                 470                 475 ggc gtg atc atc aga gcc agc caa gag aag ctg cgg gct ctg agc cag           1488
Gly Val Ile Ile Arg Ala Ser Gln Glu Lys Leu Arg Ala Leu Ser Gln
480                 485                 490 cac gcc atg tct gct gga cag agg cct tgg ggc aga aga agc tct ggc           1536
His Ala Met Ser Ala Gly Gln Arg Pro Trp Gly Arg Arg Ser Ser Gly
495                 500                 505                 510 ggc cct atc tct ctg aag tcc gag agc ccc tcc tac agc aac cag ttt           1584
Gly Pro Ile Ser Leu Lys Ser Glu Ser Pro Ser Tyr Ser Asn Gln Phe
                515                 520                 525 ggc cag ttc ttc gag gct tgc ccc gag gaa cac cgg cag ctg caa gaa           1632
Gly Gln Phe Phe Glu Ala Cys Pro Glu Glu His Arg Gln Leu Gln Glu
            530                 535                 540 atg gac gtg ctc gtg aac tac gcc gag atc aag agg ggc gcc atg atg           1680
Met Asp Val Leu Val Asn Tyr Ala Glu Ile Lys Arg Gly Ala Met Met
        545                 550                 555 gtg ccc cac tac aac agc aag gcc acc gtg gtg gtg tac gtg gtg gaa           1728
Val Pro His Tyr Asn Ser Lys Ala Thr Val Val Val Tyr Val Val Glu
560                 565                 570 ggc acc ggc aga tac gag atg gca tgc ccc cac gtg tcc agc cag tct           1776
Gly Thr Gly Arg Tyr Glu Met Ala Cys Pro His Val Ser Ser Gln Ser
575                 580                 585                 590 tac gag ggc caa gga cgc aga gag caa gaa gag gaa gag tcc acc gga           1824
Tyr Glu Gly Gln Gly Arg Arg Glu Gln Glu Glu Glu Glu Ser Thr Gly
                595                 600                 605
```

```
cgg ttc cag aaa gtg acc gcc aga ctg gcc aga ggc gac atc ttc gtg      1872
Arg Phe Gln Lys Val Thr Ala Arg Leu Ala Arg Gly Asp Ile Phe Val
            610                 615                 620 atc cca gcc gga cac cct atc gcc atc acc gcc agc cag aac gag aat      1920
Ile Pro Ala Gly His Pro Ile Ala Ile Thr Ala Ser Gln Asn Glu Asn
        625                 630                 635 ctg cgg ctg ctg ggc ttc gac atc aac ggc gag aac aac cag cgg gac      1968
Leu Arg Leu Leu Gly Phe Asp Ile Asn Gly Glu Asn Asn Gln Arg Asp
    640                 645                 650 ttt ctg gcc gga cag aac aac atc atc aac cag ctg gaa cgg gaa gcc      2016
Phe Leu Ala Gly Gln Asn Asn Ile Ile Asn Gln Leu Glu Arg Glu Ala
655                 660                 665                 670 aaa gaa ctg agc ttc aac atg ccc cgc gag gaa atc gaa gag att ttc      2064
Lys Glu Leu Ser Phe Asn Met Pro Arg Glu Glu Ile Glu Glu Ile Phe
            675                 680                 685 gag agc cag atg gaa agc tac ttc gtg ccc acc gag cgc cag agc aga      2112
Glu Ser Gln Met Glu Ser Tyr Phe Val Pro Thr Glu Arg Gln Ser Arg
        690                 695                 700 agg ggc caa ggg cgg gat cac cca ctg gcc tct att ctg gat ttc gcc      2160
Arg Gly Gln Gly Arg Asp His Pro Leu Ala Ser Ile Leu Asp Phe Ala
    705                 710                 715 ttc ttc gaattc                                                        2172
Phe Phe
    720

<210> SEQ ID NO 27
<211> LENGTH: 720
<212> TYPE: PRT
<213> ORGANISM: Artificial sequence
<220> FEATURE:
<223> OTHER INFORMATION: Synthetic Construct

<400> SEQUENCE: 27

Arg Thr Thr Ile Thr Thr Met Glu Ile Asp Glu Asp Ile Asp Asn Pro
1               5                   10                  15

Arg Arg Arg Gly Glu Gly Cys Gln Glu Gln Ile Gln Arg Gln Gln Asn
            20                  25                  30

Leu Asn His Cys Gln Tyr Tyr Leu Arg Gln Gln Ser Arg Ser Gly Gly
        35                  40                  45

Tyr Asp Glu Asp Asn Gln Arg Gln His Phe Arg Gln Cys Cys Gln Gln
    50                  55                  60

Leu Ser Gln Ile Glu Glu Gln Cys Gln Cys Glu Gly Leu Arg Gln Ala
65                  70                  75                  80

Val Arg Arg Gln Gln Gln Gln Gly Leu Arg Gly Glu Glu Met Glu
                85                  90                  95

Glu Met Val Gln Ser Ala Arg Asp Leu Pro Lys Glu Cys Gly Ile Ser
            100                 105                 110

Ser Gln Arg Cys Glu Ile Arg Arg Ser Trp Phe Gly Gly Gly Gly Arg
        115                 120                 125

Gly Arg Asp Asp Asp Glu Glu Asn Pro Arg Asp Pro Arg Glu Gln
    130                 135                 140

Tyr Arg Gln Cys Gln Glu Tyr Cys Arg Arg Gln Gly Gln Gly Gln Arg
145                 150                 155                 160

Gln Gln Gln Gln Cys Gln Ile Arg Cys Glu Glu Arg Leu Glu Glu Asp
                165                 170                 175

Gln Arg Ser Gln Glu Glu Arg Glu Arg Arg Gly Arg Asp Val Asp
            180                 185                 190

Asp Gln Asn Pro Arg Asp Pro Glu Gln Arg Tyr Glu Gln Cys Gln Gln
```

```
            195                 200                 205
Gln Cys Glu Arg Gln Arg Arg Gly Gln Glu Gln Thr Leu Cys Arg Arg
    210                 215                 220

Arg Cys Glu Gln Arg Gln Gln Glu Glu Arg Glu Arg Gln Arg Gly
225                 230                 235                 240

Arg Asp Arg Gln Asp Pro Gln Gln Tyr His Arg Cys Gln Arg Arg
                245                 250                 255

Cys Gln Ile Gln Glu Gln Ser Pro Glu Arg Gln Arg Gln Cys Gln Gln
            260                 265                 270

Arg Cys Glu Arg Gln Tyr Lys Glu Gln Gln Gly Arg Glu Arg Gly Pro
                275                 280                 285

Glu Ala Ser Pro Arg Arg Glu Ser Arg Gly Arg Glu Glu Gln Gln
    290                 295                 300

Arg His Asn Pro Tyr Tyr Phe His Ser Gln Ser Ile Arg Ser Arg His
305                 310                 315                 320

Glu Ser Glu Glu Gly Glu Val Lys Tyr Leu Glu Arg Phe Thr Glu Arg
                325                 330                 335

Thr Glu Leu Leu Arg Gly Ile Glu Asn Tyr Arg Val Val Ile Leu Asp
                340                 345                 350

Ala Asn Pro Asn Thr Ser Met Leu Pro His His Lys Asp Ala Glu Ser
            355                 360                 365

Val Ala Val Val Thr Arg Gly Arg Ala Thr Leu Thr Leu Val Ser Gln
    370                 375                 380

Glu Thr Arg Glu Ser Phe Asn Leu Glu Cys Gly Asp Val Ile Arg Val
385                 390                 395                 400

Pro Ala Gly Ala Thr Val Tyr Val Ile Asn Gln Asp Ser Asn Glu Arg
                405                 410                 415

Leu Glu Met Val Lys Leu Leu Gln Pro Val Asn Asn Pro Gly Gln Phe
                420                 425                 430

Arg Glu Tyr Tyr Ala Ala Gly Ala Lys Ser Pro Asp Gln Ser Tyr Leu
            435                 440                 445

Arg Val Phe Ser Asn Asp Ile Leu Val Ala Ala Leu Asn Thr Pro Arg
450                 455                 460

Asp Arg Leu Glu Arg Phe Phe Asp Gln Gln Glu Gln Arg Glu Gly Val
465                 470                 475                 480

Ile Ile Arg Ala Ser Gln Glu Lys Leu Arg Ala Leu Ser Gln His Ala
                485                 490                 495

Met Ser Ala Gly Gln Arg Pro Trp Gly Arg Ser Ser Gly Gly Pro
            500                 505                 510

Ile Ser Leu Lys Ser Glu Ser Pro Ser Tyr Ser Asn Gln Phe Gly Gln
            515                 520                 525

Phe Phe Glu Ala Cys Pro Glu His Arg Gln Leu Gln Glu Met Asp
    530                 535                 540

Val Leu Val Asn Tyr Ala Glu Ile Lys Arg Gly Ala Met Met Val Pro
545                 550                 555                 560

His Tyr Asn Ser Lys Ala Thr Val Val Val Tyr Val Glu Gly Thr
                565                 570                 575

Gly Arg Tyr Glu Met Ala Cys Pro His Val Ser Ser Gln Ser Tyr Glu
                580                 585                 590

Gly Gln Gly Arg Arg Glu Gln Glu Glu Glu Ser Thr Gly Arg Phe
            595                 600                 605

Gln Lys Val Thr Ala Arg Leu Ala Arg Gly Asp Ile Phe Val Ile Pro
            610                 615                 620
```

```
Ala Gly His Pro Ile Ala Ile Thr Ala Ser Gln Asn Glu Asn Leu Arg
625                 630                 635                 640

Leu Leu Gly Phe Asp Ile Asn Gly Glu Asn Asn Gln Arg Asp Phe Leu
            645                 650                 655

Ala Gly Gln Asn Asn Ile Ile Asn Gln Leu Glu Arg Glu Ala Lys Glu
                660                 665                 670

Leu Ser Phe Asn Met Pro Arg Glu Glu Ile Glu Glu Ile Phe Glu Ser
            675                 680                 685

Gln Met Glu Ser Tyr Phe Val Pro Thr Glu Arg Gln Ser Arg Arg Gly
690                 695                 700

Gln Gly Arg Asp His Pro Leu Ala Ser Ile Leu Asp Phe Ala Phe Phe
705                 710                 715                 720

<210> SEQ ID NO 28
<211> LENGTH: 1125
<212> TYPE: DNA
<213> ORGANISM: Ambrosia artemisiifolia
<220> FEATURE:
<221> NAME/KEY: CDS
<222> LOCATION: (7)..(1119)

<400> SEQUENCE: 28 ctcgag gcc gag gat ctg caa gag att ctg ccc gtg aac gag aca cgg         48
       Ala Glu Asp Leu Gln Glu Ile Leu Pro Val Asn Glu Thr Arg
       1               5                   10 cgg ctg aca aca agc ggc gcc tac aac atc atc gac ggc tgc tgg cgg        96
Arg Leu Thr Thr Ser Gly Ala Tyr Asn Ile Ile Asp Gly Cys Trp Arg
15                  20                  25                  30 ggc aag gcc gat tgg gcc gag aac aga aag gct ctg gcc gat tgc gcc       144
Gly Lys Ala Asp Trp Ala Glu Asn Arg Lys Ala Leu Ala Asp Cys Ala
                35                  40                  45 caa ggc ttc ggc aag gga aca gtg ggc ggc aag gac ggc gac atc tac       192
Gln Gly Phe Gly Lys Gly Thr Val Gly Gly Lys Asp Gly Asp Ile Tyr
            50                  55                  60 acc gtg acc agc gag ctg gac gac gac gtg gcc aat ccc aaa gag ggc       240
Thr Val Thr Ser Glu Leu Asp Asp Asp Val Ala Asn Pro Lys Glu Gly
65                  70                  75 aca ctg aga ttc gga gcc gcc cag aac cgg cct ctg tgg atc atc ttc       288
Thr Leu Arg Phe Gly Ala Ala Gln Asn Arg Pro Leu Trp Ile Ile Phe
            80                  85                  90 gag cgg gac atg gtc atc cgg ctg gac aaa gaa atg gtc gtg aac agc       336
Glu Arg Asp Met Val Ile Arg Leu Asp Lys Glu Met Val Val Asn Ser
95                  100                 105                 110 gac aag acc atc gac gga aga ggc gcc aaa gtg gaa atc atc aac gcc       384
Asp Lys Thr Ile Asp Gly Arg Gly Ala Lys Val Glu Ile Ile Asn Ala
                115                 120                 125 ggc ttc aca ctg aac ggc gtg aag aac gtg atc atc cac aac atc aac       432
Gly Phe Thr Leu Asn Gly Val Lys Asn Val Ile Ile His Asn Ile Asn
            130                 135                 140 atg cac gac gtg aaa gtg aat ccc gga gga ctg atc aag agc aac gat       480
Met His Asp Val Lys Val Asn Pro Gly Gly Leu Ile Lys Ser Asn Asp
                145                 150                 155 ggc cca gcc gcc cct aga gcc gga tct gat ggc gac gcc att tcc atc       528
Gly Pro Ala Ala Pro Arg Ala Gly Ser Asp Gly Asp Ala Ile Ser Ile
160                 165                 170 agc ggc agc tct cag atc tgg atc gac cac tgc tct ctg agc aag agc       576
Ser Gly Ser Ser Gln Ile Trp Ile Asp His Cys Ser Leu Ser Lys Ser
175                 180                 185                 190 gtg gac gga ctc gtg gac gcc aag ctg ggc acc aca aga ctg acc gtg       624
```

| | | | | | | | | | | | | |
|---|---|---|---|---|---|---|---|---|---|---|---|---|
|Val|Asp|Gly|Leu|Val|Asp|Ala|Lys|Leu|Gly|Thr|Thr|Arg|Leu|Thr|Val|
| | | |195| | | |200| | | |205| | | | |

```
tcc aac tct ctg ttc acc cag cac cag ttc gtg ctg ctg ttc ggc gct      672
Ser Asn Ser Leu Phe Thr Gln His Gln Phe Val Leu Leu Phe Gly Ala
        210                 215                 220 ggc gac gag aac atc gag gat agg ggc atg ctg gcc acc gtg gcc ttc      720
Gly Asp Glu Asn Ile Glu Asp Arg Gly Met Leu Ala Thr Val Ala Phe
            225                 230                 235 aac aca ttc acc gac aac gtg gac cag cgg atg ccc aga tgc cgg cac      768
Asn Thr Phe Thr Asp Asn Val Asp Gln Arg Met Pro Arg Cys Arg His
    240                 245                 250 ggc ttc ttc caa gtc gtg aac aac aac tac gat aag tgg ggc agc tac      816
Gly Phe Phe Gln Val Val Asn Asn Asn Tyr Asp Lys Trp Gly Ser Tyr
255                 260                 265                 270 gcc atc ggc ggc tct gcc agc cct acc att ctg agc caa ggc aac cgg      864
Ala Ile Gly Gly Ser Ala Ser Pro Thr Ile Leu Ser Gln Gly Asn Arg
                275                 280                 285 ttc tgc gcc cca gac gag cgg agc aag aag aat gtg ctg gga cgg cac      912
Phe Cys Ala Pro Asp Glu Arg Ser Lys Lys Asn Val Leu Gly Arg His
        290                 295                 300 ggc gaa gcc gcc gct gaa tcc atg aag tgg aac tgg cgg acc aac aag      960
Gly Glu Ala Ala Ala Glu Ser Met Lys Trp Asn Trp Arg Thr Asn Lys
            305                 310                 315 gac gtg ctg gaa aac ggc gcc atc ttc gtg gcc tct ggc gtg gac cca     1008
Asp Val Leu Glu Asn Gly Ala Ile Phe Val Ala Ser Gly Val Asp Pro
    320                 325                 330 gtg ctg aca cca gaa cag agc gcc ggc atg att cca gcc gag ccc ggc     1056
Val Leu Thr Pro Glu Gln Ser Ala Gly Met Ile Pro Ala Glu Pro Gly
335                 340                 345                 350 gaa tct gct ctg tct ctg aca agc tct gcc ggc gtg ctg agc tgt cag     1104
Glu Ser Ala Leu Ser Leu Thr Ser Ser Ala Gly Val Leu Ser Cys Gln
                355                 360                 365 ccc gga gca cca tgt gaattc                                          1125
Pro Gly Ala Pro Cys
        370
```

<210> SEQ ID NO 29
<211> LENGTH: 371
<212> TYPE: PRT
<213> ORGANISM: Ambrosia artemisiifolia

<400> SEQUENCE: 29

```
Ala Glu Asp Leu Gln Glu Ile Leu Pro Val Asn Glu Thr Arg Arg Leu
1               5                   10                  15

Thr Thr Ser Gly Ala Tyr Asn Ile Ile Asp Gly Cys Trp Arg Gly Lys
            20                  25                  30

Ala Asp Trp Ala Glu Asn Arg Lys Ala Leu Ala Asp Cys Ala Gln Gly
        35                  40                  45

Phe Gly Lys Gly Thr Val Gly Gly Lys Asp Gly Asp Ile Tyr Thr Val
    50                  55                  60

Thr Ser Glu Leu Asp Asp Val Ala Asn Pro Lys Glu Gly Thr Leu
65                  70                  75                  80

Arg Phe Gly Ala Ala Gln Asn Arg Pro Leu Trp Ile Ile Phe Glu Arg
                85                  90                  95

Asp Met Val Ile Arg Leu Asp Lys Glu Met Val Val Asn Ser Asp Lys
            100                 105                 110

Thr Ile Asp Gly Arg Gly Ala Lys Val Glu Ile Ile Asn Ala Gly Phe
        115                 120                 125
```

```
Thr Leu Asn Gly Val Lys Asn Val Ile Ile His Asn Ile Asn Met His
    130                 135                 140
Asp Val Lys Val Asn Pro Gly Leu Ile Lys Ser Asn Asp Gly Pro
145                 150                 155                 160
Ala Ala Pro Arg Ala Gly Ser Asp Gly Asp Ala Ile Ser Ile Ser Gly
                165                 170                 175
Ser Ser Gln Ile Trp Ile Asp His Cys Ser Leu Ser Lys Ser Val Asp
                180                 185                 190
Gly Leu Val Asp Ala Lys Leu Gly Thr Thr Arg Leu Thr Val Ser Asn
                195                 200                 205
Ser Leu Phe Thr Gln His Gln Phe Val Leu Leu Phe Gly Ala Gly Asp
    210                 215                 220
Glu Asn Ile Glu Asp Arg Gly Met Leu Ala Thr Val Ala Phe Asn Thr
225                 230                 235                 240
Phe Thr Asp Asn Val Asp Gln Arg Met Pro Arg Cys Arg His Gly Phe
                245                 250                 255
Phe Gln Val Val Asn Asn Asn Tyr Asp Lys Trp Gly Ser Tyr Ala Ile
                260                 265                 270
Gly Gly Ser Ala Ser Pro Thr Ile Leu Ser Gln Gly Asn Arg Phe Cys
                275                 280                 285
Ala Pro Asp Glu Arg Ser Lys Lys Asn Val Leu Gly Arg His Gly Glu
                290                 295                 300
Ala Ala Ala Glu Ser Met Lys Trp Asn Trp Arg Thr Asn Lys Asp Val
305                 310                 315                 320
Leu Glu Asn Gly Ala Ile Phe Val Ala Ser Gly Val Asp Pro Val Leu
                325                 330                 335
Thr Pro Glu Gln Ser Ala Gly Met Ile Pro Ala Glu Pro Gly Glu Ser
                340                 345                 350
Ala Leu Ser Leu Thr Ser Ser Ala Gly Val Leu Ser Cys Gln Pro Gly
                355                 360                 365
Ala Pro Cys
    370

<210> SEQ ID NO 30
<211> LENGTH: 2379
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(2379)

<400> SEQUENCE: 30 atg gcg ccc cgc agc gcc cgg cga ccc ctg ctg ctg cta ctg ttg       48
Met Ala Pro Arg Ser Ala Arg Arg Pro Leu Leu Leu Leu Leu Leu
1               5                   10                  15 ctg ctg ctc ggc ctc atg cat tgt gcg tca gca gca atg ttt atg gtg   96
Leu Leu Leu Gly Leu Met His Cys Ala Ser Ala Ala Met Phe Met Val
                20                  25                  30 aaa aat ggc aac ggg acc gcg tgc ata atg gcc aac ttc tct gct gcc   144
Lys Asn Gly Asn Gly Thr Ala Cys Ile Met Ala Asn Phe Ser Ala Ala
            35                  40                  45 ttc tca gtg aac tac gac acc aag agt ggc cct aag aac atg acc ctt   192
Phe Ser Val Asn Tyr Asp Thr Lys Ser Gly Pro Lys Asn Met Thr Leu
        50                  55                  60 gac ctg cca tca gat gcc aca gtg gtg ctc aac cgc agc tcc tgt gga   240
Asp Leu Pro Ser Asp Ala Thr Val Val Leu Asn Arg Ser Ser Cys Gly
```

|  |  |  |  |  |  |  |  |  |  |  |  |  |  |  |  |  |
|---|---|---|---|---|---|---|---|---|---|---|---|---|---|---|---|---|
| | | 65 | | | | 70 | | | | | 75 | | | | 80 | |

```
aaa gag aac act tct gac ccc agt ctc gtg att gct ttt gga aga gga      288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc      336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc      384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc      432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc      480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg      528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa      576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg      624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc      672
Pro Ser Pro Val Pro Lys Ser Pro Ser Val Asp Lys Tyr Asn Val Ser
    210                 215                 220 ggc acc aac ggg acc tgc ctg ctg gcc agc atg ggg ctg cag ctg aac      720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac      768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg      816
Ile Asn Pro Asn Lys Thr Ser Ala Ser Gly Ser Cys Gly Ala His Leu
            260                 265                 270 gtg act ctg gag ctg cac agc gag ggc acc acc gtc ctg ctc ttc cag      864
Val Thr Leu Glu Leu His Ser Glu Gly Thr Thr Val Leu Leu Phe Gln
        275                 280                 285 ttc ggg atg aat gca agt tct agc cgg ttt ttc cta caa gga atc cag      912
Phe Gly Met Asn Ala Ser Ser Ser Arg Phe Phe Leu Gln Gly Ile Gln
    290                 295                 300 ttg aat aca att ctt cct gac gcc aga gac cct gcc ttt aaa gct gcc      960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag     1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat     1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt     1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag gcc gag     1152
Gly Ser Val Glu Glu Cys Leu Leu Asp Glu Asn Ser Leu Glu Ala Glu
    370                 375                 380 gat ctg caa gag att ctg ccc gtg aac gag aca cgg cgg ctg aca aca     1200
```

```
Asp Leu Gln Glu Ile Leu Pro Val Asn Glu Thr Arg Arg Leu Thr Thr
385                 390                 395                 400 agc ggc gcc tac aac atc atc gac ggc tgc tgg cgg ggc aag gcc gat      1248
Ser Gly Ala Tyr Asn Ile Ile Asp Gly Cys Trp Arg Gly Lys Ala Asp
                        405                 410                 415 tgg gcc gag aac aga aag gct ctg gcc gat tgc gcc caa ggc ttc ggc      1296
Trp Ala Glu Asn Arg Lys Ala Leu Ala Asp Cys Ala Gln Gly Phe Gly
                420                 425                 430 aag gga aca gtg ggc ggc aag gac ggc gac atc tac acc gtg acc agc      1344
Lys Gly Thr Val Gly Gly Lys Asp Gly Asp Ile Tyr Thr Val Thr Ser
        435                 440                 445 gag ctg gac gac gac gtg gcc aat ccc aaa gag ggc aca ctg aga ttc      1392
Glu Leu Asp Asp Asp Val Ala Asn Pro Lys Glu Gly Thr Leu Arg Phe
450                 455                 460 gga gcc gcc cag aac cgg cct ctg tgg atc atc ttc gag cgg gac atg      1440
Gly Ala Ala Gln Asn Arg Pro Leu Trp Ile Ile Phe Glu Arg Asp Met
465                 470                 475                 480 gtc atc cgg ctg gac aaa gaa atg gtc gtg aac agc gac aag acc atc      1488
Val Ile Arg Leu Asp Lys Glu Met Val Val Asn Ser Asp Lys Thr Ile
                485                 490                 495 gac gga aga ggc gcc aaa gtg gaa atc atc aac gcc ggc ttc aca ctg      1536
Asp Gly Arg Gly Ala Lys Val Glu Ile Ile Asn Ala Gly Phe Thr Leu
            500                 505                 510 aac ggc gtg aag aac gtg atc atc cac aac atc aac atg cac gac gtg      1584
Asn Gly Val Lys Asn Val Ile Ile His Asn Ile Asn Met His Asp Val
        515                 520                 525 aaa gtg aat ccc ggc gga ctg atc aag agc aac gat ggc cca gcc gcc      1632
Lys Val Asn Pro Gly Gly Leu Ile Lys Ser Asn Asp Gly Pro Ala Ala
530                 535                 540 cct aga gcc gga tct gat ggc gac gcc att tcc atc agc ggc agc tct      1680
Pro Arg Ala Gly Ser Asp Gly Asp Ala Ile Ser Ile Ser Gly Ser Ser
545                 550                 555                 560 cag atc tgg atc gac cac tgc tct ctg agc aag agc gtg gac gga ctc      1728
Gln Ile Trp Ile Asp His Cys Ser Leu Ser Lys Ser Val Asp Gly Leu
                565                 570                 575 gtg gac gcc aag ctg ggc acc aca aga ctg acc gtg tcc aac tct ctg      1776
Val Asp Ala Lys Leu Gly Thr Thr Arg Leu Thr Val Ser Asn Ser Leu
            580                 585                 590 ttc acc cag cac cag ttc gtg ctg ctg ttc ggc gct ggc gac gag aac      1824
Phe Thr Gln His Gln Phe Val Leu Leu Phe Gly Ala Gly Asp Glu Asn
        595                 600                 605 atc gag gat agg ggc atg ctg gcc acc gtg gcc ttc aac aca ttc acc      1872
Ile Glu Asp Arg Gly Met Leu Ala Thr Val Ala Phe Asn Thr Phe Thr
610                 615                 620 gac aac gtg gac cag cgg atg ccc aga tgc cgg cac ggc ttc ttc caa      1920
Asp Asn Val Asp Gln Arg Met Pro Arg Cys Arg His Gly Phe Phe Gln
625                 630                 635                 640 gtc gtg aac aac aac tac gat aag tgg ggc agc tac gcc atc ggc ggc      1968
Val Val Asn Asn Asn Tyr Asp Lys Trp Gly Ser Tyr Ala Ile Gly Gly
                645                 650                 655 tct gcc agc cct acc att ctg agc caa ggc aac cgg ttc tgc gcc cca      2016
Ser Ala Ser Pro Thr Ile Leu Ser Gln Gly Asn Arg Phe Cys Ala Pro
            660                 665                 670 gac gag cgg agc aag aag aat gtg ctg gga cgg cac ggc gaa gcc gcc      2064
Asp Glu Arg Ser Lys Lys Asn Val Leu Gly Arg His Gly Glu Ala Ala
        675                 680                 685 gct gaa tcc atg aag tgg aac tgg cgg acc aac aag gac gtg ctg gaa      2112
Ala Glu Ser Met Lys Trp Asn Trp Arg Thr Asn Lys Asp Val Leu Glu
690                 695                 700
```

```
aac ggc gcc atc ttc gtg gcc tct ggc gtg gac cca gtg ctg aca cca    2160
Asn Gly Ala Ile Phe Val Ala Ser Gly Val Asp Pro Val Leu Thr Pro
705             710                 715                 720 gaa cag agc gcc ggc atg att cca gcc gag ccc gga gaa tct gct ctg    2208
Glu Gln Ser Ala Gly Met Ile Pro Ala Glu Pro Gly Glu Ser Ala Leu
            725                 730                 735 tct ctg aca agc tct gcc ggc gtg ctg agc tgt cag ccc gga gca cca    2256
Ser Leu Thr Ser Ser Ala Gly Val Leu Ser Cys Gln Pro Gly Ala Pro
        740                 745                 750 tgt gaa ttc acg ctg atc ccc atc gct gtg ggt ggt gcc ctg gcg ggg    2304
Cys Glu Phe Thr Leu Ile Pro Ile Ala Val Gly Gly Ala Leu Ala Gly
    755                 760                 765 ctg gtc ctc atc gtc ctc atc gcc tac ctc gtc ggc agg aag agg agt    2352
Leu Val Leu Ile Val Leu Ile Ala Tyr Leu Val Gly Arg Lys Arg Ser
770                 775                 780 cac gca ggc tac cag act atc tag taa                                 2379
His Ala Gly Tyr Gln Thr Ile
785                 790
```

<210> SEQ ID NO 31
<211> LENGTH: 791
<212> TYPE: PRT
<213> ORGANISM: Artificial sequence
<220> FEATURE:
<223> OTHER INFORMATION: Synthetic Construct

<400> SEQUENCE: 31

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240
```

```
Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Ala Glu
    370                 375                 380

Asp Leu Gln Glu Ile Leu Pro Val Asn Glu Thr Arg Arg Leu Thr Thr
385                 390                 395                 400

Ser Gly Ala Tyr Asn Ile Ile Asp Gly Cys Trp Arg Gly Lys Ala Asp
                405                 410                 415

Trp Ala Glu Asn Arg Lys Ala Leu Ala Asp Cys Ala Gln Gly Phe Gly
            420                 425                 430

Lys Gly Thr Val Gly Gly Lys Asp Gly Asp Ile Tyr Thr Val Thr Ser
        435                 440                 445

Glu Leu Asp Asp Asp Val Ala Asn Pro Lys Glu Gly Thr Leu Arg Phe
    450                 455                 460

Gly Ala Ala Gln Asn Arg Pro Leu Trp Ile Ile Phe Glu Arg Asp Met
465                 470                 475                 480

Val Ile Arg Leu Asp Lys Glu Met Val Val Asn Ser Asp Lys Thr Ile
                485                 490                 495

Asp Gly Arg Gly Ala Lys Val Glu Ile Ile Asn Ala Gly Phe Thr Leu
            500                 505                 510

Asn Gly Val Lys Asn Val Ile Ile His Asn Ile Asn Met His Asp Val
        515                 520                 525

Lys Val Asn Pro Gly Gly Leu Ile Lys Ser Asn Asp Gly Pro Ala Ala
    530                 535                 540

Pro Arg Ala Gly Ser Asp Gly Asp Ala Ile Ser Ile Ser Gly Ser Ser
545                 550                 555                 560

Gln Ile Trp Ile Asp His Cys Ser Leu Ser Lys Ser Val Asp Gly Leu
                565                 570                 575

Val Asp Ala Lys Leu Gly Thr Thr Arg Leu Thr Val Ser Asn Ser Leu
            580                 585                 590

Phe Thr Gln His Gln Phe Val Leu Leu Phe Gly Ala Gly Asp Glu Asn
        595                 600                 605

Ile Glu Asp Arg Gly Met Leu Ala Thr Val Ala Phe Asn Thr Phe Thr
    610                 615                 620

Asp Asn Val Asp Gln Arg Met Pro Arg Cys Arg His Gly Phe Phe Gln
625                 630                 635                 640

Val Val Asn Asn Asn Tyr Asp Lys Trp Gly Ser Tyr Ala Ile Gly Gly
                645                 650                 655

Ser Ala Ser Pro Thr Ile Leu Ser Gln Gly Asn Arg Phe Cys Ala Pro
```

```
                    660            665             670
Asp Glu Arg Ser Lys Lys Asn Val Leu Gly Arg His Gly Glu Ala Ala
            675             680             685

Ala Glu Ser Met Lys Trp Asn Trp Arg Thr Asn Lys Asp Val Leu Glu
            690             695             700

Asn Gly Ala Ile Phe Val Ala Ser Gly Val Asp Pro Val Leu Thr Pro
705             710             715             720

Glu Gln Ser Ala Gly Met Ile Pro Ala Glu Pro Gly Glu Ser Ala Leu
                725             730             735

Ser Leu Thr Ser Ser Ala Gly Val Leu Ser Cys Gln Pro Gly Ala Pro
            740             745             750

Cys Glu Phe Thr Leu Ile Pro Ile Ala Val Gly Gly Ala Leu Ala Gly
            755             760             765

Leu Val Leu Ile Val Leu Ile Ala Tyr Leu Val Gly Arg Lys Arg Ser
            770             775             780

His Ala Gly Tyr Gln Thr Ile
785             790
```

<210> SEQ ID NO 32
<211> LENGTH: 489
<212> TYPE: DNA
<213> ORGANISM: Betula pendula
<220> FEATURE:
<221> NAME/KEY: CDS
<222> LOCATION: (7)..(483)

<400> SEQUENCE: 32

```
ctcgag ggc gtg ttc aac tac gag aca gag aca acc agc gtg atc cca        48
       Gly Val Phe Asn Tyr Glu Thr Glu Thr Thr Ser Val Ile Pro
        1               5                  10 gcc gcc aga ctg ttc aag gcc ttc att ctg gac ggc gac aat ctg ttc       96
Ala Ala Arg Leu Phe Lys Ala Phe Ile Leu Asp Gly Asp Asn Leu Phe
15                  20                  25                  30 ccc aaa gtg gcc ccc caa gcc atc agc agc gtg gaa aac atc gag ggc      144
Pro Lys Val Ala Pro Gln Ala Ile Ser Ser Val Glu Asn Ile Glu Gly
                35                  40                  45 aat ggc gga ccc ggc acc atc aag aag atc agc ttc ccc gag ggc ttc      192
Asn Gly Gly Pro Gly Thr Ile Lys Lys Ile Ser Phe Pro Glu Gly Phe
            50                  55                  60 cca ttc aaa tac gtg aag gac cgg gtg gac gaa gtg gac cac acc aac      240
Pro Phe Lys Tyr Val Lys Asp Arg Val Asp Glu Val Asp His Thr Asn
65                  70                  75 ttc aag tac aac tac tcc gtg atc gag ggc gga ccc atc ggc gac aca      288
Phe Lys Tyr Asn Tyr Ser Val Ile Glu Gly Gly Pro Ile Gly Asp Thr
        80                  85                  90 ctg gaa aag atc agc aac gag atc aag atc gtg gcc acc ccc gac ggc      336
Leu Glu Lys Ile Ser Asn Glu Ile Lys Ile Val Ala Thr Pro Asp Gly
95                 100                 105                 110 ggc agc att ctg aag atc tcc aac aag tac cac aca aag ggc gac cac      384
Gly Ser Ile Leu Lys Ile Ser Asn Lys Tyr His Thr Lys Gly Asp His
                115                 120                 125 gaa gtg aag gcc gaa caa gtg aaa gcc agc aaa gag atg ggc gag aca      432
Glu Val Lys Ala Glu Gln Val Lys Ala Ser Lys Glu Met Gly Glu Thr
            130                 135                 140 ctg ctg cgg gcc gtg gaa agc tat ctg ctg gcc cac agc gac gcc tac      480
Leu Leu Arg Ala Val Glu Ser Tyr Leu Leu Ala His Ser Asp Ala Tyr
145                 150                 155 aac gaattc                                                            489
Asn
```

<210> SEQ ID NO 33
<211> LENGTH: 159
<212> TYPE: PRT
<213> ORGANISM: Betula pendula

<400> SEQUENCE: 33

```
Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Gly Asn Gly
        35                  40                  45

Gly Pro Gly Thr Ile Lys Lys Ile Ser Phe Pro Glu Gly Phe Pro Phe
    50                  55                  60

Lys Tyr Val Lys Asp Arg Val Asp Glu Val Asp His Thr Asn Phe Lys
65                  70                  75                  80

Tyr Asn Tyr Ser Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
            100                 105                 110

Ile Leu Lys Ile Ser Asn Lys Tyr His Thr Lys Gly Asp His Glu Val
        115                 120                 125

Lys Ala Glu Gln Val Lys Ala Ser Lys Glu Met Gly Glu Thr Leu Leu
    130                 135                 140

Arg Ala Val Glu Ser Tyr Leu Leu Ala His Ser Asp Ala Tyr Asn
145                 150                 155
```

<210> SEQ ID NO 34
<211> LENGTH: 1743
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1743)

<400> SEQUENCE: 34

```
atg gcg ccc cgc agc gcc cgg cga ccc ctg ctg ctg cta ctg ctg ttg      48
Met Ala Pro Arg Ser Ala Arg Arg Pro Leu Leu Leu Leu Leu Leu Leu
1               5                   10                  15 ctg ctg ctc ggc ctc atg cat tgt gcg tca gca gca atg ttt atg gtg      96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc     144
Lys Asn Gly Asn Gly Thr Ala Cys Ile Met Ala Asn Phe Ser Ala Ala
        35                  40                  45 ttc tca gtg aac tac gac acc aag agt ggc cct aag aac atg acc ctt     192
Phe Ser Val Asn Tyr Asp Thr Lys Ser Gly Pro Lys Asn Met Thr Leu
    50                  55                  60 gac ctg cca tca gat gcc aca gtg gtg ctc aac cgc agc tcc tgt gga     240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga     288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc     336
His Thr Leu Thr Leu Asn Phe Thr Arg Asn Ala Thr Arg Tyr Ser Val
            100                 105                 110
```

-continued

```
cag ctc atg agt ttt gtt tat aac ttg tca gac aca cac ctt ttc ccc     384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc     432
Asn Ala Ser Ser Lys Glu Ile Lys Thr Val Glu Ser Ile Thr Asp Ile
130                 135                 140 agg gca gat ata gat aaa aaa tac aga tgt gtt agt ggc acc cag gtc     480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg     528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa     576
Tyr Leu Ser Asn Ser Ser Phe Ser Arg Gly Glu Thr Arg Cys Glu Gln
        180                 185                 190 gac agg cct tcc cca acc aca gcg ccc cct gcg cca ccc agc ccc tcg     624
Asp Arg Pro Ser Pro Thr Thr Ala Pro Pro Ala Pro Pro Ser Pro Ser
    195                 200                 205 ccc tca ccc gtg ccc aag agc ccc tct gtg gac aag tac aac gtg agc     672
Pro Ser Pro Val Pro Lys Ser Pro Ser Val Asp Lys Tyr Asn Val Ser
210                 215                 220 ggc acc aac ggg acc tgc ctg ctg gcc agc atg ggg ctg cag ctg aac     720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac     768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg     816
Ile Asn Pro Asn Lys Thr Ser Ala Ser Gly Ser Cys Gly Ala His Leu
        260                 265                 270 gtg act ctg gag ctg cac agc gag ggc acc acc gtc ctg ctc ttc cag     864
Val Thr Leu Glu Leu His Ser Glu Gly Thr Thr Val Leu Leu Phe Gln
    275                 280                 285 ttc ggg atg aat gca agt tct agc cgg ttt ttc cta caa gga atc cag     912
Phe Gly Met Asn Ala Ser Ser Ser Arg Phe Phe Leu Gln Gly Ile Gln
290                 295                 300 ttg aat aca att ctt cct gac gcc aga gac cct gcc ttt aaa gct gcc     960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag    1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat    1056
Cys Asn Ala Glu Glu His Val Arg Val Thr Lys Ala Phe Ser Val Asn
        340                 345                 350 ata ttc aaa gtg tgg gtc cag gct ttc aag gtg gaa ggt ggc cag ttt    1104
Ile Phe Lys Val Trp Val Gln Ala Phe Lys Val Glu Gly Gly Gln Phe
    355                 360                 365 ggc tct gtg gag gag tgt ctg ctg gac gag aac agc ctc gag ggc gtg    1152
Gly Ser Val Glu Glu Cys Leu Leu Asp Glu Asn Ser Leu Glu Gly Val
370                 375                 380 ttc aac tac gag aca gag aca acc agc gtg atc cca gcc gcc aga ctg    1200
Phe Asn Tyr Glu Thr Glu Thr Thr Ser Val Ile Pro Ala Ala Arg Leu
385                 390                 395                 400 ttc aag gcc ttc att ctg gac ggc gac aat ctg ttc ccc aaa gtg gcc    1248
Phe Lys Ala Phe Ile Leu Asp Gly Asp Asn Leu Phe Pro Lys Val Ala
                405                 410                 415 ccc caa gcc atc agc agc gtg gaa aac atc gag ggc aat ggc gga ccc    1296
Pro Gln Ala Ile Ser Ser Val Glu Asn Ile Glu Gly Asn Gly Gly Pro
```

```
                420             425             430
ggc acc atc aag aag atc agc ttc ccc gag ggc ttc cca ttc aaa tac    1344
Gly Thr Ile Lys Lys Ile Ser Phe Pro Glu Gly Phe Pro Phe Lys Tyr
        435                 440                 445 gtg aag gac cgg gtg gac gaa gtg gac cac acc aac ttc aag tac aac    1392
Val Lys Asp Arg Val Asp Glu Val Asp His Thr Asn Phe Lys Tyr Asn
450                 455                 460 tac tcc gtg atc gag ggc gga ccc atc ggc gac aca ctg gaa aag atc    1440
Tyr Ser Val Ile Glu Gly Gly Pro Ile Gly Asp Thr Leu Glu Lys Ile
465                 470                 475                 480 agc aac gag atc aag atc gtg gcc acc ccc gac ggc ggc agc att ctg    1488
Ser Asn Glu Ile Lys Ile Val Ala Thr Pro Asp Gly Gly Ser Ile Leu
                485                 490                 495 aag atc tcc aac aag tac cac aca aag ggc gac cac gaa gtg aag gcc    1536
Lys Ile Ser Asn Lys Tyr His Thr Lys Gly Asp His Glu Val Lys Ala
            500                 505                 510 gaa caa gtg aaa gcc agc aaa gag atg ggc gag aca ctg ctg cgg gcc    1584
Glu Gln Val Lys Ala Ser Lys Glu Met Gly Glu Thr Leu Leu Arg Ala
        515                 520                 525 gtg gaa agc tat ctg ctg gcc cac agc gac gcc tac aac gaa ttc acg    1632
Val Glu Ser Tyr Leu Leu Ala His Ser Asp Ala Tyr Asn Glu Phe Thr
530                 535                 540 ctg atc ccc atc gct gtg ggt ggt gcc ctg gcg ggg ctg gtc ctc atc    1680
Leu Ile Pro Ile Ala Val Gly Gly Ala Leu Ala Gly Leu Val Leu Ile
545                 550                 555                 560 gtc ctc atc gcc tac ctc gtc ggc agg aag agg agt cac gca ggc tac    1728
Val Leu Ile Ala Tyr Leu Val Gly Arg Lys Arg Ser His Ala Gly Tyr
                565                 570                 575 cag act atc tag taa                                                1743
Gln Thr Ile <210> SEQ ID NO 35
<211> LENGTH: 579
<212> TYPE: PRT
<213> ORGANISM: Artificial sequence
<220> FEATURE:
<223> OTHER INFORMATION: Synthetic Construct

<400> SEQUENCE: 35

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
```

```
                145                 150                 155                 160
            His Met Asn Asn Val Thr Val Thr Leu His Asp Ala Thr Ile Gln Ala
                            165                 170                 175
            Tyr Leu Ser Asn Ser Ser Phe Ser Arg Gly Glu Thr Arg Cys Glu Gln
                            180                 185                 190
            Asp Arg Pro Ser Pro Thr Thr Ala Pro Pro Ala Pro Pro Ser Pro Ser
                            195                 200                 205
            Pro Ser Pro Val Pro Lys Ser Pro Ser Val Asp Lys Tyr Asn Val Ser
                            210                 215                 220
            Gly Thr Asn Gly Thr Cys Leu Leu Ala Ser Met Gly Leu Gln Leu Asn
            225                 230                 235                 240
            Leu Thr Tyr Glu Arg Lys Asp Asn Thr Thr Val Thr Arg Leu Leu Asn
                            245                 250                 255
            Ile Asn Pro Asn Lys Thr Ser Ala Ser Gly Ser Cys Gly Ala His Leu
                            260                 265                 270
            Val Thr Leu Glu Leu His Ser Glu Gly Thr Thr Val Leu Leu Phe Gln
                            275                 280                 285
            Phe Gly Met Asn Ala Ser Ser Arg Phe Phe Leu Gln Gly Ile Gln
                            290                 295                 300
            Leu Asn Thr Ile Leu Pro Asp Ala Arg Asp Pro Ala Phe Lys Ala Ala
            305                 310                 315                 320
            Asn Gly Ser Leu Arg Ala Leu Gln Ala Thr Val Gly Asn Ser Tyr Lys
                            325                 330                 335
            Cys Asn Ala Glu Glu His Val Arg Val Thr Lys Ala Phe Ser Val Asn
                            340                 345                 350
            Ile Phe Lys Val Trp Val Gln Ala Phe Lys Val Glu Gly Gly Gln Phe
                            355                 360                 365
            Gly Ser Val Glu Glu Cys Leu Leu Asp Glu Asn Ser Leu Glu Gly Val
                            370                 375                 380
            Phe Asn Tyr Glu Thr Glu Thr Thr Ser Val Ile Pro Ala Ala Arg Leu
            385                 390                 395                 400
            Phe Lys Ala Phe Ile Leu Asp Gly Asp Asn Leu Phe Pro Lys Val Ala
                            405                 410                 415
            Pro Gln Ala Ile Ser Ser Val Glu Asn Ile Glu Gly Asn Gly Gly Pro
                            420                 425                 430
            Gly Thr Ile Lys Lys Ile Ser Phe Pro Glu Gly Phe Pro Phe Lys Tyr
                            435                 440                 445
            Val Lys Asp Arg Val Asp Glu Val Asp His Thr Asn Phe Lys Tyr Asn
                            450                 455                 460
            Tyr Ser Val Ile Glu Gly Gly Pro Ile Gly Asp Thr Leu Glu Lys Ile
            465                 470                 475                 480
            Ser Asn Glu Ile Lys Ile Val Ala Thr Pro Asp Gly Gly Ser Ile Leu
                            485                 490                 495
            Lys Ile Ser Asn Lys Tyr His Thr Lys Gly Asp His Glu Val Lys Ala
                            500                 505                 510
            Glu Gln Val Lys Ala Ser Lys Glu Met Gly Glu Thr Leu Leu Arg Ala
                            515                 520                 525
            Val Glu Ser Tyr Leu Leu Ala His Ser Asp Ala Tyr Asn Glu Phe Thr
                            530                 535                 540
            Leu Ile Pro Ile Ala Val Gly Gly Ala Leu Ala Gly Leu Val Leu Ile
            545                 550                 555                 560
            Val Leu Ile Ala Tyr Leu Val Gly Arg Lys Arg Ser His Ala Gly Tyr
                            565                 570                 575
```

```
<210> SEQ ID NO 36
<211> LENGTH: 480
<212> TYPE: DNA
<213> ORGANISM: Canis lupus
<220> FEATURE:
<221> NAME/KEY: CDS
<222> LOCATION: (7)..(474)

<400> SEQUENCE: 36 ctcgag caa gac acc ccc gct ctg ggc aag gat acc gtg gcc gtg tcc         48
       Gln Asp Thr Pro Ala Leu Gly Lys Asp Thr Val Ala Val Ser
       1               5                   10 ggc aag tgg tat ctg aag gcc atg acc gcc gac caa gaa gtg ccc gag         96
Gly Lys Trp Tyr Leu Lys Ala Met Thr Ala Asp Gln Glu Val Pro Glu
15                  20                  25                  30 aag ccc gat agc gtg acc ccc atg att ctg aaa gcc cag aag ggc ggc        144
Lys Pro Asp Ser Val Thr Pro Met Ile Leu Lys Ala Gln Lys Gly Gly
                35                  40                  45 aat ctg gaa gcc aag atc acc atg ctg acc aac ggc cag tgc cag aac        192
Asn Leu Glu Ala Lys Ile Thr Met Leu Thr Asn Gly Gln Cys Gln Asn
            50                  55                  60 atc acc gtg gtg ctg cac aag acc agc gag ccc ggc aag tac aca gcc        240
Ile Thr Val Val Leu His Lys Thr Ser Glu Pro Gly Lys Tyr Thr Ala
        65                  70                  75 tac gag ggc cag cgg gtg gtg ttc atc cag cct tct cca gtg cgg gat        288
Tyr Glu Gly Gln Arg Val Val Phe Ile Gln Pro Ser Pro Val Arg Asp
    80                  85                  90 cac tac att ctg tac tgc gag ggc gag ctg cac ggc cgg cag atc aga        336
His Tyr Ile Leu Tyr Cys Glu Gly Glu Leu His Gly Arg Gln Ile Arg
95                  100                 105                 110 atg gcc aag ctg ctg ggc aga gat ccc gag cag agc caa gag gct ctg        384
Met Ala Lys Leu Leu Gly Arg Asp Pro Glu Gln Ser Gln Glu Ala Leu
                115                 120                 125 gaa gat ttc aga gag ttc agc cgg gcc aag gga ctg aac caa gag att        432
Glu Asp Phe Arg Glu Phe Ser Arg Ala Lys Gly Leu Asn Gln Glu Ile
            130                 135                 140 ctg gaa ctg gct cag agc gag aca tgc tct ccc ggc gga caa gaattc        480
Leu Glu Leu Ala Gln Ser Glu Thr Cys Ser Pro Gly Gly Gln
        145                 150                 155

<210> SEQ ID NO 37
<211> LENGTH: 156
<212> TYPE: PRT
<213> ORGANISM: Canis lupus

<400> SEQUENCE: 37

Gln Asp Thr Pro Ala Leu Gly Lys Asp Thr Val Ala Val Ser Gly Lys
1               5                   10                  15

Trp Tyr Leu Lys Ala Met Thr Ala Asp Gln Glu Val Pro Glu Lys Pro
            20                  25                  30

Asp Ser Val Thr Pro Met Ile Leu Lys Ala Gln Lys Gly Gly Asn Leu
        35                  40                  45

Glu Ala Lys Ile Thr Met Leu Thr Asn Gly Gln Cys Gln Asn Ile Thr
    50                  55                  60

Val Val Leu His Lys Thr Ser Glu Pro Gly Lys Tyr Thr Ala Tyr Glu
65                  70                  75                  80

Gly Gln Arg Val Val Phe Ile Gln Pro Ser Pro Val Arg Asp His Tyr
            85                  90                  95
```

```
Ile Leu Tyr Cys Glu Gly Glu Leu His Gly Arg Gln Ile Arg Met Ala
                100                 105                 110

Lys Leu Leu Gly Arg Asp Pro Glu Gln Ser Gln Glu Ala Leu Glu Asp
            115                 120                 125

Phe Arg Glu Phe Ser Arg Ala Lys Gly Leu Asn Gln Glu Ile Leu Glu
        130                 135                 140

Leu Ala Gln Ser Glu Thr Cys Ser Pro Gly Gly Gln
145                 150                 155

<210> SEQ ID NO 38
<211> LENGTH: 1734
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1734)

<400> SEQUENCE: 38 atg gcg ccc cgc agc gcc cgg cga ccc ctg ctg cta ctg ctg ttg        48
Met Ala Pro Arg Ser Ala Arg Arg Pro Leu Leu Leu Leu Leu Leu
1               5                   10                  15 ctg ctc ggc ctc atg cat tgt gcg tca gca gca atg ttt atg gtg        96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc    144
Lys Asn Gly Asn Gly Thr Ala Cys Ile Met Ala Asn Phe Ser Ala Ala
        35                  40                  45 ttc tca gtg aac tac gac acc aag agt ggc cct aag aac atg acc ctt    192
Phe Ser Val Asn Tyr Asp Thr Lys Ser Gly Pro Lys Asn Met Thr Leu
    50                  55                  60 gac ctg cca tca gat gcc aca gtg gtg ctc aac cgc agc tcc tgt gga    240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga    288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc    336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc    384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc    432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc    480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg    528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa    576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg    624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc    672
Pro Ser Pro Val Pro Lys Ser Pro Ser Val Asp Lys Tyr Asn Val Ser
```

-continued

```
Pro Ser Pro Val Pro Lys Ser Pro Ser Val Asp Lys Tyr Asn Val Ser
    210                 215                 220 ggc acc aac ggg acc tgc ctg ctg gcc agc atg ggg ctg cag ctg aac        720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac        768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg        816
Ile Asn Pro Asn Lys Thr Ser Ala Ser Gly Ser Cys Gly Ala His Leu
            260                 265                 270 gtg act ctg gag ctg cac agc gag ggc acc acc gtc ctg ctc ttc cag        864
Val Thr Leu Glu Leu His Ser Glu Gly Thr Thr Val Leu Leu Phe Gln
        275                 280                 285 ttc ggg atg aat gca agt tct agc cgg ttt ttc cta caa gga atc cag        912
Phe Gly Met Asn Ala Ser Ser Ser Arg Phe Phe Leu Gln Gly Ile Gln
    290                 295                 300 ttg aat aca att ctt cct gac gcc aga gac cct gcc ttt aaa gct gcc        960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag       1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat       1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt       1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag caa gac       1152
Gly Ser Val Glu Glu Cys Leu Leu Asp Glu Asn Ser Leu Glu Gln Asp
    370                 375                 380 acc ccc gct ctg ggc aag gat acc gtg gcc gtg tcc ggc aag tgg tat       1200
Thr Pro Ala Leu Gly Lys Asp Thr Val Ala Val Ser Gly Lys Trp Tyr
385                 390                 395                 400 ctg aag gcc atg acc gcc gac caa gaa gtg ccc gag aag ccc gat agc       1248
Leu Lys Ala Met Thr Ala Asp Gln Glu Val Pro Glu Lys Pro Asp Ser
                405                 410                 415 gtg acc ccc atg att ctg aaa gcc cag aag ggc ggc aat ctg gaa gcc       1296
Val Thr Pro Met Ile Leu Lys Ala Gln Lys Gly Gly Asn Leu Glu Ala
            420                 425                 430 aag atc acc atg ctg acc aac ggc cag tgc cag aac atc acc gtg gtg       1344
Lys Ile Thr Met Leu Thr Asn Gly Gln Cys Gln Asn Ile Thr Val Val
        435                 440                 445 ctg cac aag acc agc gag ccc ggc aag tac aca gcc tac gag ggc cag       1392
Leu His Lys Thr Ser Glu Pro Gly Lys Tyr Thr Ala Tyr Glu Gly Gln
    450                 455                 460 cgg gtg gtg ttc atc cag cct tct cca gtg cgg gat cac tac att ctg       1440
Arg Val Val Phe Ile Gln Pro Ser Pro Val Arg Asp His Tyr Ile Leu
465                 470                 475                 480 tac tgc gag ggc gag ctg cac ggc cgg cag atc aga atg gcc aag ctg       1488
Tyr Cys Glu Gly Glu Leu His Gly Arg Gln Ile Arg Met Ala Lys Leu
                485                 490                 495 ctg ggc aga gat ccc gag cag agc caa gag gct ctg gaa gat ttc aga       1536
Leu Gly Arg Asp Pro Glu Gln Ser Gln Glu Ala Leu Glu Asp Phe Arg
            500                 505                 510 gag ttc agc cgg gcc aag gga ctg aac caa gag att ctg gaa ctg gct       1584
Glu Phe Ser Arg Ala Lys Gly Leu Asn Gln Glu Ile Leu Glu Leu Ala
        515                 520                 525
```

-continued

| | | | | | | | | | | | | |
|---|---|---|---|---|---|---|---|---|---|---|---|---|
| cag | agc | gag | aca | tgc | tct | ccc | gga | caa | gaa | ttc | acg | ctg | atc | ccc | 1632 |
| Gln | Ser | Glu | Thr | Cys | Ser | Pro | Gly | Gly | Gln | Glu | Phe | Thr | Leu | Ile | Pro |
| | 530 | | | | 535 | | | | 540 | | | |

| atc | gct | gtg | ggt | ggt | gcc | ctg | gcg | ggg | ctg | gtc | ctc | atc | gtc | ctc | atc | 1680 |
| Ile | Ala | Val | Gly | Gly | Ala | Leu | Ala | Gly | Leu | Val | Leu | Ile | Val | Leu | Ile |
| 545 | | | | | 550 | | | | | 555 | | | | | 560 |

| gcc | tac | ctc | gtc | ggc | agg | aag | agg | agt | cac | gca | ggc | tac | cag | act | atc | 1728 |
| Ala | Tyr | Leu | Val | Gly | Arg | Lys | Arg | Ser | His | Ala | Gly | Tyr | Gln | Thr | Ile |
| | | | | 565 | | | | | 570 | | | | | 575 | tag taa 1734

<210> SEQ ID NO 39
<211> LENGTH: 576
<212> TYPE: PRT
<213> ORGANISM: Artificial sequence
<220> FEATURE:
<223> OTHER INFORMATION: Synthetic Construct

<400> SEQUENCE: 39

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln

```
                290                 295                 300
Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Gln Asp
370                 375                 380

Thr Pro Ala Leu Gly Lys Asp Thr Val Ala Val Ser Gly Lys Trp Tyr
385                 390                 395                 400

Leu Lys Ala Met Thr Ala Asp Gln Glu Val Pro Glu Lys Pro Asp Ser
                405                 410                 415

Val Thr Pro Met Ile Leu Lys Ala Gln Lys Gly Gly Asn Leu Glu Ala
            420                 425                 430

Lys Ile Thr Met Leu Thr Asn Gly Gln Cys Gln Asn Ile Thr Val Val
        435                 440                 445

Leu His Lys Thr Ser Glu Pro Gly Lys Tyr Thr Ala Tyr Glu Gly Gln
    450                 455                 460

Arg Val Val Phe Ile Gln Pro Ser Pro Val Arg Asp His Tyr Ile Leu
465                 470                 475                 480

Tyr Cys Glu Gly Glu Leu His Gly Arg Gln Ile Arg Met Ala Lys Leu
                485                 490                 495

Leu Gly Arg Asp Pro Glu Gln Ser Gln Glu Ala Leu Glu Asp Phe Arg
            500                 505                 510

Glu Phe Ser Arg Ala Lys Gly Leu Asn Gln Glu Ile Leu Glu Leu Ala
        515                 520                 525

Gln Ser Glu Thr Cys Ser Pro Gly Gly Gln Glu Phe Thr Leu Ile Pro
    530                 535                 540

Ile Ala Val Gly Gly Ala Leu Ala Gly Leu Val Leu Ile Val Leu Ile
545                 550                 555                 560

Ala Tyr Leu Val Gly Arg Lys Arg Ser His Ala Gly Tyr Gln Thr Ile
                565                 570                 575

<210> SEQ ID NO 40
<211> LENGTH: 750
<212> TYPE: DNA
<213> ORGANISM: Cynodon dactylon
<220> FEATURE:
<221> NAME/KEY: CDS
<222> LOCATION: (7)..(744)

<400> SEQUENCE: 40 ctcgag gcc atc ggc gat aag ccc gga ccc aac atc acc gcc aca tac      48
       Ala Ile Gly Asp Lys Pro Gly Pro Asn Ile Thr Ala Thr Tyr
        1               5                  10 ggc agc aag tgg ctg gaa gcc aga gcc aca ttc tac ggc tcc aac ccc     96
Gly Ser Lys Trp Leu Glu Ala Arg Ala Thr Phe Tyr Gly Ser Asn Pro
15                  20                  25                  30 aga ggc gcc gct ccc gat gat cat ggc gga gct tgc ggc tac aag gac    144
Arg Gly Ala Ala Pro Asp Asp His Gly Gly Ala Cys Gly Tyr Lys Asp
                35                  40                  45 gtg gac aag ccc ccc ttc gac ggc atg acc gct tgc ggc aac gag ccc    192
Val Asp Lys Pro Pro Phe Asp Gly Met Thr Ala Cys Gly Asn Glu Pro
            50                  55                  60
```

```
atc ttc aag gac gga ctg ggc tgc cgg gct tgc tac gag atc aag tgc    240
Ile Phe Lys Asp Gly Leu Gly Cys Arg Ala Cys Tyr Glu Ile Lys Cys
         65                  70                  75 aaa gaa ccc gtg gaa tgc agc ggc gag ccc gtg ctc gtg aag atc acc    288
Lys Glu Pro Val Glu Cys Ser Gly Glu Pro Val Leu Val Lys Ile Thr
 80                  85                  90 gac aag aac tac gag cac att gcc gcc tac cac ttc gat ctg agc ggc    336
Asp Lys Asn Tyr Glu His Ile Ala Ala Tyr His Phe Asp Leu Ser Gly
 95                 100                 105                 110 aag gcc ttt ggc gcc atg gcc aag aag ggc caa gag gac aag ctg cgg    384
Lys Ala Phe Gly Ala Met Ala Lys Lys Gly Gln Glu Asp Lys Leu Arg
                115                 120                 125 aag gcc ggc gaa ctg aca ctg cag ttt cgg aga gtg aag tgc aag tac    432
Lys Ala Gly Glu Leu Thr Leu Gln Phe Arg Arg Val Lys Cys Lys Tyr
130                 135                 140 ccc agc ggc acc aag atc aca ttc cac atc gag aag ggc agc aac gat    480
Pro Ser Gly Thr Lys Ile Thr Phe His Ile Glu Lys Gly Ser Asn Asp
        145                 150                 155 cac tat ctg gct ctg ctc gtg aaa tac gcc gct ggc gac ggc aac atc    528
His Tyr Leu Ala Leu Leu Val Lys Tyr Ala Ala Gly Asp Gly Asn Ile
    160                 165                 170 gtg gcc gtg gac atc aag ccc aga gac agc gac gag ttc atc ccc atg    576
Val Ala Val Asp Ile Lys Pro Arg Asp Ser Asp Glu Phe Ile Pro Met
175                 180                 185                 190 aag tcc agc tgg ggc gcc atc tgg cgg atc gac cca aag aag cct ctg    624
Lys Ser Ser Trp Gly Ala Ile Trp Arg Ile Asp Pro Lys Lys Pro Leu
                195                 200                 205 aag ggc ccc ttc tcc atc cgg ctg aca tct gag ggc gga gca cat ctg    672
Lys Gly Pro Phe Ser Ile Arg Leu Thr Ser Glu Gly Gly Ala His Leu
            210                 215                 220 gtg caa gac gac gtg atc ccc gcc aac tgg aag ccc gac acc gtg tac    720
Val Gln Asp Asp Val Ile Pro Ala Asn Trp Lys Pro Asp Thr Val Tyr
        225                 230                 235 acc agc aag ctg cag ttt ggc gcc gaattc                             750
Thr Ser Lys Leu Gln Phe Gly Ala
    240                 245

<210> SEQ ID NO 41
<211> LENGTH: 246
<212> TYPE: PRT
<213> ORGANISM: Cynodon dactylon

<400> SEQUENCE: 41

Ala Ile Gly Asp Lys Pro Gly Pro Asn Ile Thr Ala Thr Tyr Gly Ser
1               5                  10                  15

Lys Trp Leu Glu Ala Arg Ala Thr Phe Tyr Gly Ser Asn Pro Arg Gly
            20                  25                  30

Ala Ala Pro Asp Asp His Gly Gly Ala Cys Gly Tyr Lys Asp Val Asp
        35                  40                  45

Lys Pro Pro Phe Asp Gly Met Thr Ala Cys Gly Asn Glu Pro Ile Phe
    50                  55                  60

Lys Asp Gly Leu Gly Cys Arg Ala Cys Tyr Glu Ile Lys Cys Lys Glu
65                  70                  75                  80

Pro Val Glu Cys Ser Gly Glu Pro Val Leu Val Lys Ile Thr Asp Lys
                85                  90                  95

Asn Tyr Glu His Ile Ala Ala Tyr His Phe Asp Leu Ser Gly Lys Ala
            100                 105                 110

Phe Gly Ala Met Ala Lys Lys Gly Gln Glu Asp Lys Leu Arg Lys Ala
```

```
                115                 120                 125
Gly Glu Leu Thr Leu Gln Phe Arg Arg Val Lys Cys Lys Tyr Pro Ser
            130                 135                 140

Gly Thr Lys Ile Thr Phe His Ile Glu Lys Gly Ser Asn Asp His Tyr
145                 150                 155                 160

Leu Ala Leu Leu Val Lys Tyr Ala Ala Gly Asp Gly Asn Ile Val Ala
                    165                 170                 175

Val Asp Ile Lys Pro Arg Asp Ser Asp Glu Phe Ile Pro Met Lys Ser
            180                 185                 190

Ser Trp Gly Ala Ile Trp Arg Ile Asp Pro Lys Lys Pro Leu Lys Gly
                195                 200                 205

Pro Phe Ser Ile Arg Leu Thr Ser Glu Gly Gly Ala His Leu Val Gln
            210                 215                 220

Asp Asp Val Ile Pro Ala Asn Trp Lys Pro Asp Thr Val Tyr Thr Ser
225                 230                 235                 240

Lys Leu Gln Phe Gly Ala
                245

<210> SEQ ID NO 42
<211> LENGTH: 2004
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(2004)

<400> SEQUENCE: 42 atg gcg ccc cgc agc gcc cgg cga ccc ctg ctg ctg cta ctg ctg ttg        48
Met Ala Pro Arg Ser Ala Arg Arg Pro Leu Leu Leu Leu Leu Leu Leu
1               5                   10                  15 ctg ctg ctc ggc ctc atg cat tgt gcg tca gca gca atg ttt atg gtg        96
Leu Leu Leu Gly Leu Met His Cys Ala Ser Ala Ala Met Phe Met Val
                20                  25                  30 aaa aat ggc aac ggg acc gcg tgc ata atg gcc aac ttc tct gct gcc       144
Lys Asn Gly Asn Gly Thr Ala Cys Ile Met Ala Asn Phe Ser Ala Ala
            35                  40                  45 ttc tca gtg aac tac gac acc aag agt ggc cct aag aac atg acc ctt       192
Phe Ser Val Asn Tyr Asp Thr Lys Ser Gly Pro Lys Asn Met Thr Leu
        50                  55                  60 gac ctg cca tca gat gcc aca gtg gtg ctc aac cgc agc tcc tgt gga       240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga       288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc       336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc       384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc       432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc       480
Arg Ala Asp Ile Asp Lys Lys Tyr Arg Cys Val Ser Gly Thr Gln Val
145                 150                 155                 160
```

| | | |
|---|---|---|
| cac atg aac aac gtg acc gta acg ctc cat gat gcc acc atc cag gcg<br>His Met Asn Asn Val Thr Val Thr Leu His Asp Ala Thr Ile Gln Ala<br>                        165                    170                175 | 528 |
| tac ctt tcc aac agc agc ttc agc cgg gga gag aca cgc tgt gaa caa<br>Tyr Leu Ser Asn Ser Ser Phe Ser Arg Gly Glu Thr Arg Cys Glu Gln<br>                      180                    185              190 | 576 |
| gac agg cct tcc cca acc aca gcg ccc cct gcg cca ccc agc ccc tcg<br>Asp Arg Pro Ser Pro Thr Thr Ala Pro Pro Ala Pro Pro Ser Pro Ser<br>        195                    200                    205 | 624 |
| ccc tca ccc gtg ccc aag agc ccc tct gtg gac aag tac aac gtg agc<br>Pro Ser Pro Val Pro Lys Ser Pro Ser Val Asp Lys Tyr Asn Val Ser<br>210                    215                    220 | 672 |
| ggc acc aac ggg acc tgc ctg ctg gcc agc atg ggg ctg cag ctg aac<br>Gly Thr Asn Gly Thr Cys Leu Leu Ala Ser Met Gly Leu Gln Leu Asn<br>225                    230                    235              240 | 720 |
| ctc acc tat gag agg aag gac aac acg acg gtg aca agg ctt ctc aac<br>Leu Thr Tyr Glu Arg Lys Asp Asn Thr Thr Val Thr Arg Leu Leu Asn<br>                        245                    250              255 | 768 |
| atc aac ccc aac aag acc tcg gcc agc ggg agc tgc ggc gcc cac ctg<br>Ile Asn Pro Asn Lys Thr Ser Ala Ser Gly Ser Cys Gly Ala His Leu<br>                260                    265                    270 | 816 |
| gtg act ctg gag ctg cac agc gag ggc acc acc gtc ctg ctc ttc cag<br>Val Thr Leu Glu Leu His Ser Glu Gly Thr Thr Val Leu Leu Phe Gln<br>        275                    280                    285 | 864 |
| ttc ggg atg aat gca agt tct agc cgg ttt ttc cta caa gga atc cag<br>Phe Gly Met Asn Ala Ser Ser Ser Arg Phe Phe Leu Gln Gly Ile Gln<br>        290                    295                    300 | 912 |
| ttg aat aca att ctt cct gac gcc aga gac cct gcc ttt aaa gct gcc<br>Leu Asn Thr Ile Leu Pro Asp Ala Arg Asp Pro Ala Phe Lys Ala Ala<br>305                    310                    315              320 | 960 |
| aac ggc tcc ctg cga gcg ctg cag gcc aca gtc ggc aat tcc tac aag<br>Asn Gly Ser Leu Arg Ala Leu Gln Ala Thr Val Gly Asn Ser Tyr Lys<br>                        325                    330              335 | 1008 |
| tgc aac gcg gag gag cac gtc cgt gtc acg aag gcg ttt tca gtc aat<br>Cys Asn Ala Glu Glu His Val Arg Val Thr Lys Ala Phe Ser Val Asn<br>                340                    345                    350 | 1056 |
| ata ttc aaa gtg tgg gtc cag gct ttc aag gtg gaa ggt ggc cag ttt<br>Ile Phe Lys Val Trp Val Gln Ala Phe Lys Val Glu Gly Gly Gln Phe<br>        355                    360                    365 | 1104 |
| ggc tct gtg gag gag tgt ctg ctg gac gag aac agc ctc gag gcc atc<br>Gly Ser Val Glu Glu Cys Leu Leu Asp Glu Asn Ser Leu Glu Ala Ile<br>        370                    375                    380 | 1152 |
| ggc gat aag ccc gga ccc aac atc acc gcc aca tac ggc agc aag tgg<br>Gly Asp Lys Pro Gly Pro Asn Ile Thr Ala Thr Tyr Gly Ser Lys Trp<br>385                    390                    395              400 | 1200 |
| ctg gaa gcc aga gcc aca ttc tac ggc tcc aac ccc aga ggc gcc gct<br>Leu Glu Ala Arg Ala Thr Phe Tyr Gly Ser Asn Pro Arg Gly Ala Ala<br>                      405                    410              415 | 1248 |
| ccc gat gat cat ggc gga gct tgc ggc tac aag gac gtg gac aag ccc<br>Pro Asp Asp His Gly Gly Ala Cys Gly Tyr Lys Asp Val Asp Lys Pro<br>                420                    425                    430 | 1296 |
| ccc ttc gac ggc atg acc gct tgc ggc aac gag ccc atc ttc aag gac<br>Pro Phe Asp Gly Met Thr Ala Cys Gly Asn Glu Pro Ile Phe Lys Asp<br>        435                    440                    445 | 1344 |
| gga ctg ggc tgc cgg gct tgc tac gag atc aag tgc aaa gaa ccc gtg<br>Gly Leu Gly Cys Arg Ala Cys Tyr Glu Ile Lys Cys Lys Glu Pro Val<br>        450                    455                    460 | 1392 |
| gaa tgc agc ggc gag ccc gtg ctc gtg aag atc acc gac aag aac tac<br>Glu Cys Ser Gly Glu Pro Val Leu Val Lys Ile Thr Asp Lys Asn Tyr<br>465                    470                    475              480 | 1440 |

```
gag cac att gcc gcc tac cac ttc gat ctg agc ggc aag gcc ttt ggc      1488
Glu His Ile Ala Ala Tyr His Phe Asp Leu Ser Gly Lys Ala Phe Gly
                485                 490                 495 gcc atg gcc aag aag ggc caa gag gac aag ctg cgg aag gcc ggc gaa      1536
Ala Met Ala Lys Lys Gly Gln Glu Asp Lys Leu Arg Lys Ala Gly Glu
            500                 505                 510 ctg aca ctg cag ttt cgg aga gtg aag tgc aag tac ccc agc ggc acc      1584
Leu Thr Leu Gln Phe Arg Arg Val Lys Cys Lys Tyr Pro Ser Gly Thr
        515                 520                 525 aag atc aca ttc cac atc gag aag ggc agc aac gat cac tat ctg gct      1632
Lys Ile Thr Phe His Ile Glu Lys Gly Ser Asn Asp His Tyr Leu Ala
    530                 535                 540 ctg ctc gtg aaa tac gcc gct ggc gac ggc aac atc gtg gcc gtg gac      1680
Leu Leu Val Lys Tyr Ala Ala Gly Asp Gly Asn Ile Val Ala Val Asp
545                 550                 555                 560 atc aag ccc aga gac agc gac gag ttc atc ccc atg aag tcc agc tgg      1728
Ile Lys Pro Arg Asp Ser Asp Glu Phe Ile Pro Met Lys Ser Ser Trp
                565                 570                 575 ggc gcc atc tgg cgg atc gac cca aag aag cct ctg aag ggc ccc ttc      1776
Gly Ala Ile Trp Arg Ile Asp Pro Lys Lys Pro Leu Lys Gly Pro Phe
            580                 585                 590 tcc atc cgg ctg aca tct gag ggc gga gca cat ctg gtg caa gac gac      1824
Ser Ile Arg Leu Thr Ser Glu Gly Gly Ala His Leu Val Gln Asp Asp
        595                 600                 605 gtg atc ccc gcc aac tgg aag ccc gac acc gtg tac acc agc aag ctg      1872
Val Ile Pro Ala Asn Trp Lys Pro Asp Thr Val Tyr Thr Ser Lys Leu
    610                 615                 620 cag ttt ggc gcc gaa ttc acg ctg atc ccc atc gct gtg ggt ggt gcc      1920
Gln Phe Gly Ala Glu Phe Thr Leu Ile Pro Ile Ala Val Gly Gly Ala
625                 630                 635                 640 ctg gcg ggg ctg gtc ctc atc gtc ctc atc gcc tac ctc gtc ggc agg      1968
Leu Ala Gly Leu Val Leu Ile Val Leu Ile Ala Tyr Leu Val Gly Arg
                645                 650                 655 aag agg agt cac gca ggc tac cag act atc tag taa                      2004
Lys Arg Ser His Ala Gly Tyr Gln Thr Ile
            660                 665

<210> SEQ ID NO 43
<211> LENGTH: 666
<212> TYPE: PRT
<213> ORGANISM: Artificial sequence
<220> FEATURE:
<223> OTHER INFORMATION: Synthetic Construct

<400> SEQUENCE: 43

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110
```

```
Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
                180                 185                 190

Asp Arg Pro Ser Pro Thr Thr Ala Pro Ala Pro Pro Ser Pro Ser
                195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
                260                 265                 270

Val Thr Leu Glu Leu His Ser Glu Gly Thr Thr Val Leu Leu Phe Gln
                275                 280                 285

Phe Gly Met Asn Ala Ser Ser Ser Arg Phe Phe Leu Gln Gly Ile Gln
                290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
                340                 345                 350

Ile Phe Lys Val Trp Val Gln Ala Phe Lys Val Glu Gly Gly Gln Phe
                355                 360                 365

Gly Ser Val Glu Glu Cys Leu Leu Asp Glu Asn Ser Leu Glu Ala Ile
370                 375                 380

Gly Asp Lys Pro Gly Pro Asn Ile Thr Ala Thr Tyr Gly Ser Lys Trp
385                 390                 395                 400

Leu Glu Ala Arg Ala Thr Phe Tyr Gly Ser Asn Pro Arg Gly Ala Ala
                405                 410                 415

Pro Asp Asp His Gly Gly Ala Cys Gly Tyr Lys Asp Val Asp Lys Pro
                420                 425                 430

Pro Phe Asp Gly Met Thr Ala Cys Gly Asn Glu Pro Ile Phe Lys Asp
                435                 440                 445

Gly Leu Gly Cys Arg Ala Cys Tyr Glu Ile Lys Cys Lys Glu Pro Val
450                 455                 460

Glu Cys Ser Gly Glu Pro Val Leu Val Lys Ile Thr Asp Lys Asn Tyr
465                 470                 475                 480

Glu His Ile Ala Ala Tyr His Phe Asp Leu Ser Gly Lys Ala Phe Gly
                485                 490                 495

Ala Met Ala Lys Lys Gly Gln Glu Asp Lys Leu Arg Lys Ala Gly Glu
                500                 505                 510

Leu Thr Leu Gln Phe Arg Arg Val Lys Cys Lys Tyr Pro Ser Gly Thr
                515                 520                 525
```

```
Lys Ile Thr Phe His Ile Glu Lys Gly Ser Asn Asp His Tyr Leu Ala
    530                 535                 540

Leu Leu Val Lys Tyr Ala Ala Gly Asp Gly Asn Ile Val Ala Val Asp
545                 550                 555                 560

Ile Lys Pro Arg Asp Ser Asp Glu Phe Ile Pro Met Lys Ser Ser Trp
                565                 570                 575

Gly Ala Ile Trp Arg Ile Asp Pro Lys Lys Pro Leu Lys Gly Pro Phe
                580                 585                 590

Ser Ile Arg Leu Thr Ser Glu Gly Gly Ala His Leu Val Gln Asp Asp
            595                 600                 605

Val Ile Pro Ala Asn Trp Lys Pro Asp Thr Val Tyr Thr Ser Lys Leu
    610                 615                 620

Gln Phe Gly Ala Glu Phe Thr Leu Ile Pro Ile Ala Val Gly Gly Ala
625                 630                 635                 640

Leu Ala Gly Leu Val Leu Ile Val Leu Ile Ala Tyr Leu Val Gly Arg
                645                 650                 655

Lys Arg Ser His Ala Gly Tyr Gln Thr Ile
            660                 665

<210> SEQ ID NO 44
<211> LENGTH: 921
<212> TYPE: DNA
<213> ORGANISM: Dermatophagoides farinae
<220> FEATURE:
<221> NAME/KEY: CDS
<222> LOCATION: (7)..(915)

<400> SEQUENCE: 44 ctcgag agg ccc gcc agc atc aag aca ttc gaa gag ttc aag aag gcc        48
       Arg Pro Ala Ser Ile Lys Thr Phe Glu Glu Phe Lys Lys Ala
       1               5                   10 ttt aac aag aac tac gcc acc gtg gaa gag gaa gaa gtg gcc cgg aag       96
Phe Asn Lys Asn Tyr Ala Thr Val Glu Glu Glu Glu Val Ala Arg Lys
15                  20                  25                  30 aac ttt ctg gaa tct ctg aaa tac gtg gaa gcc aac aag ggc gcc atc      144
Asn Phe Leu Glu Ser Leu Lys Tyr Val Glu Ala Asn Lys Gly Ala Ile
                35                  40                  45 aac cat ctg agc gat ctg tct ctg gac gag ttt aag aac cgg tat ctg      192
Asn His Leu Ser Asp Leu Ser Leu Asp Glu Phe Lys Asn Arg Tyr Leu
            50                  55                  60 atg agc gcc gag gcc ttc gag cag ctg aaa acc cag ttc gat ctg aac      240
Met Ser Ala Glu Ala Phe Glu Gln Leu Lys Thr Gln Phe Asp Leu Asn
        65                  70                  75 gcc gaa acc agc gct tgc cgg atc aac agc gtg aac gtg ccc agc gag      288
Ala Glu Thr Ser Ala Cys Arg Ile Asn Ser Val Asn Val Pro Ser Glu
    80                  85                  90 ctg gat ctg aga tct ctg aga acc gtg acc ccc atc aga atg caa ggc      336
Leu Asp Leu Arg Ser Leu Arg Thr Val Thr Pro Ile Arg Met Gln Gly
95                  100                 105                 110 ggc tgc ggc agc tgc tgg gcc ttt agc gga gtg gcc gcc aca gag tct      384
Gly Cys Gly Ser Cys Trp Ala Phe Ser Gly Val Ala Ala Thr Glu Ser
                115                 120                 125 gcc tat ctg gcc tac cgg aac aca tct ctg gat ctg tcc gag caa gaa      432
Ala Tyr Leu Ala Tyr Arg Asn Thr Ser Leu Asp Leu Ser Glu Gln Glu
            130                 135                 140 ctc gtg gac tgc gcc agc cag cac ggc tgt cac ggc gat aca atc ccc      480
Leu Val Asp Cys Ala Ser Gln His Gly Cys His Gly Asp Thr Ile Pro
        145                 150                 155 aga ggc atc gag tac atc cag cag aac ggc gtc gtg gaa gaa cgg tcc      528
```

```
Arg Gly Ile Glu Tyr Ile Gln Gln Asn Gly Val Val Glu Glu Arg Ser
    160                 165                 170 tac cct tac gtg gcc cgc gag cag aga tgc aga agg ccc aac tct cag    576
Tyr Pro Tyr Val Ala Arg Glu Gln Arg Cys Arg Arg Pro Asn Ser Gln
175                 180                 185                 190 cac tac ggc atc agc aac tac tgc cag atc tac ccc ccc gac gtg aag    624
His Tyr Gly Ile Ser Asn Tyr Cys Gln Ile Tyr Pro Pro Asp Val Lys
                195                 200                 205 cag atc aga gag gct ctg acc cag acc cac acc gcc att gcc gtg atc    672
Gln Ile Arg Glu Ala Leu Thr Gln Thr His Thr Ala Ile Ala Val Ile
        210                 215                 220 atc gga atc aag gat ctg cgg gcc ttc cag cac tat gac ggc cgg acc    720
Ile Gly Ile Lys Asp Leu Arg Ala Phe Gln His Tyr Asp Gly Arg Thr
            225                 230                 235 atc atc cag cac gac aac ggc tac cag ccc aac tac cac gcc gtg aac    768
Ile Ile Gln His Asp Asn Gly Tyr Gln Pro Asn Tyr His Ala Val Asn
                240                 245                 250 atc gtg ggc tac ggc agc aca caa ggc gac gac tac tgg atc gtg cgg    816
Ile Val Gly Tyr Gly Ser Thr Gln Gly Asp Asp Tyr Trp Ile Val Arg
255                 260                 265                 270 aac agc tgg gac acc aca tgg ggc gat agc ggc tac ggc tac ttc caa    864
Asn Ser Trp Asp Thr Thr Trp Gly Asp Ser Gly Tyr Gly Tyr Phe Gln
                275                 280                 285 gcc ggc aac aat ctg atg atg atc gag cag tac ccc tac gtc gtg atc    912
Ala Gly Asn Asn Leu Met Met Ile Glu Gln Tyr Pro Tyr Val Val Ile
            290                 295                 300 atg gaattc                                                          921
Met

<210> SEQ ID NO 45
<211> LENGTH: 303
<212> TYPE: PRT
<213> ORGANISM: Dermatophagoides farinae

<400> SEQUENCE: 45

Arg Pro Ala Ser Ile Lys Thr Phe Glu Glu Phe Lys Lys Ala Phe Asn
1               5                   10                  15

Lys Asn Tyr Ala Thr Val Glu Glu Glu Val Ala Arg Lys Asn Phe
            20                  25                  30

Leu Glu Ser Leu Lys Tyr Val Glu Ala Asn Lys Gly Ala Ile Asn His
        35                  40                  45

Leu Ser Asp Leu Ser Leu Asp Glu Phe Lys Asn Arg Tyr Leu Met Ser
    50                  55                  60

Ala Glu Ala Phe Glu Gln Leu Lys Thr Gln Phe Asp Leu Asn Ala Glu
65                  70                  75                  80

Thr Ser Ala Cys Arg Ile Asn Ser Val Asn Val Pro Ser Glu Leu Asp
                85                  90                  95

Leu Arg Ser Leu Arg Thr Val Thr Pro Ile Arg Met Gln Gly Gly Cys
            100                 105                 110

Gly Ser Cys Trp Ala Phe Ser Gly Val Ala Ala Thr Glu Ser Ala Tyr
        115                 120                 125

Leu Ala Tyr Arg Asn Thr Ser Leu Asp Leu Ser Glu Gln Glu Leu Val
    130                 135                 140

Asp Cys Ala Ser Gln His Gly Cys His Gly Asp Thr Ile Pro Arg Gly
145                 150                 155                 160

Ile Glu Tyr Ile Gln Gln Asn Gly Val Val Glu Glu Arg Ser Tyr Pro
                165                 170                 175
```

```
Tyr Val Ala Arg Glu Gln Arg Cys Arg Arg Pro Asn Ser Gln His Tyr
            180                 185                 190

Gly Ile Ser Asn Tyr Cys Gln Ile Tyr Pro Pro Asp Val Lys Gln Ile
        195                 200                 205

Arg Glu Ala Leu Thr Gln Thr His Thr Ala Ile Ala Val Ile Ile Gly
    210                 215                 220

Ile Lys Asp Leu Arg Ala Phe Gln His Tyr Asp Gly Arg Thr Ile Ile
225                 230                 235                 240

Gln His Asp Asn Gly Tyr Gln Pro Asn Tyr His Ala Val Asn Ile Val
                245                 250                 255

Gly Tyr Gly Ser Thr Gln Gly Asp Asp Tyr Trp Ile Val Arg Asn Ser
            260                 265                 270

Trp Asp Thr Thr Trp Gly Asp Ser Gly Tyr Gly Tyr Phe Gln Ala Gly
        275                 280                 285

Asn Asn Leu Met Met Ile Glu Gln Tyr Pro Tyr Val Val Ile Met
    290                 295                 300

<210> SEQ ID NO 46
<211> LENGTH: 2175
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(2175)

<400> SEQUENCE: 46 atg gcg ccc cgc agc gcc cgg cga ccc ctg ctg ctg cta ctg ctg ttg      48
Met Ala Pro Arg Ser Ala Arg Arg Pro Leu Leu Leu Leu Leu Leu Leu
1               5                   10                  15 ctg ctg ctc ggc ctc atg cat tgt gcg tca gca gca atg ttt atg gtg      96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc     144
Lys Asn Gly Asn Gly Thr Ala Cys Ile Met Ala Asn Phe Ser Ala Ala
        35                  40                  45 ttc tca gtg aac tac gac acc aag agt ggc cct aag aac atg acc ctt     192
Phe Ser Val Asn Tyr Asp Thr Lys Ser Gly Pro Lys Asn Met Thr Leu
    50                  55                  60 gac ctg cca tca gat gcc aca gtg gtg ctc aac cgc agc tcc tgt gga     240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga     288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc     336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc     384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc     432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc     480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg     528
His Met Asn Asn Val Thr Val Thr Leu His Asp Ala Thr Ile Gln Ala
```

```
                        165                 170                 175
tac ctt tcc aac agc agc ttc agc cgg gga gag aca cgc tgt gaa caa      576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg      624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc      672
Pro Ser Pro Val Pro Lys Ser Pro Ser Val Asp Lys Tyr Asn Val Ser
210                 215                 220 ggc acc aac ggg acc tgc ctg ctg gcc agc atg ggg ctg cag ctg aac      720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac      768
Leu Thr Tyr Glu Arg Lys Asp Asn Thr Thr Val Thr Arg Leu Leu Asn
            245                 250                 255 atc aac ccc aac aag acc tcg gcc agc ggg agc tgc ggc gcc cac ctg      816
Ile Asn Pro Asn Lys Thr Ser Ala Ser Gly Ser Cys Gly Ala His Leu
        260                 265                 270 gtg act ctg gag ctg cac agc gag ggc acc acc gtc ctg ctc ttc cag      864
Val Thr Leu Glu Leu His Ser Glu Gly Thr Thr Val Leu Leu Phe Gln
    275                 280                 285 ttc ggg atg aat gca agt tct agc cgg ttt ttc cta caa gga atc cag      912
Phe Gly Met Asn Ala Ser Ser Ser Arg Phe Phe Leu Gln Gly Ile Gln
290                 295                 300 ttg aat aca att ctt cct gac gcc aga gac cct gcc ttt aaa gct gcc      960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag     1008
Asn Gly Ser Leu Arg Ala Leu Gln Ala Thr Val Gly Asn Ser Tyr Lys
            325                 330                 335 tgc aac gcg gag gag cac gtc cgt gtc acg aag gcg ttt tca gtc aat     1056
Cys Asn Ala Glu Glu His Val Arg Val Thr Lys Ala Phe Ser Val Asn
        340                 345                 350 ata ttc aaa gtg tgg gtc cag gct ttc aag gtg gaa ggt ggc cag ttt     1104
Ile Phe Lys Val Trp Val Gln Ala Phe Lys Val Glu Gly Gly Gln Phe
    355                 360                 365 ggc tct gtg gag gag tgt ctg ctg gac gag aac agc ctc gag agg ccc     1152
Gly Ser Val Glu Glu Cys Leu Leu Asp Glu Asn Ser Leu Glu Arg Pro
370                 375                 380 gcc agc atc aag aca ttc gaa gag ttc aag aag gcc ttt aac aag aac     1200
Ala Ser Ile Lys Thr Phe Glu Glu Phe Lys Lys Ala Phe Asn Lys Asn
385                 390                 395                 400 tac gcc acc gtg gaa gag gaa gaa gtg gcc cgg aag aac ttt ctg gaa     1248
Tyr Ala Thr Val Glu Glu Glu Glu Val Ala Arg Lys Asn Phe Leu Glu
            405                 410                 415 tct ctg aaa tac gtg gaa gcc aac aag ggc gcc atc aac cat ctg agc     1296
Ser Leu Lys Tyr Val Glu Ala Asn Lys Gly Ala Ile Asn His Leu Ser
        420                 425                 430 gat ctg tct ctg gac gag ttt aag aac cgg tat ctg atg agc gcc gag     1344
Asp Leu Ser Leu Asp Glu Phe Lys Asn Arg Tyr Leu Met Ser Ala Glu
    435                 440                 445 gcc ttc gag cag ctg aaa acc cag ttc gat ctg aac gcc gaa acc agc     1392
Ala Phe Glu Gln Leu Lys Thr Gln Phe Asp Leu Asn Ala Glu Thr Ser
450                 455                 460 gct tgc cgg atc aac agc gtg aac gtg ccc agc gag ctg gat ctg aga     1440
Ala Cys Arg Ile Asn Ser Val Asn Val Pro Ser Glu Leu Asp Leu Arg
465                 470                 475                 480 tct ctg aga acc gtg acc ccc atc aga atg caa ggc ggc tgc ggc agc     1488
```

```
                Ser Leu Arg Thr Val Thr Pro Ile Arg Met Gln Gly Gly Cys Gly Ser
                                485                 490                 495 tgc tgg gcc ttt agc gga gtg gcc gcc aca gag tct gcc tat ctg gcc              1536
Cys Trp Ala Phe Ser Gly Val Ala Ala Thr Glu Ser Ala Tyr Leu Ala
            500                 505                 510 tac cgg aac aca tct ctg gat ctg tcc gag caa gaa ctc gtg gac tgc              1584
Tyr Arg Asn Thr Ser Leu Asp Leu Ser Glu Gln Glu Leu Val Asp Cys
            515                 520                 525 gcc agc cag cac ggc tgt cac ggc gat aca atc ccc aga ggc atc gag              1632
Ala Ser Gln His Gly Cys His Gly Asp Thr Ile Pro Arg Gly Ile Glu
        530                 535                 540 tac atc cag cag aac ggc gtc gtg gaa gaa cgg tcc tac cct tac gtg              1680
Tyr Ile Gln Gln Asn Gly Val Val Glu Glu Arg Ser Tyr Pro Tyr Val
545                 550                 555                 560 gcc cgc gag cag aga tgc aga agg ccc aac tct cag cac tac ggc atc              1728
Ala Arg Glu Gln Arg Cys Arg Arg Pro Asn Ser Gln His Tyr Gly Ile
                565                 570                 575 agc aac tac tgc cag atc tac ccc ccc gac gtg aag cag atc aga gag              1776
Ser Asn Tyr Cys Gln Ile Tyr Pro Pro Asp Val Lys Gln Ile Arg Glu
            580                 585                 590 gct ctg acc cag acc cac acc gcc att gcc gtg atc atc gga atc aag              1824
Ala Leu Thr Gln Thr His Thr Ala Ile Ala Val Ile Ile Gly Ile Lys
            595                 600                 605 gat ctg cgg gcc ttc cag cac tat gac ggc cgg acc atc atc cag cac              1872
Asp Leu Arg Ala Phe Gln His Tyr Asp Gly Arg Thr Ile Ile Gln His
        610                 615                 620 gac aac ggc tac cag ccc aac tac cac gcc gtg aac atc gtg ggc tac              1920
Asp Asn Gly Tyr Gln Pro Asn Tyr His Ala Val Asn Ile Val Gly Tyr
625                 630                 635                 640 ggc agc aca caa ggc gac gac tac tgg atc gtg cgg aac agc tgg gac              1968
Gly Ser Thr Gln Gly Asp Asp Tyr Trp Ile Val Arg Asn Ser Trp Asp
                645                 650                 655 acc aca tgg ggc gat agc ggc tac ggc tac ttc caa gcc ggc aac aat              2016
Thr Thr Trp Gly Asp Ser Gly Tyr Gly Tyr Phe Gln Ala Gly Asn Asn
            660                 665                 670 ctg atg atg atc gag cag tac ccc tac gtc gtg atc atg gaa ttc acg              2064
Leu Met Met Ile Glu Gln Tyr Pro Tyr Val Val Ile Met Glu Phe Thr
            675                 680                 685 ctg atc ccc atc gct gtg ggt ggt gcc ctg gcg ggg ctg gtc ctc atc              2112
Leu Ile Pro Ile Ala Val Gly Gly Ala Leu Ala Gly Leu Val Leu Ile
        690                 695                 700 gtc ctc atc gcc tac ctc gtc ggc agg aag agg agt cac gca ggc tac              2160
Val Leu Ile Ala Tyr Leu Val Gly Arg Lys Arg Ser His Ala Gly Tyr
705                 710                 715                 720 cag act atc tag taa                                                          2175
Gln Thr Ile <210> SEQ ID NO 47
<211> LENGTH: 723
<212> TYPE: PRT
<213> ORGANISM: Artificial sequence
<220> FEATURE:
<223> OTHER INFORMATION: Synthetic Construct

<400> SEQUENCE: 47

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
```

-continued

```
                35                  40                  45
Phe Ser Val Asn Tyr Asp Thr Lys Ser Gly Pro Lys Asn Met Thr Leu
 50                  55                  60
Asp Leu Pro Ser Asp Ala Thr Val Val Leu Asn Arg Ser Ser Cys Gly
 65                  70                  75                  80
Lys Glu Asn Thr Ser Asp Pro Ser Leu Val Ile Ala Phe Gly Arg Gly
                 85                  90                  95
His Thr Leu Thr Leu Asn Phe Thr Arg Asn Ala Thr Arg Tyr Ser Val
                100                 105                 110
Gln Leu Met Ser Phe Val Tyr Asn Leu Ser Asp Thr His Leu Phe Pro
            115                 120                 125
Asn Ala Ser Ser Lys Glu Ile Lys Thr Val Glu Ser Ile Thr Asp Ile
        130                 135                 140
Arg Ala Asp Ile Asp Lys Lys Tyr Arg Cys Val Ser Gly Thr Gln Val
145                 150                 155                 160
His Met Asn Asn Val Thr Val Thr Leu His Asp Ala Thr Ile Gln Ala
                165                 170                 175
Tyr Leu Ser Asn Ser Ser Phe Ser Arg Gly Glu Thr Arg Cys Glu Gln
            180                 185                 190
Asp Arg Pro Ser Pro Thr Thr Ala Pro Pro Ala Pro Pro Ser Pro Ser
        195                 200                 205
Pro Ser Pro Val Pro Lys Ser Pro Ser Val Asp Lys Tyr Asn Val Ser
210                 215                 220
Gly Thr Asn Gly Thr Cys Leu Leu Ala Ser Met Gly Leu Gln Leu Asn
225                 230                 235                 240
Leu Thr Tyr Glu Arg Lys Asp Asn Thr Thr Val Thr Arg Leu Leu Asn
                245                 250                 255
Ile Asn Pro Asn Lys Thr Ser Ala Ser Gly Ser Cys Gly Ala His Leu
            260                 265                 270
Val Thr Leu Glu Leu His Ser Glu Gly Thr Thr Val Leu Leu Phe Gln
        275                 280                 285
Phe Gly Met Asn Ala Ser Ser Ser Arg Phe Phe Leu Gln Gly Ile Gln
    290                 295                 300
Leu Asn Thr Ile Leu Pro Asp Ala Arg Asp Pro Ala Phe Lys Ala Ala
305                 310                 315                 320
Asn Gly Ser Leu Arg Ala Leu Gln Ala Thr Val Gly Asn Ser Tyr Lys
                325                 330                 335
Cys Asn Ala Glu Glu His Val Arg Val Thr Lys Ala Phe Ser Val Asn
            340                 345                 350
Ile Phe Lys Val Trp Val Gln Ala Phe Lys Val Glu Gly Gly Gln Phe
        355                 360                 365
Gly Ser Val Glu Glu Cys Leu Leu Asp Glu Asn Ser Leu Glu Arg Pro
    370                 375                 380
Ala Ser Ile Lys Thr Phe Glu Glu Phe Lys Lys Ala Phe Asn Lys Asn
385                 390                 395                 400
Tyr Ala Thr Val Glu Glu Glu Val Ala Arg Lys Asn Phe Leu Glu
                405                 410                 415
Ser Leu Lys Tyr Val Glu Ala Asn Lys Gly Ala Ile Asn His Leu Ser
            420                 425                 430
Asp Leu Ser Leu Asp Glu Phe Lys Asn Arg Tyr Leu Met Ser Ala Glu
        435                 440                 445
Ala Phe Glu Gln Leu Lys Thr Gln Phe Asp Leu Asn Ala Glu Thr Ser
    450                 455                 460
```

Ala Cys Arg Ile Asn Ser Val Asn Val Pro Ser Glu Leu Asp Leu Arg
465                 470                 475                 480

Ser Leu Arg Thr Val Thr Pro Ile Arg Met Gln Gly Gly Cys Gly Ser
            485                 490                 495

Cys Trp Ala Phe Ser Gly Val Ala Ala Thr Glu Ser Ala Tyr Leu Ala
        500                 505                 510

Tyr Arg Asn Thr Ser Leu Asp Leu Ser Glu Gln Glu Leu Val Asp Cys
    515                 520                 525

Ala Ser Gln His Gly Cys His Gly Asp Thr Ile Pro Arg Gly Ile Glu
530                 535                 540

Tyr Ile Gln Gln Asn Gly Val Val Glu Glu Arg Ser Tyr Pro Tyr Val
545                 550                 555                 560

Ala Arg Glu Gln Arg Cys Arg Arg Pro Asn Ser Gln His Tyr Gly Ile
            565                 570                 575

Ser Asn Tyr Cys Gln Ile Tyr Pro Pro Asp Val Lys Gln Ile Arg Glu
        580                 585                 590

Ala Leu Thr Gln Thr His Thr Ala Ile Ala Val Ile Ile Gly Ile Lys
    595                 600                 605

Asp Leu Arg Ala Phe Gln His Tyr Asp Gly Arg Thr Ile Ile Gln His
610                 615                 620

Asp Asn Gly Tyr Gln Pro Asn Tyr His Ala Val Asn Ile Val Gly Tyr
625                 630                 635                 640

Gly Ser Thr Gln Gly Asp Asp Tyr Trp Ile Val Arg Asn Ser Trp Asp
            645                 650                 655

Thr Thr Trp Gly Asp Ser Gly Tyr Gly Tyr Phe Gln Ala Gly Asn Asn
        660                 665                 670

Leu Met Met Ile Glu Gln Tyr Pro Tyr Val Val Met Glu Phe Thr
    675                 680                 685

Leu Ile Pro Ile Ala Val Gly Gly Ala Leu Ala Gly Leu Val Leu Ile
    690                 695                 700

Val Leu Ile Ala Tyr Leu Val Gly Arg Lys Arg Ser His Ala Gly Tyr
705                 710                 715                 720

Gln Thr Ile

<210> SEQ ID NO 48
<211> LENGTH: 681
<212> TYPE: DNA
<213> ORGANISM: Dermatophagoides farinae
<220> FEATURE:
<221> NAME/KEY: CDS
<222> LOCATION: (7)..(675)

<400> SEQUENCE: 48 ctcgag acc agc gct tgc cgg atc aac agc gtg aac gtg ccc agc gag      48
       Thr Ser Ala Cys Arg Ile Asn Ser Val Asn Val Pro Ser Glu
         1               5                  10 ctg gat ctg aga tct ctg aga acc gtg acc ccc atc aga atg caa ggc     96
Leu Asp Leu Arg Ser Leu Arg Thr Val Thr Pro Ile Arg Met Gln Gly
 15                  20                  25                  30 ggc tgc ggc agc tgc tgg gcc ttt agc gga gtg gcc gcc aca gag tct    144
Gly Cys Gly Ser Cys Trp Ala Phe Ser Gly Val Ala Ala Thr Glu Ser
                 35                  40                  45 gcc tat ctg gcc tac cgg aac aca tct ctg gat ctg tcc gag caa gaa    192
Ala Tyr Leu Ala Tyr Arg Asn Thr Ser Leu Asp Leu Ser Glu Gln Glu
             50                  55                  60 ctc gtg gac tgc gcc agc cag cac ggc tgt cac ggc gat aca atc ccc    240

```
Leu Val Asp Cys Ala Ser Gln His Gly Cys His Gly Asp Thr Ile Pro
            65                  70                  75 aga ggc atc gag tac atc cag cag aac ggc gtc gtg gaa gaa cgg tcc      288
Arg Gly Ile Glu Tyr Ile Gln Gln Asn Gly Val Val Glu Glu Arg Ser
        80                  85                  90 tac cct tac gtg gcc cgc gag cag aga tgc aga agg ccc aac tct cag      336
Tyr Pro Tyr Val Ala Arg Glu Gln Arg Cys Arg Arg Pro Asn Ser Gln
95                  100                 105                 110 cac tac ggc atc agc aac tac tgc cag atc tac ccc ccc gac gtg aag      384
His Tyr Gly Ile Ser Asn Tyr Cys Gln Ile Tyr Pro Pro Asp Val Lys
                115                 120                 125 cag atc aga gag gct ctg acc cag acc cac acc gcc att gcc gtg atc      432
Gln Ile Arg Glu Ala Leu Thr Gln Thr His Thr Ala Ile Ala Val Ile
            130                 135                 140 atc gga atc aag gat ctg cgg gcc ttc cag cac tat gac ggc cgg acc      480
Ile Gly Ile Lys Asp Leu Arg Ala Phe Gln His Tyr Asp Gly Arg Thr
                145                 150                 155 atc atc cag cac gac aac ggc tac cag ccc aac tac cac gcc gtg aac      528
Ile Ile Gln His Asp Asn Gly Tyr Gln Pro Asn Tyr His Ala Val Asn
        160                 165                 170 atc gtg ggc tac ggc agc aca caa ggc gac gac tac tgg atc gtg cgg      576
Ile Val Gly Tyr Gly Ser Thr Gln Gly Asp Asp Tyr Trp Ile Val Arg
175                 180                 185                 190 aac agc tgg gac acc aca tgg ggc gat agc ggc tac ggc tac ttc caa      624
Asn Ser Trp Asp Thr Thr Trp Gly Asp Ser Gly Tyr Gly Tyr Phe Gln
                195                 200                 205 gcc ggc aac aat ctg atg atg atc gag cag tac ccc tac gtc gtg atc      672
Ala Gly Asn Asn Leu Met Met Ile Glu Gln Tyr Pro Tyr Val Val Ile
            210                 215                 220 atg gaattc                                                           681
Met

<210> SEQ ID NO 49
<211> LENGTH: 223
<212> TYPE: PRT
<213> ORGANISM: Dermatophagoides farinae

<400> SEQUENCE: 49

Thr Ser Ala Cys Arg Ile Asn Ser Val Asn Val Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Asn Thr Ser Leu Asp Leu Ser Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln Gln Asn Gly Val Val Glu Glu Arg Ser Tyr Pro
                85                  90                  95

Tyr Val Ala Arg Glu Gln Arg Cys Arg Arg Pro Asn Ser Gln His Tyr
            100                 105                 110

Gly Ile Ser Asn Tyr Cys Gln Ile Tyr Pro Pro Asp Val Lys Gln Ile
        115                 120                 125

Arg Glu Ala Leu Thr Gln Thr His Thr Ala Ile Ala Val Ile Ile Gly
    130                 135                 140

Ile Lys Asp Leu Arg Ala Phe Gln His Tyr Asp Gly Arg Thr Ile Ile
145                 150                 155                 160
```

```
Gln His Asp Asn Gly Tyr Gln Pro Asn Tyr His Ala Val Asn Ile Val
            165                 170                 175

Gly Tyr Gly Ser Thr Gln Gly Asp Asp Tyr Trp Ile Val Arg Asn Ser
        180                 185                 190

Trp Asp Thr Thr Trp Gly Asp Ser Gly Tyr Gly Tyr Phe Gln Ala Gly
        195                 200                 205

Asn Asn Leu Met Met Ile Glu Gln Tyr Pro Tyr Val Val Ile Met
    210                 215                 220

<210> SEQ ID NO 50
<211> LENGTH: 1935
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1935)

<400> SEQUENCE: 50 atg gcg ccc cgc agc gcc cgg cga ccc ctg ctg cta ctg ctg ttg          48
Met Ala Pro Arg Ser Ala Arg Arg Pro Leu Leu Leu Leu Leu Leu
1               5                   10                  15 ctg ctc ggc ctc atg cat tgt gcg tca gca gca atg ttt atg gtg          96
Leu Leu Leu Gly Leu Met His Cys Ala Ser Ala Ala Met Phe Met Val
                20                  25                  30 aaa aat ggc aac ggg acc gcg tgc ata atg gcc aac ttc tct gct gcc     144
Lys Asn Gly Asn Gly Thr Ala Cys Ile Met Ala Asn Phe Ser Ala Ala
            35                  40                  45 ttc tca gtg aac tac gac acc aag agt ggc cct aag aac atg acc ctt     192
Phe Ser Val Asn Tyr Asp Thr Lys Ser Gly Pro Lys Asn Met Thr Leu
        50                  55                  60 gac ctg cca tca gat gcc aca gtg gtc ctc aac cgc agc tcc tgt gga     240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga    288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc    336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc    384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc    432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc    480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg    528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa    576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg    624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc    672
Pro Ser Pro Val Pro Lys Ser Pro Ser Val Asp Lys Tyr Asn Val Ser
```

```
Pro Ser Pro Val Pro Lys Ser Pro Ser Val Asp Lys Tyr Asn Val Ser
    210                 215                 220 ggc acc aac ggg acc tgc ctg ctg gcc agc atg ggg ctg cag ctg aac      720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac      768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg      816
Ile Asn Pro Asn Lys Thr Ser Ala Ser Gly Ser Cys Gly Ala His Leu
            260                 265                 270 gtg act ctg gag ctg cac agc gag ggc acc acc gtc ctg ctc ttc cag      864
Val Thr Leu Glu Leu His Ser Glu Gly Thr Thr Val Leu Leu Phe Gln
        275                 280                 285 ttc ggg atg aat gca agt tct agc cgg ttt ttc cta caa gga atc cag      912
Phe Gly Met Asn Ala Ser Ser Ser Arg Phe Phe Leu Gln Gly Ile Gln
    290                 295                 300 ttg aat aca att ctt cct gac gcc aga gac cct gcc ttt aaa gct gcc      960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag     1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat     1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt     1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag acc agc     1152
Gly Ser Val Glu Glu Cys Leu Leu Asp Glu Asn Ser Leu Glu Thr Ser
    370                 375                 380 gct tgc cgg atc aac agc gtg aac gtg ccc agc gag ctg gat ctg aga     1200
Ala Cys Arg Ile Asn Ser Val Asn Val Pro Ser Glu Leu Asp Leu Arg
385                 390                 395                 400 tct ctg aga acc gtg acc ccc atc aga atg caa ggc ggc tgc ggc agc     1248
Ser Leu Arg Thr Val Thr Pro Ile Arg Met Gln Gly Gly Cys Gly Ser
                405                 410                 415 tgc tgg gcc ttt agc gga gtg gcc gcc aca gag tct gcc tat ctg gcc     1296
Cys Trp Ala Phe Ser Gly Val Ala Ala Thr Glu Ser Ala Tyr Leu Ala
            420                 425                 430 tac cgg aac aca tct ctg gat ctg tcc gag caa gaa ctc gtg gac tgc     1344
Tyr Arg Asn Thr Ser Leu Asp Leu Ser Glu Gln Glu Leu Val Asp Cys
        435                 440                 445 gcc agc cag cac ggc tgt cac ggc gat aca atc ccc aga ggc atc gag     1392
Ala Ser Gln His Gly Cys His Gly Asp Thr Ile Pro Arg Gly Ile Glu
    450                 455                 460 tac atc cag cag aac ggc gtc gtg gaa gaa cgg tcc tac cct tac gtg     1440
Tyr Ile Gln Gln Asn Gly Val Val Glu Glu Arg Ser Tyr Pro Tyr Val
465                 470                 475                 480 gcc cgc gag cag aga tgc aga agg ccc aac tct cag cac tac ggc atc     1488
Ala Arg Glu Gln Arg Cys Arg Arg Pro Asn Ser Gln His Tyr Gly Ile
                485                 490                 495 agc aac tac tgc cag atc tac ccc ccc gac gtg aag cag atc aga gag     1536
Ser Asn Tyr Cys Gln Ile Tyr Pro Pro Asp Val Lys Gln Ile Arg Glu
            500                 505                 510 gct ctg acc cag acc cac acc gcc att gcc gtg atc atc gga atc aag     1584
Ala Leu Thr Gln Thr His Thr Ala Ile Ala Val Ile Ile Gly Ile Lys
        515                 520                 525
```

```
gat ctg cgg gcc ttc cag cac tat gac ggc cgg acc atc atc cag cac   1632
Asp Leu Arg Ala Phe Gln His Tyr Asp Gly Arg Thr Ile Ile Gln His
        530                 535                 540 gac aac ggc tac cag ccc aac tac cac gcc gtg aac atc gtg ggc tac   1680
Asp Asn Gly Tyr Gln Pro Asn Tyr His Ala Val Asn Ile Val Gly Tyr
545                 550                 555                 560 ggc agc aca caa ggc gac gac tac tgg atc gtg cgg aac agc tgg gac   1728
Gly Ser Thr Gln Gly Asp Asp Tyr Trp Ile Val Arg Asn Ser Trp Asp
                565                 570                 575 acc aca tgg ggc gat agc ggc tac ggc tac ttc caa gcc ggc aac aat   1776
Thr Thr Trp Gly Asp Ser Gly Tyr Gly Tyr Phe Gln Ala Gly Asn Asn
            580                 585                 590 ctg atg atg atc gag cag tac ccc tac gtc gtg atc atg gaa ttc acg   1824
Leu Met Met Ile Glu Gln Tyr Pro Tyr Val Val Ile Met Glu Phe Thr
        595                 600                 605 ctg atc ccc atc gct gtg ggt ggt gcc ctg gcg ggg ctg gtc ctc atc   1872
Leu Ile Pro Ile Ala Val Gly Gly Ala Leu Ala Gly Leu Val Leu Ile
610                 615                 620 gtc ctc atc gcc tac ctc gtc ggc agg aag agg agt cac gca ggc tac   1920
Val Leu Ile Ala Tyr Leu Val Gly Arg Lys Arg Ser His Ala Gly Tyr
625                 630                 635                 640 cag act atc tag taa                                               1935
Gln Thr Ile <210> SEQ ID NO 51
<211> LENGTH: 643
<212> TYPE: PRT
<213> ORGANISM: Artificial sequence
<220> FEATURE:
<223> OTHER INFORMATION: Synthetic Construct

<400> SEQUENCE: 51

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205
```

```
Pro Ser Pro Val Pro Lys Ser Pro Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Thr Ser
370                 375                 380

Ala Cys Arg Ile Asn Ser Val Asn Val Pro Ser Glu Leu Asp Leu Arg
385                 390                 395                 400

Ser Leu Arg Thr Val Thr Pro Ile Arg Met Gln Gly Gly Cys Gly Ser
                405                 410                 415

Cys Trp Ala Phe Ser Gly Val Ala Ala Thr Glu Ser Ala Tyr Leu Ala
            420                 425                 430

Tyr Arg Asn Thr Ser Leu Asp Leu Ser Glu Gln Glu Leu Val Asp Cys
        435                 440                 445

Ala Ser Gln His Gly Cys His Gly Asp Thr Ile Pro Arg Gly Ile Glu
450                 455                 460

Tyr Ile Gln Gln Asn Gly Val Val Glu Glu Arg Ser Tyr Pro Tyr Val
465                 470                 475                 480

Ala Arg Glu Gln Arg Cys Arg Arg Pro Asn Ser Gln His Tyr Gly Ile
                485                 490                 495

Ser Asn Tyr Cys Gln Ile Tyr Pro Pro Asp Val Lys Gln Ile Arg Glu
            500                 505                 510

Ala Leu Thr Gln Thr His Thr Ala Ile Ala Val Ile Ile Gly Ile Lys
        515                 520                 525

Asp Leu Arg Ala Phe Gln His Tyr Asp Gly Arg Thr Ile Ile Gln His
530                 535                 540

Asp Asn Gly Tyr Gln Pro Asn Tyr His Ala Val Asn Ile Val Gly Tyr
545                 550                 555                 560

Gly Ser Thr Gln Gly Asp Asp Tyr Trp Ile Val Arg Asn Ser Trp Asp
                565                 570                 575

Thr Thr Trp Gly Asp Ser Gly Tyr Gly Tyr Phe Gln Ala Gly Asn Asn
            580                 585                 590

Leu Met Met Ile Glu Gln Tyr Pro Tyr Val Val Ile Met Glu Phe Thr
        595                 600                 605

Leu Ile Pro Ile Ala Val Gly Gly Ala Leu Ala Gly Leu Val Leu Ile
610                 615                 620
```

```
Val Leu Ile Ala Tyr Leu Val Gly Arg Lys Arg Ser His Ala Gly Tyr
625                 630                 635                 640

Gln Thr Ile

<210> SEQ ID NO 52
<211> LENGTH: 399
<212> TYPE: DNA
<213> ORGANISM: Dermatophagoides pteronyssinus
<220> FEATURE:
<221> NAME/KEY: CDS
<222> LOCATION: (7)..(393)

<400> SEQUENCE: 52 ctcgag gac caa gtg gac gtg aag gac tgc gcc aac cac gag atc aag        48
       Asp Gln Val Asp Val Lys Asp Cys Ala Asn His Glu Ile Lys
         1               5                  10 aaa gtg ctg gtg ccc ggc tgc cac ggc agc gag cct tgt atc atc cac       96
Lys Val Leu Val Pro Gly Cys His Gly Ser Glu Pro Cys Ile Ile His
 15              20                  25                  30 cgg ggc aag ccc ttt cag ctg gaa gcc gtg ttc gag gcc aac cag aac      144
Arg Gly Lys Pro Phe Gln Leu Glu Ala Val Phe Glu Ala Asn Gln Asn
                 35                  40                  45 acc aag acc gcc aag att gag atc aag gcc agc atc gac gga ctg gaa      192
Thr Lys Thr Ala Lys Ile Glu Ile Lys Ala Ser Ile Asp Gly Leu Glu
         50                  55                  60 gtg gat gtg ccc ggc atc gac ccc aac gct tgt cac tac atg aag tgc      240
Val Asp Val Pro Gly Ile Asp Pro Asn Ala Cys His Tyr Met Lys Cys
                 65                  70                  75 cct ctc gtg aag ggc cag cag tac gac atc aag tac aca tgg aac gtg      288
Pro Leu Val Lys Gly Gln Gln Tyr Asp Ile Lys Tyr Thr Trp Asn Val
 80                  85                  90 ccc aag atc gcc ccc aag agc gag aac gtc gtc gtg acc gtg aaa gtg      336
Pro Lys Ile Ala Pro Lys Ser Glu Asn Val Val Val Thr Val Lys Val
 95                 100                 105                 110 atg ggc gac gac ggc gtg ctg gct tgc gcc att gcc aca cac gcc aag      384
Met Gly Asp Asp Gly Val Leu Ala Cys Ala Ile Ala Thr His Ala Lys
                115                 120                 125 atc cgg gac gaattc                                                   399
Ile Arg Asp <210> SEQ ID NO 53
<211> LENGTH: 129
<212> TYPE: PRT
<213> ORGANISM: Dermatophagoides pteronyssinus

<400> SEQUENCE: 53

Asp Gln Val Asp Val Lys Asp Cys Ala Asn His Glu Ile Lys Lys Val
1               5                  10                  15

Leu Val Pro Gly Cys His Gly Ser Glu Pro Cys Ile Ile His Arg Gly
            20                  25                  30

Lys Pro Phe Gln Leu Glu Ala Val Phe Glu Ala Asn Gln Asn Thr Lys
        35                  40                  45

Thr Ala Lys Ile Glu Ile Lys Ala Ser Ile Asp Gly Leu Glu Val Asp
    50                  55                  60

Val Pro Gly Ile Asp Pro Asn Ala Cys His Tyr Met Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Val Met Gly
            100                 105                 110
```

```
                         Asp Asp Gly Val Leu Ala Cys Ala Ile Ala Thr His Ala Lys Ile Arg
                                 115                 120                 125

Asp

<210> SEQ ID NO 54
<211> LENGTH: 1653
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1653)

<400> SEQUENCE: 54 atg gcg ccc cgc agc gcc cgg cga ccc ctg ctg ctg cta ctg ctg ttg        48
Met Ala Pro Arg Ser Ala Arg Arg Pro Leu Leu Leu Leu Leu Leu Leu
1               5                  10                  15 ctg ctc ggc ctc atg cat tgt gcg tca gca gca atg ttt atg gtg              96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc         144
Lys Asn Gly Asn Gly Thr Ala Cys Ile Met Ala Asn Phe Ser Ala Ala
        35                  40                  45 ttc tca gtg aac tac gac acc aag agt ggc cct aag aac atg acc ctt         192
Phe Ser Val Asn Tyr Asp Thr Lys Ser Gly Pro Lys Asn Met Thr Leu
    50                  55                  60 gac ctg cca tca gat gcc aca gtg gtg ctc aac cgc agc tcc tgt gga         240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga         288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc         336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc         384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc         432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc         480
Arg Ala Asp Ile Asp Lys Lys Tyr Arg Cys Val Ser Gly Thr Gln Val
145                 150                 155                 160 cac atg aac aac gta acc gta acg ctc cat gat gcc acc atc cag gcg         528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa         576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg         624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc         672
Pro Ser Pro Val Pro Lys Ser Pro Ser Val Asp Lys Tyr Asn Val Ser
    210                 215                 220 ggc acc aac ggg acc tgc ctg ctg gcc agc atg ggg ctg cag ctg aac         720
Gly Thr Asn Gly Thr Cys Leu Leu Ala Ser Met Gly Leu Gln Leu Asn
225                 230                 235                 240
```

```
ctc acc tat gag agg aag gac aac acg acg gtg aca agg ctt ctc aac      768
Leu Thr Tyr Glu Arg Lys Asp Asn Thr Thr Val Thr Arg Leu Leu Asn
            245                 250                 255 atc aac ccc aac aag acc tcg gcc agc ggg agc tgc ggc gcc cac ctg      816
Ile Asn Pro Asn Lys Thr Ser Ala Ser Gly Ser Cys Gly Ala His Leu
        260                 265                 270 gtg act ctg gag ctg cac agc gag ggc acc acc gtc ctg ctc ttc cag      864
Val Thr Leu Glu Leu His Ser Glu Gly Thr Thr Val Leu Leu Phe Gln
    275                 280                 285 ttc ggg atg aat gca agt tct agc cgg ttt ttc cta caa gga atc cag      912
Phe Gly Met Asn Ala Ser Ser Ser Arg Phe Phe Leu Gln Gly Ile Gln
290                 295                 300 ttg aat aca att ctt cct gac gcc aga gac cct gcc ttt aaa gct gcc      960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag     1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat     1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt     1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag gac caa     1152
Gly Ser Val Glu Glu Cys Leu Leu Asp Glu Asn Ser Leu Glu Asp Gln
    370                 375                 380 gtg gac gtg aag gac tgc gcc aac cac gag atc aag aaa gtg ctg gtg     1200
Val Asp Val Lys Asp Cys Ala Asn His Glu Ile Lys Lys Val Leu Val
385                 390                 395                 400 ccc ggc tgc cac ggc agc gag cct tgt atc atc cac cgg ggc aag ccc     1248
Pro Gly Cys His Gly Ser Glu Pro Cys Ile Ile His Arg Gly Lys Pro
                405                 410                 415 ttt cag ctg gaa gcc gtg ttc gag gcc aac cag aac acc aag acc gcc     1296
Phe Gln Leu Glu Ala Val Phe Glu Ala Asn Gln Asn Thr Lys Thr Ala
            420                 425                 430 aag att gag atc aag gcc agc atc gac gga ctg gaa gtg gat gtg ccc     1344
Lys Ile Glu Ile Lys Ala Ser Ile Asp Gly Leu Glu Val Asp Val Pro
        435                 440                 445 ggc atc gac ccc aac gct tgt cac tac atg aag tgc cct ctc gtg aag     1392
Gly Ile Asp Pro Asn Ala Cys His Tyr Met Lys Cys Pro Leu Val Lys
    450                 455                 460 ggc cag cag tac gac atc aag tac aca tgg aac gtg ccc aag atc gcc     1440
Gly Gln Gln Tyr Asp Ile Lys Tyr Thr Trp Asn Val Pro Lys Ile Ala
465                 470                 475                 480 ccc aag agc gag aac gtc gtc gtg acc gtg aaa gtg atg ggc gac gac     1488
Pro Lys Ser Glu Asn Val Val Val Thr Val Lys Val Met Gly Asp Asp
                485                 490                 495 ggc gtg ctg gct tgc gcc att gcc aca cac gcc aag atc cgg gac gaa     1536
Gly Val Leu Ala Cys Ala Ile Ala Thr His Ala Lys Ile Arg Asp Glu
            500                 505                 510 ttc acg ctg atc ccc atc gct gtg ggt ggt gcc ctg gcg ggg ctg gtc     1584
Phe Thr Leu Ile Pro Ile Ala Val Gly Gly Ala Leu Ala Gly Leu Val
        515                 520                 525 ctc atc gtc ctc atc gcc tac ctc gtc ggc agg aag agg agt cac gca     1632
Leu Ile Val Leu Ile Ala Tyr Leu Val Gly Arg Lys Arg Ser His Ala
    530                 535                 540 ggc tac cag act atc tag taa                                         1653
Gly Tyr Gln Thr Ile
545
```

<210> SEQ ID NO 55
<211> LENGTH: 549
<212> TYPE: PRT
<213> ORGANISM: Artificial sequence
<220> FEATURE:
<223> OTHER INFORMATION: Synthetic Construct

<400> SEQUENCE: 55

Met Ala Pro Arg Ser Ala Arg Arg Pro Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
                100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
            195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
    275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

```
Gly Ser Val Glu Glu Cys Leu Leu Asp Glu Asn Ser Leu Glu Asp Gln
    370                 375                 380

Val Asp Val Lys Asp Cys Ala Asn His Glu Ile Lys Lys Val Leu Val
385                 390                 395                 400

Pro Gly Cys His Gly Ser Glu Pro Cys Ile Ile His Arg Gly Lys Pro
                405                 410                 415

Phe Gln Leu Glu Ala Val Phe Glu Ala Asn Gln Asn Thr Lys Thr Ala
            420                 425                 430

Lys Ile Glu Ile Lys Ala Ser Ile Asp Gly Leu Glu Val Asp Val Pro
        435                 440                 445

Gly Ile Asp Pro Asn Ala Cys His Tyr Met Lys Cys Pro Leu Val Lys
    450                 455                 460

Gly Gln Gln Tyr Asp Ile Lys Tyr Thr Trp Asn Val Pro Lys Ile Ala
465                 470                 475                 480

Pro Lys Ser Glu Asn Val Val Thr Val Lys Val Met Gly Asp Asp
                485                 490                 495

Gly Val Leu Ala Cys Ala Ile Ala Thr His Ala Lys Ile Arg Asp Glu
                500                 505                 510

Phe Thr Leu Ile Pro Ile Ala Val Gly Gly Ala Leu Ala Gly Leu Val
            515                 520                 525

Leu Ile Val Leu Ile Ala Tyr Leu Val Gly Arg Lys Arg Ser His Ala
    530                 535                 540

Gly Tyr Gln Thr Ile
545

<210> SEQ ID NO 56
<211> LENGTH: 399
<212> TYPE: DNA
<213> ORGANISM: Dermatophagoides farinae
<220> FEATURE:
<221> NAME/KEY: CDS
<222> LOCATION: (7)..(393)

<400> SEQUENCE: 56 ctcgag gat cag gtg gat gtc aag gac tgt gct aac aac gaa atc aag        48
       Asp Gln Val Asp Val Lys Asp Cys Ala Asn Asn Glu Ile Lys
         1               5                  10 aaa gtc atg gtg gac gga tgt cac ggg agc gac ccc tgt att atc cac       96
Lys Val Met Val Asp Gly Cys His Gly Ser Asp Pro Cys Ile Ile His
 15              20                  25                  30 cgg gga aag ccc ttc aca ctg gag gcc ctg ttt gat gct aac cag aat      144
Arg Gly Lys Pro Phe Thr Leu Glu Ala Leu Phe Asp Ala Asn Gln Asn
                 35                  40                  45 acc aag aca gca aaa atc gag gtc aaa gcc agc ctg gac ggc ctg gaa      192
Thr Lys Thr Ala Lys Ile Glu Val Lys Ala Ser Leu Asp Gly Leu Glu
             50                  55                  60 atc gat gtg cca ggg att gac acc aac gct tgc cat ttc gtc aag tgt      240
Ile Asp Val Pro Gly Ile Asp Thr Asn Ala Cys His Phe Val Lys Cys
         65                  70                  75 ccc ctg gtg aaa ggc cag cag tac gac atc aag tat act tgg aac gtc      288
Pro Leu Val Lys Gly Gln Gln Tyr Asp Ile Lys Tyr Thr Trp Asn Val
     80                  85                  90 ccc aag att gcc cct aaa tcc gaa aat gtg gtc gtg acc gtg aaa ctg      336
Pro Lys Ile Ala Pro Lys Ser Glu Asn Val Val Val Thr Val Lys Leu
 95                 100                 105                 110 att gga gac aac ggc gtc ctg gcc tgt gct atc gca act cac ggg aag      384
Ile Gly Asp Asn Gly Val Leu Ala Cys Ala Ile Ala Thr His Gly Lys
                115                 120                 125
```

-continued

```
att aga gac gaattc                                                    399
Ile Arg Asp <210> SEQ ID NO 57
<211> LENGTH: 129
<212> TYPE: PRT
<213> ORGANISM: Dermatophagoides farinae

<400> SEQUENCE: 57

Asp Gln Val Asp Val Lys Asp Cys Ala Asn Asn Glu Ile Lys Lys Val
1               5                   10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Ile Glu Val Lys Ala Ser Leu Asp Gly Leu Glu Ile Asp
    50                  55                  60

Val Pro Gly Ile Asp Thr Asn Ala Cys His Phe Val Lys Cys Pro Leu
65                  70                  75                  80

Val Lys Gly Gln Gln Tyr Asp Ile Lys Tyr Thr Trp Asn Val Pro Lys
                85                  90                  95

Ile Ala Pro Lys Ser Glu Asn Val Val Val Thr Val Lys Leu Ile Gly
            100                 105                 110

Asp Asn Gly Val Leu Ala Cys Ala Ile Ala Thr His Gly Lys Ile Arg
        115                 120                 125

Asp

<210> SEQ ID NO 58
<211> LENGTH: 1653
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1653)

<400> SEQUENCE: 58 atg gcg ccc cgc agc gcc cgg cga ccc ctg ctg ctg cta ctg ctg ttg    48
Met Ala Pro Arg Ser Ala Arg Arg Pro Leu Leu Leu Leu Leu Leu Leu
1               5                   10                  15 ctg ctc ggc ctc atg cat tgt gcg tca gca gca atg ttt atg gtg         96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc   144
Lys Asn Gly Asn Gly Thr Ala Cys Ile Met Ala Asn Phe Ser Ala Ala
        35                  40                  45 ttc tca gtg aac tac gac acc aag agt ggc cct aag aac atg acc ctt   192
Phe Ser Val Asn Tyr Asp Thr Lys Ser Gly Pro Lys Asn Met Thr Leu
    50                  55                  60 gac ctg cca tca gat gcc aca gtg gtg ctc aac cgc agc tcc tgt gga   240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga   288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc   336
His Thr Leu Thr Leu Asn Phe Thr Arg Asn Ala Thr Arg Tyr Ser Val
            100                 105                 110
```

```
cag ctc atg agt ttt gtt tat aac ttg tca gac aca cac ctt ttc ccc    384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc    432
Asn Ala Ser Ser Lys Glu Ile Lys Thr Val Glu Ser Ile Thr Asp Ile
130                 135                 140 agg gca gat ata gat aaa aaa tac aga tgt gtt agt ggc acc cag gtc    480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg    528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa    576
Tyr Leu Ser Asn Ser Ser Phe Ser Arg Gly Glu Thr Arg Cys Glu Gln
                180                 185                 190 gac agg cct tcc cca acc aca gcg ccc cct gcg cca ccc agc ccc tcg    624
Asp Arg Pro Ser Pro Thr Thr Ala Pro Pro Ala Pro Pro Ser Pro Ser
            195                 200                 205 ccc tca ccc gtg ccc aag agc ccc tct gtg gac aag tac aac gtg agc    672
Pro Ser Pro Val Pro Lys Ser Pro Ser Val Asp Lys Tyr Asn Val Ser
210                 215                 220 ggc acc aac ggg acc tgc ctg ctg gcc agc atg ggg ctg cag ctg aac    720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac    768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg    816
Ile Asn Pro Asn Lys Thr Ser Ala Ser Gly Ser Cys Gly Ala His Leu
                260                 265                 270 gtg act ctg gag ctg cac agc gag ggc acc acc gtc ctg ctc ttc cag    864
Val Thr Leu Glu Leu His Ser Glu Gly Thr Thr Val Leu Leu Phe Gln
            275                 280                 285 ttc ggg atg aat gca agt tct agc cgg ttt ttc cta caa gga atc cag    912
Phe Gly Met Asn Ala Ser Ser Ser Arg Phe Phe Leu Gln Gly Ile Gln
290                 295                 300 ttg aat aca att ctt cct gac gcc aga gac cct gcc ttt aaa gct gcc    960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag   1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat   1056
Cys Asn Ala Glu Glu His Val Arg Val Thr Lys Ala Phe Ser Val Asn
                340                 345                 350 ata ttc aaa gtg tgg gtc cag gct ttc aag gtg gaa ggt ggc cag ttt   1104
Ile Phe Lys Val Trp Val Gln Ala Phe Lys Val Glu Gly Gly Gln Phe
            355                 360                 365 ggc tct gtg gag gag tgt ctg ctg gac gag aac agc ctc gag gat cag   1152
Gly Ser Val Glu Glu Cys Leu Leu Asp Glu Asn Ser Leu Glu Asp Gln
370                 375                 380 gtg gat gtc aag gac tgt gct aac aac gaa atc aag aaa gtc atg gtg   1200
Val Asp Val Lys Asp Cys Ala Asn Asn Glu Ile Lys Lys Val Met Val
385                 390                 395                 400 gac gga tgt cac ggg agc gac ccc tgt att atc cac cgg gga aag ccc   1248
Asp Gly Cys His Gly Ser Asp Pro Cys Ile Ile His Arg Gly Lys Pro
                405                 410                 415 ttc aca ctg gag gcc ctg ttt gat gct aac cag aat acc aag aca gca   1296
Phe Thr Leu Glu Ala Leu Phe Asp Ala Asn Gln Asn Thr Lys Thr Ala
            420                 425                 430
```

```
aaa atc gag gtc aaa gcc agc ctg gac ggc ctg gaa atc gat gtg cca    1344
Lys Ile Glu Val Lys Ala Ser Leu Asp Gly Leu Glu Ile Asp Val Pro
        435                 440                 445 ggg att gac acc aac gct tgc cat ttc gtc aag tgt ccc ctg gtg aaa    1392
Gly Ile Asp Thr Asn Ala Cys His Phe Val Lys Cys Pro Leu Val Lys
450                 455                 460 ggc cag cag tac gac atc aag tat act tgg aac gtc ccc aag att gcc    1440
Gly Gln Gln Tyr Asp Ile Lys Tyr Thr Trp Asn Val Pro Lys Ile Ala
465                 470                 475                 480 cct aaa tcc gaa aat gtg gtc gtg acc gtg aaa ctg att gga gac aac    1488
Pro Lys Ser Glu Asn Val Val Val Thr Val Lys Leu Ile Gly Asp Asn
                485                 490                 495 ggc gtc ctg gcc tgt gct atc gca act cac ggg aag att aga gac gaa    1536
Gly Val Leu Ala Cys Ala Ile Ala Thr His Gly Lys Ile Arg Asp Glu
        500                 505                 510 ttc acg ctg atc ccc atc gct gtg ggt ggt gcc ctg gcg ggg ctg gtc    1584
Phe Thr Leu Ile Pro Ile Ala Val Gly Gly Ala Leu Ala Gly Leu Val
        515                 520                 525 ctc atc gtc ctc atc gcc tac ctc gtc ggc agg aag agg agt cac gca    1632
Leu Ile Val Leu Ile Ala Tyr Leu Val Gly Arg Lys Arg Ser His Ala
530                 535                 540 ggc tac cag act atc tag taa                                        1653
Gly Tyr Gln Thr Ile
545

<210> SEQ ID NO 59
<211> LENGTH: 549
<212> TYPE: PRT
<213> ORGANISM: Artificial sequence
<220> FEATURE:
<223> OTHER INFORMATION: Synthetic Construct

<400> SEQUENCE: 59

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190
```

```
Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
            245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
        290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
                340                 345                 350

Ile Phe Lys Val Trp Val Gln Ala Phe Lys Val Glu Gly Gly Gln Phe
            355                 360                 365

Gly Ser Val Glu Glu Cys Leu Leu Asp Glu Asn Ser Leu Glu Asp Gln
        370                 375                 380

Val Asp Val Lys Asp Cys Ala Asn Asn Glu Ile Lys Lys Val Met Val
385                 390                 395                 400

Asp Gly Cys His Gly Ser Asp Pro Cys Ile Ile His Arg Gly Lys Pro
                405                 410                 415

Phe Thr Leu Glu Ala Leu Phe Asp Ala Asn Gln Asn Thr Lys Thr Ala
            420                 425                 430

Lys Ile Glu Val Lys Ala Ser Leu Asp Gly Leu Glu Ile Asp Val Pro
        435                 440                 445

Gly Ile Asp Thr Asn Ala Cys His Phe Val Lys Cys Pro Leu Val Lys
450                 455                 460

Gly Gln Gln Tyr Asp Ile Lys Tyr Thr Trp Asn Val Pro Lys Ile Ala
465                 470                 475                 480

Pro Lys Ser Glu Asn Val Val Thr Val Lys Leu Ile Gly Asp Asn
                485                 490                 495

Gly Val Leu Ala Cys Ala Ile Thr His Gly Lys Ile Arg Asp Glu
            500                 505                 510

Phe Thr Leu Ile Pro Ile Ala Val Gly Gly Ala Leu Ala Gly Leu Val
        515                 520                 525

Leu Ile Val Leu Ile Ala Tyr Leu Val Gly Arg Lys Arg Ser His Ala
530                 535                 540

Gly Tyr Gln Thr Ile
545

<210> SEQ ID NO 60
<211> LENGTH: 648
<212> TYPE: DNA
<213> ORGANISM: Dermatophagoides pteronyssinus
<220> FEATURE:
<221> NAME/KEY: CDS
<222> LOCATION: (7)..(642)

<400> SEQUENCE: 60
```

```
ctcgag acc aac gct tgc tct atc aac gga aac gcc ccc gcc gaa atc        48
       Thr Asn Ala Cys Ser Ile Asn Gly Asn Ala Pro Ala Glu Ile
       1               5                   10 gac ctg agg cag atg agg act gtc aca ccc att agg tcc gga gtg gcc        96
Asp Leu Arg Gln Met Arg Thr Val Thr Pro Ile Arg Ser Gly Val Ala
15                  20                  25                  30 gct act gag tct gcc tac ctg gct tat cga aat cag agt ctg gac ctg       144
Ala Thr Glu Ser Ala Tyr Leu Ala Tyr Arg Asn Gln Ser Leu Asp Leu
                35                  40                  45 gca gag cag gaa ctg gtg gat tgc gcc agc cag cac aat ggg tgt cat       192
Ala Glu Gln Glu Leu Val Asp Cys Ala Ser Gln His Asn Gly Cys His
            50                  55                  60 gga gac acc atc cca agg gga atc gaa tac att cag cac aac ggc gtg       240
Gly Asp Thr Ile Pro Arg Gly Ile Glu Tyr Ile Gln His Asn Gly Val
65                  70                  75 gtc cag gag tca tac tat aga tat gtg gcc cgc gaa cag agc tgc cga       288
Val Gln Glu Ser Tyr Tyr Arg Tyr Val Ala Arg Glu Gln Ser Cys Arg
        80                  85                  90 aga cca aat gct cag agg ttc ggc atc agt aac tac tgt cag att tat       336
Arg Pro Asn Ala Gln Arg Phe Gly Ile Ser Asn Tyr Cys Gln Ile Tyr
95                  100                 105                 110 cct cag aac gtg aat aag atc cga gag gca ctg gca cag acc cac tcc       384
Pro Gln Asn Val Asn Lys Ile Arg Glu Ala Leu Ala Gln Thr His Ser
                115                 120                 125 gct atc gca gtc atc att ggg att aaa gac ctg gat gcc ttt cga cat       432
Ala Ile Ala Val Ile Ile Gly Ile Lys Asp Leu Asp Ala Phe Arg His
            130                 135                 140 tac gac ggg cgg aca atc att cag aga gat aac gga tac cag ccc aat       480
Tyr Asp Gly Arg Thr Ile Ile Gln Arg Asp Asn Gly Tyr Gln Pro Asn
145                 150                 155 tat cat gct gtg aac atc gtc ggc tac tcc aat gca cag ggg gtg gat       528
Tyr His Ala Val Asn Ile Val Gly Tyr Ser Asn Ala Gln Gly Val Asp
        160                 165                 170 tat tgg att gtc cgg aac tct tgg gac aca aac tgg ggc gat aat gga       576
Tyr Trp Ile Val Arg Asn Ser Trp Asp Thr Asn Trp Gly Asp Asn Gly
175                 180                 185                 190 tat ggc tat ttc gcc gcc aac att gac ctg atg atg att gaa gag tat       624
Tyr Gly Tyr Phe Ala Ala Asn Ile Asp Leu Met Met Ile Glu Glu Tyr
                195                 200                 205 cct tac gtg gtg atc ctg gaattc                                        648
Pro Tyr Val Val Ile Leu
            210
```

<210> SEQ ID NO 61
<211> LENGTH: 212
<212> TYPE: PRT
<213> ORGANISM: Dermatophagoides pteronyssinus

<400> SEQUENCE: 61

```
Thr Asn Ala Cys Ser Ile Asn Gly Asn Ala Pro Ala Glu Ile Asp Leu
1               5                   10                  15

Arg Gln Met Arg Thr Val Thr Pro Ile Arg Ser Gly Val Ala Ala Thr
                20                  25                  30

Glu Ser Ala Tyr Leu Ala Tyr Arg Asn Gln Ser Leu Asp Leu Ala Glu
            35                  40                  45

Gln Glu Leu Val Asp Cys Ala Ser Gln His Asn Gly Cys His Gly Asp
        50                  55                  60

Thr Ile Pro Arg Gly Ile Glu Tyr Ile Gln His Asn Gly Val Val Gln
65                  70                  75                  80
```

```
Glu Ser Tyr Tyr Arg Tyr Val Ala Arg Glu Gln Ser Cys Arg Arg Pro
                85                  90                  95

Asn Ala Gln Arg Phe Gly Ile Ser Asn Tyr Cys Gln Ile Tyr Pro Gln
            100                 105                 110

Asn Val Asn Lys Ile Arg Glu Ala Leu Ala Gln Thr His Ser Ala Ile
        115                 120                 125

Ala Val Ile Ile Gly Ile Lys Asp Leu Asp Ala Phe Arg His Tyr Asp
    130                 135                 140

Gly Arg Thr Ile Ile Gln Arg Asp Asn Gly Tyr Gln Pro Asn Tyr His
145                 150                 155                 160

Ala Val Asn Ile Val Gly Tyr Ser Asn Ala Gln Gly Val Asp Tyr Trp
                165                 170                 175

Ile Val Arg Asn Ser Trp Asp Thr Asn Trp Gly Asp Asn Gly Tyr Gly
            180                 185                 190

Tyr Phe Ala Ala Asn Ile Asp Leu Met Met Ile Glu Glu Tyr Pro Tyr
        195                 200                 205

Val Val Ile Leu
    210
```

<210> SEQ ID NO 62
<211> LENGTH: 1902
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1902)

<400> SEQUENCE: 62

| | | |
|---|---|---|
| atg gcg ccc cgc agc gcc cgg cga ccc ctg ctg ctg cta ctg ctg ttg<br>Met Ala Pro Arg Ser Ala Arg Arg Pro Leu Leu Leu Leu Leu Leu Leu<br>1               5                   10                  15 | | 48 |
| ctg ctg ctc ggc ctc atg cat tgt gcg tca gca gca atg ttt atg gtg<br>Leu Leu Leu Gly Leu Met His Cys Ala Ser Ala Ala Met Phe Met Val<br>            20                  25                  30 | | 96 |
| aaa aat ggc aac ggg acc gcg tgc ata atg gcc aac ttc tct gct gcc<br>Lys Asn Gly Asn Gly Thr Ala Cys Ile Met Ala Asn Phe Ser Ala Ala<br>        35                  40                  45 | | 144 |
| ttc tca gtg aac tac gac acc aag agt ggc cct aag aac atg acc ctt<br>Phe Ser Val Asn Tyr Asp Thr Lys Ser Gly Pro Lys Asn Met Thr Leu<br>    50                  55                  60 | | 192 |
| gac ctg cca tca gat gcc aca gtg gtg ctc aac cgc agc tcc tgt gga<br>Asp Leu Pro Ser Asp Ala Thr Val Val Leu Asn Arg Ser Ser Cys Gly<br>65                  70                  75                  80 | | 240 |
| aaa gag aac act tct gac ccc agt ctc gtg att gct ttt gga aga gga<br>Lys Glu Asn Thr Ser Asp Pro Ser Leu Val Ile Ala Phe Gly Arg Gly<br>                85                  90                  95 | | 288 |
| cat aca ctc act ctc aat ttc acg aga aat gca aca cgt tac agc gtc<br>His Thr Leu Thr Leu Asn Phe Thr Arg Asn Ala Thr Arg Tyr Ser Val<br>            100                 105                 110 | | 336 |
| cag ctc atg agt ttt gtt tat aac ttg tca gac aca cac ctt ttc ccc<br>Gln Leu Met Ser Phe Val Tyr Asn Leu Ser Asp Thr His Leu Phe Pro<br>        115                 120                 125 | | 384 |
| aat gcg agc tcc aaa gaa atc aag act gtg gaa tct ata act gac atc<br>Asn Ala Ser Ser Lys Glu Ile Lys Thr Val Glu Ser Ile Thr Asp Ile<br>    130                 135                 140 | | 432 |
| agg gca gat ata gat aaa aaa tac aga tgt gtt agt ggc acc cag gtc<br>Arg Ala Asp Ile Asp Lys Lys Tyr Arg Cys Val Ser Gly Thr Gln Val | | 480 |

-continued

| | | | |
|---|---|---|---|
| 145 | 150 | 155 | 160 |

| | | |
|---|---|---|
| cac atg aac aac gtg acc gta acg ctc cat gat gcc acc atc cag gcg<br>His Met Asn Asn Val Thr Val Thr Leu His Asp Ala Thr Ile Gln Ala<br>                         165                       170                    175 | 528 |
| tac ctt tcc aac agc agc ttc agc cgg gga gag aca cgc tgt gaa caa<br>Tyr Leu Ser Asn Ser Ser Phe Ser Arg Gly Glu Thr Arg Cys Glu Gln<br>           180                       185                    190 | 576 |
| gac agg cct tcc cca acc aca gcg ccc cct gcg cca ccc agc ccc tcg<br>Asp Arg Pro Ser Pro Thr Thr Ala Pro Pro Ala Pro Pro Ser Pro Ser<br>       195                    200                    205 | 624 |
| ccc tca ccc gtg ccc aag agc ccc tct gtg gac aag tac aac gtg agc<br>Pro Ser Pro Val Pro Lys Ser Pro Ser Val Asp Lys Tyr Asn Val Ser<br>210                    215                  220 | 672 |
| ggc acc aac ggg acc tgc ctg ctg gcc agc atg ggg ctg cag ctg aac<br>Gly Thr Asn Gly Thr Cys Leu Leu Ala Ser Met Gly Leu Gln Leu Asn<br>225                    230                  235                  240 | 720 |
| ctc acc tat gag agg aag gac aac acg acg gtg aca agg ctt ctc aac<br>Leu Thr Tyr Glu Arg Lys Asp Asn Thr Thr Val Thr Arg Leu Leu Asn<br>                  245                    250                  255 | 768 |
| atc aac ccc aac aag acc tcg gcc agc ggg agc tgc ggc gcc cac ctg<br>Ile Asn Pro Asn Lys Thr Ser Ala Ser Gly Ser Cys Gly Ala His Leu<br>         260                    265                    270 | 816 |
| gtg act ctg gag ctg cac agc gag ggc acc acc gtc ctg ctc ttc cag<br>Val Thr Leu Glu Leu His Ser Glu Gly Thr Thr Val Leu Leu Phe Gln<br>       275                    280                    285 | 864 |
| ttc ggg atg aat gca agt tct agc cgg ttt ttc cta caa gga atc cag<br>Phe Gly Met Asn Ala Ser Ser Ser Arg Phe Phe Leu Gln Gly Ile Gln<br>     290                    295                  300 | 912 |
| ttg aat aca att ctt cct gac gcc aga gac cct gcc ttt aaa gct gcc<br>Leu Asn Thr Ile Leu Pro Asp Ala Arg Asp Pro Ala Phe Lys Ala Ala<br>305                    310                  315                  320 | 960 |
| aac ggc tcc ctg cga gcg ctg cag gcc aca gtc ggc aat tcc tac aag<br>Asn Gly Ser Leu Arg Ala Leu Gln Ala Thr Val Gly Asn Ser Tyr Lys<br>                  325                    330                  335 | 1008 |
| tgc aac gcg gag gag cac gtc cgt gtc acg aag gcg ttt tca gtc aat<br>Cys Asn Ala Glu Glu His Val Arg Val Thr Lys Ala Phe Ser Val Asn<br>         340                    345                    350 | 1056 |
| ata ttc aaa gtg tgg gtc cag gct ttc aag gtg gaa ggt ggc cag ttt<br>Ile Phe Lys Val Trp Val Gln Ala Phe Lys Val Glu Gly Gly Gln Phe<br>       355                    360                    365 | 1104 |
| ggc tct gtg gag gag tgt ctg ctg gac gag aac agc ctc gag acc aac<br>Gly Ser Val Glu Glu Cys Leu Leu Asp Glu Asn Ser Leu Glu Thr Asn<br>     370                    375                  380 | 1152 |
| gct tgc tct atc aac gga aac gcc ccc gcc gaa atc gac ctg agg cag<br>Ala Cys Ser Ile Asn Gly Asn Ala Pro Ala Glu Ile Asp Leu Arg Gln<br>385                    390                  395                  400 | 1200 |
| atg agg act gtc aca ccc att agg tcc gga gtg gcc gct act gag tct<br>Met Arg Thr Val Thr Pro Ile Arg Ser Gly Val Ala Ala Thr Glu Ser<br>                  405                    410                  415 | 1248 |
| gcc tac ctg gct tat cga aat cag agt ctg gac ctg gca gag cag gaa<br>Ala Tyr Leu Ala Tyr Arg Asn Gln Ser Leu Asp Leu Ala Glu Gln Glu<br>         420                    425                    430 | 1296 |
| ctg gtg gat tgc gcc agc cag cac aat ggg tgt cat gga gac acc atc<br>Leu Val Asp Cys Ala Ser Gln His Asn Gly Cys His Gly Asp Thr Ile<br>       435                    440                    445 | 1344 |
| cca agg gga atc gaa tac att cag cac aac ggc gtg gtc cag gag tca<br>Pro Arg Gly Ile Glu Tyr Ile Gln His Asn Gly Val Val Gln Glu Ser<br>450                    455                  460 | 1392 |
| tac tat aga tat gtg gcc cgc gaa cag agc tgc cga aga cca aat gct | 1440 |

| | | | | | | | | | | | | | |
|---|---|---|---|---|---|---|---|---|---|---|---|---|---|
|Tyr|Tyr|Arg|Tyr|Val|Ala|Arg|Glu|Gln|Ser|Cys|Arg|Arg|Pro|Asn|Ala|
|465| | | |470| | | |475| | | |480| | |

| cag agg ttc ggc atc agt aac tac tgt cag att tat cct cag aac gtg | 1488 |
|---|---|
| Gln Arg Phe Gly Ile Ser Asn Tyr Cys Gln Ile Tyr Pro Gln Asn Val | |
|                485              490               495 | |
| aat aag atc cga gag gca ctg gca cag acc cac tcc gct atc gca gtc | 1536 |
| Asn Lys Ile Arg Glu Ala Leu Ala Gln Thr His Ser Ala Ile Ala Val | |
|  500                   505                    510 | |
| atc att ggg att aaa gac ctg gat gcc ttt cga cat tac gac ggg cgg | 1584 |
| Ile Ile Gly Ile Lys Asp Leu Asp Ala Phe Arg His Tyr Asp Gly Arg | |
|         515               520              525 | |
| aca atc att cag aga gat aac gga tac cag ccc aat tat cat gct gtg | 1632 |
| Thr Ile Ile Gln Arg Asp Asn Gly Tyr Gln Pro Asn Tyr His Ala Val | |
|  530                   535                540 | |
| aac atc gtc ggc tac tcc aat gca cag ggg gtg gat tat tgg att gtc | 1680 |
| Asn Ile Val Gly Tyr Ser Asn Ala Gln Gly Val Asp Tyr Trp Ile Val | |
| 545                 550                555              560 | |
| cgg aac tct tgg gac aca aac tgg ggc gat aat gga tat ggc tat ttc | 1728 |
| Arg Asn Ser Trp Asp Thr Asn Trp Gly Asp Asn Gly Tyr Gly Tyr Phe | |
|                  565              570              575 | |
| gcc gcc aac att gac ctg atg atg att gaa gag tat cct tac gtg gtg | 1776 |
| Ala Ala Asn Ile Asp Leu Met Met Ile Glu Glu Tyr Pro Tyr Val Val | |
|         580               585                590 | |
| atc ctg gaa ttc acg ctg atc ccc atc gct gtg ggt ggt gcc ctg gcg | 1824 |
| Ile Leu Glu Phe Thr Leu Ile Pro Ile Ala Val Gly Gly Ala Leu Ala | |
|         595               600              605 | |
| ggg ctg gtc ctc atc gtc ctc atc gcc tac ctc gtc ggc agg aag agg | 1872 |
| Gly Leu Val Leu Ile Val Leu Ile Ala Tyr Leu Val Gly Arg Lys Arg | |
|  610                   615                620 | |
| agt cac gca ggc tac cag act atc tag taa | 1902 |
| Ser His Ala Gly Tyr Gln Thr Ile | |
| 625                 630 | |

<210> SEQ ID NO 63
<211> LENGTH: 632
<212> TYPE: PRT
<213> ORGANISM: Artificial sequence
<220> FEATURE:
<223> OTHER INFORMATION: Synthetic Construct

<400> SEQUENCE: 63

| | | | | | | | | | | | | | | | |
|---|---|---|---|---|---|---|---|---|---|---|---|---|---|---|---|
|Met|Ala|Pro|Arg|Ser|Ala|Arg|Arg|Pro|Leu|Leu|Leu|Leu|Leu|Leu|Leu|
|1| | | |5| | | | |10| | | | |15| |

| | | | | | | | | | | | | | | | |
|---|---|---|---|---|---|---|---|---|---|---|---|---|---|---|---|
|Leu|Leu|Leu|Gly|Leu|Met|His|Cys|Ala|Ser|Ala|Ala|Met|Phe|Met|Val|
| | | |20| | | | |25| | | | |30| | |

| | | | | | | | | | | | | | | | |
|---|---|---|---|---|---|---|---|---|---|---|---|---|---|---|---|
|Lys|Asn|Gly|Asn|Gly|Thr|Ala|Cys|Ile|Met|Ala|Asn|Phe|Ser|Ala|Ala|
| | | |35| | | | |40| | | | |45| | |

| | | | | | | | | | | | | | | | |
|---|---|---|---|---|---|---|---|---|---|---|---|---|---|---|---|
|Phe|Ser|Val|Asn|Tyr|Asp|Thr|Lys|Ser|Gly|Pro|Lys|Asn|Met|Thr|Leu|
| | |50| | | | |55| | | | |60| | | |

| | | | | | | | | | | | | | | | |
|---|---|---|---|---|---|---|---|---|---|---|---|---|---|---|---|
|Asp|Leu|Pro|Ser|Asp|Ala|Thr|Val|Val|Leu|Asn|Arg|Ser|Ser|Cys|Gly|
|65| | | |70| | | | |75| | | | |80| | |

| | | | | | | | | | | | | | | | |
|---|---|---|---|---|---|---|---|---|---|---|---|---|---|---|---|
|Lys|Glu|Asn|Thr|Ser|Asp|Pro|Ser|Leu|Val|Ile|Ala|Phe|Gly|Arg|Gly|
| | | |85| | | | |90| | | | |95| | |

| | | | | | | | | | | | | | | | |
|---|---|---|---|---|---|---|---|---|---|---|---|---|---|---|---|
|His|Thr|Leu|Thr|Leu|Asn|Phe|Thr|Arg|Asn|Ala|Thr|Arg|Tyr|Ser|Val|
| | | |100| | | | |105| | | | |110| | |

| | | | | | | | | | | | | | | | |
|---|---|---|---|---|---|---|---|---|---|---|---|---|---|---|---|
|Gln|Leu|Met|Ser|Phe|Val|Tyr|Asn|Leu|Ser|Asp|Thr|His|Leu|Phe|Pro|
| | |115| | | | |120| | | | |125| | | |

| | | | | | | | | | | | | | | | |
|---|---|---|---|---|---|---|---|---|---|---|---|---|---|---|---|
|Asn|Ala|Ser|Ser|Lys|Glu|Ile|Lys|Thr|Val|Glu|Ser|Ile|Thr|Asp|Ile|
|130| | | |135| | | | |140| | | | | | |

```
Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gly Gln Phe
        355                 360                 365

Gly Ser Val Glu Glu Cys Leu Leu Asp Glu Asn Ser Leu Glu Thr Asn
    370                 375                 380

Ala Cys Ser Ile Asn Gly Asn Ala Pro Ala Glu Ile Asp Leu Arg Gln
385                 390                 395                 400

Met Arg Thr Val Thr Pro Ile Arg Ser Gly Val Ala Ala Thr Glu Ser
                405                 410                 415

Ala Tyr Leu Ala Tyr Arg Asn Gln Ser Leu Asp Leu Ala Glu Gln Glu
            420                 425                 430

Leu Val Asp Cys Ala Ser Gln His Asn Gly Cys His Gly Asp Thr Ile
        435                 440                 445

Pro Arg Gly Ile Glu Tyr Ile Gln His Asn Gly Val Val Gln Glu Ser
    450                 455                 460

Tyr Tyr Arg Tyr Val Ala Arg Glu Gln Ser Cys Arg Arg Pro Asn Ala
465                 470                 475                 480

Gln Arg Phe Gly Ile Ser Asn Tyr Cys Gln Ile Tyr Pro Gln Asn Val
                485                 490                 495

Asn Lys Ile Arg Glu Ala Leu Ala Gln Thr His Ser Ala Ile Ala Val
            500                 505                 510

Ile Ile Gly Ile Lys Asp Leu Asp Ala Phe Arg His Tyr Asp Gly Arg
        515                 520                 525

Thr Ile Ile Gln Arg Asp Asn Gly Tyr Gln Pro Asn Tyr His Ala Val
    530                 535                 540

Asn Ile Val Gly Tyr Ser Asn Ala Gln Gly Val Asp Tyr Trp Ile Val
545                 550                 555                 560
```

```
Arg Asn Ser Trp Asp Thr Asn Trp Gly Asp Asn Gly Tyr Gly Tyr Phe
            565                 570                 575

Ala Ala Asn Ile Asp Leu Met Met Ile Glu Glu Tyr Pro Tyr Val Val
        580                 585                 590

Ile Leu Glu Phe Thr Leu Ile Pro Ile Ala Val Gly Gly Ala Leu Ala
            595                 600                 605

Gly Leu Val Leu Ile Val Leu Ile Ala Tyr Leu Val Gly Arg Lys Arg
        610                 615                 620

Ser His Ala Gly Tyr Gln Thr Ile
625                 630

<210> SEQ ID NO 64
<211> LENGTH: 543
<212> TYPE: DNA
<213> ORGANISM: Felis catus
<220> FEATURE:
<221> NAME/KEY: CDS
<222> LOCATION: (7)..(537)

<400> SEQUENCE: 64 ctcgag gaa atc tgc cca gcc gtg aag cgg gat gtg gat ctg ttt ctg        48
       Glu Ile Cys Pro Ala Val Lys Arg Asp Val Asp Leu Phe Leu
       1               5                   10 acc ggc acc ccc gac gag tac gtg gaa caa gtg gcc cag tac aag gct       96
Thr Gly Thr Pro Asp Glu Tyr Val Glu Gln Val Ala Gln Tyr Lys Ala
15              20                  25                  30 ctg ccc gtg gtg ctg gaa aac gcc cgg att ctg aag aac tgc gtg gac      144
Leu Pro Val Val Leu Glu Asn Ala Arg Ile Leu Lys Asn Cys Val Asp
                35                  40                  45 gcc aag atg acc gaa gag gac aaa gag aac gct ctg tct ctg ctg gac      192
Ala Lys Met Thr Glu Glu Asp Lys Glu Asn Ala Leu Ser Leu Leu Asp
            50                  55                  60 aag atc tac acc agc cct ctg tgt ggc ggc gga gga tct ggc gga ggc      240
Lys Ile Tyr Thr Ser Pro Leu Cys Gly Gly Gly Gly Ser Gly Gly Gly
        65                  70                  75 gga agt ggc gga ggg ggc tct gtg aag atg gcc gag aca tgc ccc atc      288
Gly Ser Gly Gly Gly Gly Ser Val Lys Met Ala Glu Thr Cys Pro Ile
80                  85                  90 ttc tac gac gtg ttc ttc gcc gtg gcc aac ggc aac gag ctg ctg ctg      336
Phe Tyr Asp Val Phe Phe Ala Val Ala Asn Gly Asn Glu Leu Leu Leu
95                  100                 105                 110 gat ctg agt ctg acc aaa gtg aac gcc acc gag ccc gag cgg acc gcc      384
Asp Leu Ser Leu Thr Lys Val Asn Ala Thr Glu Pro Glu Arg Thr Ala
                115                 120                 125 atg aag aag atc caa gac tgc tac gtg gaa aac gga ctg atc agc cgg      432
Met Lys Lys Ile Gln Asp Cys Tyr Val Glu Asn Gly Leu Ile Ser Arg
            130                 135                 140 gtg ctg gac gga ctc gtg atg acc acc atc agc agc tcc aag gac tgc      480
Val Leu Asp Gly Leu Val Met Thr Thr Ile Ser Ser Ser Lys Asp Cys
        145                 150                 155 atg ggc gag gcc gtg cag aac acc gtg gaa gat ctg aag ctg aac aca      528
Met Gly Glu Ala Val Gln Asn Thr Val Glu Asp Leu Lys Leu Asn Thr
160                 165                 170 ctg ggc cgg gaattc                                                   543
Leu Gly Arg
175

<210> SEQ ID NO 65
<211> LENGTH: 177
<212> TYPE: PRT
<213> ORGANISM: Felis catus
```

<400> SEQUENCE: 65

```
Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
        35                  40                  45

Met Thr Glu Glu Asp Lys Glu Asn Ala Leu Ser Leu Leu Asp Lys Ile
50                  55                  60

Tyr Thr Ser Pro Leu Cys Gly Gly Gly Ser Gly Gly Gly Ser
65                  70                  75                  80

Gly Gly Gly Ser Val Lys Met Ala Glu Thr Cys Pro Ile Phe Tyr
            85                  90                  95

Asp Val Phe Phe Ala Val Ala Asn Gly Asn Glu Leu Leu Leu Asp Leu
            100                 105                 110

Ser Leu Thr Lys Val Asn Ala Thr Glu Pro Glu Arg Thr Ala Met Lys
        115                 120                 125

Lys Ile Gln Asp Cys Tyr Val Glu Asn Gly Leu Ile Ser Arg Val Leu
130                 135                 140

Asp Gly Leu Val Met Thr Thr Ile Ser Ser Lys Asp Cys Met Gly
145                 150                 155                 160

Glu Ala Val Gln Asn Thr Val Glu Asp Leu Lys Leu Asn Thr Leu Gly
            165                 170                 175

Arg
```

<210> SEQ ID NO 66
<211> LENGTH: 162
<212> TYPE: PRT
<213> ORGANISM: Felis catus

<400> SEQUENCE: 66

```
Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Leu Glu Asn Ala Arg Ile Leu Lys Asn Cys Val Asp Ala Lys
        35                  40                  45

Met Thr Glu Glu Asp Lys Glu Asn Ala Leu Ser Leu Leu Asp Lys Ile
50                  55                  60

Tyr Thr Ser Pro Leu Cys Val Lys Met Ala Glu Thr Cys Pro Ile Phe
65                  70                  75                  80

Tyr Asp Val Phe Phe Ala Val Ala Asn Gly Asn Glu Leu Leu Leu Asp
            85                  90                  95

Leu Ser Leu Thr Lys Val Asn Ala Thr Glu Pro Glu Arg Thr Ala Met
            100                 105                 110

Lys Lys Ile Gln Asp Cys Tyr Val Glu Asn Gly Leu Ile Ser Arg Val
        115                 120                 125

Leu Asp Gly Leu Val Met Thr Thr Ile Ser Ser Lys Asp Cys Met
    130                 135                 140

Gly Glu Ala Val Gln Asn Thr Val Glu Asp Leu Lys Leu Asn Thr Leu
145                 150                 155                 160

Gly Arg
```

```
<210> SEQ ID NO 67
<211> LENGTH: 1797
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1797)

<400> SEQUENCE: 67
```

| | | | | | | | | | | | | | | | | |
|---|---|---|---|---|---|---|---|---|---|---|---|---|---|---|---|---|
| atg | gcg | ccc | cgc | agc | gcc | cgg | cga | ccc | ctg | ctg | ctg | cta | ctg | ctg | ttg | 48 |
| Met | Ala | Pro | Arg | Ser | Ala | Arg | Arg | Pro | Leu | Leu | Leu | Leu | Leu | Leu | Leu | |
| 1 | | | | 5 | | | | | 10 | | | | | 15 | | |
| ctg | ctg | ctc | ggc | ctc | atg | cat | tgt | gcg | tca | gca | gca | atg | ttt | atg | gtg | 96 |
| Leu | Leu | Leu | Gly | Leu | Met | His | Cys | Ala | Ser | Ala | Ala | Met | Phe | Met | Val | |
| | | | 20 | | | | | 25 | | | | | 30 | | | |
| aaa | aat | ggc | aac | ggg | acc | gcg | tgc | ata | atg | gcc | aac | ttc | tct | gct | gcc | 144 |
| Lys | Asn | Gly | Asn | Gly | Thr | Ala | Cys | Ile | Met | Ala | Asn | Phe | Ser | Ala | Ala | |
| | | 35 | | | | | 40 | | | | | 45 | | | | |
| ttc | tca | gtg | aac | tac | gac | acc | aag | agt | ggc | cct | aag | aac | atg | acc | ctt | 192 |
| Phe | Ser | Val | Asn | Tyr | Asp | Thr | Lys | Ser | Gly | Pro | Lys | Asn | Met | Thr | Leu | |
| | 50 | | | | | 55 | | | | | 60 | | | | | |
| gac | ctg | cca | tca | gat | gcc | aca | gtg | gtg | ctc | aac | cgc | agc | tcc | tgt | gga | 240 |
| Asp | Leu | Pro | Ser | Asp | Ala | Thr | Val | Val | Leu | Asn | Arg | Ser | Ser | Cys | Gly | |
| 65 | | | | | 70 | | | | | 75 | | | | | 80 | |
| aaa | gag | aac | act | tct | gac | ccc | agt | ctc | gtg | att | gct | ttt | gga | aga | gga | 288 |
| Lys | Glu | Asn | Thr | Ser | Asp | Pro | Ser | Leu | Val | Ile | Ala | Phe | Gly | Arg | Gly | |
| | | | | 85 | | | | | 90 | | | | | 95 | | |
| cat | aca | ctc | act | ctc | aat | ttc | acg | aga | aat | gca | aca | cgt | tac | agc | gtc | 336 |
| His | Thr | Leu | Thr | Leu | Asn | Phe | Thr | Arg | Asn | Ala | Thr | Arg | Tyr | Ser | Val | |
| | | | 100 | | | | | 105 | | | | | 110 | | | |
| cag | ctc | atg | agt | ttt | gtt | tat | aac | ttg | tca | gac | aca | cac | ctt | ttc | ccc | 384 |
| Gln | Leu | Met | Ser | Phe | Val | Tyr | Asn | Leu | Ser | Asp | Thr | His | Leu | Phe | Pro | |
| | | 115 | | | | | 120 | | | | | 125 | | | | |
| aat | gcg | agc | tcc | aaa | gaa | atc | aag | act | gtg | gaa | tct | ata | act | gac | atc | 432 |
| Asn | Ala | Ser | Ser | Lys | Glu | Ile | Lys | Thr | Val | Glu | Ser | Ile | Thr | Asp | Ile | |
| | 130 | | | | | 135 | | | | | 140 | | | | | |
| agg | gca | gat | ata | gat | aaa | aaa | tac | aga | tgt | gtt | agt | ggc | acc | cag | gtc | 480 |
| Arg | Ala | Asp | Ile | Asp | Lys | Lys | Tyr | Arg | Cys | Val | Ser | Gly | Thr | Gln | Val | |
| 145 | | | | | 150 | | | | | 155 | | | | | 160 | |
| cac | atg | aac | aac | gtg | acc | gta | acg | ctc | cat | gat | gcc | acc | atc | cag | gcg | 528 |
| His | Met | Asn | Asn | Val | Thr | Val | Thr | Leu | His | Asp | Ala | Thr | Ile | Gln | Ala | |
| | | | | 165 | | | | | 170 | | | | | 175 | | |
| tac | ctt | tcc | aac | agc | agc | ttc | agc | cgg | gga | gag | aca | cgc | tgt | gaa | caa | 576 |
| Tyr | Leu | Ser | Asn | Ser | Ser | Phe | Ser | Arg | Gly | Glu | Thr | Arg | Cys | Glu | Gln | |
| | | | 180 | | | | | 185 | | | | | 190 | | | |
| gac | agg | cct | tcc | cca | acc | aca | gcg | ccc | cct | gcg | cca | ccc | agc | ccc | tcg | 624 |
| Asp | Arg | Pro | Ser | Pro | Thr | Thr | Ala | Pro | Pro | Ala | Pro | Pro | Ser | Pro | Ser | |
| | | 195 | | | | | 200 | | | | | 205 | | | | |
| ccc | tca | ccc | gtg | ccc | aag | agc | ccc | tct | gtg | gac | aag | tac | aac | gtg | agc | 672 |
| Pro | Ser | Pro | Val | Pro | Lys | Ser | Pro | Ser | Val | Asp | Lys | Tyr | Asn | Val | Ser | |
| | 210 | | | | | 215 | | | | | 220 | | | | | |
| ggc | acc | aac | ggg | acc | tgc | ctg | ctg | gcc | agc | atg | ggg | ctg | cag | ctg | aac | 720 |
| Gly | Thr | Asn | Gly | Thr | Cys | Leu | Leu | Ala | Ser | Met | Gly | Leu | Gln | Leu | Asn | |
| 225 | | | | | 230 | | | | | 235 | | | | | 240 | |
| ctc | acc | tat | gag | agg | aag | gac | aac | acg | acg | gtg | aca | agg | ctt | ctc | aac | 768 |
| Leu | Thr | Tyr | Glu | Arg | Lys | Asp | Asn | Thr | Thr | Val | Thr | Arg | Leu | Leu | Asn | |
| | | | | 245 | | | | | 250 | | | | | 255 | | |
| atc | aac | ccc | aac | aag | acc | tcg | gcc | agc | ggg | agc | tgc | ggc | gcc | cac | ctg | 816 |
| Ile | Asn | Pro | Asn | Lys | Thr | Ser | Ala | Ser | Gly | Ser | Cys | Gly | Ala | His | Leu | |
| | | | 260 | | | | | 265 | | | | | 270 | | | |

```
gtg act ctg gag ctg cac agc gag ggc acc acc gtc ctg ctc ttc cag        864
Val Thr Leu Glu Leu His Ser Glu Gly Thr Thr Val Leu Leu Phe Gln
            275                 280                 285 ttc ggg atg aat gca agt tct agc cgg ttt ttc cta caa gga atc cag        912
Phe Gly Met Asn Ala Ser Ser Ser Arg Phe Phe Leu Gln Gly Ile Gln
        290                 295                 300 ttg aat aca att ctt cct gac gcc aga gac cct gcc ttt aaa gct gcc        960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag       1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat       1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt       1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag gaa atc       1152
Gly Ser Val Glu Glu Cys Leu Leu Asp Glu Asn Ser Leu Glu Glu Ile
370                 375                 380 tgc cca gcc gtg aag cgg gat gtg gat ctg ttt ctg acc ggc acc ccc       1200
Cys Pro Ala Val Lys Arg Asp Val Asp Leu Phe Leu Thr Gly Thr Pro
385                 390                 395                 400 gac gag tac gtg gaa caa gtg gcc cag tac aag gct ctg ccc gtg gtg       1248
Asp Glu Tyr Val Glu Gln Val Ala Gln Tyr Lys Ala Leu Pro Val Val
                405                 410                 415 ctg gaa aac gcc cgg att ctg aag aac tgc gtg gac gcc aag atg acc       1296
Leu Glu Asn Ala Arg Ile Leu Lys Asn Cys Val Asp Ala Lys Met Thr
            420                 425                 430 gaa gag gac aaa gag aac gct ctg tct ctg ctg gac aag atc tac acc       1344
Glu Glu Asp Lys Glu Asn Ala Leu Ser Leu Leu Asp Lys Ile Tyr Thr
        435                 440                 445 agc cct ctg tgt ggc gga gga gga tct ggc gga ggc gga agt ggc gga       1392
Ser Pro Leu Cys Gly Gly Gly Gly Ser Gly Gly Gly Gly Ser Gly Gly
450                 455                 460 ggg ggc tct gtg aag atg gcc gag aca tgc ccc atc ttc tac gac gtg       1440
Gly Gly Ser Val Lys Met Ala Glu Thr Cys Pro Ile Phe Tyr Asp Val
465                 470                 475                 480 ttc ttc gcc gtg gcc aac ggc aac gag ctg ctg ctg gat ctg agt ctg       1488
Phe Phe Ala Val Ala Asn Gly Asn Glu Leu Leu Leu Asp Leu Ser Leu
                485                 490                 495 acc aaa gtg aac gcc acc gag ccc gag cgg acc gcc atg aag aag atc       1536
Thr Lys Val Asn Ala Thr Glu Pro Glu Arg Thr Ala Met Lys Lys Ile
            500                 505                 510 caa gac tgc tac gtg gaa aac gga ctg atc agc cgg gtg ctg gac gga       1584
Gln Asp Cys Tyr Val Glu Asn Gly Leu Ile Ser Arg Val Leu Asp Gly
        515                 520                 525 ctc gtg atg acc acc atc agc agc tcc aag gac tgc atg ggc gag gcc       1632
Leu Val Met Thr Thr Ile Ser Ser Ser Lys Asp Cys Met Gly Glu Ala
530                 535                 540 gtg cag aac acc gtg gaa gat ctg aag ctg aac aca ctg ggc cgg gaa       1680
Val Gln Asn Thr Val Glu Asp Leu Lys Leu Asn Thr Leu Gly Arg Glu
545                 550                 555                 560 ttc acg ctg atc ccc atc gct gtg ggt ggt gcc ctg gcg ggg ctg gtc       1728
Phe Thr Leu Ile Pro Ile Ala Val Gly Gly Ala Leu Ala Gly Leu Val
                565                 570                 575 ctc atc gtc ctc atc gcc tac ctc gtc ggc agg aag agg agt cac gca       1776
Leu Ile Val Leu Ile Ala Tyr Leu Val Gly Arg Lys Arg Ser His Ala
```

```
                        580             585             590
ggc tac cag act atc tag taa                                              1797
Gly Tyr Gln Thr Ile
        595
```

<210> SEQ ID NO 68
<211> LENGTH: 597
<212> TYPE: PRT
<213> ORGANISM: Artificial sequence
<220> FEATURE:
<223> OTHER INFORMATION: Synthetic Construct

<400> SEQUENCE: 68

| | | | | | | | | | | | | | | |
|---|---|---|---|---|---|---|---|---|---|---|---|---|---|---|
| Met | Ala | Pro | Arg | Ser | Ala | Arg | Arg | Pro | Leu | Leu | Leu | Leu | Leu | Leu |
| 1 | | | | 5 | | | | | 10 | | | | | 15 |
| Leu | Leu | Leu | Gly | Leu | Met | His | Cys | Ala | Ser | Ala | Ala | Met | Phe | Met | Val |
| | | | 20 | | | | | 25 | | | | | 30 | | |
| Lys | Asn | Gly | Asn | Gly | Thr | Ala | Cys | Ile | Met | Ala | Asn | Phe | Ser | Ala | Ala |
| | | | 35 | | | | | 40 | | | | | 45 | | |
| Phe | Ser | Val | Asn | Tyr | Asp | Thr | Lys | Ser | Gly | Pro | Lys | Asn | Met | Thr | Leu |
| | 50 | | | | | 55 | | | | | 60 | | | | |
| Asp | Leu | Pro | Ser | Asp | Ala | Thr | Val | Val | Leu | Asn | Arg | Ser | Ser | Cys | Gly |
| 65 | | | | | 70 | | | | | 75 | | | | | 80 |
| Lys | Glu | Asn | Thr | Ser | Asp | Pro | Ser | Leu | Val | Ile | Ala | Phe | Gly | Arg | Gly |
| | | | | 85 | | | | | 90 | | | | | 95 | |
| His | Thr | Leu | Thr | Leu | Asn | Phe | Thr | Arg | Asn | Ala | Thr | Arg | Tyr | Ser | Val |
| | | | 100 | | | | | 105 | | | | | 110 | | |
| Gln | Leu | Met | Ser | Phe | Val | Tyr | Asn | Leu | Ser | Asp | Thr | His | Leu | Phe | Pro |
| | | | 115 | | | | | 120 | | | | | 125 | | |
| Asn | Ala | Ser | Ser | Lys | Glu | Ile | Lys | Thr | Val | Glu | Ser | Ile | Thr | Asp | Ile |
| | 130 | | | | | 135 | | | | | 140 | | | | |
| Arg | Ala | Asp | Ile | Asp | Lys | Lys | Tyr | Arg | Cys | Val | Ser | Gly | Thr | Gln | Val |
| 145 | | | | | 150 | | | | | 155 | | | | | 160 |
| His | Met | Asn | Asn | Val | Thr | Val | Thr | Leu | His | Asp | Ala | Thr | Ile | Gln | Ala |
| | | | | 165 | | | | | 170 | | | | | 175 | |
| Tyr | Leu | Ser | Asn | Ser | Ser | Phe | Ser | Arg | Gly | Glu | Thr | Arg | Cys | Glu | Gln |
| | | | 180 | | | | | 185 | | | | | 190 | | |
| Asp | Arg | Pro | Ser | Pro | Thr | Thr | Ala | Pro | Pro | Ala | Pro | Ser | Pro | Ser |
| | | | 195 | | | | | 200 | | | | | 205 | | |
| Pro | Ser | Pro | Val | Pro | Lys | Ser | Pro | Ser | Val | Asp | Lys | Tyr | Asn | Val | Ser |
| | 210 | | | | | 215 | | | | | 220 | | | | |
| Gly | Thr | Asn | Gly | Thr | Cys | Leu | Leu | Ala | Ser | Met | Gly | Leu | Gln | Leu | Asn |
| 225 | | | | | 230 | | | | | 235 | | | | | 240 |
| Leu | Thr | Tyr | Glu | Arg | Lys | Asp | Asn | Thr | Thr | Val | Thr | Arg | Leu | Leu | Asn |
| | | | | 245 | | | | | 250 | | | | | 255 | |
| Ile | Asn | Pro | Asn | Lys | Thr | Ser | Ala | Ser | Gly | Ser | Cys | Gly | Ala | His | Leu |
| | | | 260 | | | | | 265 | | | | | 270 | | |
| Val | Thr | Leu | Glu | Leu | His | Ser | Glu | Gly | Thr | Thr | Val | Leu | Leu | Phe | Gln |
| | | | 275 | | | | | 280 | | | | | 285 | | |
| Phe | Gly | Met | Asn | Ala | Ser | Ser | Ser | Arg | Phe | Phe | Leu | Gln | Gly | Ile | Gln |
| | 290 | | | | | 295 | | | | | 300 | | | | |
| Leu | Asn | Thr | Ile | Leu | Pro | Asp | Ala | Arg | Asp | Pro | Ala | Phe | Lys | Ala | Ala |
| 305 | | | | | 310 | | | | | 315 | | | | | 320 |
| Asn | Gly | Ser | Leu | Arg | Ala | Leu | Gln | Ala | Thr | Val | Gly | Asn | Ser | Tyr | Lys |
| | | | | 325 | | | | | 330 | | | | | 335 | |

```
Cys Asn Ala Glu Glu His Val Arg Val Thr Lys Ala Phe Ser Val Asn
                340                 345                 350
Ile Phe Lys Val Trp Val Gln Ala Phe Lys Val Glu Gly Gly Gln Phe
            355                 360                 365
Gly Ser Val Glu Glu Cys Leu Leu Asp Glu Asn Ser Leu Glu Glu Ile
        370                 375                 380
Cys Pro Ala Val Lys Arg Asp Val Asp Leu Phe Leu Thr Gly Thr Pro
385                 390                 395                 400
Asp Glu Tyr Val Glu Gln Val Ala Gln Tyr Lys Ala Leu Pro Val Val
                405                 410                 415
Leu Glu Asn Ala Arg Ile Leu Lys Asn Cys Val Asp Ala Lys Met Thr
            420                 425                 430
Glu Glu Asp Lys Glu Asn Ala Leu Ser Leu Leu Asp Lys Ile Tyr Thr
        435                 440                 445
Ser Pro Leu Cys Gly Gly Gly Gly Ser Gly Gly Gly Ser Gly Gly
        450                 455                 460
Gly Gly Ser Val Lys Met Ala Glu Thr Cys Pro Ile Phe Tyr Asp Val
465                 470                 475                 480
Phe Phe Ala Val Ala Asn Gly Asn Glu Leu Leu Leu Asp Leu Ser Leu
                485                 490                 495
Thr Lys Val Asn Ala Thr Glu Pro Glu Arg Thr Ala Met Lys Lys Ile
            500                 505                 510
Gln Asp Cys Tyr Val Glu Asn Gly Leu Ile Ser Arg Val Leu Asp Gly
        515                 520                 525
Leu Val Met Thr Thr Ile Ser Ser Ser Lys Asp Cys Met Gly Glu Ala
        530                 535                 540
Val Gln Asn Thr Val Glu Asp Leu Lys Leu Asn Thr Leu Gly Arg Glu
545                 550                 555                 560
Phe Thr Leu Ile Pro Ile Ala Val Gly Gly Ala Leu Ala Gly Leu Val
                565                 570                 575
Leu Ile Val Leu Ile Ala Tyr Leu Val Gly Arg Lys Arg Ser His Ala
            580                 585                 590
Gly Tyr Gln Thr Ile
        595

<210> SEQ ID NO 69
<211> LENGTH: 1764
<212> TYPE: DNA
<213> ORGANISM: Felis catus
<220> FEATURE:
<221> NAME/KEY: CDS
<222> LOCATION: (7)..(1758)

<400> SEQUENCE: 69 ctcgag gaa gcc cat cag agc gag atc gcc cac cgg ttc aac gat ctg      48
       Glu Ala His Gln Ser Glu Ile Ala His Arg Phe Asn Asp Leu
       1               5                   10 ggc gag gaa cac ttc cgg gga ctg gtt ctc gtg gcc ttc agc cag tat    96
Gly Glu Glu His Phe Arg Gly Leu Val Leu Val Ala Phe Ser Gln Tyr
15                  20                  25                  30 ctg cag cag tgc ccc ttc gag gac cac gtg aag ctc gtg aac gaa gtg   144
Leu Gln Gln Cys Pro Phe Glu Asp His Val Lys Leu Val Asn Glu Val
                35                  40                  45 acc gag ttc gcc aag ggc tgc gtg gcc gat cag tct gcc gcc aac tgc   192
Thr Glu Phe Ala Lys Gly Cys Val Ala Asp Gln Ser Ala Ala Asn Cys
            50                  55                  60 gag aag tct ctg cac gag ctg ctg ggc gac aag ctg tgt acc gtg gcc   240
```

```
Glu Lys Ser Leu His Glu Leu Leu Gly Asp Lys Leu Cys Thr Val Ala
         65                  70                  75 tct ctg cgg gat aag tac ggc gag atg gcc gac tgt tgc gag aag aaa    288
Ser Leu Arg Asp Lys Tyr Gly Glu Met Ala Asp Cys Cys Glu Lys Lys
 80                  85                  90 gag ccc gag cgg aac gag tgc ttt ctg cag cac aag gac gac aac ccc    336
Glu Pro Glu Arg Asn Glu Cys Phe Leu Gln His Lys Asp Asp Asn Pro
 95                 100                 105                 110 ggc ttc ggc cag ctc gtg aca cca gag gcc gat gcc atg tgc acc gcc    384
Gly Phe Gly Gln Leu Val Thr Pro Glu Ala Asp Ala Met Cys Thr Ala
                115                 120                 125 ttc cac gag aat gag cag cgg ttt ctg ggc aag tat ctg tac gag att    432
Phe His Glu Asn Glu Gln Arg Phe Leu Gly Lys Tyr Leu Tyr Glu Ile
            130                 135                 140 gcc aga cgg cac ccc tac ttc tac gcc cca gag ctg ctg tac tac gcc    480
Ala Arg Arg His Pro Tyr Phe Tyr Ala Pro Glu Leu Leu Tyr Tyr Ala
                145                 150                 155 gaa gag tac aag ggc gtg ttc acc gag tgc tgc gag gcc gcc gat aag    528
Glu Glu Tyr Lys Gly Val Phe Thr Glu Cys Cys Glu Ala Ala Asp Lys
160                 165                 170 gcc gct tgt ctg acc ccc aaa gtg gac gca ctg cgc gag aaa gtg ctg    576
Ala Ala Cys Leu Thr Pro Lys Val Asp Ala Leu Arg Glu Lys Val Leu
175                 180                 185                 190 gcc tcc agc gcc aaa gaa cgg ctg aag tgc gct tct ctg cag aag ttc    624
Ala Ser Ser Ala Lys Glu Arg Leu Lys Cys Ala Ser Leu Gln Lys Phe
                195                 200                 205 ggc gag cgg gcc ttc aag gct tgg agc gtg gca aga ctg agc cag aag    672
Gly Glu Arg Ala Phe Lys Ala Trp Ser Val Ala Arg Leu Ser Gln Lys
            210                 215                 220 ttc ccc aag gcc gag ttt gcc gag atc agc aag ctc gtg acc gat ctg    720
Phe Pro Lys Ala Glu Phe Ala Glu Ile Ser Lys Leu Val Thr Asp Leu
        225                 230                 235 gcc aag atc cac aaa gag tgc tgc cac ggc gat ctg ctg gaa tgc gcc    768
Ala Lys Ile His Lys Glu Cys Cys His Gly Asp Leu Leu Glu Cys Ala
240                 245                 250 gac gac aga gct gat ctg gct aag tac atc tgc gag aat caa gac agc    816
Asp Asp Arg Ala Asp Leu Ala Lys Tyr Ile Cys Glu Asn Gln Asp Ser
255                 260                 265                 270 atc agc acc aag ctg aaa gag tgt tgc ggc aag ccc gtg ctg gaa aag    864
Ile Ser Thr Lys Leu Lys Glu Cys Cys Gly Lys Pro Val Leu Glu Lys
                275                 280                 285 agc cac tgc atc agc gaa gtg gaa cgg gac gag ctg ccc gct gat ctg    912
Ser His Cys Ile Ser Glu Val Glu Arg Asp Glu Leu Pro Ala Asp Leu
            290                 295                 300 cct cct ctg gcc gtg gac ttc gtg gag gac aaa gaa gtg tgc aag aac    960
Pro Pro Leu Ala Val Asp Phe Val Glu Asp Lys Glu Val Cys Lys Asn
        305                 310                 315 tac caa gag gcc aag gat gtg ttt ctg ggg aca ttt ctg tat gag tac   1008
Tyr Gln Glu Ala Lys Asp Val Phe Leu Gly Thr Phe Leu Tyr Glu Tyr
320                 325                 330 tct cgg cgg cac ccc gag tac tcc gtg tct ctg ctg ctg cgg ctg gcc   1056
Ser Arg Arg His Pro Glu Tyr Ser Val Ser Leu Leu Leu Arg Leu Ala
335                 340                 345                 350 aaa gag tac gag gcc aca ctg gaa aag tgc tgc gcc acc gac gat ccc   1104
Lys Glu Tyr Glu Ala Thr Leu Glu Lys Cys Cys Ala Thr Asp Asp Pro
                355                 360                 365 ccc gct tgt tat gcc cac gtg ttc gac gag ttc aag cca ctc gtg gaa   1152
Pro Ala Cys Tyr Ala His Val Phe Asp Glu Phe Lys Pro Leu Val Glu
            370                 375                 380
```

```
gaa ccc cac aat ctc gtg aaa aca aac tgc gag ctg ttc gag aag ctg    1200
Glu Pro His Asn Leu Val Lys Thr Asn Cys Glu Leu Phe Glu Lys Leu
        385                 390                 395 ggc gag tac ggc ttc cag aac gca ctg ctc gtg cgg tac acc aag aaa    1248
Gly Glu Tyr Gly Phe Gln Asn Ala Leu Leu Val Arg Tyr Thr Lys Lys
400                 405                 410 gtg ccc caa gtg tcc acc ccc aca ctc gtg gaa gtg tcc aga tct ctg    1296
Val Pro Gln Val Ser Thr Pro Thr Leu Val Glu Val Ser Arg Ser Leu
415                 420                 425                 430 ggc aaa gtg ggc agc aag tgc tgc acc cac ccc gag gcc gag aga ctg    1344
Gly Lys Val Gly Ser Lys Cys Cys Thr His Pro Glu Ala Glu Arg Leu
                435                 440                 445 tct tgc gcc gag gac tat ctg agc gtg gtg ctg aac cgg ctg tgc gtg    1392
Ser Cys Ala Glu Asp Tyr Leu Ser Val Val Leu Asn Arg Leu Cys Val
            450                 455                 460 ctg cac gag aaa acc ccc gtg tcc gag cgc gtg acc aag tgc tgt acc    1440
Leu His Glu Lys Thr Pro Val Ser Glu Arg Val Thr Lys Cys Cys Thr
            465                 470                 475 gag tct ctc gtg aac aga cgg cct tgc ttc agc gct ctg caa gtg gac    1488
Glu Ser Leu Val Asn Arg Arg Pro Cys Phe Ser Ala Leu Gln Val Asp
        480                 485                 490 gag aca tac gtg ccc aaa gag ttc agc gcc gag aca ttc aca ttc cac    1536
Glu Thr Tyr Val Pro Lys Glu Phe Ser Ala Glu Thr Phe Thr Phe His
495                 500                 505                 510 gcc gat ctg tgc aca ctg ccc gaa gcc gag aag cag atc aag aaa cag    1584
Ala Asp Leu Cys Thr Leu Pro Glu Ala Glu Lys Gln Ile Lys Lys Gln
                515                 520                 525 tcc gct ctc gtg gaa ctg ctg aag cac aag ccc aag gcc acc gag gaa    1632
Ser Ala Leu Val Glu Leu Leu Lys His Lys Pro Lys Ala Thr Glu Glu
            530                 535                 540 cag ctg aaa acc gtg atg ggc gac ttc ggc agc ttc gtg gat aag tgc    1680
Gln Leu Lys Thr Val Met Gly Asp Phe Gly Ser Phe Val Asp Lys Cys
        545                 550                 555 tgt gcc gct gag gac aaa gag gct tgc ttc gcc gaa gag ggc ccc aaa    1728
Cys Ala Ala Glu Asp Lys Glu Ala Cys Phe Ala Glu Glu Gly Pro Lys
560                 565                 570 ctc gtg gct gct gct caa gct gct ctg gcc gaattc                     1764
Leu Val Ala Ala Ala Gln Ala Ala Leu Ala
575                 580

<210> SEQ ID NO 70
<211> LENGTH: 584
<212> TYPE: PRT
<213> ORGANISM: Felis catus

<400> SEQUENCE: 70

Glu Ala His Gln Ser Glu Ile Ala His Arg Phe Asn Asp Leu Gly Glu
1               5                   10                  15

Glu His Phe Arg Gly Leu Val Leu Val Ala Phe Ser Gln Tyr Leu Gln
            20                  25                  30

Gln Cys Pro Phe Glu Asp His Val Lys Leu Val Asn Glu Val Thr Glu
        35                  40                  45

Phe Ala Lys Gly Cys Val Ala Asp Gln Ser Ala Ala Asn Cys Glu Lys
    50                  55                  60

Ser Leu His Glu Leu Leu Gly Asp Lys Leu Cys Thr Val Ala Ser Leu
65                  70                  75                  80

Arg Asp Lys Tyr Gly Glu Met Ala Asp Cys Cys Glu Lys Lys Glu Pro
                85                  90                  95

Glu Arg Asn Glu Cys Phe Leu Gln His Lys Asp Asp Asn Pro Gly Phe
```

```
                100                 105                 110
Gly Gln Leu Val Thr Pro Glu Ala Asp Ala Met Cys Thr Ala Phe His
            115                 120                 125
Glu Asn Glu Gln Arg Phe Leu Gly Lys Tyr Leu Tyr Glu Ile Ala Arg
        130                 135                 140
Arg His Pro Tyr Phe Tyr Ala Pro Glu Leu Leu Tyr Tyr Ala Glu Glu
145                 150                 155                 160
Tyr Lys Gly Val Phe Thr Glu Cys Cys Glu Ala Ala Asp Lys Ala Ala
                165                 170                 175
Cys Leu Thr Pro Lys Val Asp Ala Leu Arg Glu Lys Val Leu Ala Ser
            180                 185                 190
Ser Ala Lys Glu Arg Leu Lys Cys Ala Ser Leu Gln Lys Phe Gly Glu
        195                 200                 205
Arg Ala Phe Lys Ala Trp Ser Val Ala Arg Leu Ser Gln Lys Phe Pro
210                 215                 220
Lys Ala Glu Phe Ala Glu Ile Ser Lys Leu Val Thr Asp Leu Ala Lys
225                 230                 235                 240
Ile His Lys Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Thr Lys Leu Lys Glu Cys Cys Gly Lys Pro Val Leu Glu Lys Ser His
        275                 280                 285
Cys Ile Ser Glu Val Glu Arg Asp Glu Leu Pro Ala Asp Leu Pro Pro
        290                 295                 300
Leu Ala Val Asp Phe Val Glu Asp Lys Glu Val Cys Lys Asn Tyr Gln
305                 310                 315                 320
Glu Ala Lys Asp Val Phe Leu Gly Thr Phe Leu Tyr Glu Tyr Ser Arg
                325                 330                 335
Arg His Pro Glu Tyr Ser Val Ser Leu Leu Leu Arg Leu Ala Lys Glu
            340                 345                 350
Tyr Glu Ala Thr Leu Glu Lys Cys Cys Ala Thr Asp Asp Pro Pro Ala
        355                 360                 365
Cys Tyr Ala His Val Phe Asp Glu Phe Lys Pro Leu Val Glu Glu Pro
        370                 375                 380
His Asn Leu Val Lys Thr Asn Cys Glu Leu Phe Glu Lys Leu Gly Glu
385                 390                 395                 400
Tyr Gly Phe Gln Asn Ala Leu Leu Val Arg Tyr Thr Lys Lys Val Pro
                405                 410                 415
Gln Val Ser Thr Pro Thr Leu Val Glu Val Ser Arg Ser Leu Gly Lys
            420                 425                 430
Val Gly Ser Lys Cys Cys Thr His Pro Glu Ala Glu Arg Leu Ser Cys
        435                 440                 445
Ala Glu Asp Tyr Leu Ser Val Val Leu Asn Arg Leu Cys Val Leu His
        450                 455                 460
Glu Lys Thr Pro Val Ser Glu Arg Val Thr Lys Cys Cys Thr Glu Ser
465                 470                 475                 480
Leu Val Asn Arg Arg Pro Cys Phe Ser Ala Leu Gln Val Asp Glu Thr
                485                 490                 495
Tyr Val Pro Lys Glu Phe Ser Ala Glu Thr Phe Thr Phe His Ala Asp
            500                 505                 510
Leu Cys Thr Leu Pro Glu Ala Glu Lys Gln Ile Lys Lys Gln Ser Ala
        515                 520                 525
```

```
Leu Val Glu Leu Leu Lys His Lys Pro Lys Ala Thr Glu Glu Gln Leu
        530                 535                 540

Lys Thr Val Met Gly Asp Phe Gly Ser Phe Val Asp Lys Cys Cys Ala
545                 550                 555                 560

Ala Glu Asp Lys Glu Ala Cys Phe Ala Glu Glu Gly Pro Lys Leu Val
                565                 570                 575

Ala Ala Ala Gln Ala Ala Leu Ala
            580

<210> SEQ ID NO 71
<211> LENGTH: 3018
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(3018)

<400> SEQUENCE: 71
```

| | | | | | | | | | | | | | | | | |
|---|---|---|---|---|---|---|---|---|---|---|---|---|---|---|---|---|
| atg | gcg | ccc | cgc | agc | gcc | cgg | cga | ccc | ctg | ctg | ctg | cta | ctg | ctg | ttg | 48 |
| Met | Ala | Pro | Arg | Ser | Ala | Arg | Arg | Pro | Leu | Leu | Leu | Leu | Leu | Leu | Leu | |
| 1 | | | | 5 | | | | | 10 | | | | | 15 | | |
| ctg | ctg | ctc | ggc | ctc | atg | cat | tgt | gcg | tca | gca | gca | atg | ttt | atg | gtg | 96 |
| Leu | Leu | Leu | Gly | Leu | Met | His | Cys | Ala | Ser | Ala | Ala | Met | Phe | Met | Val | |
| | | | 20 | | | | | 25 | | | | | 30 | | | |
| aaa | aat | ggc | aac | ggg | acc | gcg | tgc | ata | atg | gcc | aac | ttc | tct | gct | gcc | 144 |
| Lys | Asn | Gly | Asn | Gly | Thr | Ala | Cys | Ile | Met | Ala | Asn | Phe | Ser | Ala | Ala | |
| | | 35 | | | | | 40 | | | | | 45 | | | | |
| ttc | tca | gtg | aac | tac | gac | acc | aag | agt | ggc | cct | aag | aac | atg | acc | ctt | 192 |
| Phe | Ser | Val | Asn | Tyr | Asp | Thr | Lys | Ser | Gly | Pro | Lys | Asn | Met | Thr | Leu | |
| | 50 | | | | | 55 | | | | | 60 | | | | | |
| gac | ctg | cca | tca | gat | gcc | aca | gtg | gtg | ctc | aac | cgc | agc | tcc | tgt | gga | 240 |
| Asp | Leu | Pro | Ser | Asp | Ala | Thr | Val | Val | Leu | Asn | Arg | Ser | Ser | Cys | Gly | |
| 65 | | | | | 70 | | | | | 75 | | | | | 80 | |
| aaa | gag | aac | act | tct | gac | ccc | agt | ctc | gtg | att | gct | ttt | gga | aga | gga | 288 |
| Lys | Glu | Asn | Thr | Ser | Asp | Pro | Ser | Leu | Val | Ile | Ala | Phe | Gly | Arg | Gly | |
| | | | | 85 | | | | | 90 | | | | | 95 | | |
| cat | aca | ctc | act | ctc | aat | ttc | acg | aga | aat | gca | aca | cgt | tac | agc | gtc | 336 |
| His | Thr | Leu | Thr | Leu | Asn | Phe | Thr | Arg | Asn | Ala | Thr | Arg | Tyr | Ser | Val | |
| | | | 100 | | | | | 105 | | | | | 110 | | | |
| cag | ctc | atg | agt | ttt | gtt | tat | aac | ttg | tca | gac | aca | cac | ctt | ttc | ccc | 384 |
| Gln | Leu | Met | Ser | Phe | Val | Tyr | Asn | Leu | Ser | Asp | Thr | His | Leu | Phe | Pro | |
| | | 115 | | | | | 120 | | | | | 125 | | | | |
| aat | gcg | agc | tcc | aaa | gaa | atc | aag | act | gtg | gaa | tct | ata | act | gac | atc | 432 |
| Asn | Ala | Ser | Ser | Lys | Glu | Ile | Lys | Thr | Val | Glu | Ser | Ile | Thr | Asp | Ile | |
| | 130 | | | | | 135 | | | | | 140 | | | | | |
| agg | gca | gat | ata | gat | aaa | aaa | tac | aga | tgt | gtt | agt | ggc | acc | cag | gtc | 480 |
| Arg | Ala | Asp | Ile | Asp | Lys | Lys | Tyr | Arg | Cys | Val | Ser | Gly | Thr | Gln | Val | |
| 145 | | | | | 150 | | | | | 155 | | | | | 160 | |
| cac | atg | aac | aac | gtg | acc | gta | acg | ctc | cat | gat | gcc | acc | atc | cag | gcg | 528 |
| His | Met | Asn | Asn | Val | Thr | Val | Thr | Leu | His | Asp | Ala | Thr | Ile | Gln | Ala | |
| | | | | 165 | | | | | 170 | | | | | 175 | | |
| tac | ctt | tcc | aac | agc | agc | ttc | agc | cgg | gga | gag | aca | cgc | tgt | gaa | caa | 576 |
| Tyr | Leu | Ser | Asn | Ser | Ser | Phe | Ser | Arg | Gly | Glu | Thr | Arg | Cys | Glu | Gln | |
| | | | 180 | | | | | 185 | | | | | 190 | | | |
| gac | agg | cct | tcc | cca | acc | aca | gcg | ccc | cct | gcg | cca | ccc | agc | ccc | tcg | 624 |
| Asp | Arg | Pro | Ser | Pro | Thr | Thr | Ala | Pro | Pro | Ala | Pro | Pro | Ser | Pro | Ser | |
| | | 195 | | | | | 200 | | | | | 205 | | | | |
| ccc | tca | ccc | gtg | ccc | aag | agc | ccc | tct | gtg | gac | aag | tac | aac | gtg | agc | 672 |

```
                    Pro Ser Pro Val Pro Lys Ser Pro Val Asp Lys Tyr Asn Val Ser
                        210             215             220 ggc acc aac ggg acc tgc ctg ctg gcc agc atg ggg ctg cag ctg aac        720
Gly Thr Asn Gly Thr Cys Leu Leu Ala Ser Met Gly Leu Gln Leu Asn
225                 230             235                 240 ctc acc tat gag agg aag gac aac acg acg gtg aca agg ctt ctc aac        768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg        816
Ile Asn Pro Asn Lys Thr Ser Ala Ser Gly Ser Cys Gly Ala His Leu
            260                 265                 270 gtg act ctg gag ctg cac agc gag ggc acc acc gtc ctg ctc ttc cag        864
Val Thr Leu Glu Leu His Ser Glu Gly Thr Thr Val Leu Leu Phe Gln
        275                 280                 285 ttc ggg atg aat gca agt tct agc cgg ttt ttc cta caa gga atc cag        912
Phe Gly Met Asn Ala Ser Ser Ser Arg Phe Phe Leu Gln Gly Ile Gln
    290                 295                 300 ttg aat aca att ctt cct gac gcc aga gac cct gcc ttt aaa gct gcc        960
Leu Asn Thr Ile Leu Pro Asp Ala Arg Asp Pro Ala Phe Lys Ala Ala
305                 310             315                 320 aac ggc tcc ctg cga gcg ctg cag gcc aca gtc ggc aat tcc tac aag       1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat       1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt       1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag gaa gcc       1152
Gly Ser Val Glu Glu Cys Leu Leu Asp Glu Asn Ser Leu Glu Glu Ala
    370                 375                 380 cat cag agc gag atc gcc cac cgg ttc aac gat ctg ggc gag gaa cac       1200
His Gln Ser Glu Ile Ala His Arg Phe Asn Asp Leu Gly Glu Glu His
385                 390                 395                 400 ttc cgg gga ctg gtt ctc gtg gcc ttc agc cag tat ctg cag cag tgc       1248
Phe Arg Gly Leu Val Leu Val Ala Phe Ser Gln Tyr Leu Gln Gln Cys
                405                 410                 415 ccc ttc gag gac cac gtg aag ctc gtg aac gaa gtg acc gag ttc gcc       1296
Pro Phe Glu Asp His Val Lys Leu Val Asn Glu Val Thr Glu Phe Ala
            420                 425                 430 aag ggc tgc gtg gcc gat cag tct gcc gcc aac tgc gag aag tct ctg       1344
Lys Gly Cys Val Ala Asp Gln Ser Ala Ala Asn Cys Glu Lys Ser Leu
        435                 440                 445 cac gag ctg ctg ggc gac aag ctg tgt acc gtg gcc tct ctg cgg gat       1392
His Glu Leu Leu Gly Asp Lys Leu Cys Thr Val Ala Ser Leu Arg Asp
    450                 455                 460 aag tac ggc gag atg gcc gac tgt tgc gag aag aaa gag ccc gag cgg       1440
Lys Tyr Gly Glu Met Ala Asp Cys Cys Glu Lys Lys Glu Pro Glu Arg
465                 470                 475                 480 aac gag tgc ttt ctg cag cac aag gac gac aac ccc ggc ttc ggc cag       1488
Asn Glu Cys Phe Leu Gln His Lys Asp Asp Asn Pro Gly Phe Gly Gln
                485                 490                 495 ctc gtg aca cca gag gcc gat gcc atg tgc acc gcc ttc cac gag aat       1536
Leu Val Thr Pro Glu Ala Asp Ala Met Cys Thr Ala Phe His Glu Asn
            500                 505                 510 gag cag cgg ttt ctg ggc aag tat ctg tac gag att gcc aga cgg cac       1584
Glu Gln Arg Phe Leu Gly Lys Tyr Leu Tyr Glu Ile Ala Arg Arg His
        515                 520                 525
```

-continued

| | | |
|---|---|---|
| ccc tac ttc tac gcc cca gag ctg ctg tac tac gcc gaa gag tac aag<br>Pro Tyr Phe Tyr Ala Pro Glu Leu Leu Tyr Tyr Ala Glu Glu Tyr Lys<br>530                       535                     540 | 1632 |
| ggc gtg ttc acc gag tgc tgc gag gcc gcc gat aag gcc gct tgt ctg<br>Gly Val Phe Thr Glu Cys Cys Glu Ala Ala Asp Lys Ala Ala Cys Leu<br>545                       550                     555                  560 | 1680 |
| acc ccc aaa gtg gac gca ctg cgc gag aaa gtg ctg gcc tcc agc gcc<br>Thr Pro Lys Val Asp Ala Leu Arg Glu Lys Val Leu Ala Ser Ser Ala<br>                  565                     570                  575 | 1728 |
| aaa gaa cgg ctg aag tgc gct tct ctg cag aag ttc ggc gag cgg gcc<br>Lys Glu Arg Leu Lys Cys Ala Ser Leu Gln Lys Phe Gly Glu Arg Ala<br>            580                     585                     590 | 1776 |
| ttc aag gct tgg agc gtg gca aga ctg agc cag aag ttc ccc aag gcc<br>Phe Lys Ala Trp Ser Val Ala Arg Leu Ser Gln Lys Phe Pro Lys Ala<br>            595                     600                     605 | 1824 |
| gag ttt gcc gag atc agc aag ctc gtg acc gat ctg gcc aag atc cac<br>Glu Phe Ala Glu Ile Ser Lys Leu Val Thr Asp Leu Ala Lys Ile His<br>610                       615                     620 | 1872 |
| aaa gag tgc tgc cac ggc gat ctg ctg gaa tgc gcc gac gac aga gct<br>Lys Glu Cys Cys His Gly Asp Leu Leu Glu Cys Ala Asp Asp Arg Ala<br>625                       630                     635                  640 | 1920 |
| gat ctg gct aag tac atc tgc gag aat caa gac agc atc agc acc aag<br>Asp Leu Ala Lys Tyr Ile Cys Glu Asn Gln Asp Ser Ile Ser Thr Lys<br>                    645                     650                  655 | 1968 |
| ctg aaa gag tgt tgc ggc aag ccc gtg ctg gaa aag agc cac tgc atc<br>Leu Lys Glu Cys Cys Gly Lys Pro Val Leu Glu Lys Ser His Cys Ile<br>            660                     665                     670 | 2016 |
| agc gaa gtg gaa cgg gac gag ctg ccc gct gat ctg cct cct ctg gcc<br>Ser Glu Val Glu Arg Asp Glu Leu Pro Ala Asp Leu Pro Pro Leu Ala<br>                  675                     680                  685 | 2064 |
| gtg gac ttc gtg gag gac aaa gaa gtg tgc aag aac tac caa gag gcc<br>Val Asp Phe Val Glu Asp Lys Glu Val Cys Lys Asn Tyr Gln Glu Ala<br>            690                     695                     700 | 2112 |
| aag gat gtg ttt ctg ggg aca ttt ctg tat gag tac tct cgg cgg cac<br>Lys Asp Val Phe Leu Gly Thr Phe Leu Tyr Glu Tyr Ser Arg Arg His<br>705                       710                     715                  720 | 2160 |
| ccc gag tac tcc gtg tct ctg ctg cgg ctg gcc aaa gag tac gag<br>Pro Glu Tyr Ser Val Ser Leu Leu Leu Arg Leu Ala Lys Glu Tyr Glu<br>                  725                     730                  735 | 2208 |
| gcc aca ctg gaa aag tgc tgc gcc acc gac gat ccc ccc gct tgt tat<br>Ala Thr Leu Glu Lys Cys Cys Ala Thr Asp Asp Pro Pro Ala Cys Tyr<br>            740                     745                     750 | 2256 |
| gcc cac gtg ttc gac gag ttc aag cca ctc gtg gaa gaa ccc cac aat<br>Ala His Val Phe Asp Glu Phe Lys Pro Leu Val Glu Glu Pro His Asn<br>                  755                     760                  765 | 2304 |
| ctc gtg aaa aca aac tgc gag ctg ttc gag aag ctg ggc gag tac ggc<br>Leu Val Lys Thr Asn Cys Glu Leu Phe Glu Lys Leu Gly Glu Tyr Gly<br>770                       775                     780 | 2352 |
| ttc cag aac gca ctg ctc gtg cgg tac acc aag aaa gtg ccc caa gtg<br>Phe Gln Asn Ala Leu Leu Val Arg Tyr Thr Lys Lys Val Pro Gln Val<br>785                       790                     795                  800 | 2400 |
| tcc acc ccc aca ctc gtg gaa gtg tcc aga tct ctg ggc aaa gtg ggc<br>Ser Thr Pro Thr Leu Val Glu Val Ser Arg Ser Leu Gly Lys Val Gly<br>                  805                     810                  815 | 2448 |
| agc aag tgc tgc acc cac ccc gag gcc gag aga ctg tct tgc gcc gag<br>Ser Lys Cys Cys Thr His Pro Glu Ala Glu Arg Leu Ser Cys Ala Glu<br>            820                     825                     830 | 2496 |
| gac tat ctg agc gtg gtg ctg aac cgg ctg tgc gtg ctg cac gag aaa<br>Asp Tyr Leu Ser Val Val Leu Asn Arg Leu Cys Val Leu His Glu Lys<br>            835                     840                  845 | 2544 |

```
acc ccc gtg tcc gag cgc gtg acc aag tgc tgt acc gag tct ctc gtg       2592
Thr Pro Val Ser Glu Arg Val Thr Lys Cys Cys Thr Glu Ser Leu Val
    850                 855                 860 aac aga cgg cct tgc ttc agc gct ctg caa gtg gac gag aca tac gtg       2640
Asn Arg Arg Pro Cys Phe Ser Ala Leu Gln Val Asp Glu Thr Tyr Val
865                 870                 875                 880 ccc aaa gag ttc agc gcc gag aca ttc aca ttc cac gcc gat ctg tgc       2688
Pro Lys Glu Phe Ser Ala Glu Thr Phe Thr Phe His Ala Asp Leu Cys
                885                 890                 895 aca ctg ccc gaa gcc gag aag cag atc aag aaa cag tcc gct ctc gtg       2736
Thr Leu Pro Glu Ala Glu Lys Gln Ile Lys Lys Gln Ser Ala Leu Val
            900                 905                 910 gaa ctg ctg aag cac aag ccc aag gcc acc gag gaa cag ctg aaa acc       2784
Glu Leu Leu Lys His Lys Pro Lys Ala Thr Glu Glu Gln Leu Lys Thr
        915                 920                 925 gtg atg ggc gac ttc ggc agc ttc gtg gat aag tgc tgt gcc gct gag       2832
Val Met Gly Asp Phe Gly Ser Phe Val Asp Lys Cys Cys Ala Ala Glu
    930                 935                 940 gac aaa gag gct tgc ttc gcc gaa gag ggc ccc aaa ctc gtg gct gct       2880
Asp Lys Glu Ala Cys Phe Ala Glu Glu Gly Pro Lys Leu Val Ala Ala
945                 950                 955                 960 gct caa gct gct ctg gcc gaa ttc acg ctg atc ccc atc gct gtg ggt       2928
Ala Gln Ala Ala Leu Ala Glu Phe Thr Leu Ile Pro Ile Ala Val Gly
                965                 970                 975 ggt gcc ctg gcg ggg ctg gtc ctc atc gtc ctc atc gcc tac ctc gtc       2976
Gly Ala Leu Ala Gly Leu Val Leu Ile Val Leu Ile Ala Tyr Leu Val
            980                 985                 990 ggc agg aag agg agt cac gca ggc tac cag act atc tag taa               3018
Gly Arg Lys Arg Ser His Ala Gly Tyr Gln Thr Ile
        995                 1000

<210> SEQ ID NO 72
<211> LENGTH: 1004
<212> TYPE: PRT
<213> ORGANISM: Artificial sequence
<220> FEATURE:
<223> OTHER INFORMATION: Synthetic Construct

<400> SEQUENCE: 72

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
```

```
              145                 150                 155                 160
    His Met Asn Asn Val Thr Val Thr Leu His Asp Ala Thr Ile Gln Ala
                        165                 170                 175
    Tyr Leu Ser Asn Ser Ser Phe Ser Arg Gly Glu Thr Arg Cys Glu Gln
                        180                 185                 190
    Asp Arg Pro Ser Pro Thr Thr Ala Pro Pro Ala Pro Pro Ser Pro Ser
                        195                 200                 205
    Pro Ser Pro Val Pro Lys Ser Pro Ser Val Asp Lys Tyr Asn Val Ser
    210                 215                 220
    Gly Thr Asn Gly Thr Cys Leu Leu Ala Ser Met Gly Leu Gln Leu Asn
    225                 230                 235                 240
    Leu Thr Tyr Glu Arg Lys Asp Asn Thr Thr Val Thr Arg Leu Leu Asn
                        245                 250                 255
    Ile Asn Pro Asn Lys Thr Ser Ala Ser Gly Ser Cys Gly Ala His Leu
                        260                 265                 270
    Val Thr Leu Glu Leu His Ser Glu Gly Thr Thr Val Leu Leu Phe Gln
                        275                 280                 285
    Phe Gly Met Asn Ala Ser Ser Ser Arg Phe Phe Leu Gln Gly Ile Gln
                        290                 295                 300
    Leu Asn Thr Ile Leu Pro Asp Ala Arg Asp Pro Ala Phe Lys Ala Ala
    305                 310                 315                 320
    Asn Gly Ser Leu Arg Ala Leu Gln Ala Thr Val Gly Asn Ser Tyr Lys
                        325                 330                 335
    Cys Asn Ala Glu Glu His Val Arg Val Thr Lys Ala Phe Ser Val Asn
                        340                 345                 350
    Ile Phe Lys Val Trp Val Gln Ala Phe Lys Val Glu Gly Gly Gln Phe
                        355                 360                 365
    Gly Ser Val Glu Glu Cys Leu Leu Asp Glu Asn Ser Leu Glu Glu Ala
                        370                 375                 380
    His Gln Ser Glu Ile Ala His Arg Phe Asn Asp Leu Gly Glu Glu His
    385                 390                 395                 400
    Phe Arg Gly Leu Val Leu Val Ala Phe Ser Gln Tyr Leu Gln Gln Cys
                        405                 410                 415
    Pro Phe Glu Asp His Val Lys Leu Val Asn Glu Val Thr Glu Phe Ala
                        420                 425                 430
    Lys Gly Cys Val Ala Asp Gln Ser Ala Ala Asn Cys Glu Lys Ser Leu
                        435                 440                 445
    His Glu Leu Leu Gly Asp Lys Leu Cys Thr Val Ala Ser Leu Arg Asp
    450                 455                 460
    Lys Tyr Gly Glu Met Ala Asp Cys Cys Glu Lys Lys Glu Pro Glu Arg
    465                 470                 475                 480
    Asn Glu Cys Phe Leu Gln His Lys Asp Asp Asn Pro Gly Phe Gly Gln
                        485                 490                 495
    Leu Val Thr Pro Glu Ala Asp Ala Met Cys Thr Ala Phe His Glu Asn
                        500                 505                 510
    Glu Gln Arg Phe Leu Gly Lys Tyr Leu Tyr Glu Ile Ala Arg Arg His
                        515                 520                 525
    Pro Tyr Phe Tyr Ala Pro Glu Leu Leu Tyr Tyr Ala Glu Glu Tyr Lys
                        530                 535                 540
    Gly Val Phe Thr Glu Cys Cys Glu Ala Ala Asp Lys Ala Ala Cys Leu
    545                 550                 555                 560
    Thr Pro Lys Val Asp Ala Leu Arg Glu Lys Val Leu Ala Ser Ser Ala
                        565                 570                 575
```

```
Lys Glu Arg Leu Lys Cys Ala Ser Leu Gln Lys Phe Gly Glu Arg Ala
            580                 585                 590
Phe Lys Ala Trp Ser Val Ala Arg Leu Ser Gln Lys Phe Pro Lys Ala
            595                 600                 605
Glu Phe Ala Glu Ile Ser Lys Leu Val Thr Asp Leu Ala Lys Ile His
            610                 615                 620
Lys Glu Cys Cys His Gly Asp Leu Leu Glu Cys Ala Asp Asp Arg Ala
625                 630                 635                 640
Asp Leu Ala Lys Tyr Ile Cys Glu Asn Gln Asp Ser Ile Ser Thr Lys
            645                 650                 655
Leu Lys Glu Cys Cys Gly Lys Pro Val Leu Glu Lys Ser His Cys Ile
            660                 665                 670
Ser Glu Val Glu Arg Asp Glu Leu Pro Ala Asp Leu Pro Pro Leu Ala
            675                 680                 685
Val Asp Phe Val Glu Asp Lys Glu Val Cys Lys Asn Tyr Gln Glu Ala
            690                 695                 700
Lys Asp Val Phe Leu Gly Thr Phe Leu Tyr Glu Tyr Ser Arg Arg His
705                 710                 715                 720
Pro Glu Tyr Ser Val Ser Leu Leu Arg Leu Ala Lys Glu Tyr Glu
            725                 730                 735
Ala Thr Leu Glu Lys Cys Cys Ala Thr Asp Asp Pro Pro Ala Cys Tyr
            740                 745                 750
Ala His Val Phe Asp Glu Phe Lys Pro Leu Val Glu Glu Pro His Asn
            755                 760                 765
Leu Val Lys Thr Asn Cys Glu Leu Phe Glu Lys Leu Gly Glu Tyr Gly
            770                 775                 780
Phe Gln Asn Ala Leu Leu Val Arg Tyr Thr Lys Lys Val Pro Gln Val
785                 790                 795                 800
Ser Thr Pro Thr Leu Val Glu Val Ser Arg Ser Leu Gly Lys Val Gly
            805                 810                 815
Ser Lys Cys Cys Thr His Pro Glu Ala Glu Arg Leu Ser Cys Ala Glu
            820                 825                 830
Asp Tyr Leu Ser Val Val Leu Asn Arg Leu Cys Val Leu His Glu Lys
            835                 840                 845
Thr Pro Val Ser Glu Arg Val Thr Lys Cys Cys Thr Glu Ser Leu Val
            850                 855                 860
Asn Arg Arg Pro Cys Phe Ser Ala Leu Gln Val Asp Glu Thr Tyr Val
865                 870                 875                 880
Pro Lys Glu Phe Ser Ala Glu Thr Phe Thr Phe His Ala Asp Leu Cys
            885                 890                 895
Thr Leu Pro Glu Ala Glu Lys Gln Ile Lys Lys Gln Ser Ala Leu Val
            900                 905                 910
Glu Leu Leu Lys His Lys Pro Lys Ala Thr Glu Glu Gln Leu Lys Thr
            915                 920                 925
Val Met Gly Asp Phe Gly Ser Phe Val Asp Lys Cys Cys Ala Ala Glu
            930                 935                 940
Asp Lys Glu Ala Cys Phe Ala Glu Glu Gly Pro Lys Leu Val Ala Ala
945                 950                 955                 960
Ala Gln Ala Ala Leu Ala Glu Phe Thr Leu Ile Pro Ile Ala Val Gly
            965                 970                 975
Gly Ala Leu Ala Gly Leu Val Leu Ile Val Leu Ile Ala Tyr Leu Val
            980                 985                 990
```

Gly Arg Lys Arg Ser His Ala Gly Tyr Gln Thr Ile
      995                  1000

<210> SEQ ID NO 73
<211> LENGTH: 525
<212> TYPE: DNA
<213> ORGANISM: Felis catus
<220> FEATURE:
<221> NAME/KEY: CDS
<222> LOCATION: (7)..(519)

<400> SEQUENCE: 73

```
ctcgag cac gag gaa gag aac gtc gtg cgg agc aac atc gac atc agc         48
       His Glu Glu Glu Asn Val Val Arg Ser Asn Ile Asp Ile Ser
       1               5                   10 aag atc agc ggc gag tgg tac agc att ctg ctg gcc tcc gac gtg aaa         96
Lys Ile Ser Gly Glu Trp Tyr Ser Ile Leu Leu Ala Ser Asp Val Lys
15              20                  25                  30 gag aag atc gaa gaa aac ggc agc atg cgg gtg ttc gtg gaa cac atc        144
Glu Lys Ile Glu Glu Asn Gly Ser Met Arg Val Phe Val Glu His Ile
                35                  40                  45 aag gct ctg gac aac agc tct ctg agc ttc gtg ttc cac acc aaa gaa        192
Lys Ala Leu Asp Asn Ser Ser Leu Ser Phe Val Phe His Thr Lys Glu
            50                  55                  60 aat ggc aag tgc acc gag atc ttt ctc gtg gcc gac aag acc aag gac        240
Asn Gly Lys Cys Thr Glu Ile Phe Leu Val Ala Asp Lys Thr Lys Asp
65                  70                  75 ggc gtg tac acc gtg gtg tac gac ggc tac aac gtg ttc agc atc gtg        288
Gly Val Tyr Thr Val Val Tyr Asp Gly Tyr Asn Val Phe Ser Ile Val
        80                  85                  90 gaa acc gtg tac gat gag tac att ctg ctg cat ctg ctg aac ttc gac        336
Glu Thr Val Tyr Asp Glu Tyr Ile Leu Leu His Leu Leu Asn Phe Asp
95                  100                 105                 110 aag aca cgg ccc ttc caa ctc gtg gag ttc tac gcc aga gaa ccc gac        384
Lys Thr Arg Pro Phe Gln Leu Val Glu Phe Tyr Ala Arg Glu Pro Asp
                115                 120                 125 gtg tcc cag aag ctg aaa gaa aag ttc gtg aag tac tgc caa gag cac        432
Val Ser Gln Lys Leu Lys Glu Lys Phe Val Lys Tyr Cys Gln Glu His
            130                 135                 140 ggc atc gtg aac att ctg gat ctg acc gaa gtg gac cgg tgt ctg caa        480
Gly Ile Val Asn Ile Leu Asp Leu Thr Glu Val Asp Arg Cys Leu Gln
        145                 150                 155 gcc aga ggc agc gaa gtg gcc caa gac agc agc gtg gaa gaattc             525
Ala Arg Gly Ser Glu Val Ala Gln Asp Ser Ser Val Glu
160                 165                 170
```

<210> SEQ ID NO 74
<211> LENGTH: 171
<212> TYPE: PRT
<213> ORGANISM: Felis catus

<400> SEQUENCE: 74

His Glu Glu Glu Asn Val Val Arg Ser Asn Ile Asp Ile Ser Lys Ile
1               5                   10                  15

Ser Gly Glu Trp Tyr Ser Ile Leu Leu Ala Ser Asp Val Lys Glu Lys
            20                  25                  30

Ile Glu Glu Asn Gly Ser Met Arg Val Phe Val Glu His Ile Lys Ala
        35                  40                  45

Leu Asp Asn Ser Ser Leu Ser Phe Val Phe His Thr Lys Glu Asn Gly
    50                  55                  60

Lys Cys Thr Glu Ile Phe Leu Val Ala Asp Lys Thr Lys Asp Gly Val

```
                    65                  70                  75                  80
Tyr Thr Val Val Tyr Asp Gly Tyr Asn Val Phe Ser Ile Val Glu Thr
                            85                  90                  95

Val Tyr Asp Glu Tyr Ile Leu Leu His Leu Leu Asn Phe Asp Lys Thr
                100                 105                 110

Arg Pro Phe Gln Leu Val Glu Phe Tyr Ala Arg Glu Pro Asp Val Ser
            115                 120                 125

Gln Lys Leu Lys Glu Lys Phe Val Lys Tyr Cys Gln Glu His Gly Ile
        130                 135                 140

Val Asn Ile Leu Asp Leu Thr Glu Val Asp Arg Cys Leu Gln Ala Arg
145                 150                 155                 160

Gly Ser Glu Val Ala Gln Asp Ser Ser Val Glu
                165                 170

<210> SEQ ID NO 75
<211> LENGTH: 1779
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1779)

<400> SEQUENCE: 75
```

| | |
|---|---:|
| atg gcg ccc cgc agc gcc cgg cga ccc ctg ctg ctg cta ctg ctg ttg<br>Met Ala Pro Arg Ser Ala Arg Arg Pro Leu Leu Leu Leu Leu Leu Leu<br>1               5                  10                  15 | 48 |
| ctg ctg ctc ggc ctc atg cat tgt gcg tca gca gca atg ttt atg gtg<br>Leu Leu Leu Gly Leu Met His Cys Ala Ser Ala Ala Met Phe Met Val<br>            20                  25                  30 | 96 |
| aaa aat ggc aac ggg acc gcg tgc ata atg gcc aac ttc tct gct gcc<br>Lys Asn Gly Asn Gly Thr Ala Cys Ile Met Ala Asn Phe Ser Ala Ala<br>        35                  40                  45 | 144 |
| ttc tca gtg aac tac gac acc aag agt ggc cct aag aac atg acc ctt<br>Phe Ser Val Asn Tyr Asp Thr Lys Ser Gly Pro Lys Asn Met Thr Leu<br>    50                  55                  60 | 192 |
| gac ctg cca tca gat gcc aca gtg gtg ctc aac cgc agc tcc tgt gga<br>Asp Leu Pro Ser Asp Ala Thr Val Val Leu Asn Arg Ser Ser Cys Gly<br>65                  70                  75                  80 | 240 |
| aaa gag aac act tct gac ccc agt ctc gtg att gct ttt gga aga gga<br>Lys Glu Asn Thr Ser Asp Pro Ser Leu Val Ile Ala Phe Gly Arg Gly<br>                85                  90                  95 | 288 |
| cat aca ctc act ctc aat ttc acg aga aat gca aca cgt tac agc gtc<br>His Thr Leu Thr Leu Asn Phe Thr Arg Asn Ala Thr Arg Tyr Ser Val<br>            100                 105                 110 | 336 |
| cag ctc atg agt ttt gtt tat aac ttg tca gac aca cac ctt ttc ccc<br>Gln Leu Met Ser Phe Val Tyr Asn Leu Ser Asp Thr His Leu Phe Pro<br>        115                 120                 125 | 384 |
| aat gcg agc tcc aaa gaa atc aag act gtg gaa tct ata act gac atc<br>Asn Ala Ser Ser Lys Glu Ile Lys Thr Val Glu Ser Ile Thr Asp Ile<br>    130                 135                 140 | 432 |
| agg gca gat ata gat aaa aaa tac aga tgt gtt agt ggc acc cag gtc<br>Arg Ala Asp Ile Asp Lys Lys Tyr Arg Cys Val Ser Gly Thr Gln Val<br>145                 150                 155                 160 | 480 |
| cac atg aac aac gtg acc gta acg ctc cat gat gcc acc atc cag gcg<br>His Met Asn Asn Val Thr Val Thr Leu His Asp Ala Thr Ile Gln Ala<br>                165                 170                 175 | 528 |
| tac ctt tcc aac agc agc ttc agc cgg gga gag aca cgc tgt gaa caa<br>Tyr Leu Ser Asn Ser Ser Phe Ser Arg Gly Glu Thr Arg Cys Glu Gln | 576 |

-continued

```
              180                 185                 190
gac agg cct tcc cca acc aca gcg ccc cct gcg cca ccc agc ccc tcg      624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc      672
Pro Ser Pro Val Pro Lys Ser Pro Ser Val Asp Lys Tyr Asn Val Ser
210                 215                 220 ggc acc aac ggg acc tgc ctg ctg gcc agc atg ggg ctg cag ctg aac      720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac      768
Leu Thr Tyr Glu Arg Lys Asp Asn Thr Thr Val Thr Arg Leu Leu Asn
            245                 250                 255 atc aac ccc aac aag acc tcg gcc agc ggg agc tgc ggc gcc cac ctg      816
Ile Asn Pro Asn Lys Thr Ser Ala Ser Gly Ser Cys Gly Ala His Leu
        260                 265                 270 gtg act ctg gag ctg cac agc gag ggc acc acc gtc ctg ctc ttc cag      864
Val Thr Leu Glu Leu His Ser Glu Gly Thr Thr Val Leu Leu Phe Gln
    275                 280                 285 ttc ggg atg aat gca agt tct agc cgg ttt ttc cta caa gga atc cag      912
Phe Gly Met Asn Ala Ser Ser Ser Arg Phe Phe Leu Gln Gly Ile Gln
290                 295                 300 ttg aat aca att ctt cct gac gcc aga gac cct gcc ttt aaa gct gcc      960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag     1008
Asn Gly Ser Leu Arg Ala Leu Gln Ala Thr Val Gly Asn Ser Tyr Lys
            325                 330                 335 tgc aac gcg gag gag cac gtc cgt gtc acg aag gcg ttt tca gtc aat     1056
Cys Asn Ala Glu Glu His Val Arg Val Thr Lys Ala Phe Ser Val Asn
        340                 345                 350 ata ttc aaa gtg tgg gtc cag gct ttc aag gtg gaa ggt ggc cag ttt     1104
Ile Phe Lys Val Trp Val Gln Ala Phe Lys Val Glu Gly Gly Gln Phe
    355                 360                 365 ggc tct gtg gag gag tgt ctg ctg gac gag aac agc ctc gag cac gag     1152
Gly Ser Val Glu Glu Cys Leu Leu Asp Glu Asn Ser Leu Glu His Glu
370                 375                 380 gaa gag aac gtc gtg cgg agc aac atc gac atc agc aag atc agc ggc     1200
Glu Glu Asn Val Val Arg Ser Asn Ile Asp Ile Ser Lys Ile Ser Gly
385                 390                 395                 400 gag tgg tac agc att ctg ctg gcc tcc gac gtg aaa gag aag atc gaa     1248
Glu Trp Tyr Ser Ile Leu Leu Ala Ser Asp Val Lys Glu Lys Ile Glu
            405                 410                 415 gaa aac ggc agc atg cgg gtg ttc gtg gaa cac atc aag gct ctg gac     1296
Glu Asn Gly Ser Met Arg Val Phe Val Glu His Ile Lys Ala Leu Asp
        420                 425                 430 aac agc tct ctg agc ttc gtg ttc cac acc aaa gaa aat ggc aag tgc     1344
Asn Ser Ser Leu Ser Phe Val Phe His Thr Lys Glu Asn Gly Lys Cys
    435                 440                 445 acc gag atc ttt ctc gtg gcc gac aag acc aag gac ggc gtg tac acc     1392
Thr Glu Ile Phe Leu Val Ala Asp Lys Thr Lys Asp Gly Val Tyr Thr
450                 455                 460 gtg gtg tac gac ggc tac aac gtg ttc agc atc gtg gaa acc gtg tac     1440
Val Val Tyr Asp Gly Tyr Asn Val Phe Ser Ile Val Glu Thr Val Tyr
465                 470                 475                 480 gat gag tac att ctg ctg cat ctg ctg aac ttc gac aag aca cgg ccc     1488
Asp Glu Tyr Ile Leu Leu His Leu Leu Asn Phe Asp Lys Thr Arg Pro
            485                 490                 495 ttc caa ctc gtg gag ttc tac gcc aga gaa ccc gac gtg tcc cag aag     1536
Phe Gln Leu Val Glu Phe Tyr Ala Arg Glu Pro Asp Val Ser Gln Lys
```

```
                Phe Gln Leu Val Glu Phe Tyr Ala Arg Glu Pro Asp Val Ser Gln Lys
                                500                 505                 510 ctg aaa gaa aag ttc gtg aag tac tgc caa gag cac ggc atc gtg aac          1584
Leu Lys Glu Lys Phe Val Lys Tyr Cys Gln Glu His Gly Ile Val Asn
            515                 520                 525 att ctg gat ctg acc gaa gtg gac cgg tgt ctg caa gcc aga ggc agc          1632
Ile Leu Asp Leu Thr Glu Val Asp Arg Cys Leu Gln Ala Arg Gly Ser
530                 535                 540 gaa gtg gcc caa gac agc agc gtg gaa gaa ttc acg ctg atc ccc atc          1680
Glu Val Ala Gln Asp Ser Ser Val Glu Glu Phe Thr Leu Ile Pro Ile
545                 550                 555                 560 gct gtg ggt ggt gcc ctg gcg ggg ctg gtc ctc atc gtc ctc atc gcc          1728
Ala Val Gly Gly Ala Leu Ala Gly Leu Val Leu Ile Val Leu Ile Ala
                565                 570                 575 tac ctc gtc ggc agg aag agg agt cac gca ggc tac cag act atc tag          1776
Tyr Leu Val Gly Arg Lys Arg Ser His Ala Gly Tyr Gln Thr Ile
                580                 585                 590 taa                                                                       1779

<210> SEQ ID NO 76
<211> LENGTH: 591
<212> TYPE: PRT
<213> ORGANISM: Artificial sequence
<220> FEATURE:
<223> OTHER INFORMATION: Synthetic Construct

<400> SEQUENCE: 76

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
                100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
        195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240
```

Leu Thr Tyr Glu Arg Lys Asp Asn Thr Thr Val Thr Arg Leu Leu Asn
             245                 250                 255

Ile Asn Pro Asn Lys Thr Ser Ala Ser Gly Ser Cys Gly Ala His Leu
         260                 265                 270

Val Thr Leu Glu Leu His Ser Glu Gly Thr Thr Val Leu Leu Phe Gln
             275                 280                 285

Phe Gly Met Asn Ala Ser Ser Ser Arg Phe Phe Leu Gln Gly Ile Gln
         290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
             325                 330                 335

Cys Asn Ala Glu Glu His Val Arg Val Thr Lys Ala Phe Ser Val Asn
         340                 345                 350

Ile Phe Lys Val Trp Val Gln Ala Phe Lys Val Glu Gly Gly Gln Phe
             355                 360                 365

Gly Ser Val Glu Glu Cys Leu Leu Asp Glu Asn Ser Leu Glu His Glu
         370                 375                 380

Glu Glu Asn Val Val Arg Ser Asn Ile Asp Ile Ser Lys Ile Ser Gly
385                 390                 395                 400

Glu Trp Tyr Ser Ile Leu Leu Ala Ser Asp Val Lys Glu Lys Ile Glu
             405                 410                 415

Glu Asn Gly Ser Met Arg Val Phe Val Glu His Ile Lys Ala Leu Asp
         420                 425                 430

Asn Ser Ser Leu Ser Phe Val Phe His Thr Lys Glu Asn Gly Lys Cys
             435                 440                 445

Thr Glu Ile Phe Leu Val Ala Asp Lys Thr Lys Asp Gly Val Tyr Thr
         450                 455                 460

Val Val Tyr Asp Gly Tyr Asn Val Phe Ser Ile Val Glu Thr Val Tyr
465                 470                 475                 480

Asp Glu Tyr Ile Leu Leu His Leu Leu Asn Phe Asp Lys Thr Arg Pro
             485                 490                 495

Phe Gln Leu Val Glu Phe Tyr Ala Arg Glu Pro Asp Val Ser Gln Lys
         500                 505                 510

Leu Lys Glu Lys Phe Val Lys Tyr Cys Gln Glu His Gly Ile Val Asn
             515                 520                 525

Ile Leu Asp Leu Thr Glu Val Asp Arg Cys Leu Gln Ala Arg Gly Ser
530                 535                 540

Glu Val Ala Gln Asp Ser Ser Val Glu Glu Phe Thr Leu Ile Pro Ile
545                 550                 555                 560

Ala Val Gly Gly Ala Leu Ala Gly Leu Val Leu Ile Val Leu Ile Ala
             565                 570                 575

Tyr Leu Val Gly Arg Lys Arg Ser His Ala Gly Tyr Gln Thr Ile
         580                 585                 590

<210> SEQ ID NO 77
<211> LENGTH: 864
<212> TYPE: DNA
<213> ORGANISM: Litopenaeus vannamei
<220> FEATURE:
<221> NAME/KEY: CDS
<222> LOCATION: (7)..(858)

<400> SEQUENCE: 77 ctcgag atg gac gcc atc aag aag aaa atg caa gcc atg aag ctg gaa          48

```
        Met Asp Ala Ile Lys Lys Met Gln Ala Met Lys Leu Glu
        1               5                  10 aag gac aac gcc atg gac cgg gcc gac aca ctg gaa cag cag aac aaa        96
Lys Asp Asn Ala Met Asp Arg Ala Asp Thr Leu Glu Gln Gln Asn Lys
 15                  20                  25                  30 gag gcc aac aat cgg gcc gag aag tcc gag gaa gaa gtg cac aat ctg       144
Glu Ala Asn Asn Arg Ala Glu Lys Ser Glu Glu Glu Val His Asn Leu
                 35                  40                  45 cag aaa cgg atg cag cag ctg gaa aac gat ctg gac caa gtg caa gag       192
Gln Lys Arg Met Gln Gln Leu Glu Asn Asp Leu Asp Gln Val Gln Glu
             50                  55                  60 tct ctg ctg aag gcc aac atc caa ctc gtg gaa aag gat aag gct ctg       240
Ser Leu Leu Lys Ala Asn Ile Gln Leu Val Glu Lys Asp Lys Ala Leu
         65                  70                  75 agc aac gcc gag ggc gaa gtg gcc gct ctg aac aga cgg att cag ctg       288
Ser Asn Ala Glu Gly Glu Val Ala Ala Leu Asn Arg Arg Ile Gln Leu
     80                  85                  90 ctg gaa gag gat ctg gaa aga agc gag gaa cgg ctg aac acc gcc aca       336
Leu Glu Glu Asp Leu Glu Arg Ser Glu Glu Arg Leu Asn Thr Ala Thr
 95                 100                 105                 110 aca aag ctg gcc gaa gcc agc caa gcc gcc gac gag agc gag cgg atg       384
Thr Lys Leu Ala Glu Ala Ser Gln Ala Ala Asp Glu Ser Glu Arg Met
                115                 120                 125 cgg aaa gtg ctg gaa aac cgc tct ctg agc gac gag gaa aga atg gac       432
Arg Lys Val Leu Glu Asn Arg Ser Leu Ser Asp Glu Glu Arg Met Asp
            130                 135                 140 gct ctg gaa aat cag ctg aaa gag gcc cgg ttt ctg gcc gag gaa gcc       480
Ala Leu Glu Asn Gln Leu Lys Glu Ala Arg Phe Leu Ala Glu Glu Ala
        145                 150                 155 gac cgg aag tac gat gaa gtg gcc cgg aag ctg gcc atg gtc gag gct       528
Asp Arg Lys Tyr Asp Glu Val Ala Arg Lys Leu Ala Met Val Glu Ala
    160                 165                 170 gat ctg gaa cgg gcc gaa gag aga gcc gaa acc ggc gag agc aag atc       576
Asp Leu Glu Arg Ala Glu Glu Arg Ala Glu Thr Gly Glu Ser Lys Ile
175                 180                 185                 190 gtg gaa ctg gaa gag gaa ctg cgg gtc gtg ggc aac aat ctg aag tct       624
Val Glu Leu Glu Glu Glu Leu Arg Val Val Gly Asn Asn Leu Lys Ser
                195                 200                 205 ctg gaa gtg tcc gaa gag aag gcc aat cag aga gag gaa gcc tac aaa       672
Leu Glu Val Ser Glu Glu Lys Ala Asn Gln Arg Glu Glu Ala Tyr Lys
            210                 215                 220 gag cag atc aag aca ctg acc aac aag ctg aag gct gcc gag gcc aga       720
Glu Gln Ile Lys Thr Leu Thr Asn Lys Leu Lys Ala Ala Glu Ala Arg
        225                 230                 235 gcc gag ttc gcc gag aga agc gtg cag aaa ctg cag aaa gaa gtg gac       768
Ala Glu Phe Ala Glu Arg Ser Val Gln Lys Leu Gln Lys Glu Val Asp
    240                 245                 250 cgg ctg gaa gat gag ctc gtg aac gag aaa gag aag tac aag agc atc       816
Arg Leu Glu Asp Glu Leu Val Asn Glu Lys Glu Lys Tyr Lys Ser Ile
255                 260                 265                 270 acc gac gag ctg gac cag aca ttc agc gag ctg agc ggc tac gaattc       864
Thr Asp Glu Leu Asp Gln Thr Phe Ser Glu Leu Ser Gly Tyr
                275                 280
```

<210> SEQ ID NO 78
<211> LENGTH: 284
<212> TYPE: PRT
<213> ORGANISM: Litopenaeus vannamei

<400> SEQUENCE: 78

```
Met Asp Ala Ile Lys Lys Met Gln Ala Met Lys Leu Glu Lys Asp
1               5                   10                  15

Asn Ala Met Asp Arg Ala Asp Thr Leu Glu Gln Gln Asn Lys Glu Ala
            20                  25                  30

Asn Asn Arg Ala Glu Lys Ser Glu Glu Val His Asn Leu Gln Lys
        35                  40                  45

Arg Met Gln Gln Leu Glu Asn Asp Leu Asp Gln Val Gln Glu Ser Leu
    50                  55                  60

Leu Lys Ala Asn Ile Gln Leu Val Glu Lys Asp Lys Ala Leu Ser Asn
65                  70                  75                  80

Ala Glu Gly Glu Val Ala Ala Leu Asn Arg Arg Ile Gln Leu Leu Glu
                    85                  90                  95

Glu Asp Leu Glu Arg Ser Glu Glu Arg Leu Asn Thr Ala Thr Thr Lys
            100                 105                 110

Leu Ala Glu Ala Ser Gln Ala Ala Asp Glu Ser Glu Arg Met Arg Lys
            115                 120                 125

Val Leu Glu Asn Arg Ser Leu Ser Asp Glu Glu Arg Met Asp Ala Leu
        130                 135                 140

Glu Asn Gln Leu Lys Glu Ala Arg Phe Leu Ala Glu Glu Ala Asp Arg
145                 150                 155                 160

Lys Tyr Asp Glu Val Ala Arg Lys Leu Ala Met Val Glu Ala Asp Leu
                165                 170                 175

Glu Arg Ala Glu Glu Arg Ala Glu Thr Gly Glu Ser Lys Ile Val Glu
            180                 185                 190

Leu Glu Glu Glu Leu Arg Val Val Gly Asn Asn Leu Lys Ser Leu Glu
        195                 200                 205

Val Ser Glu Glu Lys Ala Asn Gln Arg Glu Glu Ala Tyr Lys Glu Gln
    210                 215                 220

Ile Lys Thr Leu Thr Asn Lys Leu Lys Ala Ala Glu Ala Arg Ala Glu
225                 230                 235                 240

Phe Ala Glu Arg Ser Val Gln Lys Leu Gln Lys Glu Val Asp Arg Leu
                245                 250                 255

Glu Asp Glu Leu Val Asn Glu Lys Glu Lys Tyr Lys Ser Ile Thr Asp
            260                 265                 270

Glu Leu Asp Gln Thr Phe Ser Glu Leu Ser Gly Tyr
        275                 280

<210> SEQ ID NO 79
<211> LENGTH: 2118
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(2118)

<400> SEQUENCE: 79 atg gcg ccc cgc agc gcc cgg cga ccc ctg ctg ctg cta ctg ctg ttg      48
Met Ala Pro Arg Ser Ala Arg Arg Pro Leu Leu Leu Leu Leu Leu Leu
1               5                   10                  15 ctg ctg ctc ggc ctc atg cat tgt gcg tca gca gca atg ttt atg gtg      96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc     144
Lys Asn Gly Asn Gly Thr Ala Cys Ile Met Ala Asn Phe Ser Ala Ala
        35                  40                  45
```

-continued

| | | |
|---|---|---|
| ttc tca gtg aac tac gac acc aag agt ggc cct aag aac atg acc ctt<br>Phe Ser Val Asn Tyr Asp Thr Lys Ser Gly Pro Lys Asn Met Thr Leu<br>50                              55                          60 | | 192 |
| gac ctg cca tca gat gcc aca gtg gtg ctc aac cgc agc tcc tgt gga<br>Asp Leu Pro Ser Asp Ala Thr Val Val Leu Asn Arg Ser Ser Cys Gly<br>65                            70                        75                        80 | | 240 |
| aaa gag aac act tct gac ccc agt ctc gtg att gct ttt gga aga gga<br>Lys Glu Asn Thr Ser Asp Pro Ser Leu Val Ile Ala Phe Gly Arg Gly<br>                            85                        90                        95 | | 288 |
| cat aca ctc act ctc aat ttc acg aga aat gca aca cgt tac agc gtc<br>His Thr Leu Thr Leu Asn Phe Thr Arg Asn Ala Thr Arg Tyr Ser Val<br>                100                       105                       110 | | 336 |
| cag ctc atg agt ttt gtt tat aac ttg tca gac aca cac ctt ttc ccc<br>Gln Leu Met Ser Phe Val Tyr Asn Leu Ser Asp Thr His Leu Phe Pro<br>                115                       120                       125 | | 384 |
| aat gcg agc tcc aaa gaa atc aag act gtg gaa tct ata act gac atc<br>Asn Ala Ser Ser Lys Glu Ile Lys Thr Val Glu Ser Ile Thr Asp Ile<br>130                            135                        140 | | 432 |
| agg gca gat ata gat aaa aaa tac aga tgt gtt agt ggc acc cag gtc<br>Arg Ala Asp Ile Asp Lys Lys Tyr Arg Cys Val Ser Gly Thr Gln Val<br>145                            150                        155                       160 | | 480 |
| cac atg aac aac gtg acc gta acg ctc cat gat gcc acc atc cag gcg<br>His Met Asn Asn Val Thr Val Thr Leu His Asp Ala Thr Ile Gln Ala<br>                            165                        170                       175 | | 528 |
| tac ctt tcc aac agc agc ttc agc cgg gga gag aca cgc tgt gaa caa<br>Tyr Leu Ser Asn Ser Ser Phe Ser Arg Gly Glu Thr Arg Cys Glu Gln<br>                180                       185                       190 | | 576 |
| gac agg cct tcc cca acc aca gcg ccc cct gcg cca ccc agc ccc tcg<br>Asp Arg Pro Ser Pro Thr Thr Ala Pro Pro Ala Pro Pro Ser Pro Ser<br>                            195                       200                       205 | | 624 |
| ccc tca ccc gtg ccc aag agc ccc tct gtg gac aag tac aac gtg agc<br>Pro Ser Pro Val Pro Lys Ser Pro Ser Val Asp Lys Tyr Asn Val Ser<br>210                            215                        220 | | 672 |
| ggc acc aac ggg acc tgc ctg ctg gcc agc atg ggg ctg cag ctg aac<br>Gly Thr Asn Gly Thr Cys Leu Leu Ala Ser Met Gly Leu Gln Leu Asn<br>225                            230                                     240 | | 720 |
| ctc acc tat gag agg aag gac aac acg acg gtg aca agg ctt ctc aac<br>Leu Thr Tyr Glu Arg Lys Asp Asn Thr Thr Val Thr Arg Leu Leu Asn<br>                            245                       250                       255 | | 768 |
| atc aac ccc aac aag acc tcg gcc agc ggg agc tgc ggc gcc cac ctg<br>Ile Asn Pro Asn Lys Thr Ser Ala Ser Gly Ser Cys Gly Ala His Leu<br>                260                       265                       270 | | 816 |
| gtg act ctg gag ctg cac agc gag ggc acc acc gtc ctg ctc ttc cag<br>Val Thr Leu Glu Leu His Ser Glu Gly Thr Thr Val Leu Leu Phe Gln<br>                275                       280                       285 | | 864 |
| ttc ggg atg aat gca agt tct agc cgg ttt ttc cta caa gga atc cag<br>Phe Gly Met Asn Ala Ser Ser Ser Arg Phe Phe Leu Gln Gly Ile Gln<br>                290                       295                       300 | | 912 |
| ttg aat aca att ctt cct gac gcc aga gac cct gcc ttt aaa gct gcc<br>Leu Asn Thr Ile Leu Pro Asp Ala Arg Asp Pro Ala Phe Lys Ala Ala<br>305                            310                        315                       320 | | 960 |
| aac ggc tcc ctg cga gcg ctg cag gcc aca gtc ggc aat tcc tac aag<br>Asn Gly Ser Leu Arg Ala Leu Gln Ala Thr Val Gly Asn Ser Tyr Lys<br>                            325                       330                       335 | | 1008 |
| tgc aac gcg gag gag cac gtc cgt gtc acg aag gcg ttt tca gtc aat<br>Cys Asn Ala Glu Glu His Val Arg Val Thr Lys Ala Phe Ser Val Asn<br>                340                       345                       350 | | 1056 |
| ata ttc aaa gtg tgg gtc cag gct ttc aag gtg gaa ggt ggc cag ttt<br>Ile Phe Lys Val Trp Val Gln Ala Phe Lys Val Glu Gly Gly Gln Phe<br>                            355                       360                       365 | | 1104 |

```
ggc tct gtg gag gag tgt ctg ctg gac gag aac agc ctc gag atg gac      1152
Gly Ser Val Glu Glu Cys Leu Leu Asp Glu Asn Ser Leu Glu Met Asp
    370             375                 380 gcc atc aag aag aaa atg caa gcc atg aag ctg gaa aag gac aac gcc      1200
Ala Ile Lys Lys Lys Met Gln Ala Met Lys Leu Glu Lys Asp Asn Ala
385             390                 395                 400 atg gac cgg gcc gac aca ctg gaa cag cag aac aaa gag gcc aac aat      1248
Met Asp Arg Ala Asp Thr Leu Glu Gln Gln Asn Lys Glu Ala Asn Asn
                405                 410                 415 cgg gcc gag aag tcc gag gaa gaa gtg cac aat ctg cag aaa cgg atg      1296
Arg Ala Glu Lys Ser Glu Glu Glu Val His Asn Leu Gln Lys Arg Met
            420                 425                 430 cag cag ctg gaa aac gat ctg gac caa gtg caa gag tct ctg ctg aag      1344
Gln Gln Leu Glu Asn Asp Leu Asp Gln Val Gln Glu Ser Leu Leu Lys
        435                 440                 445 gcc aac atc caa ctc gtg gaa aag gat aag gct ctg agc aac gcc gag      1392
Ala Asn Ile Gln Leu Val Glu Lys Asp Lys Ala Leu Ser Asn Ala Glu
    450                 455                 460 ggc gaa gtg gcc gct ctg aac aga cgg att cag ctg ctg gaa gag gat      1440
Gly Glu Val Ala Ala Leu Asn Arg Arg Ile Gln Leu Leu Glu Glu Asp
465             470                 475                 480 ctg gaa aga agc gag gaa cgg ctg aac acc gcc aca aca aag ctg gcc      1488
Leu Glu Arg Ser Glu Glu Arg Leu Asn Thr Ala Thr Thr Lys Leu Ala
                485                 490                 495 gaa gcc agc caa gcc gcc gac gag agc gag cgg atg cgg aaa gtg ctg      1536
Glu Ala Ser Gln Ala Ala Asp Glu Ser Glu Arg Met Arg Lys Val Leu
            500                 505                 510 gaa aac cgc tct ctg agc gac gag gaa aga atg gac gct ctg gaa aat      1584
Glu Asn Arg Ser Leu Ser Asp Glu Glu Arg Met Asp Ala Leu Glu Asn
        515                 520                 525 cag ctg aaa gag gcc cgg ttt ctg gcc gag gaa gcc gac cgg aag tac      1632
Gln Leu Lys Glu Ala Arg Phe Leu Ala Glu Glu Ala Asp Arg Lys Tyr
    530                 535                 540 gat gaa gtg gcc cgg aag ctg gcc atg gtc gag gct gat ctg gaa cgg      1680
Asp Glu Val Ala Arg Lys Leu Ala Met Val Glu Ala Asp Leu Glu Arg
545             550                 555                 560 gcc gaa gag aga gcc gaa acc ggc gag agc aag atc gtg gaa ctg gaa      1728
Ala Glu Glu Arg Ala Glu Thr Gly Glu Ser Lys Ile Val Glu Leu Glu
                565                 570                 575 gag gaa ctg cgg gtc gtg ggc aac aat ctg aag tct ctg gaa gtg tcc      1776
Glu Glu Leu Arg Val Val Gly Asn Asn Leu Lys Ser Leu Glu Val Ser
            580                 585                 590 gaa gag aag gcc aat cag aga gag gaa gcc tac aaa gag cag atc aag      1824
Glu Glu Lys Ala Asn Gln Arg Glu Glu Ala Tyr Lys Glu Gln Ile Lys
        595                 600                 605 aca ctg acc aac aag ctg aag gct gcc gag gcc aga gcc gag ttc gcc      1872
Thr Leu Thr Asn Lys Leu Lys Ala Ala Glu Ala Arg Ala Glu Phe Ala
    610                 615                 620 gag aga agc gtg cag aaa ctg cag aaa gaa gtg gac cgg ctg gaa gat      1920
Glu Arg Ser Val Gln Lys Leu Gln Lys Glu Val Asp Arg Leu Glu Asp
625             630                 635                 640 gag ctc gtg aac gag aaa gag aag tac aag agc atc acc gac gag ctg      1968
Glu Leu Val Asn Glu Lys Glu Lys Tyr Lys Ser Ile Thr Asp Glu Leu
                645                 650                 655 gac cag aca ttc agc gag ctg agc ggc tac gaa ttc acg ctg atc ccc      2016
Asp Gln Thr Phe Ser Glu Leu Ser Gly Tyr Glu Phe Thr Leu Ile Pro
            660                 665                 670 atc gct gtg ggt ggt gcc ctg gcg ggg ctg gtc ctc atc gtc ctc atc      2064
Ile Ala Val Gly Gly Ala Leu Ala Gly Leu Val Leu Ile Val Leu Ile
```

-continued

```
              675                 680                 685
gcc tac ctc gtc ggc agg aag agg agt cac gca ggc tac cag act atc    2112
Ala Tyr Leu Val Gly Arg Lys Arg Ser His Ala Gly Tyr Gln Thr Ile
690                 695                 700 tag taa                                                              2118
```

<210> SEQ ID NO 80
<211> LENGTH: 704
<212> TYPE: PRT
<213> ORGANISM: Artificial sequence
<220> FEATURE:
<223> OTHER INFORMATION: Synthetic Construct

<400> SEQUENCE: 80

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
                20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
        50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Pro Ser Pro Ser
        195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                245                 250                 255

Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
```

```
                    325                 330                 335
Cys Asn Ala Glu Glu His Val Arg Val Thr Lys Ala Phe Ser Val Asn
                340                 345                 350

Ile Phe Lys Val Trp Val Gln Ala Phe Lys Val Glu Gly Gly Gln Phe
            355                 360                 365

Gly Ser Val Glu Glu Cys Leu Leu Asp Glu Asn Ser Leu Glu Met Asp
        370                 375                 380

Ala Ile Lys Lys Met Gln Ala Met Lys Leu Glu Lys Asp Asn Ala
385                 390                 395                 400

Met Asp Arg Ala Asp Thr Leu Glu Gln Gln Asn Lys Glu Ala Asn Asn
                405                 410                 415

Arg Ala Glu Lys Ser Glu Glu Val His Asn Leu Gln Lys Arg Met
                420                 425                 430

Gln Gln Leu Glu Asn Asp Leu Asp Gln Val Gln Glu Ser Leu Leu Lys
                435                 440                 445

Ala Asn Ile Gln Leu Val Glu Lys Asp Lys Ala Leu Ser Asn Ala Glu
                450                 455                 460

Gly Glu Val Ala Ala Leu Asn Arg Arg Ile Gln Leu Leu Glu Glu Asp
465                 470                 475                 480

Leu Glu Arg Ser Glu Glu Arg Leu Asn Thr Ala Thr Lys Leu Ala
                485                 490                 495

Glu Ala Ser Gln Ala Ala Asp Glu Ser Glu Arg Met Arg Lys Val Leu
                500                 505                 510

Glu Asn Arg Ser Leu Ser Asp Glu Glu Arg Met Asp Ala Leu Glu Asn
                515                 520                 525

Gln Leu Lys Glu Ala Arg Phe Leu Ala Glu Glu Ala Asp Arg Lys Tyr
                530                 535                 540

Asp Glu Val Ala Arg Lys Leu Ala Met Val Glu Ala Asp Leu Glu Arg
545                 550                 555                 560

Ala Glu Glu Arg Ala Glu Thr Gly Glu Ser Lys Ile Val Glu Leu Glu
                565                 570                 575

Glu Glu Leu Arg Val Val Gly Asn Asn Leu Lys Ser Leu Glu Val Ser
                580                 585                 590

Glu Glu Lys Ala Asn Gln Arg Glu Glu Ala Tyr Lys Glu Gln Ile Lys
                595                 600                 605

Thr Leu Thr Asn Lys Leu Lys Ala Ala Glu Ala Arg Ala Glu Phe Ala
                610                 615                 620

Glu Arg Ser Val Gln Lys Leu Gln Lys Glu Val Asp Arg Leu Glu Asp
625                 630                 635                 640

Glu Leu Val Asn Glu Lys Glu Lys Tyr Lys Ser Ile Thr Asp Glu Leu
                645                 650                 655

Asp Gln Thr Phe Ser Glu Leu Ser Gly Tyr Glu Phe Thr Leu Ile Pro
                660                 665                 670

Ile Ala Val Gly Gly Ala Leu Ala Gly Leu Val Leu Ile Val Leu Ile
                675                 680                 685

Ala Tyr Leu Val Gly Arg Lys Arg Ser His Ala Gly Tyr Gln Thr Ile
                690                 695                 700

<210> SEQ ID NO 81
<211> LENGTH: 753
<212> TYPE: DNA
<213> ORGANISM: Lolium perenne
<220> FEATURE:
<221> NAME/KEY: CDS
<222> LOCATION: (7)..(747)
```

<400> SEQUENCE: 81

```
ctcgag gcc gat gcc ggc tac aca cca gcc gct gct aca cca gcc         48
       Ala Asp Ala Gly Tyr Thr Pro Ala Ala Ala Thr Pro Ala
       1               5                   10 act cca gca gca aca cca gca gcc gct ggc ggc aag gcc aca acc gat    96
Thr Pro Ala Ala Thr Pro Ala Ala Ala Gly Gly Lys Ala Thr Thr Asp
15                  20                  25                  30 gag cag aaa ctg ctg gaa gat gtg aac gcc ggc ttc aag gcc gcc gtg    144
Glu Gln Lys Leu Leu Glu Asp Val Asn Ala Gly Phe Lys Ala Ala Val
                35                  40                  45 gct gct gct gca aat gcc cct ccc gcc gac aag ttc aag atc ttc gag    192
Ala Ala Ala Ala Asn Ala Pro Pro Ala Asp Lys Phe Lys Ile Phe Glu
            50                  55                  60 gcc gcc ttc agc gag agc agc aag gga ctg ctg gcc aca tct gcc gcc    240
Ala Ala Phe Ser Glu Ser Ser Lys Gly Leu Leu Ala Thr Ser Ala Ala
        65                  70                  75 aaa gcc ccc gga ctg atc ccc aag ctg gac acc gcc tac gac gtg gcc    288
Lys Ala Pro Gly Leu Ile Pro Lys Leu Asp Thr Ala Tyr Asp Val Ala
    80                  85                  90 tac aaa gcc gcc gag gcc acc cca gag gcc aaa tac gat gcc ttc gtg    336
Tyr Lys Ala Ala Glu Ala Thr Pro Glu Ala Lys Tyr Asp Ala Phe Val
95                  100                 105                 110 acc gct ctg acc gag gct ctg aga gtg att gcc ggc gct ctg gaa gtg    384
Thr Ala Leu Thr Glu Ala Leu Arg Val Ile Ala Gly Ala Leu Glu Val
                115                 120                 125 cac gcc gtg aag cca gcc acc gaa gaa gtg ctg gcc gcc aag att cct    432
His Ala Val Lys Pro Ala Thr Glu Glu Val Leu Ala Ala Lys Ile Pro
            130                 135                 140 acc ggc gag ctg cag atc gtg gac aag atc gac gcc gcc ttt aag atc    480
Thr Gly Glu Leu Gln Ile Val Asp Lys Ile Asp Ala Ala Phe Lys Ile
        145                 150                 155 gcc gcc acc gcc gca aat gcc gcc cct acc aac gat aag ttc acc gtg    528
Ala Ala Thr Ala Ala Asn Ala Ala Pro Thr Asn Asp Lys Phe Thr Val
    160                 165                 170 ttc gag agc gcc ttc aac aag gct ctg aac gag tgc acc ggc gga gcc    576
Phe Glu Ser Ala Phe Asn Lys Ala Leu Asn Glu Cys Thr Gly Gly Ala
175                 180                 185                 190 tac gag aca tac aag ttc atc cca tct ctg gaa gcc gct gtg aag caa    624
Tyr Glu Thr Tyr Lys Phe Ile Pro Ser Leu Glu Ala Ala Val Lys Gln
                195                 200                 205 gcc tac gcc gcc aca gtg gcc gct gcc ccc gaa gtg aag tac gcc gtg    672
Ala Tyr Ala Ala Thr Val Ala Ala Ala Pro Glu Val Lys Tyr Ala Val
            210                 215                 220 ttt gag gcc gca ctg acc aag gcc atc acc gcc atg aca caa gcc cag    720
Phe Glu Ala Ala Leu Thr Lys Ala Ile Thr Ala Met Thr Gln Ala Gln
        225                 230                 235 aag gcc ggc aaa cca gct gct gca gct gaattc                        753
Lys Ala Gly Lys Pro Ala Ala Ala Ala
    240                 245
```

<210> SEQ ID NO 82
<211> LENGTH: 247
<212> TYPE: PRT
<213> ORGANISM: Lolium perenne

<400> SEQUENCE: 82

```
Ala Asp Ala Gly Tyr Thr Pro Ala Ala Ala Thr Pro Ala Thr Pro
1               5                   10                  15

Ala Ala Thr Pro Ala Ala Ala Gly Gly Lys Ala Thr Thr Asp Glu Gln
```

```
                    20                  25                  30

Lys Leu Leu Glu Asp Val Asn Ala Gly Phe Lys Ala Val Ala Ala
                35                  40                  45

Ala Ala Asn Ala Pro Pro Ala Asp Lys Phe Lys Ile Phe Glu Ala Ala
 50                  55                  60

Phe Ser Glu Ser Ser Lys Gly Leu Leu Ala Thr Ser Ala Ala Lys Ala
65                  70                  75                  80

Pro Gly Leu Ile Pro Lys Leu Asp Thr Ala Tyr Asp Val Ala Tyr Lys
                85                  90                  95

Ala Ala Glu Ala Thr Pro Glu Ala Lys Tyr Asp Ala Phe Val Thr Ala
               100                 105                 110

Leu Thr Glu Ala Leu Arg Val Ile Ala Gly Ala Leu Glu Val His Ala
               115                 120                 125

Val Lys Pro Ala Thr Glu Glu Val Leu Ala Ala Lys Ile Pro Thr Gly
               130                 135                 140

Glu Leu Gln Ile Val Asp Lys Ile Asp Ala Ala Phe Lys Ile Ala Ala
145                 150                 155                 160

Thr Ala Ala Asn Ala Ala Pro Thr Asn Asp Lys Phe Thr Val Phe Glu
               165                 170                 175

Ser Ala Phe Asn Lys Ala Leu Asn Glu Cys Thr Gly Gly Ala Tyr Glu
               180                 185                 190

Thr Tyr Lys Phe Ile Pro Ser Leu Glu Ala Ala Val Lys Gln Ala Tyr
               195                 200                 205

Ala Ala Thr Val Ala Ala Ala Pro Glu Val Lys Tyr Ala Val Phe Glu
               210                 215                 220

Ala Ala Leu Thr Lys Ala Ile Thr Ala Met Thr Gln Ala Gln Lys Ala
225                 230                 235                 240

Gly Lys Pro Ala Ala Ala Ala
               245

<210> SEQ ID NO 83
<211> LENGTH: 2007
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(2007)

<400> SEQUENCE: 83 atg gcg ccc cgc agc gcc cgg cga ccc ctg ctg ctg cta ctg ctg ttg      48
Met Ala Pro Arg Ser Ala Arg Arg Pro Leu Leu Leu Leu Leu Leu Leu
1               5                  10                  15 ctg ctc ggc ctc atg cat tgt gcg tca gca gca atg ttt atg gtg           96
Leu Leu Gly Leu Met His Cys Ala Ser Ala Ala Met Phe Met Val
            20                  25                  30 aaa aat ggc aac ggg acc gcg tgc ata atg gcc aac ttc tct gct gcc      144
Lys Asn Gly Asn Gly Thr Ala Cys Ile Met Ala Asn Phe Ser Ala Ala
            35                  40                  45 ttc tca gtg aac tac gac acc aag agt ggc cct aag aac atg acc ctt      192
Phe Ser Val Asn Tyr Asp Thr Lys Ser Gly Pro Lys Asn Met Thr Leu
 50                  55                  60 gac ctg cca tca gat gcc aca gtg gtg ctc aac cgc agc tcc tgt gga      240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga      288
Lys Glu Asn Thr Ser Asp Pro Ser Leu Val Ile Ala Phe Gly Arg Gly
```

-continued

|  | 85 |  |  |  | 90 |  |  |  | 95 |  |  |  |  |
|---|---|---|---|---|---|---|---|---|---|---|---|---|---|
| cat | aca | ctc | act | ctc | aat | ttc | acg | aga | aat | gca | aca | cgt | tac agc gtc | 336 |
| His | Thr | Leu | Thr | Leu | Asn | Phe | Thr | Arg | Asn | Ala | Thr | Arg | Tyr Ser Val |  |
|  |  | 100 |  |  |  | 105 |  |  |  | 110 |  |  |  |  | cag ctc atg agt ttt gtt tat aac ttg tca gac aca cac ctt ttc ccc  384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc  432
Asn Ala Ser Ser Lys Glu Ile Lys Thr Val Glu Ser Ile Thr Asp Ile
130                 135                 140 agg gca gat ata gat aaa aaa tac aga tgt gtt agt ggc acc cag gtc  480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg  528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa  576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg  624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc  672
Pro Ser Pro Val Pro Lys Ser Pro Ser Val Asp Lys Tyr Asn Val Ser
210                 215                 220 ggc acc aac ggg acc tgc ctg ctg gcc agc atg ggg ctg cag ctg aac  720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac  768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg  816
Ile Asn Pro Asn Lys Thr Ser Ala Ser Gly Ser Cys Gly Ala His Leu
            260                 265                 270 gtg act ctg gag ctg cac agc gag ggc acc acc gtc ctg ctc ttc cag  864
Val Thr Leu Glu Leu His Ser Glu Gly Thr Thr Val Leu Leu Phe Gln
        275                 280                 285 ttc ggg atg aat gca agt tct agc cgg ttt ttc cta caa gga atc cag  912
Phe Gly Met Asn Ala Ser Ser Ser Arg Phe Phe Leu Gln Gly Ile Gln
290                 295                 300 ttg aat aca att ctt cct gac gcc aga gac cct gcc ttt aaa gct gcc  960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag  1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat  1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt  1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag gcc gat  1152
Gly Ser Val Glu Glu Cys Leu Leu Asp Glu Asn Ser Leu Glu Ala Asp
370                 375                 380 gcc ggc tac aca cca gcc gct gct gct aca cca gcc act cca gca gca  1200
Ala Gly Tyr Thr Pro Ala Ala Ala Ala Thr Pro Ala Thr Pro Ala Ala
385                 390                 395                 400 aca cca gca gcc gct ggc ggc aag gcc aca acc gat gag cag aaa ctg  1248

```
                Thr Pro Ala Ala Ala Gly Gly Lys Ala Thr Thr Asp Glu Gln Lys Leu
                                405                 410                 415 ctg gaa gat gtg aac gcc ggc ttc aag gcc gcc gtg gct gct gct gca          1296
Leu Glu Asp Val Asn Ala Gly Phe Lys Ala Ala Val Ala Ala Ala Ala
            420                 425                 430 aat gcc cct ccc gcc gac aag ttc aag atc ttc gag gcc gcc ttc agc          1344
Asn Ala Pro Pro Ala Asp Lys Phe Lys Ile Phe Glu Ala Ala Phe Ser
        435                 440                 445 gag agc agc aag gga ctg ctg gcc aca tct gcc gcc aaa gcc ccc gga          1392
Glu Ser Ser Lys Gly Leu Leu Ala Thr Ser Ala Ala Lys Ala Pro Gly
    450                 455                 460 ctg atc ccc aag ctg gac acc gcc tac gac gtg gcc tac aaa gcc gcc          1440
Leu Ile Pro Lys Leu Asp Thr Ala Tyr Asp Val Ala Tyr Lys Ala Ala
465                 470                 475                 480 gag gcc acc cca gag gcc aaa tac gat gcc ttc gtg acc gct ctg acc          1488
Glu Ala Thr Pro Glu Ala Lys Tyr Asp Ala Phe Val Thr Ala Leu Thr
                485                 490                 495 gag gct ctg aga gtg att gcc ggc gct ctg gaa gtg cac gcc gtg aag          1536
Glu Ala Leu Arg Val Ile Ala Gly Ala Leu Glu Val His Ala Val Lys
            500                 505                 510 cca gcc acc gaa gaa gtg ctg gcc gcc aag att cct acc ggc gag ctg          1584
Pro Ala Thr Glu Glu Val Leu Ala Ala Lys Ile Pro Thr Gly Glu Leu
        515                 520                 525 cag atc gtg gac aag atc gac gcc gcc ttt aag atc gcc gcc acc gcc          1632
Gln Ile Val Asp Lys Ile Asp Ala Ala Phe Lys Ile Ala Ala Thr Ala
    530                 535                 540 gca aat gcc gcc cct acc aac gat aag ttc acc gtg ttc gag agc gcc          1680
Ala Asn Ala Ala Pro Thr Asn Asp Lys Phe Thr Val Phe Glu Ser Ala
545                 550                 555                 560 ttc aac aag gct ctg aac gag tgc acc ggc gga gcc tac gag aca tac          1728
Phe Asn Lys Ala Leu Asn Glu Cys Thr Gly Gly Ala Tyr Glu Thr Tyr
                565                 570                 575 aag ttc atc cca tct ctg gaa gcc gct gtg aag caa gcc tac gcc gcc          1776
Lys Phe Ile Pro Ser Leu Glu Ala Ala Val Lys Gln Ala Tyr Ala Ala
            580                 585                 590 aca gtg gcc gct gcc ccc gaa gtg aag tac gcc gtg ttt gag gcc gca          1824
Thr Val Ala Ala Ala Pro Glu Val Lys Tyr Ala Val Phe Glu Ala Ala
        595                 600                 605 ctg acc aag gcc atc acc gcc atg aca caa gcc cag aag gcc ggc aaa          1872
Leu Thr Lys Ala Ile Thr Ala Met Thr Gln Ala Gln Lys Ala Gly Lys
    610                 615                 620 cca gct gct gca gct gaa ttc acg ctg atc ccc atc gct gtg ggt ggt          1920
Pro Ala Ala Ala Ala Glu Phe Thr Leu Ile Pro Ile Ala Val Gly Gly
625                 630                 635                 640 gcc ctg gcg ggg ctg gtc ctc atc gtc ctc atc gcc tac ctc gtc ggc          1968
Ala Leu Ala Gly Leu Val Leu Ile Val Leu Ile Ala Tyr Leu Val Gly
                645                 650                 655 agg aag agg agt cac gca ggc tac cag act atc tag taa                      2007
Arg Lys Arg Ser His Ala Gly Tyr Gln Thr Ile
            660                 665

<210> SEQ ID NO 84
<211> LENGTH: 667
<212> TYPE: PRT
<213> ORGANISM: Artificial sequence
<220> FEATURE:
<223> OTHER INFORMATION: Synthetic Construct

<400> SEQUENCE: 84

Met Ala Pro Arg Ser Ala Arg Arg Pro Leu Leu Leu Leu Leu Leu Leu
1               5                   10                  15
```

```
Leu Leu Leu Gly Leu Met His Cys Ala Ser Ala Ala Met Phe Met Val
             20                  25                  30

Lys Asn Gly Asn Gly Thr Ala Cys Ile Met Ala Asn Phe Ser Ala Ala
         35                  40                  45

Phe Ser Val Asn Tyr Asp Thr Lys Ser Gly Pro Lys Asn Met Thr Leu
     50                  55                  60

Asp Leu Pro Ser Asp Ala Thr Val Val Leu Asn Arg Ser Ser Cys Gly
 65                  70                  75                  80

Lys Glu Asn Thr Ser Asp Pro Ser Leu Val Ile Ala Phe Gly Arg Gly
                 85                  90                  95

His Thr Leu Thr Leu Asn Phe Thr Arg Asn Ala Thr Arg Tyr Ser Val
             100                 105                 110

Gln Leu Met Ser Phe Val Tyr Asn Leu Ser Asp Thr His Leu Phe Pro
             115                 120                 125

Asn Ala Ser Ser Lys Glu Ile Lys Thr Val Glu Ser Ile Thr Asp Ile
 130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
                 165                 170                 175

Tyr Leu Ser Asn Ser Ser Phe Ser Arg Gly Glu Thr Arg Cys Glu Gln
             180                 185                 190

Asp Arg Pro Ser Pro Thr Thr Ala Pro Pro Ala Pro Pro Ser Pro Ser
             195                 200                 205

Pro Ser Pro Val Pro Lys Ser Pro Ser Val Asp Lys Tyr Asn Val Ser
     210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
                 245                 250                 255

Ile Asn Pro Asn Lys Thr Ser Ala Ser Gly Ser Cys Gly Ala His Leu
             260                 265                 270

Val Thr Leu Glu Leu His Ser Glu Gly Thr Thr Val Leu Leu Phe Gln
             275                 280                 285

Phe Gly Met Asn Ala Ser Ser Ser Arg Phe Phe Leu Gln Gly Ile Gln
 290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                 325                 330                 335

Cys Asn Ala Glu Glu His Val Arg Val Thr Lys Ala Phe Ser Val Asn
             340                 345                 350

Ile Phe Lys Val Trp Val Gln Ala Phe Lys Val Glu Gly Gly Gln Phe
             355                 360                 365

Gly Ser Val Glu Glu Cys Leu Leu Asp Glu Asn Ser Leu Glu Ala Asp
         370                 375                 380

Ala Gly Tyr Thr Pro Ala Ala Ala Thr Pro Ala Thr Pro Ala Ala
385                 390                 395                 400

Thr Pro Ala Ala Ala Gly Gly Lys Ala Thr Thr Asp Glu Gln Lys Leu
             405                 410                 415

Leu Glu Asp Val Asn Ala Gly Phe Lys Ala Ala Val Ala Ala Ala Ala
             420                 425                 430
```

```
Asn Ala Pro Pro Ala Asp Lys Phe Lys Ile Phe Glu Ala Ala Phe Ser
            435                 440                 445

Glu Ser Ser Lys Gly Leu Leu Ala Thr Ser Ala Ala Lys Ala Pro Gly
        450                 455                 460

Leu Ile Pro Lys Leu Asp Thr Ala Tyr Asp Val Ala Tyr Lys Ala Ala
465                 470                 475                 480

Glu Ala Thr Pro Glu Ala Lys Tyr Asp Ala Phe Val Thr Ala Leu Thr
                485                 490                 495

Glu Ala Leu Arg Val Ile Ala Gly Leu Glu Val His Ala Val Lys
            500                 505                 510

Pro Ala Thr Glu Glu Val Leu Ala Ala Lys Ile Pro Thr Gly Glu Leu
            515                 520                 525

Gln Ile Val Asp Lys Ile Asp Ala Ala Phe Lys Ile Ala Ala Thr Ala
        530                 535                 540

Ala Asn Ala Ala Pro Thr Asn Asp Lys Phe Thr Val Phe Glu Ser Ala
545                 550                 555                 560

Phe Asn Lys Ala Leu Asn Glu Cys Thr Gly Gly Ala Tyr Glu Thr Tyr
                565                 570                 575

Lys Phe Ile Pro Ser Leu Glu Ala Val Lys Gln Ala Tyr Ala Ala
            580                 585                 590

Thr Val Ala Ala Pro Glu Val Lys Tyr Ala Val Phe Glu Ala Ala
        595                 600                 605

Leu Thr Lys Ala Ile Thr Ala Met Thr Gln Ala Gln Lys Ala Gly Lys
            610                 615                 620

Pro Ala Ala Ala Ala Glu Phe Thr Leu Ile Pro Ile Ala Val Gly Gly
625                 630                 635                 640

Ala Leu Ala Gly Leu Val Leu Ile Val Leu Ile Ala Tyr Leu Val Gly
                645                 650                 655

Arg Lys Arg Ser His Ala Gly Tyr Gln Thr Ile
            660                 665

<210> SEQ ID NO 85
<211> LENGTH: 732
<212> TYPE: DNA
<213> ORGANISM: Phleum pratense
<220> FEATURE:
<221> NAME/KEY: CDS
<222> LOCATION: (7)..(726)

<400> SEQUENCE: 85 ctcgag atc ccc aaa gtg cct ccc ggc cca aac atc acc gcc aca tac      48
       Ile Pro Lys Val Pro Pro Gly Pro Asn Ile Thr Ala Thr Tyr
       1               5                  10 ggc gac aag tgg ctg gac gcc aag agc act tgg tac ggc aag cct act    96
Gly Asp Lys Trp Leu Asp Ala Lys Ser Thr Trp Tyr Gly Lys Pro Thr
15                  20                  25                  30 ggc gcc gga ccc aag gac aat ggc ggc gct tgt ggc tac aag gac gtg  144
Gly Ala Gly Pro Lys Asp Asn Gly Gly Ala Cys Gly Tyr Lys Asp Val
                35                  40                  45 gac aag ccc ccc ttc tct ggc atg acc ggc tgc ggc aac acc ccc atc  192
Asp Lys Pro Pro Phe Ser Gly Met Thr Gly Cys Gly Asn Thr Pro Ile
            50                  55                  60 ttc aag agc ggc aga ggc tgt ggc agc tgc ttc gag atc aag tgc acc  240
Phe Lys Ser Gly Arg Gly Cys Gly Ser Cys Phe Glu Ile Lys Cys Thr
        65                  70                  75 aag ccc gag gct tgc agc ggc gaa cca gtc gtg gtg cac atc acc gac  288
Lys Pro Glu Ala Cys Ser Gly Glu Pro Val Val Val His Ile Thr Asp
80                  85                  90
```

```
gac aac gag gaa ccc att gcc ccc tac cac ttc gat ctg agc ggc cac      336
Asp Asn Glu Glu Pro Ile Ala Pro Tyr His Phe Asp Leu Ser Gly His
 95             100                 105                 110 gcc ttt ggc gcc atg gcc aag aaa ggc gac gag cag aag ctg aga tct      384
Ala Phe Gly Ala Met Ala Lys Lys Gly Asp Glu Gln Lys Leu Arg Ser
                115                 120                 125 gcc ggc gag ctg gaa ctg cag ttt cgg aga gtg aag tgc aag tac ccc      432
Ala Gly Glu Leu Glu Leu Gln Phe Arg Arg Val Lys Cys Lys Tyr Pro
        130                 135                 140 gag ggc acc aaa gtg aca ttt cac gtg gaa aag ggc agc aac ccc aac      480
Glu Gly Thr Lys Val Thr Phe His Val Glu Lys Gly Ser Asn Pro Asn
145                 150                 155 tat ctg gct ctg ctc gtg aaa tac gtg aac ggc gac ggc gac gtc gtg      528
Tyr Leu Ala Leu Leu Val Lys Tyr Val Asn Gly Asp Gly Asp Val Val
    160                 165                 170 gcc gtg gac atc aaa gag aag ggc aag gac aag tgg atc gag ctg aaa      576
Ala Val Asp Ile Lys Glu Lys Gly Lys Asp Lys Trp Ile Glu Leu Lys
175                 180                 185                 190 gag agc tgg ggc gcc atc tgg cgg atc gac acc cca gat aag ctg acc      624
Glu Ser Trp Gly Ala Ile Trp Arg Ile Asp Thr Pro Asp Lys Leu Thr
                195                 200                 205 ggc cct ttc acc gtg cgg tac aca aca gag ggc ggc acc aag aca gag      672
Gly Pro Phe Thr Val Arg Tyr Thr Thr Glu Gly Gly Thr Lys Thr Glu
            210                 215                 220 gcc gag gat gtg atc cca gag ggc tgg aag gcc gac acc agc tac gag      720
Ala Glu Asp Val Ile Pro Glu Gly Trp Lys Ala Asp Thr Ser Tyr Glu
        225                 230                 235 agc aaa gaattc                                                       732
Ser Lys
    240
```

<210> SEQ ID NO 86
<211> LENGTH: 240
<212> TYPE: PRT
<213> ORGANISM: Phleum pratense

<400> SEQUENCE: 86

```
Ile Pro Lys Val Pro Gly Pro Asn Ile Thr Ala Thr Tyr Gly Asp
 1               5                  10                  15

Lys Trp Leu Asp Ala Lys Ser Thr Trp Tyr Gly Lys Pro Thr Gly Ala
             20                  25                  30

Gly Pro Lys Asp Asn Gly Gly Ala Cys Gly Tyr Lys Asp Val Asp Lys
         35                  40                  45

Pro Pro Phe Ser Gly Met Thr Gly Cys Gly Asn Thr Pro Ile Phe Lys
     50                  55                  60

Ser Gly Arg Gly Cys Gly Ser Cys Phe Glu Ile Lys Cys Thr Lys Pro
 65                  70                  75                  80

Glu Ala Cys Ser Gly Glu Pro Val Val His Ile Thr Asp Asp Asn
                 85                  90                  95

Glu Glu Pro Ile Ala Pro Tyr His Phe Asp Leu Ser Gly His Ala Phe
            100                 105                 110

Gly Ala Met Ala Lys Lys Gly Asp Glu Gln Lys Leu Arg Ser Ala Gly
        115                 120                 125

Glu Leu Glu Leu Gln Phe Arg Arg Val Lys Cys Lys Tyr Pro Glu Gly
    130                 135                 140

Thr Lys Val Thr Phe His Val Glu Lys Gly Ser Asn Pro Asn Tyr Leu
145                 150                 155                 160
```

```
Ala Leu Leu Val Lys Tyr Val Asn Gly Asp Gly Asp Val Val Ala Val
            165                 170                 175

Asp Ile Lys Glu Lys Gly Lys Asp Lys Trp Ile Glu Leu Lys Glu Ser
        180                 185                 190

Trp Gly Ala Ile Trp Arg Ile Asp Thr Pro Asp Lys Leu Thr Gly Pro
            195                 200                 205

Phe Thr Val Arg Tyr Thr Thr Glu Gly Gly Lys Thr Glu Ala Glu
        210                 215                 220

Asp Val Ile Pro Glu Gly Trp Lys Ala Asp Thr Ser Tyr Glu Ser Lys
225                 230                 235                 240

<210> SEQ ID NO 87
<211> LENGTH: 1986
<212> TYPE: DNA
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(1986)

<400> SEQUENCE: 87 atg gcg ccc cgc agc gcc cgg cga ccc ctg ctg ctg cta ctg ctg ttg      48
Met Ala Pro Arg Ser Ala Arg Arg Pro Leu Leu Leu Leu Leu Leu Leu
1               5                   10                  15 ctg ctg ctc ggc ctc atg cat tgt gcg tca gca gca atg ttt atg gtg      96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc     144
Lys Asn Gly Asn Gly Thr Ala Cys Ile Met Ala Asn Phe Ser Ala Ala
        35                  40                  45 ttc tca gtg aac tac gac acc aag agt ggc cct aag aac atg acc ctt     192
Phe Ser Val Asn Tyr Asp Thr Lys Ser Gly Pro Lys Asn Met Thr Leu
    50                  55                  60 gac ctg cca tca gat gcc aca gtg gtg ctc aac cgc agc tcc tgt gga     240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga     288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc     336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc     384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc     432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc     480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg     528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa     576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg     624
Asp Arg Pro Ser Pro Thr Thr Ala Pro Pro Ala Pro Pro Ser Pro Ser
        195                 200                 205
```

| | | |
|---|---|---|
| ccc tca ccc gtg ccc aag agc ccc tct gtg gac aag tac aac gtg agc<br>Pro Ser Pro Val Pro Lys Ser Pro Ser Val Asp Lys Tyr Asn Val Ser<br>210                             215                         220 | 672 |
| ggc acc aac ggg acc tgc ctg ctg gcc agc atg ggg ctg cag ctg aac<br>Gly Thr Asn Gly Thr Cys Leu Leu Ala Ser Met Gly Leu Gln Leu Asn<br>225                       230                   235                    240 | 720 |
| ctc acc tat gag agg aag gac aac acg acg gtg aca agg ctt ctc aac<br>Leu Thr Tyr Glu Arg Lys Asp Asn Thr Thr Val Thr Arg Leu Leu Asn<br>                    245                   250                    255 | 768 |
| atc aac ccc aac aag acc tcg gcc agc ggg agc tgc ggc gcc cac ctg<br>Ile Asn Pro Asn Lys Thr Ser Ala Ser Gly Ser Cys Gly Ala His Leu<br>              260                   265                   270 | 816 |
| gtg act ctg gag ctg cac agc gag ggc acc acc gtc ctg ctc ttc cag<br>Val Thr Leu Glu Leu His Ser Glu Gly Thr Thr Val Leu Leu Phe Gln<br>275                           280                   285 | 864 |
| ttc ggg atg aat gca agt tct agc cgg ttt ttc cta caa gga atc cag<br>Phe Gly Met Asn Ala Ser Ser Ser Arg Phe Phe Leu Gln Gly Ile Gln<br>         290                   295                   300 | 912 |
| ttg aat aca att ctt cct gac gcc aga gac cct gcc ttt aaa gct gcc<br>Leu Asn Thr Ile Leu Pro Asp Ala Arg Asp Pro Ala Phe Lys Ala Ala<br>305                         310                   315                320 | 960 |
| aac ggc tcc ctg cga gcg ctg cag gcc aca gtc ggc aat tcc tac aag<br>Asn Gly Ser Leu Arg Ala Leu Gln Ala Thr Val Gly Asn Ser Tyr Lys<br>                    325                   330                   335 | 1008 |
| tgc aac gcg gag gag cac gtc cgt gtc acg aag gcg ttt tca gtc aat<br>Cys Asn Ala Glu Glu His Val Arg Val Thr Lys Ala Phe Ser Val Asn<br>              340                   345                   350 | 1056 |
| ata ttc aaa gtg tgg gtc cag gct ttc aag gtg gaa ggt ggc cag ttt<br>Ile Phe Lys Val Trp Val Gln Ala Phe Lys Val Glu Gly Gly Gln Phe<br>355                         360                   365 | 1104 |
| ggc tct gtg gag gag tgt ctg ctg gac gag aac agc ctc gag atc ccc<br>Gly Ser Val Glu Glu Cys Leu Leu Asp Glu Asn Ser Leu Glu Ile Pro<br>         370                   375                   380 | 1152 |
| aaa gtg cct ccc ggc cca aac atc acc gcc aca tac ggc gac aag tgg<br>Lys Val Pro Pro Gly Pro Asn Ile Thr Ala Thr Tyr Gly Asp Lys Trp<br>385                         390                   395                400 | 1200 |
| ctg gac gcc aag agc act tgg tac ggc aag cct act ggc gcc gga ccc<br>Leu Asp Ala Lys Ser Thr Trp Tyr Gly Lys Pro Thr Gly Ala Gly Pro<br>                    405                   410                   415 | 1248 |
| aag gac aat ggc ggc gct tgt ggc tac aag gac gtg gac aag ccc ccc<br>Lys Asp Asn Gly Gly Ala Cys Gly Tyr Lys Asp Val Asp Lys Pro Pro<br>              420                   425                   430 | 1296 |
| ttc tct ggc atg acc ggc tgc ggc aac acc ccc atc ttc aag agc ggc<br>Phe Ser Gly Met Thr Gly Cys Gly Asn Thr Pro Ile Phe Lys Ser Gly<br>435                         440                   445 | 1344 |
| aga ggc tgt ggc agc tgc ttc gag atc aag tgc acc aag ccc gag gct<br>Arg Gly Cys Gly Ser Cys Phe Glu Ile Lys Cys Thr Lys Pro Glu Ala<br>         450                   455                   460 | 1392 |
| tgc agc ggc gaa cca gtc gtg gtg cac atc acc gac gac aac gag gaa<br>Cys Ser Gly Glu Pro Val Val Val His Ile Thr Asp Asp Asn Glu Glu<br>465                         470                   475                480 | 1440 |
| ccc att gcc ccc tac cac ttc gat ctg agc ggc cac gcc ttt ggc gcc<br>Pro Ile Ala Pro Tyr His Phe Asp Leu Ser Gly His Ala Phe Gly Ala<br>                    485                   490                   495 | 1488 |
| atg gcc aag aaa ggc gac gag cag aag ctg aga tct gcc ggc gag ctg<br>Met Ala Lys Lys Gly Asp Glu Gln Lys Leu Arg Ser Ala Gly Glu Leu<br>              500                   505                   510 | 1536 |
| gaa ctg cag ttt cgg aga gtg aag tgc aag tac ccc gag ggc acc aaa<br>Glu Leu Gln Phe Arg Arg Val Lys Cys Lys Tyr Pro Glu Gly Thr Lys | 1584 |

-continued

```
               515                 520                 525
gtg aca ttt cac gtg gaa aag ggc agc aac ccc aac tat ctg gct ctg    1632
Val Thr Phe His Val Glu Lys Gly Ser Asn Pro Asn Tyr Leu Ala Leu
        530                 535                 540 ctc gtg aaa tac gtg aac ggc gac ggc gac gtc gtg gcc gtg gac atc    1680
Leu Val Lys Tyr Val Asn Gly Asp Gly Asp Val Val Ala Val Asp Ile
545                 550                 555                 560 aaa gag aag ggc aag gac aag tgg atc gag ctg aaa gag agc tgg ggc    1728
Lys Glu Lys Gly Lys Asp Lys Trp Ile Glu Leu Lys Glu Ser Trp Gly
                565                 570                 575 gcc atc tgg cgg atc gac acc cca gat aag ctg acc ggc cct ttc acc    1776
Ala Ile Trp Arg Ile Asp Thr Pro Asp Lys Leu Thr Gly Pro Phe Thr
            580                 585                 590 gtg cgg tac aca aca gag ggc ggc acc aag aca gag gcc gag gat gtg    1824
Val Arg Tyr Thr Thr Glu Gly Gly Thr Lys Thr Glu Ala Glu Asp Val
        595                 600                 605 atc cca gag ggc tgg aag gcc gac acc agc tac gag agc aaa gaa ttc    1872
Ile Pro Glu Gly Trp Lys Ala Asp Thr Ser Tyr Glu Ser Lys Glu Phe
610                 615                 620 acg ctg atc ccc atc gct gtg ggt ggt gcc ctg gcg ggg ctg gtc ctc    1920
Thr Leu Ile Pro Ile Ala Val Gly Gly Ala Leu Ala Gly Leu Val Leu
625                 630                 635                 640 atc gtc ctc atc gcc tac ctc gtc ggc agg aag agg agt cac gca ggc    1968
Ile Val Leu Ile Ala Tyr Leu Val Gly Arg Lys Arg Ser His Ala Gly
                645                 650                 655 tac cag act atc tag taa                                            1986
Tyr Gln Thr Ile
            660
```

<210> SEQ ID NO 88
<211> LENGTH: 660
<212> TYPE: PRT
<213> ORGANISM: Artificial sequence
<220> FEATURE:
<223> OTHER INFORMATION: Synthetic Construct

<400> SEQUENCE: 88

```
Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
        35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
                85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
        115                 120                 125

Asn Ala Ser Ser Lys Glu Ile Lys Thr Val Glu Ser Ile Thr Asp Ile
    130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
```

-continued

```
                165                 170                 175
Tyr Leu Ser Asn Ser Ser Phe Ser Arg Gly Glu Thr Arg Cys Glu Gln
                180                 185                 190

Asp Arg Pro Ser Pro Thr Thr Ala Pro Pro Ala Pro Pro Ser Pro Ser
                195                 200                 205

Pro Ser Pro Val Pro Lys Ser Pro Ser Val Asp Lys Tyr Asn Val Ser
210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Val Thr Arg Leu Leu Asn
                245                 250                 255

Ile Asn Pro Asn Lys Thr Ser Ala Ser Gly Ser Cys Gly Ala His Leu
                260                 265                 270

Val Thr Leu Glu Leu His Ser Glu Gly Thr Thr Val Leu Leu Phe Gln
                275                 280                 285

Phe Gly Met Asn Ala Ser Ser Ser Arg Phe Phe Leu Gln Gly Ile Gln
                290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
                340                 345                 350

Ile Phe Lys Val Trp Val Gln Ala Phe Lys Val Glu Gly Gly Gln Phe
                355                 360                 365

Gly Ser Val Glu Glu Cys Leu Leu Asp Glu Asn Ser Leu Glu Ile Pro
370                 375                 380

Lys Val Pro Pro Gly Pro Asn Ile Thr Ala Thr Tyr Gly Asp Lys Trp
385                 390                 395                 400

Leu Asp Ala Lys Ser Thr Trp Tyr Gly Lys Pro Thr Gly Ala Gly Pro
                405                 410                 415

Lys Asp Asn Gly Gly Ala Cys Gly Tyr Lys Asp Val Asp Lys Pro Pro
                420                 425                 430

Phe Ser Gly Met Thr Gly Cys Gly Asn Thr Pro Ile Phe Lys Ser Gly
                435                 440                 445

Arg Gly Cys Gly Ser Cys Phe Glu Ile Lys Cys Thr Lys Pro Glu Ala
                450                 455                 460

Cys Ser Gly Glu Pro Val Val His Ile Thr Asp Asp Asn Glu Glu
465                 470                 475                 480

Pro Ile Ala Pro Tyr His Phe Asp Leu Ser Gly His Ala Phe Gly Ala
                485                 490                 495

Met Ala Lys Lys Gly Asp Glu Gln Lys Leu Arg Ser Ala Gly Glu Leu
                500                 505                 510

Glu Leu Gln Phe Arg Arg Val Lys Cys Lys Tyr Pro Glu Gly Thr Lys
                515                 520                 525

Val Thr Phe His Val Glu Lys Gly Ser Asn Pro Asn Tyr Leu Ala Leu
                530                 535                 540

Leu Val Lys Tyr Val Asn Gly Asp Gly Asp Val Val Ala Val Asp Ile
545                 550                 555                 560

Lys Glu Lys Gly Lys Asp Lys Trp Ile Glu Leu Lys Glu Ser Trp Gly
                565                 570                 575

Ala Ile Trp Arg Ile Asp Thr Pro Asp Lys Leu Thr Gly Pro Phe Thr
                580                 585                 590
```

```
Val Arg Tyr Thr Thr Glu Gly Gly Thr Lys Thr Glu Ala Glu Asp Val
        595                 600                 605

Ile Pro Glu Gly Trp Lys Ala Asp Thr Ser Tyr Glu Ser Lys Glu Phe
    610                 615                 620

Thr Leu Ile Pro Ile Ala Val Gly Gly Ala Leu Ala Gly Leu Val Leu
625                 630                 635                 640

Ile Val Leu Ile Ala Tyr Leu Val Gly Arg Lys Arg Ser His Ala Gly
                645                 650                 655

Tyr Gln Thr Ile
            660

<210> SEQ ID NO 89
<211> LENGTH: 804
<212> TYPE: DNA
<213> ORGANISM: Phleum pratense
<220> FEATURE:
<221> NAME/KEY: CDS
<222> LOCATION: (7)..(798)

<400> SEQUENCE: 89 ctcgag gcc gcc gat ctg ggc tat ggc cca gct aca cca gct gcc cca         48
       Ala Ala Asp Leu Gly Tyr Gly Pro Ala Thr Pro Ala Ala Pro
       1               5                   10 gcc gcc gga tac aca cca gca act cca gcc gct cca gct gaa gca gcc        96
Ala Ala Gly Tyr Thr Pro Ala Thr Pro Ala Ala Pro Ala Glu Ala Ala
15              20                  25                  30 cca gct gga aag gcc aca acc gag gaa cag aag ctg atc gag aag atc       144
Pro Ala Gly Lys Ala Thr Thr Glu Glu Gln Lys Leu Ile Glu Lys Ile
                35                  40                  45 aac gcc ggc ttc aag gcc gct ctg gct gca gct gct ggg gtg cag cca       192
Asn Ala Gly Phe Lys Ala Ala Leu Ala Ala Ala Ala Gly Val Gln Pro
            50                  55                  60 gcc gac aag tac aga aca ttc gtg gcc aca ttc gga gcc gcc agc aac       240
Ala Asp Lys Tyr Arg Thr Phe Val Ala Thr Phe Gly Ala Ala Ser Asn
        65                  70                  75 aag gcc ttt gcc gag gga ctg agc ggc gag cct aaa ggc gcc gct gag       288
Lys Ala Phe Ala Glu Gly Leu Ser Gly Glu Pro Lys Gly Ala Ala Glu
80                  85                  90 tct agc agc aag gcc gca ctg acc agc aag ctg gac gcc gcc tac aag       336
Ser Ser Ser Lys Ala Ala Leu Thr Ser Lys Leu Asp Ala Ala Tyr Lys
95                  100                 105                 110 ctg gcc tac aag aca gcc gaa ggc gcc acc ccc gag gcc aaa tac gat       384
Leu Ala Tyr Lys Thr Ala Glu Gly Ala Thr Pro Glu Ala Lys Tyr Asp
                115                 120                 125 gcc tac gtg gcc act ctg agc gag gct ctg aga atc att gcc ggc aca       432
Ala Tyr Val Ala Thr Leu Ser Glu Ala Leu Arg Ile Ile Ala Gly Thr
            130                 135                 140 ctg gaa gtg cac gcc gtg aag cca gcc gct gag gaa gtg aaa gtg atc       480
Leu Glu Val His Ala Val Lys Pro Ala Ala Glu Glu Val Lys Val Ile
        145                 150                 155 cca gcc ggc gag ctc caa gtg att gag aaa gtg gat gcc gcc ttc aaa       528
Pro Ala Gly Glu Leu Gln Val Ile Glu Lys Val Asp Ala Ala Phe Lys
    160                 165                 170 gtg gcc gcc acc gct gcc aat gcc gcc cca gcc aat gac aag ttc acc       576
Val Ala Ala Thr Ala Ala Asn Ala Ala Pro Ala Asn Asp Lys Phe Thr
175                 180                 185                 190 gtg ttt gag gcc gcc ttt aac gac gcc atc aag gcc tct acc ggc gga       624
Val Phe Glu Ala Ala Phe Asn Asp Ala Ile Lys Ala Ser Thr Gly Gly
                195                 200                 205
```

```
gcc tac gag agc tac aag ttc atc ccc gct ctg gaa gcc gcc gtg aaa    672
Ala Tyr Glu Ser Tyr Lys Phe Ile Pro Ala Leu Glu Ala Ala Val Lys
            210                 215                 220 caa gcc tat gcc gcc aca gtg gcc aca gcc ccc gaa gtg aag tac aca    720
Gln Ala Tyr Ala Ala Thr Val Ala Thr Ala Pro Glu Val Lys Tyr Thr
225                 230                 235 gtg ttc gag aca gct ctg aag aaa gcc atc acc gcc atg tcc gag gcc    768
Val Phe Glu Thr Ala Leu Lys Lys Ala Ile Thr Ala Met Ser Glu Ala
    240                 245                 250 cag aag gcc gcc aaa cca gct gct gct gct gaattc                     804
Gln Lys Ala Ala Lys Pro Ala Ala Ala Ala
255                 260
```

<210> SEQ ID NO 90
<211> LENGTH: 264
<212> TYPE: PRT
<213> ORGANISM: Phleum pratense

<400> SEQUENCE: 90

```
Ala Ala Asp Leu Gly Tyr Gly Pro Ala Thr Pro Ala Ala Pro Ala Ala
1               5                   10                  15

Gly Tyr Thr Pro Ala Thr Pro Ala Ala Pro Ala Glu Ala Ala Pro Ala
            20                  25                  30

Gly Lys Ala Thr Thr Glu Glu Gln Lys Leu Ile Glu Lys Ile Asn Ala
        35                  40                  45

Gly Phe Lys Ala Ala Leu Ala Ala Ala Gly Val Gln Pro Ala Asp
    50                  55                  60

Lys Tyr Arg Thr Phe Val Ala Thr Phe Gly Ala Ala Ser Asn Lys Ala
65                  70                  75                  80

Phe Ala Glu Gly Leu Ser Gly Glu Pro Lys Gly Ala Ala Glu Ser Ser
                85                  90                  95

Ser Lys Ala Ala Leu Thr Ser Lys Leu Asp Ala Ala Tyr Lys Leu Ala
            100                 105                 110

Tyr Lys Thr Ala Glu Gly Ala Thr Pro Glu Ala Lys Tyr Asp Ala Tyr
        115                 120                 125

Val Ala Thr Leu Ser Glu Ala Leu Arg Ile Ile Ala Gly Thr Leu Glu
    130                 135                 140

Val His Ala Val Lys Pro Ala Ala Glu Glu Val Lys Val Ile Pro Ala
145                 150                 155                 160

Gly Glu Leu Gln Val Ile Glu Lys Val Asp Ala Ala Phe Lys Val Ala
                165                 170                 175

Ala Thr Ala Ala Asn Ala Ala Pro Ala Asn Asp Lys Phe Thr Val Phe
            180                 185                 190

Glu Ala Ala Phe Asn Asp Ala Ile Lys Ala Ser Thr Gly Gly Ala Tyr
        195                 200                 205

Glu Ser Tyr Lys Phe Ile Pro Ala Leu Glu Ala Ala Val Lys Gln Ala
    210                 215                 220

Tyr Ala Ala Thr Val Ala Thr Ala Pro Glu Val Lys Tyr Thr Val Phe
225                 230                 235                 240

Glu Thr Ala Leu Lys Lys Ala Ile Thr Ala Met Ser Glu Ala Gln Lys
                245                 250                 255

Ala Ala Lys Pro Ala Ala Ala Ala
            260
```

<210> SEQ ID NO 91
<211> LENGTH: 2058
<212> TYPE: DNA

```
<213> ORGANISM: Artificial sequence
<220> FEATURE:
<223> OTHER INFORMATION: Synthetic Construct
<220> FEATURE:
<221> NAME/KEY: CDS
<222> LOCATION: (1)..(2058)

<400> SEQUENCE: 91 atg gcg ccc cgc agc gcc cgg cga ccc ctg ctg ctg cta ctg ctg ttg      48
Met Ala Pro Arg Ser Ala Arg Arg Pro Leu Leu Leu Leu Leu Leu Leu
1               5                   10                  15 ctg ctg ctc ggc ctc atg cat tgt gcg tca gca gca atg ttt atg gtg      96
Leu Leu Leu Gly Leu Met His Cys Ala Ser Ala Ala Met Phe Met Val
            20                  25                  30 aaa aat ggc aac ggg acc gcg tgc ata atg gcc aac ttc tct gct gcc     144
Lys Asn Gly Asn Gly Thr Ala Cys Ile Met Ala Asn Phe Ser Ala Ala
        35                  40                  45 ttc tca gtg aac tac gac acc aag agt ggc cct aag aac atg acc ctt     192
Phe Ser Val Asn Tyr Asp Thr Lys Ser Gly Pro Lys Asn Met Thr Leu
    50                  55                  60 gac ctg cca tca gat gcc aca gtg gtg ctc aac cgc agc tcc tgt gga     240
Asp Leu Pro Ser Asp Ala Thr Val Val Leu Asn Arg Ser Ser Cys Gly
65                  70                  75                  80 aaa gag aac act tct gac ccc agt ctc gtg att gct ttt gga aga gga     288
Lys Glu Asn Thr Ser Asp Pro Ser Leu Val Ile Ala Phe Gly Arg Gly
                85                  90                  95 cat aca ctc act ctc aat ttc acg aga aat gca aca cgt tac agc gtc     336
His Thr Leu Thr Leu Asn Phe Thr Arg Asn Ala Thr Arg Tyr Ser Val
            100                 105                 110 cag ctc atg agt ttt gtt tat aac ttg tca gac aca cac ctt ttc ccc     384
Gln Leu Met Ser Phe Val Tyr Asn Leu Ser Asp Thr His Leu Phe Pro
        115                 120                 125 aat gcg agc tcc aaa gaa atc aag act gtg gaa tct ata act gac atc     432
Asn Ala Ser Ser Lys Glu Ile Lys Thr Val Glu Ser Ile Thr Asp Ile
    130                 135                 140 agg gca gat ata gat aaa aaa tac aga tgt gtt agt ggc acc cag gtc     480
Arg Ala Asp Ile Asp Lys Lys Tyr Arg Cys Val Ser Gly Thr Gln Val
145                 150                 155                 160 cac atg aac aac gtg acc gta acg ctc cat gat gcc acc atc cag gcg     528
His Met Asn Asn Val Thr Val Thr Leu His Asp Ala Thr Ile Gln Ala
                165                 170                 175 tac ctt tcc aac agc agc ttc agc cgg gga gag aca cgc tgt gaa caa     576
Tyr Leu Ser Asn Ser Ser Phe Ser Arg Gly Glu Thr Arg Cys Glu Gln
            180                 185                 190 gac agg cct tcc cca acc aca gcg ccc cct gcg cca ccc agc ccc tcg     624
Asp Arg Pro Ser Pro Thr Thr Ala Pro Pro Ala Pro Pro Ser Pro Ser
        195                 200                 205 ccc tca ccc gtg ccc aag agc ccc tct gtg gac aag tac aac gtg agc     672
Pro Ser Pro Val Pro Lys Ser Pro Ser Val Asp Lys Tyr Asn Val Ser
    210                 215                 220 ggc acc aac ggg acc tgc ctg ctg gcc agc atg ggg ctg cag ctg aac     720
Gly Thr Asn Gly Thr Cys Leu Leu Ala Ser Met Gly Leu Gln Leu Asn
225                 230                 235                 240 ctc acc tat gag agg aag gac aac acg acg gtg aca agg ctt ctc aac     768
Leu Thr Tyr Glu Arg Lys Asp Asn Thr Thr Val Thr Arg Leu Leu Asn
                245                 250                 255 atc aac ccc aac aag acc tcg gcc agc ggg agc tgc ggc gcc cac ctg     816
Ile Asn Pro Asn Lys Thr Ser Ala Ser Gly Ser Cys Gly Ala His Leu
            260                 265                 270 gtg act ctg gag ctg cac agc gag ggc acc acc gtc ctg ctc ttc cag     864
Val Thr Leu Glu Leu His Ser Glu Gly Thr Thr Val Leu Leu Phe Gln
```

-continued

|  |  | 275 |  |  |  | 280 |  |  |  | 285 |  |  |  |  |
|---|---|---|---|---|---|---|---|---|---|---|---|---|---|---|
| ttc | ggg | atg | aat | gca | agt | tct | agc | cgg | ttt | ttc | cta | caa | gga | atc cag | 912 |
| Phe | Gly | Met | Asn | Ala | Ser | Ser | Ser | Arg | Phe | Phe | Leu | Gln | Gly | Ile Gln |  |
|  |  | 290 |  |  |  | 295 |  |  |  | 300 |  |  |  |  |

```
ttc ggg atg aat gca agt tct agc cgg ttt ttc cta caa gga atc cag      912
Phe Gly Met Asn Ala Ser Ser Ser Arg Phe Phe Leu Gln Gly Ile Gln
        290                 295                 300 ttg aat aca att ctt cct gac gcc aga gac cct gcc ttt aaa gct gcc      960
Leu Asn Thr Ile Leu Pro Asp Ala Arg Asp Pro Ala Phe Lys Ala Ala
305                 310                 315                 320 aac ggc tcc ctg cga gcg ctg cag gcc aca gtc ggc aat tcc tac aag     1008
Asn Gly Ser Leu Arg Ala Leu Gln Ala Thr Val Gly Asn Ser Tyr Lys
                325                 330                 335 tgc aac gcg gag gag cac gtc cgt gtc acg aag gcg ttt tca gtc aat     1056
Cys Asn Ala Glu Glu His Val Arg Val Thr Lys Ala Phe Ser Val Asn
            340                 345                 350 ata ttc aaa gtg tgg gtc cag gct ttc aag gtg gaa ggt ggc cag ttt     1104
Ile Phe Lys Val Trp Val Gln Ala Phe Lys Val Glu Gly Gly Gln Phe
        355                 360                 365 ggc tct gtg gag gag tgt ctg ctg gac gag aac agc ctc gag gcc gcc     1152
Gly Ser Val Glu Glu Cys Leu Leu Asp Glu Asn Ser Leu Glu Ala Ala
370                 375                 380 gat ctg ggc tat ggc cca gct aca cca gct gcc cca gcc gcc gga tac     1200
Asp Leu Gly Tyr Gly Pro Ala Thr Pro Ala Ala Pro Ala Ala Gly Tyr
385                 390                 395                 400 aca cca gca act cca gcc gct cca gct gaa gca gcc cca gct gga aag     1248
Thr Pro Ala Thr Pro Ala Ala Pro Ala Glu Ala Ala Pro Ala Gly Lys
                405                 410                 415 gcc aca acc gag gaa cag aag ctg atc gag aag atc aac gcc ggc ttc     1296
Ala Thr Thr Glu Glu Gln Lys Leu Ile Glu Lys Ile Asn Ala Gly Phe
            420                 425                 430 aag gcc gct ctg gct gca gct gct ggg gtg cag cca gcc gac aag tac     1344
Lys Ala Ala Leu Ala Ala Ala Ala Gly Val Gln Pro Ala Asp Lys Tyr
        435                 440                 445 aga aca ttc gtg gcc aca ttc gga gcc gcc agc aac aag gcc ttt gcc     1392
Arg Thr Phe Val Ala Thr Phe Gly Ala Ala Ser Asn Lys Ala Phe Ala
450                 455                 460 gag gga ctg agc ggc gag cct aaa ggc gcc gct gag tct agc agc aag     1440
Glu Gly Leu Ser Gly Glu Pro Lys Gly Ala Ala Glu Ser Ser Ser Lys
465                 470                 475                 480 gcc gca ctg acc agc aag ctg gac gcc gcc tac aag ctg gcc tac aag     1488
Ala Ala Leu Thr Ser Lys Leu Asp Ala Ala Tyr Lys Leu Ala Tyr Lys
                485                 490                 495 aca gcc gaa ggc gcc acc ccc gag gcc aaa tac gat gcc tac gtg gcc     1536
Thr Ala Glu Gly Ala Thr Pro Glu Ala Lys Tyr Asp Ala Tyr Val Ala
            500                 505                 510 act ctg agc gag gct ctg aga atc att gcc ggc aca ctg gaa gtg cac     1584
Thr Leu Ser Glu Ala Leu Arg Ile Ile Ala Gly Thr Leu Glu Val His
        515                 520                 525 gcc gtg aag cca gcc gct gag gaa gtg aaa gtg atc cca gcc ggc gag     1632
Ala Val Lys Pro Ala Ala Glu Glu Val Lys Val Ile Pro Ala Gly Glu
530                 535                 540 ctc caa gtg att gag aaa gtg gat gcc gcc ttc aaa gtg gcc gcc acc     1680
Leu Gln Val Ile Glu Lys Val Asp Ala Ala Phe Lys Val Ala Ala Thr
545                 550                 555                 560 gct gcc aat gcc gcc cca gcc aat gac aag ttc acc gtg ttt gag gcc     1728
Ala Ala Asn Ala Ala Pro Ala Asn Asp Lys Phe Thr Val Phe Glu Ala
                565                 570                 575 gcc ttt aac gac gcc atc aag gcc tct acc ggc gga gcc tac gag agc     1776
Ala Phe Asn Asp Ala Ile Lys Ala Ser Thr Gly Gly Ala Tyr Glu Ser
            580                 585                 590 tac aag ttc atc ccc gct ctg gaa gcc gcc gtg aaa caa gcc tat gcc     1824
```

```
Tyr Lys Phe Ile Pro Ala Leu Glu Ala Ala Val Lys Gln Ala Tyr Ala
            595                 600                 605 gcc aca gtg gcc aca gcc ccc gaa gtg aag tac aca gtg ttc gag aca         1872
Ala Thr Val Ala Thr Ala Pro Glu Val Lys Tyr Thr Val Phe Glu Thr
610                 615                 620 gct ctg aag aaa gcc atc acc gcc atg tcc gag gcc cag aag gcc gcc         1920
Ala Leu Lys Lys Ala Ile Thr Ala Met Ser Glu Ala Gln Lys Ala Ala
625                 630                 635                 640 aaa cca gct gct gct gct gaa ttc acg ctg atc ccc atc gct gtg ggt         1968
Lys Pro Ala Ala Ala Ala Glu Phe Thr Leu Ile Pro Ile Ala Val Gly
            645                 650                 655 ggt gcc ctg gcg ggg ctg gtc ctc atc gtc ctc atc gcc tac ctc gtc         2016
Gly Ala Leu Ala Gly Leu Val Leu Ile Val Leu Ile Ala Tyr Leu Val
            660                 665                 670 ggc agg aag agg agt cac gca ggc tac cag act atc tag taa                 2058
Gly Arg Lys Arg Ser His Ala Gly Tyr Gln Thr Ile
            675                 680

<210> SEQ ID NO 92
<211> LENGTH: 684
<212> TYPE: PRT
<213> ORGANISM: Artificial sequence
<220> FEATURE:
<223> OTHER INFORMATION: Synthetic Construct

<400> SEQUENCE: 92

Met Ala Pro Arg Ser Ala Arg Arg Pro Leu Leu Leu Leu Leu Leu Leu
1               5                   10                  15

Leu Leu Leu Gly Leu Met His Cys Ala Ser Ala Ala Met Phe Met Val
            20                  25                  30

Lys Asn Gly Asn Gly Thr Ala Cys Ile Met Ala Asn Phe Ser Ala Ala
            35                  40                  45

Phe Ser Val Asn Tyr Asp Thr Lys Ser Gly Pro Lys Asn Met Thr Leu
    50                  55                  60

Asp Leu Pro Ser Asp Ala Thr Val Val Leu Asn Arg Ser Ser Cys Gly
65                  70                  75                  80

Lys Glu Asn Thr Ser Asp Pro Ser Leu Val Ile Ala Phe Gly Arg Gly
            85                  90                  95

His Thr Leu Thr Leu Asn Phe Thr Arg Asn Ala Thr Arg Tyr Ser Val
            100                 105                 110

Gln Leu Met Ser Phe Val Tyr Asn Leu Ser Asp Thr His Leu Phe Pro
            115                 120                 125

Asn Ala Ser Ser Lys Glu Ile Lys Thr Val Glu Ser Ile Thr Asp Ile
130                 135                 140

Arg Ala Asp Ile Asp Lys Lys Tyr Arg Cys Val Ser Gly Thr Gln Val
145                 150                 155                 160

His Met Asn Asn Val Thr Val Thr Leu His Asp Ala Thr Ile Gln Ala
            165                 170                 175

Tyr Leu Ser Asn Ser Ser Phe Ser Arg Gly Glu Thr Arg Cys Glu Gln
            180                 185                 190

Asp Arg Pro Ser Pro Thr Thr Ala Pro Pro Ala Pro Ser Pro Ser
            195                 200                 205

Pro Ser Pro Val Pro Lys Ser Pro Ser Val Asp Lys Tyr Asn Val Ser
    210                 215                 220

Gly Thr Asn Gly Thr Cys Leu Leu Ala Ser Met Gly Leu Gln Leu Asn
225                 230                 235                 240

Leu Thr Tyr Glu Arg Lys Asp Asn Thr Thr Val Thr Arg Leu Leu Asn
```

-continued

```
                245                 250                 255
Ile Asn Pro Asn Lys Thr Ser Ala Ser Gly Ser Cys Gly Ala His Leu
            260                 265                 270

Val Thr Leu Glu Leu His Ser Glu Gly Thr Thr Val Leu Leu Phe Gln
        275                 280                 285

Phe Gly Met Asn Ala Ser Ser Ser Arg Phe Phe Leu Gln Gly Ile Gln
    290                 295                 300

Leu Asn Thr Ile Leu Pro Asp Ala Arg Asp Pro Ala Phe Lys Ala Ala
305                 310                 315                 320

Asn Gly Ser Leu Arg Ala Leu Gln Ala Thr Val Gly Asn Ser Tyr Lys
                325                 330                 335

Cys Asn Ala Glu Glu His Val Arg Val Thr Lys Ala Phe Ser Val Asn
            340                 345                 350

Ile Phe Lys Val Trp Val Gln Ala Phe Lys Val Glu Gly Gln Phe
        355                 360                 365

Gly Ser Val Glu Glu Cys Leu Leu Asp Glu Asn Ser Leu Glu Ala Ala
    370                 375                 380

Asp Leu Gly Tyr Gly Pro Ala Thr Pro Ala Ala Pro Ala Ala Gly Tyr
385                 390                 395                 400

Thr Pro Ala Thr Pro Ala Ala Pro Ala Glu Ala Ala Pro Ala Gly Lys
                405                 410                 415

Ala Thr Thr Glu Glu Gln Lys Leu Ile Glu Lys Ile Asn Ala Gly Phe
            420                 425                 430

Lys Ala Ala Leu Ala Ala Ala Gly Val Gln Pro Ala Asp Lys Tyr
        435                 440                 445

Arg Thr Phe Val Ala Thr Phe Gly Ala Ala Ser Asn Lys Ala Phe Ala
    450                 455                 460

Glu Gly Leu Ser Gly Glu Pro Lys Gly Ala Ala Glu Ser Ser Ser Lys
465                 470                 475                 480

Ala Ala Leu Thr Ser Lys Leu Asp Ala Ala Tyr Lys Leu Ala Tyr Lys
                485                 490                 495

Thr Ala Glu Gly Ala Thr Pro Glu Ala Lys Tyr Asp Ala Tyr Val Ala
            500                 505                 510

Thr Leu Ser Glu Ala Leu Arg Ile Ile Ala Gly Thr Leu Glu Val His
        515                 520                 525

Ala Val Lys Pro Ala Ala Glu Glu Val Lys Val Ile Pro Ala Gly Glu
    530                 535                 540

Leu Gln Val Ile Glu Lys Val Asp Ala Ala Phe Lys Val Ala Ala Thr
545                 550                 555                 560

Ala Ala Asn Ala Ala Pro Ala Asn Asp Lys Phe Thr Val Phe Glu Ala
                565                 570                 575

Ala Phe Asn Asp Ala Ile Lys Ala Ser Thr Gly Gly Ala Tyr Glu Ser
            580                 585                 590

Tyr Lys Phe Ile Pro Ala Leu Glu Ala Val Lys Gln Ala Tyr Ala
        595                 600                 605

Ala Thr Val Ala Thr Ala Pro Glu Val Lys Tyr Thr Val Phe Glu Thr
    610                 615                 620

Ala Leu Lys Lys Ala Ile Thr Ala Met Ser Glu Ala Gln Lys Ala Ala
625                 630                 635                 640

Lys Pro Ala Ala Ala Ala Glu Phe Thr Leu Ile Pro Ile Ala Val Gly
                645                 650                 655

Gly Ala Leu Ala Gly Leu Val Leu Ile Val Leu Ile Ala Tyr Leu Val
            660                 665                 670
```

Gly Arg Lys Arg Ser His Ala Gly Tyr Gln Thr Ile
        675                 680

<210> SEQ ID NO 93
<211> LENGTH: 536
<212> TYPE: PRT
<213> ORGANISM: Dermatophagoides farinae

<400> SEQUENCE: 93

Ser Ile Lys Arg Asp His Asn Asp Tyr Ser Lys Asn Pro Met Arg Ile
1               5                   10                  15

Val Cys Tyr Val Gly Thr Trp Ser Val Tyr His Lys Val Asp Pro Tyr
            20                  25                  30

Thr Ile Glu Asp Ile Asp Pro Phe Lys Cys Thr His Leu Met Tyr Gly
        35                  40                  45

Phe Ala Lys Ile Asp Glu Tyr Lys Tyr Thr Ile Gln Val Phe Asp Pro
    50                  55                  60

Tyr Gln Asp Asp Asn His Asn Ser Trp Glu Lys Arg Gly Tyr Glu Arg
65                  70                  75                  80

Phe Asn Asn Leu Arg Leu Lys Asn Pro Glu Leu Thr Thr Met Ile Ser
                85                  90                  95

Leu Gly Gly Trp Tyr Glu Gly Ser Glu Lys Tyr Ser Asp Met Ala Ala
            100                 105                 110

Asn Pro Thr Tyr Arg Gln Gln Phe Ile Gln Ser Val Leu Asp Phe Leu
        115                 120                 125

Gln Glu Tyr Lys Phe Asp Gly Leu Asp Leu Asp Trp Glu Tyr Pro Gly
    130                 135                 140

Ser Arg Leu Gly Asn Pro Lys Ile Asp Lys Gln Asn Tyr Leu Ala Leu
145                 150                 155                 160

Val Arg Glu Leu Lys Asp Ala Phe Glu Pro His Gly Tyr Leu Leu Thr
                165                 170                 175

Ala Ala Val Ser Pro Gly Lys Asp Lys Ile Asp Arg Ala Tyr Asp Ile
            180                 185                 190

Lys Glu Leu Asn Lys Leu Phe Asp Trp Met Asn Val Met Thr Tyr Asp
        195                 200                 205

Tyr His Gly Gly Trp Glu Asn Phe Tyr Gly His Asn Ala Pro Leu Tyr
    210                 215                 220

Lys Arg Pro Asp Glu Thr Asp Glu Leu His Thr Tyr Phe Asn Val Asn
225                 230                 235                 240

Tyr Thr Met His Tyr Tyr Leu Asn Asn Gly Ala Thr Arg Asp Lys Leu
                245                 250                 255

Val Met Gly Val Pro Phe Tyr Gly Arg Ala Trp Ser Ile Glu Asp Arg
            260                 265                 270

Ser Lys Leu Lys Leu Gly Asp Pro Ala Lys Gly Met Ser Pro Pro Gly
        275                 280                 285

Phe Ile Ser Gly Glu Glu Gly Val Leu Ser Tyr Ile Glu Leu Cys Gln
    290                 295                 300

Leu Phe Gln Lys Glu Glu Trp His Ile Gln Tyr Asp Glu Tyr Tyr Asn
305                 310                 315                 320

Ala Pro Tyr Gly Tyr Asn Asp Lys Ile Trp Val Gly Tyr Asp Asp Leu
                325                 330                 335

Ala Ser Ile Ser Cys Lys Leu Ala Phe Leu Lys Glu Leu Gly Val Ser
            340                 345                 350

Gly Val Met Val Trp Ser Leu Glu Asn Asp Asp Phe Lys Gly His Cys

-continued

```
                355                 360                 365
Gly Pro Lys Asn Pro Leu Leu Asn Lys Val His Asn Met Ile Asn Gly
    370                 375                 380

Asp Glu Lys Asn Ser Phe Glu Cys Ile Leu Gly Pro Ser Thr Thr Thr
385                 390                 395                 400

Pro Thr Pro Thr Thr Thr Pro Thr Thr Thr Thr Thr Thr Pro Thr Thr
                405                 410                 415

Pro Ser Pro Thr Thr Pro Thr Thr Thr Pro Ser Pro Thr Thr Pro Thr
                420                 425                 430

Thr Thr Pro Ser Pro Thr Thr Pro Thr Thr Thr Pro Ser Pro Thr Thr
                435                 440                 445

Pro Thr Pro Thr Thr Pro Thr Pro Ala Pro Thr Thr Ser Thr Pro Ser
                450                 455                 460

Pro Thr Thr Thr Glu His Thr Ser Glu Thr Pro Lys Tyr Thr Thr Tyr
465                 470                 475                 480

Val Asp Gly His Leu Ile Lys Cys Tyr Lys Glu Gly Asp Ile Pro His
                485                 490                 495

Pro Thr Asn Ile His Lys Tyr Leu Val Cys Glu Phe Val Asn Gly Gly
                500                 505                 510

Trp Trp Val His Ile Met Pro Cys Pro Pro Gly Thr Ile Trp Cys Gln
                515                 520                 525

Glu Lys Leu Thr Cys Ile Gly Glu
                530                 535

<210> SEQ ID NO 94
<211> LENGTH: 424
<212> TYPE: PRT
<213> ORGANISM: Dermatophagoides farinae

<400> SEQUENCE: 94

Ser Asn Ile Arg Pro Asn Val Ala Thr Leu Glu Pro Lys Thr Val Cys
1               5                   10                  15

Tyr Tyr Glu Ser Trp Val His Trp Arg Gln Gly Glu Gly Lys Met Asp
                20                  25                  30

Pro Glu Asp Ile Asp Thr Ser Leu Cys Thr His Ile Val Tyr Ser Tyr
                35                  40                  45

Phe Gly Ile Asp Ala Ala Thr His Glu Ile Lys Leu Leu Asp Glu Tyr
    50                  55                  60

Leu Met Lys Asp Leu His Asp Met Glu His Phe Thr Gln His Lys Gly
65              70                  75                  80

Asn Ala Lys Ala Met Ile Ala Val Gly Gly Ser Thr Met Ser Asp Gln
                85                  90                  95

Phe Ser Lys Thr Ala Ala Val Glu His Tyr Arg Glu Thr Phe Val Val
                100                 105                 110

Ser Thr Val Asp Leu Met Thr Arg Tyr Gly Phe Asp Gly Val Met Ile
                115                 120                 125

Asp Trp Ser Gly Met Gln Ala Lys Asp Ser Asp Asn Phe Ile Lys Leu
    130                 135                 140

Leu Asp Lys Phe Asp Glu Asn Tyr Asn Ile Pro Ala Ile Ser Asn Tyr
145                 150                 155                 160

Val Asp Phe Met Asn Val Leu Ser Leu Asp Tyr Thr Gly Ser Trp Ala
                165                 170                 175

His Thr Val Gly His Ala Ser Pro Phe Pro Glu Gln Leu Lys Thr Leu
                180                 185                 190
```

Glu Ala Tyr His Lys Arg Gly Ala Pro Arg His Lys Met Val Met Ala
            195                 200                 205

Val Pro Phe Tyr Ala Arg Thr Trp Ile Leu Glu Lys Met Asn Lys Gln
    210                 215                 220

Asp Ile Gly Asp Lys Ala Ser Gly Pro Gly Pro Arg Gly Gln Phe Thr
225                 230                 235                 240

Gln Thr Asp Gly Phe Leu Ser Tyr Asn Glu Leu Cys Val Gln Ile Gln
                245                 250                 255

Ala Glu Thr Asn Ala Phe Thr Ile Thr Arg Asp His Asp Asn Thr Ala
            260                 265                 270

Ile Tyr Ala Val Tyr Val His Ser Asn His Ala Glu Trp Ile Ser Phe
    275                 280                 285

Glu Asp Arg His Thr Leu Gly Glu Lys Ala Lys Asn Ile Thr Gln Gln
290                 295                 300

Gly Tyr Ala Gly Met Ser Val Tyr Thr Leu Ser Asn Glu Asp Val His
305                 310                 315                 320

Gly Val Cys Gly Asp Lys Asn Pro Leu Leu His Ala Ile Gln Ser Asn
                325                 330                 335

Tyr Tyr His Gly Val Val Thr Glu Pro Thr Val Val Thr Leu Pro Pro
            340                 345                 350

Val Thr His Thr Thr Glu His Val Thr Asp Ile Pro Gly Val Phe His
    355                 360                 365

Cys His Glu Glu Gly Phe Phe Arg Asp Lys Thr Tyr Cys Ala Thr Tyr
370                 375                 380

Tyr Glu Cys Lys Lys Gly Asp Phe Gly Leu Glu Lys Thr Val His His
385                 390                 395                 400

Cys Ala Asn His Leu Gln Ala Phe Asp Glu Val Ser Arg Thr Cys Ile
                405                 410                 415

Asp His Thr Lys Ile Pro Gly Cys
            420

<210> SEQ ID NO 95
<211> LENGTH: 478
<212> TYPE: PRT
<213> ORGANISM: Dermatophagoides farinae

<400> SEQUENCE: 95

Asn Pro Arg Phe Lys Arg Asp Asn Arg Asp Asp Val Leu Lys Gln Thr
1               5                   10                  15

Glu Glu Leu Ile Lys Ser Ala Gln Asp Val Leu Glu Lys Leu Pro Asp
            20                  25                  30

Ser Asp Leu Lys Asp Glu Ile Ala Glu Lys Leu Ala Thr Met Lys His
        35                  40                  45

Tyr Lys His Glu Leu Glu Asn Ala Lys Asn Pro Ile Lys Ile Ala His
    50                  55                  60

Phe Glu Leu Glu Leu Leu Thr Met Phe Lys Lys Phe Gln Ser Leu Leu
65                  70                  75                  80

Asn Glu Ala Asn Glu Ile Ile Lys Ser Leu Thr Thr Thr Thr Thr Glu
                85                  90                  95

Pro Thr Thr Pro Thr Pro Glu Pro Thr Thr Thr Pro Glu Pro Thr
            100                 105                 110

Thr Lys Thr Pro Glu Pro Thr Thr Lys Thr Pro Glu Pro Thr Thr Pro
        115                 120                 125

Thr Pro Glu Pro Thr Thr Lys Thr Pro Glu Pro Thr Thr Lys Thr Pro
    130                 135                 140

Glu Pro Thr Thr Pro Thr Pro Glu Pro Thr Thr Lys Thr Pro Glu Pro
145                 150                 155                 160

Thr Thr Pro Thr Pro Glu Pro Thr Thr Lys Thr Pro Glu Pro Thr Thr
                165                 170                 175

Lys Thr Pro Glu Pro Ser Thr Pro Thr Pro Glu Pro Thr Thr Lys Thr
            180                 185                 190

Pro Glu Pro Thr Thr Lys Thr Pro Glu Pro Ser Thr Pro Thr Pro Glu
        195                 200                 205

Pro Thr Thr Lys Thr Pro Glu Pro Ser Thr Pro Thr Pro Glu Pro Thr
    210                 215                 220

Thr Lys Thr Pro Glu Pro Thr Thr Lys Thr Pro Glu Pro Ser Thr Pro
225                 230                 235                 240

Thr Pro Glu Pro Thr Thr Lys Thr Pro Glu Pro Ser Thr Pro Thr Pro
                245                 250                 255

Glu Pro Thr Thr Lys Thr Pro Glu Pro Ser Thr Thr Lys Lys Pro Asn
            260                 265                 270

Arg Asp Asp Val Leu Lys Gln Ala Glu Glu Leu Ile Lys Arg Ala Glu
        275                 280                 285

Asp Val Phe Glu Lys Leu Pro Asp Ser Asp Leu Lys Asn Glu Ile Ala
    290                 295                 300

Glu Lys Leu Ala Thr Met Lys Asn Tyr Lys His Glu Leu Glu Asn Ala
305                 310                 315                 320

Lys Asn Pro Ile Lys Ile Ala His Leu Glu Ser Glu Leu Leu Thr Met
                325                 330                 335

Phe Lys Met Phe Gln Ser Leu Leu Asn Glu Ala Asp Glu Ile Ile Arg
            340                 345                 350

Ser Leu Thr Thr Thr Thr Glu Pro Thr Thr Leu Asn Ser Thr Thr Pro
        355                 360                 365

Glu Pro Thr Thr Leu Asn Ser Thr Thr Pro Glu Pro Thr Thr Leu Asn
    370                 375                 380

Ser Thr Thr Pro Glu Pro Thr Thr Leu Asn Ser Thr Thr Pro Glu Pro
385                 390                 395                 400

Thr Thr Leu Asn Ser Thr Thr Pro Glu Pro Thr Thr Leu Asn Ser Thr
                405                 410                 415

Thr Pro Glu Pro Thr Thr Leu Asn Ser Thr Thr Pro Glu Pro Thr Thr
            420                 425                 430

Leu Asn Ser Thr Thr Pro Glu Pro Thr Thr Ser Asn Ser Thr Thr Ser
        435                 440                 445

Glu Pro Thr Asn Ser Ile Asn Arg Lys Thr Ser Glu Ile Ser Phe Leu
    450                 455                 460

Ser Asp Trp Phe His Lys Ile Arg Thr Arg Phe Asn Ile Phe
465                 470                 475

<210> SEQ ID NO 96
<211> LENGTH: 158
<212> TYPE: PRT
<213> ORGANISM: Ctenocephalides felis

<400> SEQUENCE: 96

Glu Asp Ile Trp Lys Val Asn Lys Lys Cys Thr Ser Gly Gly Lys Asn
1               5                   10                  15

Gln Asp Arg Lys Leu Asp Gln Ile Ile Gln Lys Gly Gln Gln Val Lys
            20                  25                  30

Ile Gln Asn Ile Cys Lys Leu Ile Arg Asp Lys Pro His Thr Asn Gln

-continued

```
                35                  40                  45
Glu Lys Glu Lys Cys Met Lys Phe Cys Lys Lys Val Cys Gly Tyr
 50                  55                  60

Arg Gly Ala Cys Asp Gly Asn Ile Cys Tyr Cys Ser Arg Pro Ser Asn
 65                  70                  75                  80

Leu Gly Pro Asp Trp Lys Val Ser Lys Glu Cys Lys Asp Pro Asn Asn
                 85                  90                  95

Lys Asp Ser Arg Pro Thr Glu Ile Val Pro Tyr Arg Gln Gln Leu Ala
            100                 105                 110

Ile Pro Asn Ile Cys Lys Leu Lys Asn Ser Glu Thr Asn Glu Asp Ser
            115                 120                 125

Lys Cys Lys Lys His Cys Lys Glu Lys Cys Arg Gly Gly Asn Asp Ala
130                 135                 140

Gly Cys Asp Gly Asn Phe Cys Tyr Cys Arg Pro Lys Asn Lys
145                 150                 155

<210> SEQ ID NO 97
<211> LENGTH: 30
<212> TYPE: PRT
<213> ORGANISM: Unknown
<220> FEATURE:
<223> OTHER INFORMATION: The species is not known as it may be one of
      several possibilities.
<220> FEATURE:
<221> NAME/KEY: UNSURE
<222> LOCATION: (1)..(10)
<223> OTHER INFORMATION: Each Xaa can be des-Xaa or any naturally
      occurring amino acid
<220> FEATURE:
<221> NAME/KEY: UNSURE
<222> LOCATION: (17)..(21)
<223> OTHER INFORMATION: Each Xaa can be des-Xaa or any naturally
      occurring amino acid
<220> FEATURE:
<221> NAME/KEY: UNSURE
<222> LOCATION: (26)..(30)
<223> OTHER INFORMATION: Each Xaa can be des-Xaa or any naturally
      occurring amino acid

<400> SEQUENCE: 97

Xaa Xaa Xaa Xaa Xaa Xaa Xaa Xaa Xaa Xaa Glu Lys Gln Pro Leu Leu
 1               5                  10                  15

Xaa Xaa Xaa Xaa Xaa Tyr His Ser Leu Xaa Xaa Xaa Xaa Xaa
            20                  25                  30

<210> SEQ ID NO 98
<211> LENGTH: 26
<212> TYPE: PRT
<213> ORGANISM: Unknown
<220> FEATURE:
<223> OTHER INFORMATION: The species is not known as it may be one of
      several possibilities.
<220> FEATURE:
<221> NAME/KEY: UNSURE
<222> LOCATION: (1)..(7)
<223> OTHER INFORMATION: Each Xaa can be des-Xaa or any naturally
      occurring amino acid
<220> FEATURE:
<221> NAME/KEY: UNSURE
<222> LOCATION: (15)..(26)
<223> OTHER INFORMATION: Each Xaa can be des-Xaa or any naturally
      occurring amino acid

<400> SEQUENCE: 98

Xaa Xaa Xaa Xaa Xaa Xaa Xaa Glu Ala Asn Gln Pro Leu Leu Xaa Xaa
 1               5                  10                  15
```

```
Xaa Xaa Xaa Xaa Xaa Xaa Xaa Xaa Xaa
            20                  25
```

<210> SEQ ID NO 99
<211> LENGTH: 45
<212> TYPE: PRT
<213> ORGANISM: Unknown
<220> FEATURE:
<223> OTHER INFORMATION: The species is not known as it may be one of
      several possibilities.
<220> FEATURE:
<221> NAME/KEY: UNSURE
<222> LOCATION: (1)..(34)
<223> OTHER INFORMATION: Each Xaa can be des-Xaa or any naturally
      occurring amino acid
<220> FEATURE:
<221> NAME/KEY: UNSURE
<222> LOCATION: (41)..(45)
<223> OTHER INFORMATION: Each Xaa can be des-Xaa or any naturally
      occurring amino acid

<400> SEQUENCE: 99

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Glu Asn Ser Pro Leu Leu Xaa Xaa Xaa Xaa Xaa
        35                  40                  45
```

<210> SEQ ID NO 100
<211> LENGTH: 10
<212> TYPE: PRT
<213> ORGANISM: Homo sapiens

<400> SEQUENCE: 100

```
Lys His His His Ala Gly Tyr Glu Gln Phe
1               5                   10
```

<210> SEQ ID NO 101
<211> LENGTH: 10
<212> TYPE: PRT
<213> ORGANISM: Homo sapiens

<400> SEQUENCE: 101

```
Lys Ser Ile Arg Ser Gly Tyr Glu Val Met
1               5                   10
```

<210> SEQ ID NO 102
<211> LENGTH: 18
<212> TYPE: PRT
<213> ORGANISM: Unknown
<220> FEATURE:
<223> OTHER INFORMATION: The species is not known as it may be one of
      several possibilities.

<400> SEQUENCE: 102

```
Arg Met Glu Ala Pro Pro Gly Tyr Arg His Val Ala Asp Gly Gln Asp
1               5                   10                  15

His Ala
```

<210> SEQ ID NO 103
<211> LENGTH: 4
<212> TYPE: PRT
<213> ORGANISM: Artificial sequence
<220> FEATURE:
<223> OTHER INFORMATION: Synthetic Construct

```
<400> SEQUENCE: 103

Tyr Gln Thr Leu
1

<210> SEQ ID NO 104
<211> LENGTH: 4
<212> TYPE: PRT
<213> ORGANISM: Artificial Sequence
<220> FEATURE:
<223> OTHER INFORMATION: Synthetic Construct

<400> SEQUENCE: 104

Tyr Gln Thr Phe
1

<210> SEQ ID NO 105
<211> LENGTH: 4
<212> TYPE: PRT
<213> ORGANISM: Artificial Sequence
<220> FEATURE:
<223> OTHER INFORMATION: Synthetic Construct

<400> SEQUENCE: 105

Tyr Gln Thr Thr
1

<210> SEQ ID NO 106
<211> LENGTH: 4
<212> TYPE: PRT
<213> ORGANISM: Artificial Sequence
<220> FEATURE:
<223> OTHER INFORMATION: Synthetic Construct

<400> SEQUENCE: 106

Tyr Ala Thr Ile
1

<210> SEQ ID NO 107
<211> LENGTH: 4
<212> TYPE: PRT
<213> ORGANISM: Artificial Sequence
<220> FEATURE:
<223> OTHER INFORMATION: Synthetic Construct

<400> SEQUENCE: 107

Tyr Gln Ala Ile
1

<210> SEQ ID NO 108
<211> LENGTH: 4
<212> TYPE: PRT
<213> ORGANISM: Artificial Sequence
<220> FEATURE:
<223> OTHER INFORMATION: Synthetic Construct

<400> SEQUENCE: 108

Tyr Ala Ala Ile
1

<210> SEQ ID NO 109
<211> LENGTH: 965
<212> TYPE: PRT
<213> ORGANISM: Artificial Sequence
<220> FEATURE:
<223> OTHER INFORMATION: Synthetic Construct

<400> SEQUENCE: 109
```

-continued

```
Ser Ile Lys Arg Asp His Asn Asp Tyr Ser Lys Asn Pro Met Arg Ile
  1               5                  10                  15

Val Cys Tyr Val Gly Thr Trp Ser Val Tyr His Lys Val Asp Pro Tyr
             20                  25                  30

Thr Ile Glu Asp Ile Asp Pro Phe Lys Cys Thr His Leu Met Tyr Gly
             35                  40                  45

Phe Ala Lys Ile Asp Glu Tyr Lys Tyr Thr Ile Gln Val Phe Asp Pro
         50                  55                  60

Tyr Gln Asp Asp Asn His Asn Ser Trp Glu Lys Arg Gly Tyr Glu Arg
 65                  70                  75                  80

Phe Asn Asn Leu Arg Leu Lys Asn Pro Glu Leu Thr Thr Met Ile Ser
                 85                  90                  95

Leu Gly Gly Trp Tyr Glu Gly Ser Glu Lys Tyr Ser Asp Met Ala Ala
            100                 105                 110

Asn Pro Thr Tyr Arg Gln Gln Phe Ile Gln Ser Val Leu Asp Phe Leu
            115                 120                 125

Gln Glu Tyr Lys Phe Asp Gly Leu Asp Leu Asp Trp Glu Tyr Pro Gly
        130                 135                 140

Ser Arg Leu Gly Asn Pro Lys Ile Asp Lys Gln Asn Tyr Leu Ala Leu
145                 150                 155                 160

Val Arg Glu Leu Lys Asp Ala Phe Glu Pro His Gly Tyr Leu Leu Thr
                165                 170                 175

Ala Ala Val Ser Pro Gly Lys Asp Lys Ile Asp Arg Ala Tyr Asp Ile
            180                 185                 190

Lys Glu Leu Asn Lys Leu Phe Asp Trp Met Asn Val Met Thr Tyr Asp
            195                 200                 205

Tyr His Gly Gly Trp Glu Asn Phe Tyr Gly His Asn Ala Pro Leu Tyr
        210                 215                 220

Lys Arg Pro Asp Glu Thr Asp Glu Leu His Thr Tyr Phe Asn Val Asn
225                 230                 235                 240

Tyr Thr Met His Tyr Tyr Leu Asn Asn Gly Ala Thr Arg Asp Lys Leu
                245                 250                 255

Val Met Gly Val Pro Phe Tyr Gly Arg Ala Trp Ser Ile Glu Asp Arg
            260                 265                 270

Ser Lys Leu Lys Leu Gly Asp Pro Ala Lys Gly Met Ser Pro Pro Gly
        275                 280                 285

Phe Ile Ser Gly Glu Glu Gly Val Leu Ser Tyr Ile Glu Leu Cys Gln
        290                 295                 300

Leu Phe Gln Lys Glu Glu Trp His Ile Gln Tyr Asp Glu Tyr Tyr Asn
305                 310                 315                 320

Ala Pro Tyr Gly Tyr Asn Asp Lys Ile Trp Val Gly Tyr Asp Asp Leu
                325                 330                 335

Ala Ser Ile Ser Cys Lys Leu Ala Phe Leu Lys Glu Leu Gly Val Ser
            340                 345                 350

Gly Val Met Val Trp Ser Leu Glu Asn Asp Asp Phe Lys Gly His Cys
        355                 360                 365

Gly Pro Lys Asn Pro Leu Leu Asn Lys Val His Asn Met Ile Asn Gly
370                 375                 380

Asp Glu Lys Asn Ser Phe Glu Cys Ile Leu Gly Pro Ser Thr Thr Thr
385                 390                 395                 400

Pro Thr Pro Thr Thr Thr Pro Thr Thr Pro Thr Thr Pro Thr Thr
                405                 410                 415
```

```
Pro Ser Pro Thr Thr Pro Thr Thr Pro Ser Pro Thr Thr Pro Thr
            420                 425                 430

Thr Thr Pro Ser Pro Thr Thr Pro Thr Thr Thr Pro Ser Pro Thr Thr
        435                 440                 445

Pro Thr Pro Thr Thr Pro Thr Pro Ala Pro Thr Ser Thr Pro Ser
450                 455                 460

Pro Thr Thr Thr Glu His Thr Ser Glu Thr Pro Lys Tyr Thr Thr Tyr
465                 470                 475                 480

Val Asp Gly His Leu Ile Lys Cys Tyr Lys Glu Gly Asp Ile Pro His
                485                 490                 495

Pro Thr Asn Ile His Lys Tyr Leu Val Cys Glu Phe Val Asn Gly Gly
            500                 505                 510

Trp Trp Val His Ile Met Pro Cys Pro Gly Thr Ile Trp Cys Gln
            515                 520                 525

Glu Lys Leu Thr Cys Ile Gly Glu Gly Pro Gly Pro Gly Ser Asn Ile
            530                 535                 540

Arg Pro Asn Val Ala Thr Leu Glu Pro Lys Thr Val Cys Tyr Tyr Glu
545                 550                 555                 560

Ser Trp Val His Trp Arg Gln Gly Gly Lys Met Asp Pro Glu Asp
                565                 570                 575

Ile Asp Thr Ser Leu Cys Thr His Ile Val Tyr Ser Tyr Phe Gly Ile
            580                 585                 590

Asp Ala Ala Thr His Glu Ile Lys Leu Leu Asp Glu Tyr Leu Met Lys
            595                 600                 605

Asp Leu His Asp Met Glu His Phe Thr Gln His Lys Gly Asn Ala Lys
610                 615                 620

Ala Met Ile Ala Val Gly Gly Ser Thr Met Ser Asp Gln Phe Ser Lys
625                 630                 635                 640

Thr Ala Ala Val Glu His Tyr Arg Glu Thr Phe Val Val Ser Thr Val
                645                 650                 655

Asp Leu Met Thr Arg Tyr Gly Phe Asp Gly Val Met Ile Asp Trp Ser
                660                 665                 670

Gly Met Gln Ala Lys Asp Ser Asp Asn Phe Ile Lys Leu Leu Asp Lys
            675                 680                 685

Phe Asp Glu Asn Tyr Asn Ile Pro Ala Ile Ser Asn Tyr Val Asp Phe
690                 695                 700

Met Asn Val Leu Ser Leu Asp Tyr Thr Gly Ser Trp Ala His Thr Val
705                 710                 715                 720

Gly His Ala Ser Pro Phe Pro Glu Gln Leu Lys Thr Leu Glu Ala Tyr
                725                 730                 735

His Lys Arg Gly Ala Pro Arg His Lys Met Val Met Ala Val Pro Phe
                740                 745                 750

Tyr Ala Arg Thr Trp Ile Leu Glu Lys Met Asn Lys Gln Asp Ile Gly
            755                 760                 765

Asp Lys Ala Ser Gly Pro Gly Pro Arg Gly Gln Phe Thr Gln Thr Asp
770                 775                 780

Gly Phe Leu Ser Tyr Asn Glu Leu Cys Val Gln Ile Gln Ala Glu Thr
785                 790                 795                 800

Asn Ala Phe Thr Ile Thr Arg Asp His Asp Asn Thr Ala Ile Tyr Ala
                805                 810                 815

Val Tyr Val His Ser Asn His Ala Glu Trp Ile Ser Phe Glu Asp Arg
                820                 825                 830

His Thr Leu Gly Glu Lys Ala Lys Asn Ile Thr Gln Gln Gly Tyr Ala
```

```
                835                 840                 845
Gly Met Ser Val Tyr Thr Leu Ser Asn Glu Asp Val His Gly Val Cys
        850                 855                 860

Gly Asp Lys Asn Pro Leu Leu His Ala Ile Gln Ser Asn Tyr Tyr His
865                 870                 875                 880

Gly Val Val Thr Glu Pro Thr Val Val Thr Leu Pro Pro Val Thr His
                885                 890                 895

Thr Thr Glu His Val Thr Asp Ile Pro Gly Val Phe His Cys His Glu
            900                 905                 910

Glu Gly Phe Phe Arg Asp Lys Thr Tyr Cys Ala Thr Tyr Tyr Glu Cys
        915                 920                 925

Lys Lys Gly Asp Phe Gly Leu Glu Lys Thr Val His His Cys Ala Asn
930                 935                 940

His Leu Gln Ala Phe Asp Glu Val Ser Arg Thr Cys Ile Asp His Thr
945                 950                 955                 960

Lys Ile Pro Gly Cys
                965

<210> SEQ ID NO 110
<211> LENGTH: 965
<212> TYPE: PRT
<213> ORGANISM: Artificial
<220> FEATURE:
<223> OTHER INFORMATION: Synthetic Construct

<400> SEQUENCE: 110

Ser Ile Lys Arg Asp His Asn Asp Tyr Ser Lys Asn Pro Met Arg Ile
1               5                   10                  15

Val Cys Tyr Val Gly Thr Trp Ser Val Tyr His Lys Val Asp Pro Tyr
            20                  25                  30

Thr Ile Glu Asp Ile Asp Pro Phe Lys Cys Thr His Leu Met Tyr Gly
        35                  40                  45

Phe Ala Lys Ile Asp Glu Tyr Lys Tyr Thr Ile Gln Val Phe Asp Pro
    50                  55                  60

Tyr Gln Asp Asp Asn His Asn Ser Trp Glu Lys Arg Gly Tyr Glu Arg
65                  70                  75                  80

Phe Asn Asn Leu Arg Leu Lys Asn Pro Glu Leu Thr Thr Met Ile Ser
                85                  90                  95

Leu Gly Gly Trp Tyr Glu Gly Ser Glu Lys Tyr Ser Asp Met Ala Ala
            100                 105                 110

Asn Pro Thr Tyr Arg Gln Gln Phe Ile Gln Ser Val Leu Asp Phe Leu
        115                 120                 125

Gln Glu Tyr Lys Phe Asp Gly Leu Asp Leu Asp Trp Glu Tyr Pro Gly
    130                 135                 140

Ser Arg Leu Gly Asn Pro Lys Ile Asp Lys Gln Asn Tyr Leu Ala Leu
145                 150                 155                 160

Val Arg Glu Leu Lys Asp Ala Phe Glu Pro His Gly Tyr Leu Leu Thr
                165                 170                 175

Ala Ala Val Ser Pro Gly Lys Asp Lys Ile Asp Arg Ala Tyr Asp Ile
            180                 185                 190

Lys Glu Leu Asn Lys Leu Phe Asp Trp Met Asn Val Met Thr Tyr Asp
        195                 200                 205

Tyr His Gly Gly Trp Glu Asn Phe Tyr Gly His Asn Ala Pro Leu Tyr
    210                 215                 220

Lys Arg Pro Asp Glu Thr Asp Glu Leu His Thr Tyr Phe Asn Val Asn
```

-continued

```
              225                 230                 235                 240
Tyr Thr Met His Tyr Leu Asn Asn Gly Ala Thr Arg Asp Lys Leu
              245                 250                 255

Val Met Gly Val Pro Phe Tyr Gly Arg Ala Trp Ser Ile Glu Asp Arg
              260                 265                 270

Ser Lys Leu Lys Leu Gly Asp Pro Ala Lys Gly Met Ser Pro Gly
              275                 280                 285

Phe Ile Ser Gly Glu Glu Gly Val Leu Ser Tyr Ile Glu Leu Cys Gln
              290                 295                 300

Leu Phe Gln Lys Glu Glu Trp His Ile Gln Tyr Asp Glu Tyr Asn
305                 310                 315                 320

Ala Pro Tyr Gly Tyr Asn Asp Lys Ile Trp Val Gly Tyr Asp Asp Leu
                    325                 330                 335

Ala Ser Ile Ser Cys Lys Leu Ala Phe Leu Lys Glu Leu Gly Val Ser
                    340                 345                 350

Gly Val Met Val Trp Ser Leu Glu Asn Asp Asp Phe Lys Gly His Cys
                    355                 360                 365

Gly Pro Lys Asn Pro Leu Leu Asn Lys Val His Asn Met Ile Asn Gly
370                 375                 380

Asp Glu Lys Asn Ser Phe Glu Cys Ile Leu Gly Pro Ser Thr Thr Thr
385                 390                 395                 400

Pro Thr Pro Thr Thr Pro Thr Thr Pro Thr Thr Thr Pro Thr Thr
                    405                 410                 415

Pro Ser Pro Thr Thr Pro Thr Thr Thr Pro Ser Pro Thr Thr Pro Thr
                    420                 425                 430

Thr Thr Pro Ser Pro Thr Thr Pro Thr Thr Thr Pro Ser Pro Thr Thr
                    435                 440                 445

Pro Thr Pro Thr Thr Pro Thr Pro Ala Pro Thr Thr Ser Thr Pro Ser
                    450                 455                 460

Pro Thr Thr Thr Glu His Thr Ser Glu Thr Pro Lys Tyr Thr Thr Tyr
465                 470                 475                 480

Val Asp Gly His Leu Ile Lys Cys Tyr Lys Glu Gly Asp Ile Pro His
                    485                 490                 495

Pro Thr Asn Ile His Lys Tyr Leu Val Cys Glu Phe Val Asn Gly Gly
                    500                 505                 510

Trp Trp Val His Ile Met Pro Cys Pro Pro Gly Thr Ile Trp Cys Gln
                    515                 520                 525

Glu Lys Leu Thr Cys Ile Gly Glu Gly Pro Gly Pro Gly Ser Asn Ile
                    530                 535                 540

Arg Pro Asn Val Ala Thr Leu Glu Pro Lys Thr Val Cys Tyr Tyr Glu
545                 550                 555                 560

Ser Trp Val His Trp Arg Gln Gly Glu Gly Lys Met Asp Pro Glu Asp
                    565                 570                 575

Ile Asp Thr Ser Leu Cys Thr His Ile Val Tyr Ser Tyr Phe Gly Ile
                    580                 585                 590

Asp Ala Ala Thr His Glu Ile Lys Leu Leu Asp Glu Tyr Leu Met Lys
                    595                 600                 605

Asp Leu His Asp Met Glu His Phe Thr Gln His Lys Gly Asn Ala Lys
                    610                 615                 620

Ala Met Ile Ala Val Gly Gly Ser Thr Met Ser Asp Gln Phe Ser Lys
625                 630                 635                 640

Thr Ala Ala Val Glu His Tyr Arg Glu Thr Phe Val Val Ser Thr Val
                    645                 650                 655
```

```
Asp Leu Met Thr Arg Tyr Gly Phe Asp Gly Val Met Ile Asp Trp Ser
            660             665             670

Gly Met Gln Ala Lys Asp Ser Asp Asn Phe Ile Lys Leu Leu Asp Lys
        675             680             685

Phe Asp Glu Asn Tyr Asn Ile Pro Ala Ile Ser Asn Tyr Val Asp Phe
    690             695             700

Met Asn Val Leu Ser Leu Asp Tyr Thr Gly Ser Trp Ala His Thr Val
705             710             715                     720

Gly His Ala Ser Pro Phe Pro Glu Gln Leu Lys Thr Leu Glu Ala Tyr
                725             730             735

His Lys Arg Gly Ala Pro Arg His Lys Met Val Met Ala Val Pro Phe
            740             745             750

Tyr Ala Arg Thr Trp Ile Leu Glu Lys Met Asn Lys Gln Asp Ile Gly
            755             760             765

Asp Lys Ala Ser Gly Pro Gly Pro Arg Gly Gln Phe Thr Gln Thr Asp
    770             775             780

Gly Phe Leu Ser Tyr Asn Glu Leu Cys Val Gln Ile Gln Ala Glu Thr
785             790             795                     800

Asn Ala Phe Thr Ile Thr Arg Asp His Asp Asn Thr Ala Ile Tyr Ala
            805             810             815

Val Tyr Val His Ser Asn His Ala Glu Trp Ile Ser Phe Glu Asp Arg
            820             825             830

His Thr Leu Gly Glu Lys Ala Lys Asn Ile Thr Gln Gln Gly Tyr Ala
            835             840             845

Gly Met Ser Val Tyr Thr Leu Ser Asn Glu Asp Val His Gly Val Cys
    850             855             860

Gly Asp Lys Asn Pro Leu Leu His Ala Ile Gln Ser Asn Tyr Tyr His
865             870             875                     880

Gly Val Val Thr Glu Pro Thr Val Val Thr Leu Pro Pro Val Thr His
            885             890             895

Thr Thr Glu His Val Thr Asp Ile Pro Gly Val Phe His Cys His Glu
            900             905             910

Glu Gly Phe Phe Arg Asp Lys Thr Tyr Cys Ala Thr Tyr Tyr Glu Cys
            915             920             925

Lys Lys Gly Asp Phe Gly Leu Glu Lys Thr Val His His Cys Ala Asn
    930             935             940

His Leu Gln Ala Phe Asp Glu Val Ser Arg Thr Cys Ile Asp His Thr
945             950             955                     960

Lys Ile Pro Gly Cys
            965
```